United States Patent
Bourque et al.

(10) Patent No.: US 9,139,580 B2
(45) Date of Patent: Sep. 22, 2015

(54) GLUCOSYLCERAMIDE SYNTHASE INHIBITORS

(71) Applicant: GENZYME CORPORATION, Cambridge, MA (US)

(72) Inventors: Elyse Bourque, Blaine, WA (US); Bradford Hirth, Framingham, MA (US); Renato Sklerj, West Newton, MA (US); Elina Makino, Winchester, MA (US); Fazeela Morshed, Waltham, MA (US); Lingyun Li, Waltham, MA (US); Paul Mason, Natick, MA (US); John P. Leonard, Manchester, NH (US); James Lillie, Wellesley, MA (US); Hanlan Liu, Lexington, MA (US); Mary A. Cromwell, Groton, MA (US); Bing Wang, Newton, MA (US); Thomas O'Shea, Wellesley, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 14/030,725

(22) Filed: Sep. 18, 2013

(65) Prior Publication Data

US 2014/0255381 A1  Sep. 11, 2014

Related U.S. Application Data

(63) Continuation of application No. PCT/US2012/029417, filed on Mar. 16, 2012.

(60) Provisional application No. 61/590,711, filed on Jan. 25, 2012, provisional application No. 61/454,034, filed on Mar. 18, 2011.

(51) Int. Cl.
| | |
|---|---|
| *A01N 43/90* | (2006.01) |
| *A61K 31/44* | (2006.01) |
| *C07D 453/02* | (2006.01) |
| *A61K 38/47* | (2006.01) |
| *A61K 31/439* | (2006.01) |
| *A61K 31/454* | (2006.01) |
| *C07D 453/00* | (2006.01) |

(52) U.S. Cl.
CPC ............ *C07D 453/02* (2013.01); *A61K 31/439* (2013.01); *A61K 31/454* (2013.01); *A61K 38/47* (2013.01); *C07D 453/00* (2013.01)

(58) Field of Classification Search
CPC .. C07D 453/00; C07D 453/02; A61K 31/439; A61K 31/454; A61K 38/47
USPC .......................... 546/137; 514/305; 424/94.61
See application file for complete search history.

(56) References Cited

U.S. PATENT DOCUMENTS

| | | |
|---|---|---|
| 3,119,742 A | 1/1964 | Heimlich et al. |
| 3,492,397 A | 1/1970 | Peters et al. |
| 3,538,214 A | 11/1970 | Poli et al. |
| 4,060,598 A | 11/1977 | Groppenbacher et al. |
| 4,173,626 A | 11/1979 | Dempski et al. |
| 4,983,600 A | 1/1991 | Ward et al. |
| 5,236,838 A | 8/1993 | Rasmussen et al. |
| 5,272,071 A | 12/1993 | Chappel |
| 5,549,892 A | 8/1996 | Friedman et al. |
| 5,968,502 A | 10/1999 | Treco et al. |
| 6,066,626 A | 5/2000 | Yew et al. |
| 2004/0002513 A1 | 1/2004 | Mazurov et al. |
| 2006/0058349 A1 | 3/2006 | Ali et al. |
| 2009/0163500 A1 | 6/2009 | Lingwood et al. |
| 2011/0052559 A1 | 3/2011 | Schuchman et al. |

FOREIGN PATENT DOCUMENTS

| | | |
|---|---|---|
| EP | 0747355 | 12/1996 |
| WO | WO 00/58311 | 10/2000 |
| WO | WO 2004/007453 | 1/2004 |
| WO | WO 2005/068426 | 7/2005 |
| WO | WO 2006/053043 | 5/2006 |
| WO | WO 2010/014554 | 2/2010 |
| WO | WO 2010/091104 | 8/2010 |
| WO | WO 2010/091164 | 8/2010 |

OTHER PUBLICATIONS

Aerts et al., Elevated globotriaosylsphingosine is a hallmark of Fabry disease, PNAS USA, vol. 105, pp. 2812-2817 (2008).
Auray-Blais et al., How well does urinary lyso-Gb3 function as a biomarker in Fabry disease?, Clin. Chim. Acta, vol. 411, pp. 1906-1914 (2010).
Barranger, Glucosylceramide lipidosis: Gaucher disease. In: Scriver CR BA, Sly WS, Valle D, editor. The Metabolic Basis of Inherited Disease. New York: McGraw-Hill. pp. 3635-3668 (2001).
Barton et al., Replacement Therapy for Inherited Enzyme Deficiency—Macrophage-targeted Glucocerebrosidase for Gaucher's Disease, New England Journal of Medicine 324, 1464-1470 (1991).
Beniaminovitz et al., Prevention of Rejection in Cardiac Transplantation by Blockade of the Interleukin-2 Receptor With a Monoclonal Antibody, (2000), N. Engl J. Med. 342, 613-619.
Berard et al., A Review of Interleukin-2 Receptor Antagonists in Solid Organ Transplantation, (1999), Pharmacotherapy 19, 1127-1137.
Branco et al., Selective Deletion of Antigen-Specific, Activated T Cells by a Humanized MAB to CD2 (MEDI-507) is Mediated by NK Cells, (1999), Transplantation 68, 1588-1596.
Brenkert et al., Synthesis of Galactosyl Ceramide and Glucosyl Ceramide by Rat Brain: Assay Procedures and Changes With Age, Brain Research 36: 183-193 (1972).
Bundgard, Design of Prodrugs, pp. 7-9, 21-24 (1985).
Cabrera-Salazar et al., Intracerebroventricular delivery of glucocerebrosidase reduces substrates and increases lifespan in a mouse model of neuronopathic Gaucher disease, Experimental Neurology 225: 436-444 (2010).

(Continued)

*Primary Examiner* — Uma Ramachandran
(74) *Attorney, Agent, or Firm* — Jennifer D. Tousignant

(57) ABSTRACT

The invention relates to inhibitors of glucosylceramide synthase (GCS) useful for the treatment metabolic diseases, such as lysosomal storage diseases, either alone or in combination with enzyme replacement therapy, and for the treatment of cancer.

1 Claim, 20 Drawing Sheets

(56) References Cited

OTHER PUBLICATIONS

Chirmule et al., Readministration of Adenovirus Vector in Nonhuman PrimateLungs by Blockade of CD40-CD40 Ligand Interactions, (2000), J. Virol. 74, 3345-3352.
Conradi et al., Neuropathology of the Norrbottnian Type of Gaucher Disease, Acta Neuropathologica 65: 99-109(1984).
Conradi et al., Late-infantile Gaucher disease in a child with myoclonus andbulbar signs: neuropathological and neurochemical findings, Acta Neuropathologica 82: 152-157 (1991).
Czartoryska et al., Changes in Serum Chitotriosidase Activity with Cessation of Replacement Enzyme (Cerebrosidase) Administration in Gaucher Disease, (2000), Clin. Biochem. 33, 147-149.
Czartoryska et al., Serum Chitotriosidase Activity in Gaucher Patients on Enzyme Replacement Therapy (ERT), 1998, Clin. Biochem. 31, 417-420.
Davidson et al., The Neuronal Ceroid Lipofuscinosis, Clinical Features and Molecular Basis of Disease, Lysosomal Storage Disorders, (2007), pp. 371-388. Springer, New York, U.S.A.
Den Tandt et al., Marked increase of methylumbelliteryl-tetra-N-acetylchitotetraoside hydrolase activity inplasma from Gaucher disease patients, (1996), J. Inherit. Metab. Dis. 19, 344-350.
International Search Report for WO2012/0129084 dated Jul. 2, 2013.
Desnick RJ et al., (1995), alpha.-Galactosidase A Deficiency: Fabry Disease, In: The Metabolic and Molecular Bases of Inherited Disease, Scriver et al., eds., McGraw-Hill, N.Y., 7.sup.th ed., pp. 2741-2784.
Dodelson de Kremer et al., (1997), Medicina (Buenos Aires) 57, 677-684.
Eckhoff et al., The Safety and Efficacy of a Two-Dose Daclizumab (Zenapax) Induction Therapy in Liver Transplant Recipients, (2000), Transplantation 69, 1867-1872.
Ekberg et al., Daclizumab Prevents Acute Rejection and Improves Patient Survival Post Transplantation: 1 Year Pooled Analysis, (2000), Transpl. Int. 13, 151-159.
El Alwani et al., Regulation of the sphingolipidsignaling pathways in the growing andhypoxic rat heart, Prostaglandins & Other Lipid Mediators, (2005), 78(1-4), 249-263.
Young et al., Plasma chitotriosidase activity in Gaucher disease patients who have been treated either by bone marrow transplantation or by enzyme replacement therapy with alglucerase, (1997), J. Inherit. Metab. Dis. 20, 595-602.
Enquist et al., Murine models of acute neuronopathicGaucher disease, PNAS 104: 17483-17488 (2007).
Fernandez et al., Synthesis of Ethylenediamines-alpha, alpha-disubstituted, Anales de la Real Academia de Farmacia (1988), 54, 502.
Fishwild et al., Differential Effects of Administration of a Human Anti-CD4 MonoclonalAntibody, HM6G, in Nonhuman Primates, (1999), Clin. Immunol. 92, 138-152.
Gaziev et al., Chronic graft-versus-host disease: is there an alternative to theconventional treatment?, (2000), Bone Marrow Transplant. 25, 689-696.
Giri et al., Krabbe disease: psychosine-mediated activation ofphospholipase A2 in oligodendrocyte cell death, Journal of lipid research 47: 1478-1492 (2006).
Goker-Alpan et al., Phenotypic Continuum in Neuronopathic Gaucher Disease: An intermediate Phenotype Between Type 2 and Type 3, The Journal of Pediatrics 143: 273-276 (2003).
Grabowski et al., (1995), Enzyme Therapy in Type 1 Gaucher Disease: Comparative Efficacy of Mannose-terminated Glucocerebrosidase from Natural and Recombinant Sources, Annals of Internal Medicine 122, 33-39.
Graler et al., Lysophospholipids and their G protein-coupled receptorsin inflammation and immunity, Molecular and Cell Biology of Lipids 1582: 168-174 (2002).
Gummert et al., Newer Immunosuppressive Drugs: A Review, (1999), J. Am. Soc. Nephrol. 10, 1366-1380.
Guo et al., Elevated plasma chitotriosidase activity invarious lysosomal storage disorders, (1995), J. Inherit. Metab. Dis. 18, 717-722.

Henry, Cyclosporine and tacrolimus (FK506): Acomparison of efficacy and safety profiles, (1999), Clin. Transplant. 13, 209-220.
Hers, Inborn Lysosomal Diseases, (1965), Gastroenterology 48, 625.
Hirschhorn R, Glycogen Storage Disease Type II: Acid alpha-Glucosidase (Acid Maltase) Deficiency, In: The Metabolic and Molecular Bases of Inherited Disease, Scriver et al., eds., McGraw-Hill, N.Y., 7.sup.th ed., pp. 2443-2464, (1995).
Hollak et al., Marked Elevation of Plasma Chitotriosidase ActivityA Novel Hallmark of Gaucher Disease, (1994), J. Clin. Invest. 93, 1288-1292.
Hong et al., Immunosuppressive Agents in Organ Transplantation: Past, Present, and Future, (2000), Semin. Nephrol. 20, 108-125.
Ida et al., Clinical and genetic: studies of Japanese homozygotes for the Gaucher disease L444P mutation, Human Genetics 105: 120-126 (1999).
Ideguchi et al., Local Adenovirus-mediated CTLA4-immunoglobulin Expression Suppresses the Immune Responses to Adenovirus Vectors in the Brain, (2000), Neuroscience 95, 217-226.
Ito et al., Induction of CTL Responses by Simultaneous Administration of Liposomal Peptide Vaccine with Anti-CD40 and Anti-CTLA-4 mAb, (2000), J. Immunol. 164, 1230-1235.
Kurlberg et al., Blockade of the B7-CD28 Pathway by CTLA4±Ig CounteractsRejection and Prolongs Survival in Small Bowel Transplantation, (2000), Scand. J. Immunol. 51, 224-230.
Leonard et al., Cytokine receptor signaling pathways, (2000), J. Allergy Clin. Immunol. 105, 877-888.
Liu et al., Mice with type 2 and 3 Gaucher disease point mutations generatedby a single insertion mutagenesis procedure (SIMP), PNAS 95: 2503-2508 (1998).
Marinova-Mutafchieva et al., A Comparative Study into the Mechanisms of Action of Anti-Tumor Necrosis Factor a/Anti-CD4, and Combined Anti-Tumor Necrosis Factor a/Anti-CD4 Treatment in Early Collagen-Induced Arthritis, (2000), Arthritis Rheum. 43, 638-644.
Marks et al., Identification of Active Site Residues in Glucosylceramide Synthase, Journal of Biological Chemistry, (2001), 276, pp. 26492-26498.
Marshall et al., Substrate Reduction Augments the Efficacy of EnzymeTherapy in a Mouse Model of Fabry Disease, PLoS ONE 5:e15033 (2010).
Merrill et al., Sphingolipidomics: High-throughput, structure-speciWc,and quantitative analysis of sphingolipids by liquid chromatographytandem mass spectrometry, Methods 36: 207-224 (2005).
Mistry et al., A practical approach to diagnosis and management of Gaucher's disease, (1997), Baillieres Clin Haematol. 10, 817-838.
Moder, New medications for use in patients with rheumatoid arthritis, (2000), Ann. Allergy Asthma Immunol. 84, 280-284.
Morales, Gaucher's Disease: A Review, The Annals of Pharmacotherapy 30, 381-388, (1996).
Nevins, Overview of new immunosuppressive therapies, (2000), Curr. Opin. Pediatr. 12, 146-150.
Nilsson, Accumulation of Glucosylceramide andGlucosylsphingosine (Psychosine) in Cerebrum andCerebellum in Infantile and Juvenile Gaucher Disease, J Neurochem 39: 709-718 (1982).
Oberholzer et al., Cytokine signaling—regulation of the immune response in normal and critically ill states, (2000), Crit. Care Med. 28 (4 Suppl.), N3-N12.
Orvisky et al., Glucosylsphingosine accumulation in tissues from patients with Gaucher disease: correlation with phenotype and genotype. Molecular Genetics and Metabolism 76: 262-270 (2002).
Orvisky et al., Glucosylsphingosine Accumulation in Mice and Patients with Type 2 Gaucher Disease Begins Early in Gestation, Pediatric Research 48: 233-237 (2000).
Pastores et al., Enzyme Therapy in Gaucher Disease Type 1: Dosage Efficacy and Adverse Effects in 33 Patients treated for 6 to 24 Months, (1993), Blood 82, 408-416.
Pelled et al., The increased sensitivity of neurons with elevated glucocerebroside to neurotoxic agents can be reversed by imiglucerase, Journal of Inherited Metabolic Disease 23: 175-184 (2000).

(56) References Cited

OTHER PUBLICATIONS

Ponticelli et al., Promising New Agents in the Prevention of Transplant Rejection, (1999), Drugs R. D. 1, 55-60.

Potter et al., Review—The Use of immunosuppressive Agents to Prevent Neutralizing Antibodies Against a Transgene Product, (1999), Ann. N.Y. Acad. Sci. 875. 159-174.

Przepiorka et al., A Phase II Study of BTI-322, a Monoclonal Anti-CD2 Antibody, for Treatment of Steroid-Resistant Acute Graft-Versus-Host Disease, (1998), Blood 92, 4066-4071.

Qi et al., Effect of Tacrolimus (FK506) and Sirolimus (Rapamycin) Mono- and Combination Therapy in Prolongation of Renal Allograft Survival in the Monkey, (2000), Transplantation 69, 1275-1283.

Rosenthal et al., Enzyme Replacement Therapy for Gaucher Disease: Skeletal Responses to Macrophage-targeted Glucocerebrosidase, (1995), Pediatrics 96, 629-637.

Rubinstein et al., Recent Advances in Cytokines, Cytokine Receptors and Signal Transduction, (1998), Cytokine Growth Factor Rev. 9, 175-181.

Ryan et al., Clinical Outcomes and insulin Secretion After Islet Transplantation With the Edmonton Protocol, (2001), Diabetes 50, 710-719.

Schueler et al., Toxicity of glucosylsphingosine (glucopsychosine) to cultured neuronalcells: a model system for assessing neuronal damage in Gaucher disease type 2 and 3, Neurobiology of Disease 14: 595-601 (2003).

Shapiro et al., Jul. 27, 2000, "Islet Transplantation in Seven Patients With Type 1 Diabetes Mellitus Using a Glucocorticoid-Free Immunosuppressive Regimen", N. Engl. J. Med. 343, 230-238.

Silverman, Prodrugs and Drug Delivery Systems, The Organic Chemistry of Drug Design and Drug Action, pp. 352-401, Academic Press, San Diego, Calif., (1992).

Slavik et al., CDIS/CTALA-4 and CDS0/CD86 Families: Signaling and Function, (1999), Immunol. Res. 19, 1-24.

Sun et al., Neuronopathic Gaucher disease in the mouse:viable combined selective saposin C deficiency andmutant glucocerebrosidase (V394L) mice withglucosylsphingosine and glucosylceramide accumulation and progressive neurological deficits, Hum Mol Genet 19: 1088-1097 (2010).

Treiber et al., The pharmacokinetics and tissue distribution of the glucosylceramide synthase inhibitor miglustat in the rat, Xenobiotica, (2007), 37(3), 298-314.

Turzanski et al., P-glycoprotein is implicated in the inhibition of ceramide-induced apoptosis in TF-1 acute myeloid leukemia cells by modulation of the glucosylceramide synthase pathway, Experimental Hematology (2005), 33 (1), 62-72.

Weinreb et al., Effectiveness of Enzyme Replacement Therapy in1028 Patients with Type 1 Gaucher Disease after 2 to 5 Years of Treatment: A Report from the Gaucher Registry, Am. J. Med.;113(2):112-9 (2002).

Wiseman et al., Daclizumab a Review of its Use in the Prevention ofAcute Rejection in Renal Transplant Recipients, (1999), Drugs 58, 1029-1042.

Wong et al., Neuropathology provides clues to the pathophysiology of Gaucher disease, Molecular Genetics and Metabolism 82: 192-207 (2004).

Yamashita et al., A vital role for glycosphingolipid synthesis during development and differentiation, Proc. Natl. Acad. Sci. USA (1999), 96(16), 9142-9147.

European Search Report for EP2685986 entitled "Glucosylceraminde Synthase Inhibitors", date of mailing Feb. 4, 2015.

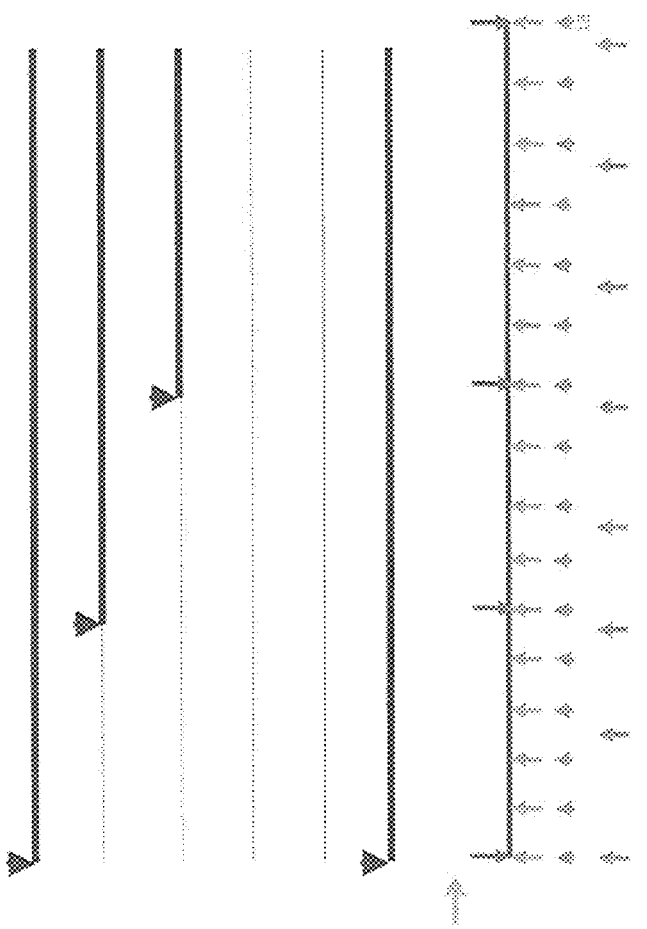

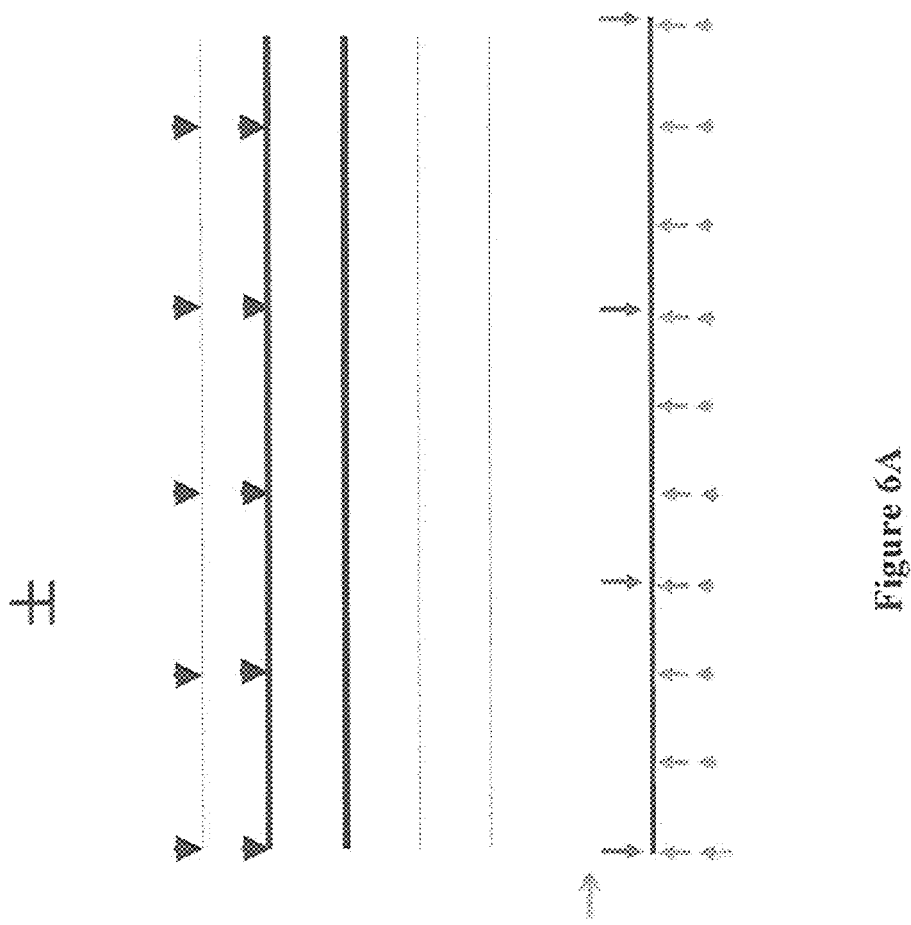

SEQUENCE LISTING

<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 1
tgttccccaa cacaatgctc ttt                                              23

<210> SEQ ID NO 2
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 2
tctgtgactc tgatgccacc ttg                                              23

<210> SEQ ID NO 3
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 3
aagacagaat aaaacgcacg ggtg                                             24

GLUCOSYLCERAMIDE SYNTHASE INHIBITORS

This application is a continuation of PCT Application No. PCT/US2012/029417, filed Mar. 16, 2012, which claims priority under 35 U.S.C. §119(e) to U.S. Provisional Application Nos. 61/454,034, filed Mar. 18, 2011 and U.S. Provisional Application No. 61/590,711, filed Jan. 25, 2012. The contents of these applications are hereby incorporated by reference into the present disclosure.

BACKGROUND OF THE INVENTION

1. Field of the Invention

The present invention relates generally to the field of therapeutics for cancer and metabolic diseases. More specifically, the invention relates to inhibitors of glucosylceramide synthase (GCS) useful for the treatment of metabolic diseases, such as lysosomal storage diseases, either alone or in combination with enzyme replacement therapy, and for the treatment of cancer.

2. Summary of the Related Art

Glucosylceramide synthase (GCS) is a pivotal enzyme which catalyzes the initial glycosylation step in the biosynthesis of glucosylceramide-base glycosphingolipids (GSLs) namely via the pivotal transfer of glucose from UDP-glucose (UDP-Glc) to ceramide to form glucosylceramide (See FIG. 1). GCS is a transmembrane, type III integral protein localized in the cis/medial Golgi. Glycosphingolipids (GSLs) are believed to be integral for the dynamics of many cell membrane events, including cellular interactions, signaling and trafficking. Synthesis of GSL structures has been shown (see, Yamashita et al., Proc. Natl. Acad. Sci. USA 1999, 96(16), 9142-9147) to be essential for embryonic development and for the differentiation of some tissues. Ceramide plays a central role in sphingolipid metabolism and downregulation of GCS activity has been shown to have marked effects on the sphingolipid pattern with diminished expression of glycosphingolipids. Sphingolipids (SLs) have a biomodulatory role in physiological as well as pathological cardiovascular conditions. In particular, sphingolipids and their regulating enzymes appear to play a role in adaptive responses to chronic hypoxia in the neonatal rat heart (see, El Alwanit et al., Prostaglandins & Other Lipid Mediators 2005, 78(1-4), 249-263).

GCS inhibitors have been proposed for the treatment of a variety of diseases (see for example, WO2005068426). Such treatments include treatment of glycolipid storage diseases (e.g., Tay Sachs, Sandhoffs, GM2 Activator deficiency, GM1 gangliosidosis and Fabry diseases), diseases associated with glycolipid accumulation (e.g., Gaucher disease; Miglustat (Zavesca), a GCS inhibitor, has been approved for therapy in type 1 Gaucher disease patients, see, Treiber et al., Xenobiotica 2007, 37(3), 298-314), diseases that cause renal hypertrophy or hyperplasia such as diabetic nephropathy; diseases that cause hyperglycemia or hyperinsulemia; cancers in which glycolipid synthesis is abnormal, infectious diseases caused by organisms which use cell surface glycolipids as receptors, infectious diseases in which synthesis of glucosylceramide is essential or important, diseases in which synthesis of glucosylceramide is essential or important, diseases in which excessive glycolipid synthesis occurs (e.g., atherosclerosis, polycystic kidney disease, and renal hypertrophy), neuronal disorders, neuronal injury, inflammatory diseases or disorders associated with macrophage recruitment and activation (e.g., rheumatoid arthritis, Crohn's disease, asthma and sepsis) and diabetes mellitus and obesity (see, WO 2006053043).

In particular, it has been shown that overexpression of GCS is implicated in multi-drug resistance and disrupts ceramide-induced apoptosis. For example, Turzanski et al., (Experimental Hematology 2005, 33 (1), 62-72 have shown that ceramide induces apoptosis in acute myeloid leukemia (AML) cells and that P-glycoprotein (p-gp) confers resistance to ceramide-induced apoptosis, with modulation of the ceramide-glucosylceramide pathway making a marked contribution to this resistance in TF-1 cells. Thus, GCS inhibitors can be useful for treatment of proliferative disorders by inducing apoptosis in diseased cells.

SUMMARY OF THE INVENTION

The present invention refers to a compound represented by the following structural formula,

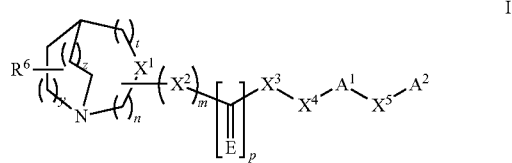

I or a pharmaceutically acceptable salt or prodrug thereof, wherein:
n is 1, 2 or 3;
m is 0 or 1;
p is 0 or 1;
t is 0, 1 or 2;
y is 1 or 2;
z is 0, 1 or 2;
E is S, O, NH, NOH, $NNO_2$, NCN, NR, NOR or $NSO_2R$;
$X^1$ is $CR^1$ when m is 1 or N when m is 0;
$X^2$ is O, —NH, —$CH_2$—, $SO_2$, NH—$SO_2$; $CH(C_1-C_6)$alkyl or —$NR^2$;
$X^3$ is O, —NH, —$CH_2$—, CO, —$CH(C_1-C_6)$alkyl, $SO_2NH$, —CO—NH— or —NR;
$X^4$ is $CR^4R^5$, $CH_2CR^4R^5$ or $CH_2$—$(C_1-C_6)$alkyl-$CR^4R^5$;
$X^5$ is a direct bond, O, S, $SO_2$, $CR^4R^5$; $(C_1-C_6)$alkyl, $(C_1-C_6)$alkyloxy, $(C_1-C_6)$alkenyl, $(C_1-C_6)$alkenyloxy;
R is $(C_6-C_{12})$aryl, $(C_2-C_9)$heteroaryl, $(C_1-C_6)$alkyl, $(C_2-C_9)$heteroaryl$(C_1-C_6)$alkyl;
$R^1$ is H, CN, $(C_1-C_6)$alkylcarbonyl, or $(C_1-C_6)$alkyl;
$R^2$ and $R^3$ are each independently —H, $(C_1-C_6)$alkyl optionally substituted by one or more substituents selected from the group consisting of halogen, $(C_1-C_6)$alkyl, $(C_6-C_{12})$aryl, $(C_2-C_9)$heteroaryl, $(C_1-C_6)$alkyl$(C_6-C_{12})$aryl, halo$(C_6-C_{12})$aryl, and halo$(C_2-C_9)$heteroaryl, or optionally when $X^2$ is —$NR^2$ and $X^3$ is —$NR^3$, $R^2$ and $R^3$ may be taken together with the nitrogen atoms to which they are attached form a non-aromatic heterocyclic ring optionally substituted by with one or more substituents selected from halogen, $(C_1-C_6)$alkyl, $(C_6-C_{12})$aryl, $(C_2-C_9)$heteroaryl, $(C_1-C_6)$alkyl$(C_6-C_{12})$aryl, halo$(C_6-C_{12})$aryl, and halo$(C_2-C_9)$heteroaryl;
$R^4$ and $R^5$ are independently selected from H, $(C_1-C_6)$alkyl, or taken together with the carbon to which they are attached to form a spiro $(C_3-C_{10})$cycloalkyl ring or spiro $(C_3-C_{10})$cycloalkoxy ring;
$R^6$ is —H, halogen, —CN, $(C_6-C_{12})$aryl, $(C_6-C_{12})$aryloxy, $(C_1-C_6)$alkyloxy; $(C_1-C_6)$alkyl optionally substituted by one to four halo or $(C_1-C_6)$alkyl;
$A^1$ is $(C_2-C_6)$alkynyl; $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkenyl, amino, $(C_1-C_6)$alkylamino, $(C_1-C_6)$ dialkylamino, $(C_1-C_6)$alkoxy, nitro, CN, —OH, $(C_1-C_6)$alkyloxy optionally substituted by one to three halo; $(C_1-C_6)$alkoxycarbonyl, and $(C_1-C_6)$alkylcarbonyl;

$A^2$ is H, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkylenyl, amino, $(C_1-C_6)$alkylamino, $(C_1-C_6)$dialkylamino, $(C_1-C_6)$alkoxy, O(C3-C6 cycloalkyl), $(C_3-C_6)$ cycloalkoxy, nitro, CN, OH, $(C_1-C_6)$alkyloxy optionally substituted by one to three halo; $(C_3-C_6)$ cycloalkyl, $(C_1-C_6)$alkoxycarbonyl, $(C_1-C_6)$alkylcarbonyl, $(C_1-C_6)$ haloalkyl;

with the proviso that the sum of n+t+y+z is not greater than 6;

with the proviso that when p is 0; $X^2$ is NH—$SO_2$ and $X^3$ is NH;

with the proviso that when n is 1; t is 0; y is 1; z is 1; $X^2$ is NH; E is O; $X^3$ is NH; $A^2$ is H and $X^5$ is a direct bond; $A^1$ is not unsubstituted phenyl, halophenyl or isopropenyl phenyl;

with the proviso that when n is 1; t is 0; y is 1; z is 1; $X^2$ is O; E is O; $X^3$ is NH; $A^1$ is $(C_6-C_{12})$aryl and $X^5$ is a direct bond; $A^2$ is H and $R^4$ is H then $R^5$ is not cyclohexyl; and with the proviso that when n is 1; t is 0; y is 1; z is 1; $X^2$ is NH; E is O; $X^3$ is $CH_2$; $R^4$ and $R^5$ are both hydrogen; $A^2$ is H and $X^5$ is a direct bond; then $A^1$ is not unsubstituted phenyl. Certain aspects of the invention include administering the foregoing compound to a patient as part of combination therapy that includes an enzyme replacement therapy (ERT) and small molecule therapy (SMT) to reduce the amount of and/or inhibit substrate accumulation in a patient diagnosed with a lysosomal storage disease.

The present invention further relates to the compound of Formula I, wherein n is 1; t is 0; y is 1 and z is 1.

The present invention further relates to the compound of Formula I, wherein n is 1; t is 1; y is 1 and z is 1.

The present invention further relates to the compound of Formula I, wherein n is 2; t is 0; y is 1 and z is 1.

The present invention further relates to the compound of Formula I, wherein n is 2; t is 1; y is 1 and z is 1.

The present invention further relates to the compound of Formula I, wherein n is 3; t is 0; y is 1 and z is 1.

The present invention further relates to the compound of Formula I, wherein n is 1; t is 2; y is 1 and z is 1.

The present invention further relates to the compound of Formula I, wherein n is 1; t is 0; y is 1 and z is 0.

The present invention further relates to the compound of Formula I, wherein n is 1; t is 1; y is 1 and z is 0.

The present invention further relates to the compound of Formula I, wherein n is 2; t is 0; y is 1 and z is 0.

The present invention further relates to the compound of Formula I, wherein n is 2; t is 1; y is 1 and z is 0.

The present invention further relates to the compound of Formula I, wherein n is 3; t is 0; y is 1 and z is 0.

The present invention further relates to the compound of Formula I, wherein n is 1; t is 2; y is 1 and z is 0.

The present invention further relates to the compound of Formula I, wherein n is 1; t is 1; y is 2 and z is 0.

The present invention further relates to the compound of Formula I, wherein n is 2; t is 0; y is 2 and z is 0.

The present invention further relates to the compound of Formula I, wherein m is 1 and $X^1$ is $CR^1$.

The present invention further relates to the compound of Formula I, wherein m is 0 and $X^1$ is N.

The present invention further relates to the compound of Formula I, wherein m is 1; E is O; $X^2$ is O and $X^3$ is NH.

The present invention further relates to the compound of Formula I, wherein m is 1; E is O; $X^2$ is NH and $X^3$ is NH.

The present invention further relates to the compound of Formula I, wherein m is 1; E is O; $X^2$ is $CH^2$ and $X^3$ is NH.

The present invention further relates to the compound of Formula I, wherein m is 1; E is O; $X^2$ is NH and $X^3$ is $CH^2$.

The present invention further relates to the compound of Formula I, wherein m is 1; E is S; $X^2$ is NH and $X^3$ is NH.

The present invention further relates to the compound of Formula I, wherein m is 0; E is O; $X^1$ is NH and $X^3$ is NH.

The present invention further relates to the compound of Formula I, wherein m is 1; E is O; $X^2$ is NH and $X^3$ is CO—NH.

The present invention further relates to the compound of Formula I, wherein m is 1; p is 0; $X^2$ is NH—$SO_2$ and $X^3$ is NH.

The present invention further relates to the compound of Formula I, wherein $R^4$ and $R^5$ are each $(C_1-C_6)$alkyl or taken together with the carbon to which they are attached to form a spiro $(C_3-C_{10})$cyclo-alkyl ring or a spiro $(C_3-C_{10})$cycloalkoxy ring.

The present invention further relates to the compound of Formula I, wherein $R^4$ and $R^5$ are each methyl.

The present invention further relates to the compound of Formula I, wherein $R^4$ and $R^5$ are taken together with the carbon to which they are attached to form a spiro $(C_3-C_{10})$ cycloalkyl ring.

The present invention further relates to the compound of Formula I, wherein $R^4$ and $R^5$ are taken together with the carbon to which they are attached to form a spiro cyclopropyl ring.

The present invention further relates to the compound of Formula I, wherein $R^4$ and $R^5$ are taken together with the carbon to which they are attached to form a spiro $(C_3-C_{10})$ cycloalkoxy ring.

The present invention further relates to the compound of Formula I, wherein $A^1$ is $(C_2-C_6)$alkynyl or $(C_6-C_{12})$aryl.

The present invention further relates to the compound of Formula I, wherein $A^1$ is $(C_2-C_9)$heteroaryl.

The present invention further relates to the compound of Formula I, wherein $A^1$ is thiophene, thiazole, isothiazole, furane, oxazole, isoxazole, pyrrole, imidazole, pyrazole, triazole, pyridine, pymiridine, pyridazine, indole, benzothiazole, benzoisoxazole, benzopyrazole, benzoimidazole, benzofuran, benzooxazole or benzoisoxazole.

The present invention further relates to the compound of Formula I, wherein $A^1$ is $(C_2-C_9)$heterocycloalkyl.

The present invention further relates to the compound of Formula I, wherein $A^1$ is pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]

hexanyl 2-azaspiro[4.4]nonanyl, 7-oxa-1-aza-spiro[4.4] nonanyl, 7-azabicyclo[2.2.2]heptanyl or octahydro-1H-indolyl.

The present invention further relates to the compound of Formula I, wherein $A^1$ is benzo($C_2$-$C_9$)heterocycloalkyl.

The present invention further relates to the compound of Formula I, wherein $A^1$ is 2,3-dihydrobenzo[b][1,4]dioxine or 2,2-difluorobenzo[d][1,3]dioxole.

The present invention further relates to the compound of Formula I, wherein $R^6$ is H.

The present invention further relates to the compound of Formula I, $X^5$ is a direct bond.

The present invention further relates to the compound of Formula I, $X^5$ is a $CR^4R^5$.

The present invention further relates to the compound of Formula I, wherein $R^4$ and $R^5$ are each methyl.

The present invention further relates to the compound of Formula I, wherein $R^4$ and $R^5$ are taken together with the carbon to which they are attached to form a spiro ($C_3$-$C_{10}$) cycloalkyl ring.

The present invention further relates to the compound of Formula I, wherein $R^4$ and $R^5$ are taken together with the carbon to which they are attached to form a spiro cyclopropyl ring.

The present invention further relates to the compound of Formula I, wherein $R^4$ and $R^5$ are taken together with the carbon to which they are attached to form a spiro ($C_3$-$C_{10}$) cycloalkoxy ring.

The present invention further relates to the compound of Formula I, wherein $A^2$ is ($C_6$-$C_{12}$)aryl.

The present invention further relates to the compound of Formula I, wherein $A^2$ is ($C_2$-$C_9$)heteroaryl.

The present invention further relates to the compound of Formula I, wherein $A^2$ is pyridine.

The present invention further relates to the compound of Formula I, wherein $A^2$ is ($C_2$-$C_9$)heterocycloalkyl.

The present invention further relates to the compound of Formula I, wherein $A^2$ is pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0] hexanyl 2-azaspiro[4.4]nonanyl, 7-oxa-1-aza-spiro[4.4] nonanyl, 7-azabicyclo[2.2.2]heptanyl or octahydro-1H-indolyl.

The present invention further relates to the compound of Formula I, wherein $A^2$ is benzo($C_2$-$C_9$)heterocycloalkyl.

The present invention further relates to the compound of Formula I, where $R^1$ is hydrogen or methyl.

The present further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is ($C_6$-$C_{12}$)aryl; $X^1$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is ($C_6$-$C_{12}$)aryl; $X^1$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^1$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^z$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$ is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; R$^6$ is a hydrogen or methyl; A$^1$ is (C$_2$-C$_9$)heterocycloalkyl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is N; m is 0; E is O; X$^3$ is NH; R$^4$ and R$^5$ are each independently methyl; R$^6$ is a hydrogen or methyl; A$^1$ is (C$_2$-C$_9$)heterocycloalkyl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CO—NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heterocycloalkyl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CO—NH; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heterocycloalkyl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CO—NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heterocycloalkyl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CO—NH; R$^4$ and R$^5$ are each independently methyl; R$^6$ is a hydrogen or methyl; A$^1$ is (C$_2$-C$_9$)heterocycloalkyl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; p is 1; E is O; X$^2$ is O; X$^3$ is NH; R$^1$ is H; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; p is 1; E is O; X$^2$ is O; X$^3$ is NH; R$^1$ is H; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is NH; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CH$_2$; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CH$_2$; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is CH$_2$; X$^3$ is NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^{5s}$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is CH$_2$; X$^3$ is NH; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is S; X$^2$ is NH; X$^3$ is NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0.1 or 2; y is 0 or 1; z is 0, 1 or 2; X$^1$ is CR$^1$; m is 1; E is S; X$^2$ is NH; X$^3$ is NH; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is SO$_2$; X$^2$ is NH; X$^3$ is NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is SO$_2$; X$^2$ is NH; X$^3$ is NH; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is N; m is 0; E is O; X$^3$ is NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is N; m is 0; E is O; X$^3$ is NH; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_1$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_3$-$C_{10})$cycloalkyl; $X^5$ is a direct bond, O or $CR^4R^5$ and $A^2$ is $(C_1$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_3\text{-}C_{10})$cycloalkyl; $X^5$ is a direct bond, O or $CR^4R^5$ and $A^2$ is $(C_2\text{-}C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_3\text{-}C_{10})$cycloalkyl; $X^5$ is a direct bond, O or $CR^4R^5$ and $A^2$ is $(C_2\text{-}C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_3\text{-}C_{10})$cycloalkyl; $X^5$ is a direct bond, O or $CR^4R^5$ and $A^2$ is $(C_2\text{-}C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_3\text{-}C_{10})$cycloalkyl; $X^5$ is a direct bond, O or $CR^4R^5$ and $A^2$ is $(C_2\text{-}C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_3\text{-}C_{10})$cycloalkyl; $X^5$ is a direct bond, O or $CR^4R^5$ and $A^2$ is $(C_2\text{-}C_9)$heteroaryl.

The present invention further relates to the compound of Formula I, wherein n is 1; 2 or 3; t is 0, or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_3\text{-}C_{10})$cycloalkyl; $X^5$ is a direct bond, O or $CR^4R^5$ and $A^2$ is $(C_2\text{-}C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_3\text{-}C_{10})$cycloalkyl; $X^5$ is a direct bond, O or $CR^4R^5$ and $A^2$ is $(C_2\text{-}C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_3\text{-}C_{10})$cycloalkyl; $X^5$ is a direct bond, O or $CR^4R^5$ and $A^2$ is $(C_2\text{-}C_9)$heteroaryl.

The present invention further relates to the compound of Formula I, wherein n is 1; 2 or 3; t is 0.1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_3\text{-}C_{10})$cycloalkyl.

The present invention further relates to the compound of Formula I, wherein n is 1; 2 or 3; t is 0, 1 or 2; y is 0 or 1; z is 0.1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_3\text{-}C_{10})$cycloalkyl; $X^5$ is a direct bond, O or $CR^4R^5$ and $A^2$ is $(C_2\text{-}C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and R$^5$ are each independently methyl; R$^6$ is a hydrogen or methyl; A$^1$ is (C$_3$-C$_{10}$)cycloalkyl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is N; m is 0; E is O; X$^3$ is NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^5$ and A$^2$ is (C$_3$-C$_{10}$)cycloalkyl.

The present invention further relates to the compound of Formula I, wherein n is 1; 2 or 3; t is 0, 1 or 2; y is 0 or 1; z is 0, 1 or 2; X$^1$ is N; m is 0; E is O; X$^2$ is NH; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_3$-C$_{10}$)cycloalkyl.

The present invention further relates to the compound of Formula I, wherein n is 1; 2 or 3; t is 0, 1 or 2; y is 0 or 1; z is 0, 1 or 2; X$^1$ is N; m is 0; E is O; X$^3$ is NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_3$-C$_{10}$)cycloalkyl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is N; m is 0; E is O; X$^3$ is NH; R$^4$ and R$^5$ are each independently methyl; R$^6$ is a hydrogen or methyl; A$^1$ is (C$_3$-C$_{10}$)cycloalkyl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CO—NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_2$-C$_9$)heteroaryl; X$^5$ is a direct bond, O or CR$^4$R$^5$ and A$^2$ is (C$_3$-C$_{10}$)cycloalkyl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CO—NH; R$^4$ and R$^5$ are each independently methyl; R$^6$ is a hydrogen or methyl; A$^1$ is (C$_2$-C$_9$)heteroaryl; X$^5$ is a direct bond, O or CR$^4$R$^5$ and A$^2$ is (C$_3$-C$_{10}$)cycloalkyl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CO—NH; R$^4$ and R$^5$ are taken together with the carbon to which they are attached to form a spiro (C$_3$-C$_{10}$)cycloalkyl ring or spiro (C$_3$-C$_{10}$)cycloalkoxy ring; R$^6$ is a hydrogen or methyl; A$^1$ is (C$_3$-C$_{10}$)cycloalkyl; X$^5$ is a direct bond, O or CR$^4$R$^5$ and A$^2$ is (C$_2$-C$_9$)heteroaryl.

The present invention further relates to the compound of Formula I, wherein n is 1; 2 or 3; t is 0, 1 or 2; y is 0 or 1; z is 0, 1 or 2; X$^1$ is CR$^1$; m is 1; E is O; X$^2$ is NH; X$^3$ is CO—NH; R$^4$ and R$^5$ are each independently methyl; R$^6$ is a hydrogen or methyl; A$^1$ is (C$_3$-C$_{10}$)cycloalkyl; X$^5$ is a direct bond, O or CR$^4$R$^5$ and A$^2$ is (C$_2$-C$_9$)heteroaryl.

The present invention further relates to the compound of Formula I, wherein A$^1$ is (C$_3$-C$_{10}$)cycloalkyl.

The present invention further relates to the compound of Formula I, wherein A$^2$ is (C$_3$-C$_{10}$)cycloalkyl.

The present invention further relates to the compound of Formula I, or a pharmaceutically acceptable salt or prodrug thereof, selected from the group consisting of:

1-azabicyclo[2.2.2]oct-3-yl[2-(2,4'-difluorobiphenyl-4-yl) propan-2-yl]carbamate;

1-azabicyclo[2.2.2]oct-3-yl {2-[4-(1,3-benzothiazol-6-yl) phenyl]propan-2-yl}carbamate;

1-azabicyclo[3.2.2]non-4-yl {1-[5-(4-fluorophenyl)pyridin-2-yl]cyclopropyl}carbamate;

1-azabicyclo[2.2.2]oct-3-yl {1-[3-(4-fluorophenoxy)phenyl] cyclopropyl}carbamate;

1-azabicyclo[2.2.2]oct-3-yl {1-[4-(1,3-benzothiazol-5-yl) phenyl]cyclopropyl}carbamate;

1-azabicyclo[2.2.2]oct-3-yl[1-(4'-fluoro-3'-methoxybiphenyl-4-yl)cyclopropyl]carbamate;

1-azabicyclo[2.2.2]oct-3-yl[3-(4'-fluorobiphenyl-4-yl)oxetan-3-yl]carbamate;

1-azabicyclo[2.2.2]oct-3-yl{1-[6-(4-fluorophenoxy)pyridin-2-yl]cyclopropyl}carbamate;

1-azabicyclo[2.2.2]oct-3-yl[3-(4'-fluorobiphenyl-4-yl)pentan-3-yl]carbamate;

1-azabicyclo[2.2.2]oct-3-yl {2-[2-(4-fluorophenyl)-2H-indazol-6-yl]propan-2yl}carbamate;

1-azabicyclo[2.2.2]oct-3-yl {2-[2-(1H-pyrrol-1-yl)pyridin-4-yl]propan-2-yl}carbamate;

1-(3-ethyl-1-azabicyclo[2.2.2]oct-3-yl)-3-[1-(4'-fluorobiphenyl-4-yl)cyclopropyl]urea;

N-(1-azabicyclo[2.2.2]oct-3-yl)-N'-[1-(4'-fluorobiphenyl-4-yl)cyclopropyl]ethanediamide;

1-azabicyclo[2.2.2]oct-3-yl (1-{4-[(4,4difluorocyclohexyl) oxy]phenyl}cyclopropyl)carbamate;

1-(4-methyl-1-azabicyclo[3.2.2]non-4-yl)-3-[1-(5-phenylpyridin-2-yl)cyclopropyl]urea;

1-[1-(4'-fluorobiphenyl-4-yl)cyclopropyl]-1-methyl-3-(3-methyl-1-azabicyclo[2.2.2]oct-3-yl)urea;

1-[4'-fluorobiphenyl-4-yl)cyclopropyl]-1-methyl-3-(3-methyl-1-azabicyclo[2.2.2]oct-3-yl)urea;

1-{2-[4'-(2-methoxyethoxy)biphenyl-4-yl]propan-2-yl}-3-(3-methyl-1-azabicyclo[2.2.2]oct-3-yl)urea;

2-(1-azabicyclo[3.2.2]non-4-yl)-N-[1-(5-phenylpyridin-2-yl)cyclopropyl]acetamide;

3-(4'-fluorobiphenyl-4-yl)-3-methyl-N-(4-methyl-1-azabicyclo[3.2.2]non-4-yl)butanamide;

N-[2-(biphenyl-4-yl)propan-2-yl]-N'-(3-methyl-1-azabicyclo[2.2.2]oct-3-yl)sulfuric diamide;

N-[2-4-fluorobiphenyl-4-yl)propan-2-yl]-N'-(3-methyl-1-azabicyclo[2.2.2]oct-3-yl)sulfuric diamide;

1-(3-butyl-1-azabicyclo[2.2.2]oct-3-yl)-3-{2-[1-(4-fluorophenyl)-1H-pyrazol-4-yl]propan-2-yl}urea;

1-azabicyclo[2.2.2]oct-3-yl[4-(4-fluorophenyl)-2-methylbut-3-yn-2-yl]carbamate;

1-(3-butyl-1-azabicyclo[2.2.2]oct-3-yl)-3-[4-(4-fluorophenyl)-2-methylbut-3-yn-2-yl]urea;

N-[1-(4'-fluorobiphenyl-4-yl)cyclopropyl]-1,4-diazabicyclo [3.2.2]nonane-4-carboxamide;

1-(2-(4'-fluoro-[1,1'-biphenyl]-4-yl)propan-2-yl)-3-(3-methyl-1-azabicyclo[3.2.2]nonan-3-yl)urea;

1-(2-(4'-fluoro-[1,1'-biphenyl]-4-yl)propan-2-yl)-3-(4-methyl-1-azabicyclo[4.2.2]decan-4-yl)urea;

1-(2-(4'-fluoro-[1,1'-biphenyl]-4-yl)propan-2-yl)-3-(3-methyl-1-azabicyclo[4.2.2]decan-3-yl)urea; and 1-(2-(4'-fluoro-[1,1'-biphenyl]-4-yl)propan-2-yl)-3-(5-methyl-1-azabicyclo[4.2.2]decan-5-yl)urea.

The present invention further relates to a pharmaceutical composition for treating a disease or disorder mediated by glucosylceramide synthase (GCS) or a disease or disorder in which GCS is implicated in a subject in need of such treatment comprising administering to the subject an effective amount of the compound of Formula I.

The present invention further relates to a method for treating a disease or disorder mediated by glucosylceramide synthase (GCS) or a disease or disorder in which GCS is implicated in a subject in need of such treatment comprising administering to the subject an effective amount of the compound of Formula I.

The present invention further relates to a method for treating a disease or disorder such as cancer.

The present invention further relates to a method for treating a disease or disorder such as a metabolic disorder.

The present invention further relates to a method for treating a disease or disorder such as a neuropathic disease.

The present invention further relates to a method wherein the neuropathic disease is Alzheimers disease.

The present invention further relates to a method wherein the neuropathic disease is Parkinsons disease.

The present invention further relates to the method for inducing decreased glucosylceramide synthase catalytic activity in a cell, in vitro, comprising contacting the cell with an effect amount of the compound of Formula I.

The present invention further relates to the compound of formula I, represented by the following structural formula, or a pharmaceutically acceptable salt or prodrug thereof.

The present invention further relates to the compound of formula I, represented by the following structural formula, or a pharmaceutically acceptable salt or prodrug thereof.

The present invention further relates to a method of treating a subject diagnosed as having a lysosomal storage disease, the method including administering to the subject an effective amount of the compound of formula I, and in certain embodiments the compound is represented by following structural formulas, or a pharmaceutically acceptable salt or prodrug thereof, or or a pharmaceutically acceptable salt or prodrug thereof.

In certain embodiments of the invention, the lysosomal storage disease results from a defect in the glycosphingolipid pathway.

In certain embodiments of the invention, the lysosomal storage disease is Gaucher, Fabry, $G_{M1}$-gangliosidosis, $G_{M2}$ Activator deficiency, Tay-Sachs or Sandhoff.

The present invention further relates to a method of treating a subject diagnosed as having a lysosomal storage disease, the method including administering to the subject an effective amount of the compound of formula I and administering to the subject a therapeutically effective amount of a lysosomal enzyme.

In certain embodiments of the invention, the lysosomal enzyme is glucocerebrosidase, alpha-galactosidase A, Hexosaminidase A, Hexosaminidase B or $G_{M1}$-ganglioside-β-galactosidase.

In certain embodiments of the invention, the subject has elevated levels of a lysosomal substrate prior to treatment and once undergoing treatment the subject has lower combined amounts of the lysosomal substrate in the urine and plasma than a subject treated with either the lysosomal enzyme or compound alone.

In certain embodiments of the invention, the substrate is globotriaosylceramide or lyso-globotriaosylceramide, and combinations thereof.

The present invention further relates to a method of reducing glucosylceramide synthase (GCS) activity in a subject diagnosed as having a lysosomal storage disease, including administering to the patient an effective amount of the compound of formula I, either alone or as a combination therapy with an enzyme replacement therapy.

The present invention further relates to a method of reducing accumulation of a GCS-derived material in a subject diagnosed as having a lysosomal storage disease, including administering to the patient an effective amount of the compound of formula I, either alone or as a combination therapy with an enzyme replacement therapy.

This invention provides a method of combination therapy for treatment of a subject diagnosed as having a lysosomal storage disease comprising alternating between administration of an enzyme replacement therapy and a small molecule therapy.

This invention provides a method of combination therapy for treatment of a subject diagnosed as having a lysosomal storage disease comprising simultaneously administering an enzyme replacement therapy and a small molecule therapy.

In the various combination therapies of the invention, it will be understood that administering small molecule therapy may occur prior to, concurrently with, or after, administration of enzyme replacement therapy. Similarly, administering enzyme replacement therapy may occur prior to, concurrently with, or after, administration of small molecule therapy.

DEFINITIONS

As used herein, the term "pharmaceutically acceptable salt" means either a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

As used herein, the term "prodrug" means a pharmacological derivative of a parent drug molecule that requires biotransformation, either spontaneous or enzymatic, within the organism to release the active drug. For example, prodrugs are variations or derivatives of the compounds of Formula I that have groups cleavable under certain metabolic conditions, which when cleaved, become the compounds of Formula I. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substituents disclosed herein.

As used herein, the term "$(C_1-C_6)$alkyl" means a saturated linear or branched free radical consisting essentially of 1 to 6 carbon atoms and a corresponding number of hydrogen atoms. Exemplary $(C_1-C_6)$alkyl groups include methyl, ethyl, n-propyl, isopropyl, n-butyl, isobutyl, etc. Of course, other $(C_1-C_6)$alkyl groups will be readily apparent to those of skill in the art given the benefit of the present disclosure.

As used herein, the term "$(C_3-C_{10})$cycloalkyl" means a nonaromatic saturated free radical forming at least one ring consisting essentially of 3 to 10 carbon atoms and a corresponding number of hydrogen atoms. As such, $(C_3-C_{10})$cycloalkyl groups can be monocyclic or multicyclic. Individual rings of such multicyclic cycloalkyl groups can have different connectivities, e.g., fused, bridged, spiro, etc. in addition to covalent bond substitution. Exemplary $(C_3-C_{10})$cycloalkyl groups include cyclopropyl, cyclobutyl, cyclopentyl, cyclohexyl, norbornanyl, bicyclo[3.2.1]octanyl, octahydro-pentalenyl, spiro[4.5]decanyl, cyclopropyl substituted with cyclobutyl, cyclobutyl substituted with cyclopentyl, cyclohexyl substituted with cyclopropyl, etc. Of course, other $(C_3-C_{10})$cycloalkyl groups will be readily apparent to those of skill in the art given the benefit of the present disclosure.

As used herein, the term "$(C_2-C_9)$heterocycloalkyl" means a nonaromatic free radical having 3 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, $(C_2-C_9)$heterocycloalkyl groups can be monocyclic or multicyclic. Individual rings of such multicyclic heterocycloalkyl groups can have different connectivities, e.g., fused, bridged, spiro, etc. in addition to covalent bond substitution. Exemplary $(C_2-C_9)$heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl, octahydro-1H-indolyl, etc. In general, the $(C_2-C_9)$heterocycloalkyl group typically is attached to the main structure via a carbon atom or a nitrogen atom. Of course, other $(C_2-C_9)$heterocycloalkyl groups will be readily apparent to those of skill in the art given the benefit of the present disclosure.

As used herein, the term "$(C_2-C_9)$heteroaryl" means an aromatic free radical having 5 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, $(C_2-C_9)$heteroaryl groups can be monocyclic or multicyclic. Individual rings of such multicyclic heteroaryl groups can have different connectivities, e.g., fused, etc. in addition to covalent bond substitution. Exemplary $(C_2-C_9)$heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. In general, the $(C_2-C_9)$heteroaryl group typically is attached to the main structure via a carbon atom, however, those of skill in the art will realize when certain other atoms, e.g., hetero ring atoms, can be attached to the main structure. Of course, other ($C_2$-$C_9$)heteroaryl groups will be readily apparent to those of skill in the art given the benefit of the present disclosure.

As used herein, the term "($C_6$-$C_{10}$)aryl" means phenyl or naphthyl.

As used herein, the term "halo" means fluorine, chlorine, bromine, or iodine.

As used herein, the term "amino" means a free radical having a nitrogen atom and 1 to 2 hydrogen atoms. As such, the term amino generally refers to primary and secondary amines. In that regard, as used herein and in the appended claims, a tertiary amine is represented by the general formula RR'N—, wherein R and R' are carbon radicals that may or may not be identical. Nevertheless, the term "amino" generally may be used herein to describe a primary, secondary, or tertiary amine, and those of skill in the art will readily be able to ascertain the identification of which in view of the context in which this term is used in the present disclosure.

As used herein, the term "combination therapy" means treating a patient with two or more therapeutic platforms (e.g., enzyme replacement therapy and small molecule therapy) in rotating, alternating and/or simultaneous treatment schedules. Examples of treatment schedules may include, but are not limited to: (1) enzyme replacement therapy, then small molecule therapy; (2) small molecule therapy, then enzyme replacement therapy; (3) enzyme replacement therapy concurrent with small molecule therapy, and (4) and any combination of the foregoing. Combination therapy may provide a temporal overlap of therapeutic platforms, as needed, depending on the clinical course of a given storage disease in a given subject.

As used herein, the term "enzyme replacement therapy", or "ERT" means administering an exogenously-produced natural or recombinant enzyme to a patient who is in need thereof. In the case of a lyosomal storage disease, for example, the patient accumulates harmful levels of a substrate (i.e., material stored) in lysosomes due to a deficiency or defect in an enzyme responsible for metabolizing the substrate, or due to a deficiency in an enzymatic activator required for proper enzymatic function. Enzyme replacement therapy is provided to the patient to reduce the levels of (i.e., debulk) accumulated substrate in affected tissues. Table 1 provides a list of lysosomal storage diseases and identifies the corresponding enzyme deficiency and accumulated substrate for each disease. Enzyme replacement therapies for treating lysosomal storage diseases are known in the art. In accordance with a combination therapy of the invention, the lysosomal enzymes identified in Table 1 can be used for enzyme replacement therapy to reduce the levels of corresponding substrate in a patient diagnosed with the respective lysosomal storage disease.

As used herein, "effective amount" of an enzyme or small molecule, when delivered to a subject in a combination therapy of the invention, is an amount sufficient to improve the clinical course of a lysosomal storage disease, where clinical improvement is measured by any of the variety of defined parameters well known to the skilled artisan.

ABBREVIATIONS

ACN refers to acetonitrile.
DMF refers to N,N-dimethylformamide.
DMSO refers to dimethylsulfoxide.
EtOAc refers to ethyl acetate.
EtOH refers to ethanol.

Hunig's Base refers to diisopropylethyl amine ("DIPEA").
MeOH refers to methanol.
NaOH refers to sodium hydroxide.
THF refers to tetrahydrofuran.
TFA refers to trifluoroacetic acid.

Additional features and advantages of compounds disclosed herein will be apparent from the following detailed description of certain embodiments.

BRIEF DESCRIPTION OF THE DRAWINGS

FIG. 4A
Study timeline showing Fabry mice starting treatment with 60 mg/kg/day GZ 452 starting at 3, 8 and 12 months of age. Periodic blood-draws, urine collection, hot-plate and activity chamber assays were performed as indicated.

FIG. 6A
Study timeline showing Fabry mice being treated with alpha-galactosidase A (1 mg/kg every 2 months) or with 60 mg/kg/day GZ 452 or a combination of the 2 treatments starting at 3 months of age. Periodic blood-draws, urine collection and hot-plate assays were performed as indicated.

FIG. 1 Systemic administration of GZ 161 reduces CD68 staining throughout the brain of K14 mice. (Upper panels) Representative immunohistochemical CD68 staining at P10 in the hippocampus, thalamus, brainstem and cerebellum of K14 mice treated daily (IP) beginning at postnatal day 4 (P4) with vehicle or GZ 161 and WT mice. (Lower panels) Quantitation of staining in the groups shown above, showing that systemic treatment with GZ 161 results in significant reductions the CD68+ cells in all brain regions. Similar reductions were observed in other structures such as the olfactory bulb and frontal cortex (data not shown). $p<0.01$. N=4/group FIG. 12** Systemic administration of GZ 161 reduces F4/80 staining in some brain regions of K14 mice. (Upper panels) Representative immunohistochemical F4/80 staining at P10 in the hippocampus, thalamus, brainstem and cerebellum of K14 mice treated daily (IP) beginning at P4 with vehicle or GZ 161, and WT mice. (Lower panels) Quantitation of staining in the groups shown above, showing that systemic treatment with GZ 161 results in significant reductions the F4/80+ cells in the thalamus and brainstem. Similar reductions were observed in other structures such as the olfactory bulb and frontal cortex; statistical differences were observed in both structures (data not shown). *$p<0.05$. N=4/group FIG. 13 Systemic administration of GZ 161 decreases gliosis in K14 mice. (Upper panels) Representative immunohistochemical GFAP staining at P10 in the hippocampus, thalamus, brainstem and cerebellum of K14 mice treated daily (IP) beginning at P4 with vehicle or GZ 161, and WT mice. (Lower panels) Quantitation of staining in the groups shown above, showing that systemic treatment with GZ 161 results in significant reductions the GFAP+ cells in the hippocampus and cerebellum; statistical differences were observed in both structures (data not shown).

DETAILED DESCRIPTION

Figure 1:
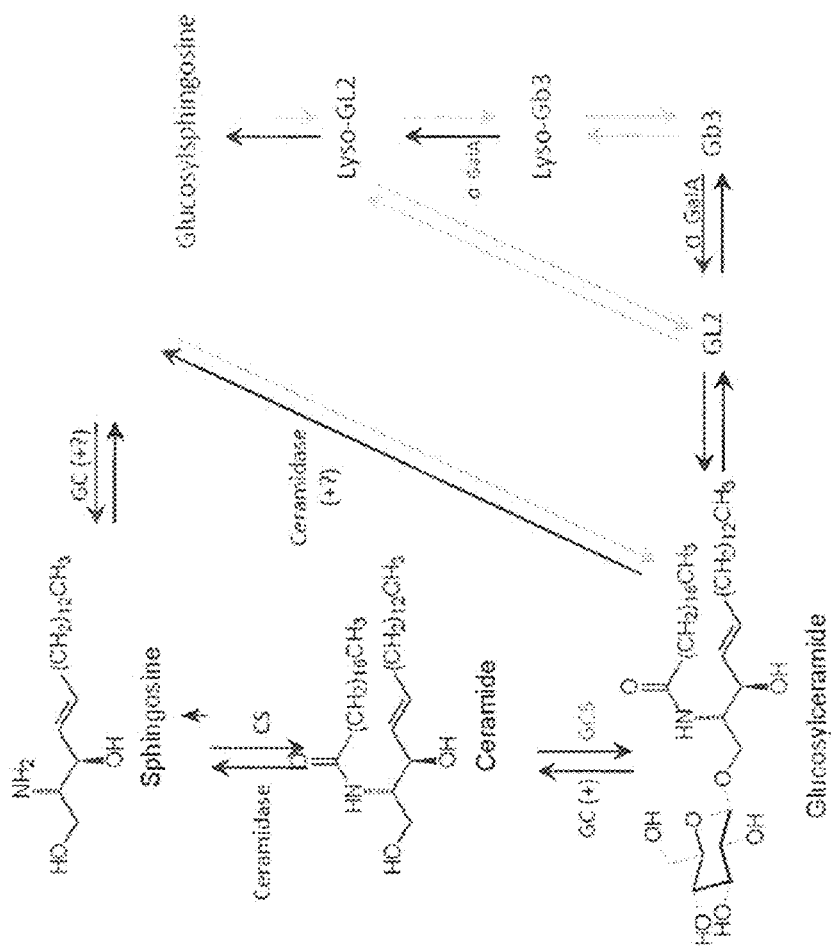
FIG. 1 Presents the metabolic pathway for the potential synthesis of Gb3 and lyso-Gb3. Documented synthetic pathways are shown with black arrows and undocumented (potential) pathways are shown with grey arrows.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

Preparation A

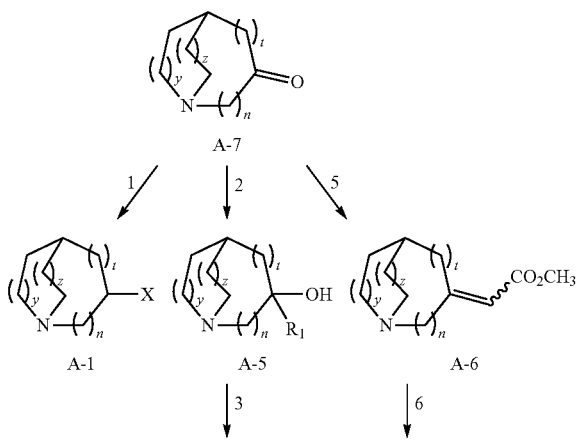

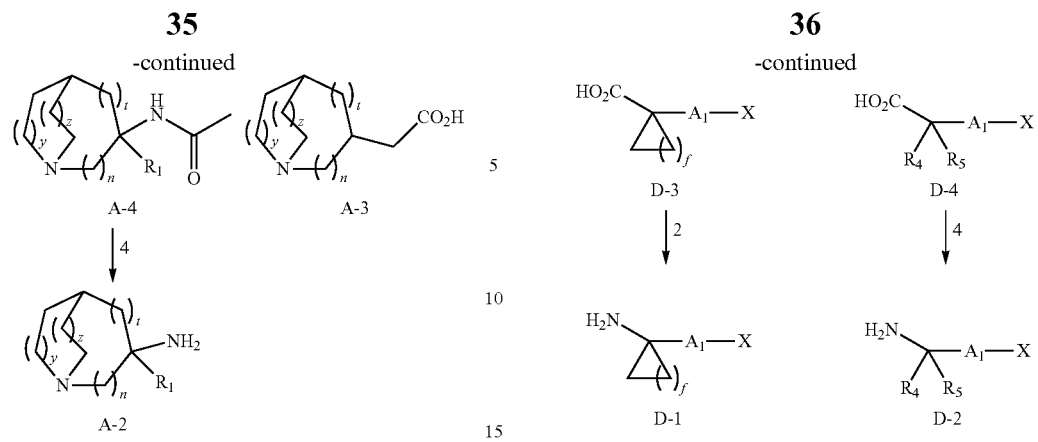
Preparation B
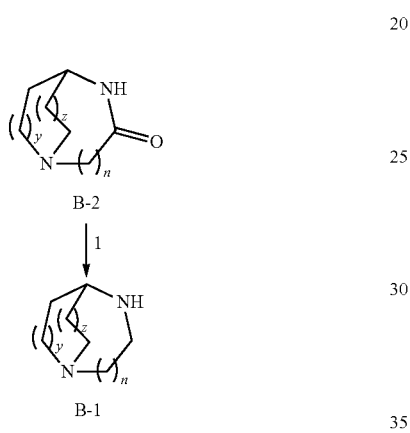
Preparation C
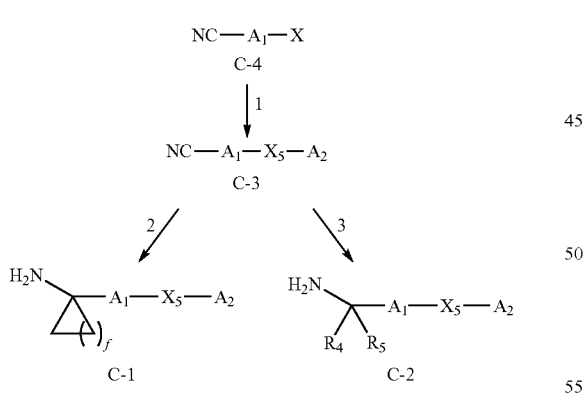
Preparation D
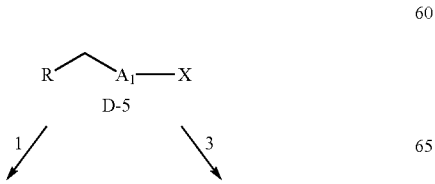
Preparation E
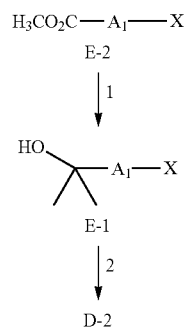
SCHEME 1
A-1 or A-2
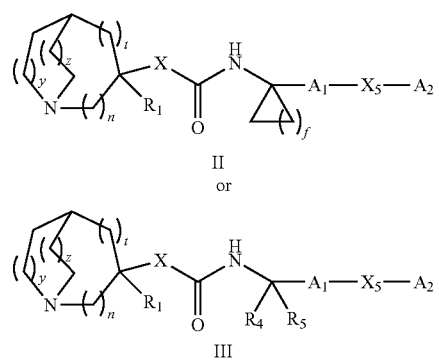
SCHEME 2
A-1 or A-2 or B-1

-continued

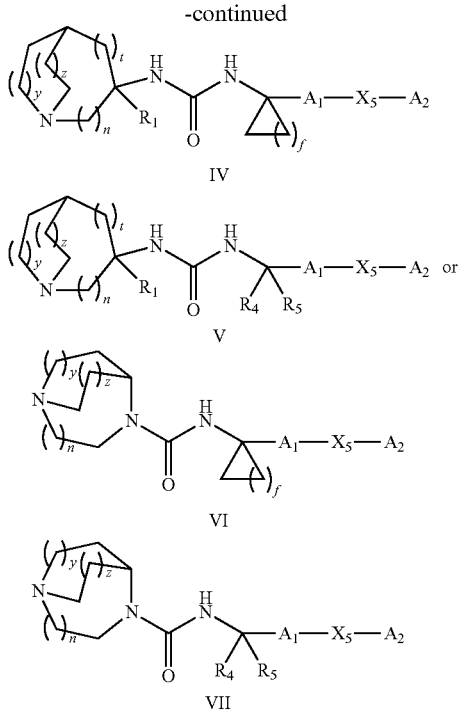

IV

V

VI

VII

SCHEME 3

A-3
↓ 1

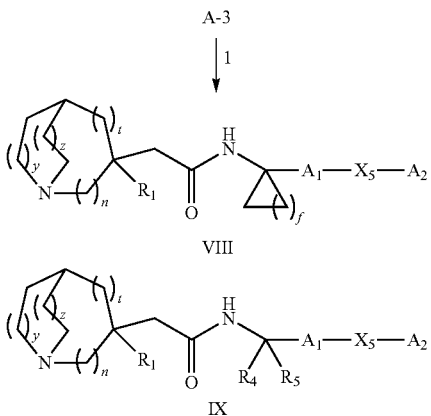

VIII

IX

In reaction 1 of Preparation A, the compound of formula A-7 is converted to the corresponding compound of formula A-1, wherein X is OH, by reducing A-7 with a reducing agent, preferably lithium aluminum hydride in aprotic solvent such tetrahydrofuran. The reaction is stirred at a temperature between 0° C. and room temperature for a time period between about 15 minutes to about 2 hours, preferably about 30 minutes. Alternatively, the compound of formula A-7 is converted to the corresponding compound of formula A-1, wherein X is OH, by reducing A-7 under approximately 1 atmosphere of hydrogen in presence of a catalyst, preferably platinum oxide, and a polar solvent such methanol or ethanol for a period of 2 hours to 6 hours, preferably 4 hours. Alternatively, the compound of formula A-7 is converted to the corresponding compound of formula A-1, wherein X is NH, by reacting A-7 with hydroxylamine hydrochloride and sodium acetate in a polar solvent such ethanol, methanol, isopropanol, preferably isopropanol. The reaction mixture is stirred at a temperature between 50-80° C. for a period of 2 hours to 7 hours, preferably 3 hours. Subsequently, the compound so formed above is converted to compound of formula A-1 with a reducing agent, preferably sodium metallic in a polar protic solvent such ethanol, methanol, propanol, preferably n-propanol. The reaction is stirred overnight at 50-80° C., preferably solvent reflux temperature.

In reaction 2 of Preparation A, the compound of formula A-7 is converted to the corresponding compound of formula A-5, wherein R1, n and z are as defined above, by adding a solution of R1-magnesium bromide in ether to a solution of A-7 in a aprotic solvent, such as ether, at a temperature between about −60° C. to about −90° C., preferably about −78° C. for a time period between about 1 hour to about 4 hours, preferably about 2 hours. Alternatively, the compound of formula A-7 can be reacted with R1-lithium to afford the compound of formula A-5.

In reaction 3 of Preparation A, the compound of formula A-5 is converted to the corresponding compound of formula A-4, wherein R1, n and z are as defined above, by treating A-5 with a strong acid, preferably sulfuric acid, in the presence of acetonitrile. The reaction is stirred overnight at room temperature.

In reaction 4 of Preparation A, the compound of formula A-4 is converted to the corresponding compound of formula A-3, wherein R1, n and z are as defined above, by treating A-4 with an acid, preferably hydrochloric acid. The reaction is stirred at reflux for a period of 18 hours to 72 hours, preferably 24 hours and basified to pH=8 by treatment with an inorganic base in aqueous solution, such as sodium hydroxide.

In reaction 5 of Preparation A, the compound of formula A-7 is converted to the corresponding compound of formula A-6, wherein R1, n and z are as defined above, by reacting A-7 with a triphenyl phosphonium ylide to give the corresponding alkene compound of formula A-6. The reaction is stirred at room temperature for overnight.

In reaction 6 of Preparation A, the compound of formula A-6 is converted to the corresponding compound of formula A-3, wherein R1, n and z are as defined above, by reducing A-6 under approximately 1 atmosphere of hydrogen in the presence of a catalyst, preferably palladium on carbon, and a polar solvent, such as methanol, ethanol or ethyl acetate. The reaction is stirred at room temperature for a time period between about 2 hours to about 24 hour, preferably about 18 hours. Subsequently, the compound so formed is treated with a base, preferably lithium hydroxide, in a mixture of solvent such tetrahydrofuran, methanol and water to afford the compound of A-3. The reaction is stirred overnight at room temperature.

In reaction 1 of Preparation B, the compound of formula B-2 is converted to the corresponding compound of formula B-1, by reducing B-2 with a reducing agent, preferably lithium aluminum hydride in aprotic solvent such tetrahydrofuran. The reaction is stirred at a temperature between 0° C. and room temperature for a time period between about 15 minutes to about 2 hours, preferably about 30 minutes.

In reaction 1 of Preparation C, the compound of C-4 is converted to the corresponding compound of formula C-3, wherein X is bromine or chloride, by reacting C-4 with boronic acid in the presence of a catalyst, preferably 1,1′-bis(diphenylphosphino)ferrocene-palladium(II)-dichloride, and potassium carbonate. The reaction is microwaved in a mixture of dimethoxyethane and water at a temperature between about 130° C. to about 170° C. preferably about 150° C., for a time period between about 15 min to about 1 hour, preferably about 30 min. Alternatively, the reaction can be performed using solvent such dioxane and stirred overnight at 100° C. under conventional heating.

In reaction 2 of Preparation C, the compound of C-3 is converted to the corresponding compound of formula C-1, wherein f is 1 to 8 and A1, X5 and A2 are as defined above, by adding ethyl magnesium bromide dropwise to a mixture of C-3 and titanium isopropoxide in ether. The reaction is stirred at a temperature between about −50° C. to about −90° C., preferably about −70° C. The resulting reaction mixture is allowed to warm to about 20° C. to about 30° C., preferably about 25° C., and allowed to stir for an additional time period between about 30 minutes to about 2 hours, preferably about 1 hour. Boron trifluoride diethyl etherate is then added to the mixture dropwise at a temperature between about 20° C. to about 30° C., preferably about 25° C.

In reaction 3 of Preparation C, the compound of C-3 is converted to the corresponding compound of formula C-2, wherein A1, X5 and A2 are as defined above, by first stirring a suspension of cerium (III) chloride in an aprotic solvent, such as tetrahyrofuran, at room temperature for time period between about 30 minutes to about 2 hours, preferably about 1 hour. The resulting suspension is cooled to a temperature between about −60° C. to about −90° C., preferably about −78° C. and an organolithium agent is added, preferably methyl lithium in an ether solution. The resulting organocerium complex is allowed to form for a time period between about 30 minutes to about 2 hours, preferably about 1 hour, followed by the addition of C-3 in an aprotic solvent, such as tetrahydrofuran. The resulting reaction mixture is then warmed to room temperature and allowed to stir for time period between about 16 hours to about 20 hours, preferably about 18 hours.

In reaction 1 of Preparation D, the compound of D-5, wherein R is CO2Et or CN and X is bromine or chloride, is converted to the corresponding compound of formula D-3, by reacting D-5 with an alkyl dihalide such 1,2-dibromoethane. Subsequently, the compound so formed is treated with an inorganic base such lithium hydroxide or potassium hydroxide, in a mixture of solvent such tetrahydrofuran, methanol, glycol and water to afford the compound of D-3, wherein f is 1 to 8. The reaction is stirred overnight at a temperature between 25° C. and 130° C. Alternatively, to form the corresponding compound of formula D-3, wherein X is X5-A2, D-5 must first be reacted according to the procedure discussed above in reaction 1 of Preparation C.

In reaction 2 of Preparation D, the compound of D-3 is converted to the corresponding compound of formula D-1 by reacting D-3 with a base such triethylamine and diphenylphosphoryl azide in aprotic solvent such toluene. The reaction was heated to a temperature range between 80° C.-110° C., preferably at 110° C. for 15 min to 1 hour, preferably 30 minutes. The so formed intermediate is then treated with tert-butyl alcohol for overnight period at 60-110° C., preferably 90° C. Subsequently, the so formed carbamate is converted to the corresponding compound of formula D-1, wherein f is 1 to 8, by a treatment under acidic media using preferably trifluoroacetic acid in dichloromethane at room temperature for a period of 30 min to 5 hours, preferably 2 hours.

In reaction 3 of Preparation D, the compound of D-5, wherein R is CO2Et or CN and X is bromine or chloride, is converted to the corresponding compound of formula D-4, by reacting D-5 with an alkyl halide such MeI. Subsequently, the compound so formed is treated with an inorganic base such lithium hydroxide or potassium hydroxide, in a mixture of solvent such tetrahydrofuran, methanol, glycol and water to afford the compound of D-4. The reaction is stirred overnight at a temperature between 25° C. and 130° C. Alternatively, to form the corresponding compound of formula D-4, wherein X is X5-A2, D-5 must first be reacted according to the procedure discussed above in reaction 1 of Preparation C.

In reaction 4 of Preparation D, the compound of D-4 is converted to the corresponding compound of formula D-2, by reacting D-4 with a base such triethylamine and diphenylphosphoryl azide in aprotic solvent such toluene. The reaction was heated to a temperature range between 80° C.-110° C., preferably at 110° C. for 15 min to 1 hour, preferably 30 minutes. The so formed intermediate is then treated with tert-butyl alcohol for overnight period at 60-110° C., preferably 90° C. Subsequently, the so formed carbamate is converted to the corresponding compound of formula D-1 by a treatment under acidic media using preferably trifluoroacetic acid in dichloromethane at room temperature for a period of 30 min to 5 hours, preferably 2 hours.

In reaction 1 of Preparation E, the compound of formula E-2, wherein X is bromide or chloride, is converted to the corresponding compound of formula E-1, by reacting E-2 with methyl magnesium bromide in ether, at a temperature between about −60° C. to about −90° C., preferably about −78° C. for a time period between about 30 min to about 3 hours, preferably about 2 hours. Alternatively, to form the corresponding compound of formula E-1, wherein X is X5-A2, E-2 must first be reacted according to the procedure discussed above in reaction 1 of Preparation C.

In reaction 2 of Preparation E, the compound of formula E-1 is converted to the corresponding compound of D-2 by treating E-1 with a strong acid, preferably sulfuric acid, in the presence of chloroacetonitrile. The reaction is stirred overnight at room temperature. Subsequently, the so formed compound is treated with thiourea in a polar protic solvent such ethanol for an overnight period at 80° C. to form the corresponding compound of formula D-2. Alternatively, E-1 is treated with sodium azide and trifluoroacetic acid in an aprotic solvent such dichloromethane at a temperature range of −10° C. to room temperature, preferably 0° C. The so formed compound is reduced in presence of triphenylphosphine in a solution of tetrahydrofuran and water to form corresponding compound of formula D-2. The reaction is stirred at a temperature range 25-80° C., preferably at room temperature for a period of 2 hours to 24 hours, preferably 18 hours.

In reaction 1 of Scheme 1, the compounds of formula A-1 or A-2 are converted to the corresponding compounds of Formula II, wherein f is 1 to 8, or III, respectively, by adding triphosgene to a suspension of C-1 or C-2 and triethylamine in a aprotic solvent, such as tetrahydrofuran. The reaction is stirred at room temperature for a time period between about 5 minutes to about 20 minutes, preferably about 15 minutes, and a small amount of ether was added. The triethylammonium salt generated is filtered off. Separately, sodium hydride is added to a suspension of A-1 or A-2, wherein X is OH or NH, in an aprotic solvent, such as tetrahydrofuran, at 0° C. or room temperature. The reaction is stirred at room temperature for a time period between about 5 minutes to about 20 minutes, preferably about 15 minutes, and the isocyanate tetrahydrofuran/ether solution so formed above is added dropwise. Alternatively, the compounds of Formula II and III may be formed by reacting the compounds of D3 or D4 with A-1 and A-2 in presence of a base such triethylamine and diphenylphosphoryl azide in aprotic solvent such toluene as described in procedure discussed above in reaction 4 of Preparation D.

In reaction 1 of Scheme 2, the compounds of formula A-1, A-2 or B-1 are converted to the corresponding compounds of Formula IV, V, VI and VII, wherein f is 1 to 8, respectively, by adding triphosgene to a suspension of C-1, C-2, D-1 or D-2 and triethylamine in a aprotic solvent, such as tetrahydrofuran or toluene. The reaction is stirred at room temperature for a time period between about 5 minutes to about 20 minutes, preferably about 15 minutes, and a small amount of ether was added. Subsequently, A-1 or A-2, wherein X is NH, is added to the isocyanate solution so formed above and the reaction is stirred at a temperature range of 25-100° C., preferably at room temperature for a period of about 2 hours to 24 hours, preferably 18 hours.

In reaction 1 of Scheme 3, the compound of formula A-3 is converted to the corresponding compounds of Formula VIII, wherein f is 1 to 8, and IX, respectively by reacting A3 with C1, C-2, D-1 or D-2 via peptidic coupling using carbodiimide coupling agent such 1-ethyl-3-(3-dimethylaminopropyl)carbodiimide and 1-hydroxy-benzotriazole or 2-(1H-7-Azabenzotriazol-1-yl)-1,1,3,3-tetramethyl uronium hexafluorophosphate in solvent such tetrahydrofuran or dimethylformamide. The reaction is stirred at room temperature for overnight.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

All pharmaceutically acceptable salts, prodrugs, tautomers, hydrates and solvates of the compounds presently disclosed are also within the scope of the present disclosure.

Presently disclosed compounds that are basic in nature are generally capable of forming a wide variety of different salts with various inorganic and/or organic acids. Although such salts are generally pharmaceutically acceptable for administration to animals and humans, it is often desirable in practice to initially isolate a compound from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds can be readily prepared using conventional techniques, e.g., by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained.

Acids which can be used to prepare the pharmaceutically acceptable acid addition salts of the base compounds are those which can form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Presently disclosed compounds that are acidic in nature, e.g., contain a COOH or tetrazole moiety, are generally capable of forming a wide variety of different salts with various inorganic and/or organic bases. Although such salts are generally pharmaceutically acceptable for administration to animals and humans, it is often desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations, and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields of the desired solid salt.

Bases which can be used to prepare the pharmaceutically acceptable base addition salts of the base compounds are those which can form non-toxic base addition salts, i.e., salts containing pharmacologically acceptable cations, such as, alkali metal cations (e.g., potassium and sodium), alkaline earth metal cations (e.g., calcium and magnesium), ammonium or other water-soluble amine addition salts such as N-methylglucamine-(meglumine), lower alkanolammonium and other such bases of organic amines.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts and prodrugs thereof, can be prepared by any means known in the art.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

The compounds, salts, prodrugs, hydrates, and solvates presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Atropisomers are also within the scope of the present disclosure. Atropisomers refer to compounds that can be separated into rotationally restricted isomers.

The present disclosure also provides pharmaceutical compositions comprising at least one presently disclosed compound and at least one pharmaceutically acceptable carrier. The pharmaceutically acceptable carrier can be any such carrier known in the art including those described in, for example, Remington's Pharmaceutical Sciences, Mack Publishing Co., (A. R. Gennaro edit. 1985). Pharmaceutical compositions of the compounds presently disclosed may be prepared by conventional means known in the art including, for example, mixing at least one presently disclosed compound with a pharmaceutically acceptable carrier.

Presently disclosed pharmaceutical compositions can be used in an animal or human. Thus, a presently disclosed compound can be formulated as a pharmaceutical composition for oral, buccal, parenteral (e.g., intravenous, intramuscular or subcutaneous), topical, rectal or intranasal administration or in a form suitable for administration by inhalation or insufflation.

The compounds presently disclosed may also be formulated for sustained delivery according to methods well known to those of ordinary skill in the art. Examples of such formulations can be found in U.S. Pat. Nos. 3,119,742, 3,492,397, 3,538,214, 4,060,598, and 4,173,626.

For oral administration, the pharmaceutical composition may take the form of, for example, a tablet or capsule prepared by conventional means with a pharmaceutically acceptable excipient(s) such as a binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g., potato starch or sodium starch glycolate); and/or wetting agent (e.g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional means with a pharmaceutically acceptable additive(s) such as a suspending agent (e.g., sorbitol syrup, methyl cellulose or hydrogenated edible fats); emulsifying agent (e.g., lecithin or acacia); non-aqueous vehicle (e.g., almond oil, oily esters or ethyl alcohol); and/or preservative (e.g., methyl or propyl p-hydroxybenzoates or sorbic acid).

For buccal administration, the composition may take the form of tablets or lozenges formulated in a conventional manner.

Presently disclosed compounds may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent recognized by those of skill in the art. Alternatively, the active ingredient may be in powder form for reconstitution with a suitable vehicle, e.g., sterile pyrogen-free water, before use.

For topical administration, a presently disclosed compound may be formulated as an ointment or cream.

Presently disclosed compounds may also be formulated in rectal compositions such as suppositories or retention enemas, e.g., containing conventional suppository bases such as cocoa butter or other glycerides.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

A proposed dose of a presently disclosed compound for oral, parenteral or buccal administration to the average adult human for the treatment or prevention of a TPO-related disease state is about 0.1 mg to about 2000 mg. In certain embodiments, the proposed dose is from about 0.1 mg to about 200 mg of the active ingredient per unit dose. Irrespective of the amount of the proposed dose, administration of the compound can occur, for example, 1 to 4 times per day.

Aerosol formulations for the treatment or prevention of the conditions referred to above in the average adult human are preferably arranged so that each metered dose or "puff" of aerosol contains about 20 mg to about 10,000 mg, preferably, about 20 mg to about 1000 mg of a presently disclosed compound. The overall daily dose with an aerosol will be within the range from about 100 mg to about 100 mg. In certain embodiments, the overall daily dose with an aerosol generally will be within the range from about 100 mg to about 10 mg. Administration may be several times daily, for example 2, 3, 4 or 8 times, giving for example, 1, 2 or 3 doses each time.

Aerosol combination formulations for the treatment or prevention of the conditions referred to above in the average adult human are preferably arranged so that each metered dose or "puff" of aerosol contains from about 0.01 mg to about 1000 mg of a combination comprising a presently disclosed compound. In certain embodiments, each metered dose or "puff" of aerosol contains about 0.01 mg to about 100 mg of a combination comprising a presently disclosed compound. In certain embodiments, each metered dose or "puff" of aerosol contains about 1 mg to about 10 mg of a combination comprising a presently disclosed compound. Administration may be several times daily, for example 2, 3, 4 or 8 times, giving for example, 1, 2 or 3 doses each time.

Pharmaceutical compositions and methods of treatment or prevention comprising administering prodrugs of at least one presently disclosed compound are also within the scope of the present disclosure.

Glucosylceramide Synthase Assay

An enzyme assay using microsomes as a source of glucosylceramide synthase activity. Fluorescent ceramide substrate is delivered to membrane-bound enzyme as a complex with albumin. After reaction, ceramide and glucosylceramide are separated and quantitated by reverse-phase HPLC with fluorescence detection.

Procedure

Preparation of Microsomes from A375 Human Melanoma Cells

Cell suspension was sonicated on ice to complete cell lysis followed by centrifugation at spin down at 10,000 g for 10 min. at 4° C.

Supernatant was cleared by centrifugation again at 100,000 g for 1 hour at 4° C. in the Pellet was resuspended in lysis buffer, aliquoted and stored at −80° C.

Glucosylceramide Synthase Assay

Substrate and microsome were combined 1:1, mix well on a plate shaker seal the plate and incubate 1 hour at room temperature in the dark The was stop with stop solution into the reaction plate and transferred analysis plate;

RP-HPLC Analysis column: MercuryMS™ (Phenomenex) replaceable cartridge (Luna $C_8$, 3 □m, 20×4 mm)

system: Agilent 1100 with Agilent 1200 series fluorescence detector mobile phase: 1% formic acid in 81% methanol, 19% water, flow rate 0.5 mL/min, isocratic run, 4 min sample diluent: 0.1 mM $C_8$ ceramide (adsorption blocker) in 50% isopropanol, 50% water (v/v)

fluorescence detection: $\square_{ex}$=470 nm. $\square_{em}$=530 nm under these conditions, NBD $C_6$ GluCer had a retention time of about 1.7 min and NBD $C_6$ Cer ran at about 2.1 min; the peaks were clearly separate to the baseline and were integrated automatically by the HPLC software % conversion of substrate to product was used as the readout for inhibitor testing to avoid variability due to dilution error or sample evaporation All of the exemplified compounds had an $IC_{50}$ value of less than 5 μM in the Reporter Assay.

EXPERIMENTAL

General Procedure A

Carbamate/Urea Formation with Triphosgene

To a suspension of amine hydrochloride (1 equivalent) and triethylamine (3-4 equivalents) in a THF (concentration ~0.2M) at room temperature was added triphosgene (0.35 equivalent). The reaction mixture was stirred for 10 min and small amount of ether (1-2 mL) was added. The triethylammonium salt was filtered off to afford a clear solution of isocyanate in THF/ether.

To a solution of alcohol (1.5 equivalents) in THF (concentration ~0.2M) at room temperature was added NaH [60%, oil](1.5 equivalents). The reaction mixture was stirred for 15 min and the above solution (isocyanate in THF/ether) was added dropwise.

In a standard workup, the reaction was quenched with brine. The solution was extracted with EtOAc and the organic layer was dried over $Na_2SO_4$, filtered and concentrated. The crude material was purified on combiflash ($SiO_2$ cartridge, $CHCl_3$ and 2N $NH_3$ in MeOH) to afford the corresponding carbamate.

Alternatively. To a suspension of amine hydrochloride A (1 equivalent) and triethylamine (3-4 equivalents) in a THF (concentration ~0.2M) at room temperature was added triphosgene (0.35 equivalent). The reaction mixture was stirred for 10 min and small amount of ether (1-2 mL) was added. The triethylammonium salt was filtered off to afford a clear solution of isocyanate in THF/ether.

To a solution of amine B (1 equivalent) in THF (concentration ~11.0M) at room temperature was added the above solution (isocyanate in THF/ether) dropwise. The reaction was stirred for a period of 18 h and concentrated. The crude material was purified on combiflash ($SiO_2$ cartridge, $CHCl_3$ and 2N $NH_3$ in MeOH) to afford the corresponding urea.

General Procedure B

Alkylation with Organocerium

A suspension of $CeCl_3$ (4 equivalents) in THF (concentration ~0.2M) was stirred at room temperature for 1 h. The suspension was cooled to −78° C. and MeLi/Ether [1.6M] (4 equivalents) was added dropwise. The organocerium complex was allowed to form for a period of 1 h and a solution of nitrile (1 equivalent) in THF (concentration 2.0M) was added dropwise. The reaction mixture was warmed up to room temperature and stirred for 18 h. The solution was cooled to 0° C. and quenched with water (~1 mL) followed by addition of 50% aqueous solution of ammonium hydroxide (~3 mL) until precipitated formed and settled to the bottom of the flask. The mixture was filtered through a pad of celite and concentrated. The crude material was treated with a solution of HCl/dioxane [4.0M]. The intermediate arylpropan-2-amine hydrochloride was triturated in ether and used as is for the next step. Alternatively, the crude free base amine was purified on combiflash ($SiO_2$ cartridge, $CHCl_3$ and 2N $NH_3$ in MeOH) to afford the corresponding arylpropylamine.

General Procedure C

Urea Formation with Carbonyl Diimidazole (CDI)

A solution of amine A (1 equivalent) and CDI (1.3 equivalent) in THF (concentration ~0.15M) was stirred at reflux for 1 h. A solution of amine B (1.3 equivalent) in THF was added and the reaction mixture was stirred for an additional 1.5 h. The reaction was cooled to room temperature and diluted with ether. The desired compound precipitated and was filtered off. The crude material was purified on combiflash (basic $Al_2O_3$ cartridge, $CHCl_3$ and MeOH) or ($SiO_2$ cartridge, $CHCl_3$ and 2N $NH_3$ in MeOH) to afford the corresponding urea.

General Procedure D

Urea Formation with Triphosgene

To a suspension of amine A (1 equivalent) and triethylamine (4 equivalents) in a THF (concentration ~0.15M) at room temperature was added triphosgene (0.35 equivalent). The reaction mixture was stirred for 15 min and amine B (1.1 equivalent) was added. The reaction mixture was stirred at room temperature for 18 h and then diluted with EtOAc. The organic layer was washed with aqueous NaOH [1.0 M], dried over $Na_2SO_4$, filtered and concentrated. The crude material was purified on combiflash ($SiO_2$ cartridge, $CHCl_3$ and 2N $NH_3$ in MeOH) to afford the corresponding urea.

General Procedure E

Suzuki Coupling

To a solution of aryl halide (1 equivalent) in a mixture of DME/water [4:1](concentration ~0.2M) was added boronic acid (2 equivalents), palladium catalyst (0.1-0.25 equivalent) and sodium carbonate (2 equivalents). The reaction mixture was microwaved 25 min at 150° C. After filtering through a celite plug and concentrating, the crude product was purified on combiflash ($SiO_2$ cartridge, $CHCl_3$ and 2N $NH_3$ in MeOH) to afford the corresponding coupling adduct.

Alternatively: To a solution of aryl halide (1 equivalent) in a mixture of toluene/water [20:1](concentration ~0.2 M) was added boronic acid (1.3-2.5 equivalents), palladium catalyst (0.05-0.15 equivalent), tricyclohexylphosphine (0.15-0.45 equivalent) and potassium phosphate (5 equivalents). The reaction mixture was microwaved 25 min at 150° C. After filtering through a celite plug and concentrating, the crude product was purified on combiflash ($SiO_2$ cartridge, $CHCl_3$ and 2N $NH_3$ in MeOH) to afford the corresponding coupling adduct.

General Procedure F

Hydrogenation

To a solution of substrate in methanol, ethanol or EtOAc (concentration ~0.2M) was added palladium catalyst (20% w/w of substrate). The reaction mixture was stirred at room temperature under 1 atm of $H_2$ until completion. The reaction was filtered through a celite plug followed by two rinses with chloroform. The crude product was concentrated and purified on combiflash ($SiO_2$ cartridge, $CHCl_3$ and 2N $NH_3$ in MeOH) to afford the hydrogenated product. Alternatively, the final material was purified by precipitation or recrystallization.

General Procedure G

Cyclopropanation

To a mixture of arylnitrile (1 equivalent) and $Ti(Oi-Pr)_4$ (1.7 equivalents) stirring at −70° C., was added dropwise EtMgBr [3.0 M in ether] (1.1 equivalents). The reaction mixture was allowed to warm to 25° C. and stirred for 1 h. To the above mixture was added $BF_3.Et_2O$ (3 equivalents) dropwise at 25° C. After the addition, the mixture was stirred for another 2 h. and then quenched with aqueous HCl [2M]. The resulting solution was then basified by adding aqueous NaOH [2M]. The organic material was extracted with ethyl ether. The organic layers were combined, dried over $Na_2SO_4$, filtered and concentrated. The crude material was purified by silica gel column chromatography (eluting with petroleum ether/EtOAc:10/1 to 1/1) to give the corresponding 1-arylcyclopropanamine.

General Procedure H

Coupling Via In-Situ Curtius Rearrangement

A mixture of acid (1 equivalent), triethylamine (2.5 equivalents), DPPA (1.0 equivalent) in toluene (concentration ~0.3M) was refluxed for 30 min. The mixture was cooled to room temperature and alcohol (1 equivalent) was added. After addition, the mixture was heated at 90° C. for 18 h. The reaction was cool down to room temperature, diluted with EtOAc and washed with saturated aqueous sodium dicarbonate. The organic phase was dried over $Na_2SO_4$, concentrated and purified by prep-TLC (EtOAc/MeOH 5:1, containing 1% of TEA) to afford the corresponding carbamate.

General Procedure I

Amide Formation Using EDCI

To a solution of amine (1 equivalent) in DMF or THF (concentration ~0.3M) was added EDCI (1.2-2.5 equivalents), HOBT (1.2-2.5 equivalents), DIPEA (1.2-2.5 equivalents) and triethylamine (few drops). The reaction mixture was stirred and the acid (1.2 equivalents) was added. The reaction was stirred at room temperature for 18 h and then concentrated. The residue was dissolved in EtOAc and washed with brine. The organic layer was dried over $Na_2SO_4$ and concentrated. The crude material was purified by prep-HPLCMS or by combiflash ($SiO_2$ cartridge, $CHCl_3$ and 2N $NH_3$ in MeOH).

Preparation A

Intermediate 1

2-(3-bromophenyl)propan-2-amine hydrochloride

To a solution of methyl 3-bromobenzoate (15.0 g, 69.8 mmol) in THF (140 mL) at −78° C. was added dropwise a solution of MeMgBr/diethyl ether [3.0M] (58 mL). The reaction mixture was warmed up to room temperature and stirred for 2 h. The solution was poured to an aqueous saturated solution of ammonium chloride and the organic material was extracted with EtOAc. The organic layer was dried over $Na_2SO_4$, filtered and concentrated to afford the corresponding alcohol (14.9 g) which was used without further purification.

To a solution of 2-(3-bromophenyl)propan-2-ol (17.2 g, 79.8 mmol) in chloroacetonitrile (160 mL) was added acetic acid (14 mL). The reaction mixture was cooled to 0° C. and $H_2SO_4$ (14 mL) was added dropwise. The reaction mixture was warmed to room temperature and stirred for 18 h. The reaction was then poured into ice and extracted with EtOAc. The organic layer was washed with aqueous NaOH [1.0M] solution and brine, dried over $Na_2SO_4$ and concentrated to afford the corresponding chloroacetamide (21.4 g) which was used without further purification.

To a solution of N-(2-(3-bromophenyl)propan-2-yl)-2-chloroacetamide (20.3 g) in ethanol (120 mL) was added acetic acid (20 mL). The reaction mixture was stirred at reflux for 18 h. The solution was cooled to room temperature and the precipitate was filtered off on a celite pad. The filtrate was concentrated and the residue was dissolved in EtOAc. The organic layer was treated with aqueous NaOH [1.0M] solution, dried over $Na_2SO_4$ and concentrated. The crude material was treated with a solution of HCl/dioxane [4M]. The intermediate 2-(3-bromophenyl)propan-2-amine hydrochloride was triturated in ether and used as is for the next step (7.50 g, 43%). $^1$H NMR (400 MHz, $CD_3OD$) δ 7.69 (q, J=1.8 Hz, 1H), 7.55 (ddd, J=1.0, 1.8, 7.9 Hz, 1H), 7.49 (ddd, J=1.0, 2.0, 8.0 Hz, 1H), 7.38 (t, J=8.0 Hz, 1H), 1.71 (s, 6H) ppm.

Preparation B

Intermediate 2

2-(5-bromo-2-fluorophenyl)propan-2-amine hydrochloride

To a solution of 5-bromo-2-fluorobenzoic acid (4.85 g, 22.8 mmol) in methanol (45 mL) was added $H_2SO_4$ (4.5 mL). The reaction mixture was stirred at room temperature for 18 h and the solution was concentrated. The residue was treated with an aqueous NaOH [10% w/v] solution and the organic material was extracted with CHCl$_3$. The organic layer was dried over Na$_2$SO$_4$, filtered and concentrated to afford the corresponding ester (4.69 g, 91%) which was used without further purification.

The ester intermediate (4.69 g, 20.1 mmol) was converted to intermediate 2 using the same procedure reported in example intermediate 1 to afford the corresponding ammonium salt (3.94 g, 67% overall yield) as a white solid. $^1$H NMR (400 MHz, CD$_3$OD) δ 7.67-7.57 (m, 2H), 7.21 (dd, J=8.7, 12.3 Hz, 1H), 1.77 (s, 6H) ppm.

Intermediate 3

2-(3-bromo-4-fluorophenyl)propan-2-amine hydrochloride

5-Bromo-2-fluorobenzoic acid was transformed to intermediate 3 using the same procedure reported in example intermediate 2 to afford the corresponding ammonium salt (2.79 g, 49% overall yield) as a white solid.

Intermediate 4

2-(3-bromo-2-fluorophenyl)propan-2-amine

3-Bromo-2-fluorobenzoic acid was transformed to intermediate 4 using the same procedure reported in example intermediate 2 to afford the corresponding amine as pale yellow oil.

Intermediate 5

2-(4-bromophenyl)propan-2-amine hydrochloride

Using general procedure B, bromobenzonitrile (2.00 g, 11.0 mmol) was converted to the corresponding 2-(4-bromophenyl)propan-2-amine, which was afforded as a brown oil (1.20 g, 51%).

Preparation C

Intermediate 6

1,4-Diazabicyclo[3.2.2]nonane

To a stirred solution of 1,4-diazabicyclo[3.2.2]nonan-3-one (1.0 g, 7.2 mmol) in 1,4-dioxane (7.2 mL) at room temperature was added lithium aluminum hydride [2.0M/THF] (4.1 mL, 8.2 mmol). The reaction mixture was then heated at reflux for 6 hours before cooling to room temperature. The reaction was quenched by the stepwise addition of 200 □L of H$_2$O, 200 □L of 15% aqueous NaOH, and 600 □L of H$_2$O. The mixture was filtered through Celite which was subsequently washed with EtOAc. The combined filtrate was concentrated in vacuo to afford the product (0.82 g, 90%) which was used without further purification. $^1$H NMR (400 MHz, CDCl$_3$) δ 3.28-3.25 (m, 1H), 2.99-2.95 (m, 8H), 1.86-1.80 (m, 3H), 1.69-1.64 (m, 2H) ppm.

Preparation D

Intermediate 7

2-Methylquinuclidin-3-ol

A solution of potassium carbonate (11.4 g, 82.8 mmol) and quinuclidine hydrate (5.00 g, 20.4 mmol) was dissolved in H$_2$O (15.6 mL). When completely dissolved, dichloromethane (20.4 mL) was added and the reaction was stirred at room temperature overnight. The organic phase was separated and the aqueous phase extracted with chloroform (3×50 mL). The combined organic layers were dried over MgSO$_4$, filtered and concentrated in vacuo. The product was used without further purification. $^1$H NMR (400 MHz, CDCl$_3$) 2.79 (s, 1H), 5.19 (s, 1H), 3.14-3.06 (m, 2H), 2.99-2.91 (m, 2H), 2.57-2.55 (m, 1H), 1.98-1.93 (m, 4H) ppm.

The 2-methylenequinuclidin-3-one (3.50 g) in ethanol (30 mL) was reduced over 10% Pd/C (50 wt %) under a H$_2$ atmosphere. When judged complete by TLC (~3 days), the catalyst was filtered off and the filter cake washed with ethyl acetate. The solvent was removed in vacuo to afford the desired product (2.80 g, 80%) was obtained and used without further purification. $^1$H NMR (400 MHz, CDCl$_3$) 3.37-3.31 (m, 1H), 3.21-3.13 (m, 2H), 3.09-3.00 (m, 1H), 2.97-2.89 (m, 1H), 2.46-2.43 (m, 1H), 2.05-1.91 (m, 4H), 1.34 (d, J=7.6 Hz, 3H) ppm.

To 2-methylquinuclidin-3-one (0.50 g, 3.60 mmol) in 1,4-dioxane (18 mL) at room temperature was added lithium aluminum hydride [1.0M/THF] (4.1, 4.1 mmol). The reaction mixture was stirred at room temperature for 15 minutes. The reaction was quenched by the stepwise addition of 116 □L of H$_2$O, 116 □L of 15% aqueous NaOH, and 348 □L of H$_2$O. The mixture was filtered through Celite which was subsequently washed with EtOAc. The solvent was removed in vacuo to afford the product (0.48 g, 95%) which was used without further purification as a 2:1 mixture of diastereomers.

Preparation E

Intermediate 8

1-azabicyclo[3.2.2]nonan-4-ol

To 1-azabicyclo[3.2.2]nonan-4-one (0.20 g, 1.4 mmol) in 1,4-dioxane (2.8 mL) at 0° C. was added lithium aluminum hydride [1.0M/THF] (1.7 mL, 1.7 mmol). The reaction mixture was maintained at 0° C. for 15 minutes. The reaction was quenched by the stepwise addition of 46 □L of H$_2$O, 46 □L of 15% aqueous NaOH, and 138 □L of H$_2$O. The mixture was filtered through Celite which was subsequently washed with EtOAc. The solvent was removed in vacuo to afford the product (0.19 g, 96%) which was used without further purification. $^1$H NMR (400 MHz, CDCl$_3$) δ 3.90-3.86 (m, 1H), 3.09-3.03 (m, 1H), 2.96-2.91 (dd, J=9.2, 6.8 Hz, 1H), 2.86-2.75 (m, 3H), 2.71-2.64 (m, 1H), 2.34-2.27 (bs s, 1H), 1.98-1.86 (m, 3H), 1.71-1.59 (m, 3H), 1.51-1.35 (m, 1H) ppm.

Preparation F

Intermediate 9

1-Azabicyclo[2.2.1]heptan-3-ol

To a mixture of sodium methoxide (2.00 g, 37.9 mmol) in methanol (9 mL) at 0° C. was added glycine methyl ester hydrochloride (4.76 g, 37.9 mmol) and dimethyl itaconate (5.00 g, 31.6 mmol.) The reaction was heated at reflux for 16 hours before cooling to room temperature. The solid was filtered off and washed with dichloromethane. The filtrate was concentrated and the residue diluted with 5N HCl (50 mL). The aqueous layer was extracted with dichloromethane (4×50 mL), dried over MgSO$_4$, filtered and concentrated in vacuo. The product was used without further purification. $^1$H NMR (400 MHz, CDCl$_3$) δ 4.04 (dd, J=82.0, 17.6 Hz), 3.74-3.64 (m, 8H), 3.32-3.24 (m, 1H), 2.77-2.63 (m, 2H) ppm.

To methyl 1-(2-methoxy-2-oxoethyl)-5-oxopyrrolidine-3-carboxylate (3.40 g, 16.0 mmol) in THF (20 mL) at 0° C. was added borane-THF [1.0M/THF] (32.0 mL, 32.0 mmol). The reaction was stirred at reflux for 1 hour and then cooled to room temperature where it was allowed to stir an additional 12 hours. The reaction was quenched by the addition of a saturated solution of potassium carbonate (5.52 g in 20 mL H$_2$O) and heated at reflux for an additional 1 hour before cooling to room temperature. The solvent was removed in vacuo and the residue made acidic by the addition of 5N HCl (25 mL). The aqueous layer was extracted with dichloromethane (2×30 mL). The pH of the aqueous layer was then made basic by the addition of solid potassium carbonate. The aqueous layer was further extracted with dichloromethane (5×30 mL). The combined organic layers were dried over MgSO$_4$, filtered and concentrated in vacuo. The product was used without further purification. $^1$H NMR (400 MHz, CDCl$_3$) δ 3.66 (s, 3H), 3.63 (s, 3H), 3.29 (ABq, 2H, J=24.0, 16.8 Hz), 3.06-3.02 (m, 2H), 2.87-2.81 (m, 1H), 2.71-2.65 (m, 1H), 2.56-2.50 (m, 1H), 2.09-2.04 (m, 2H) ppm.

To a refluxing solution of potassium tert-butoxide (2.46 g, 22.0 mmol) in toluene (32 mL) was added dropwise a solution of methyl 1-(2-methoxy-2-oxoethyl)pyrrolidine-3-carboxylate (2.00 g, 10.0 mmol) in toluene (10 mL) over 1 hour. The reaction was allowed to stir and additional 3 hours at reflux before first cooling to room temperature then cooling to −10° C. Acetic acid (1.3 mL) was then added with stirring. The toluene layer was extracted with 5N HCl (4×50 mL). The combined aqueous layers were heated at 110° C. for 8 hours. The reaction was then cooled to room temperature and the volume reduced by half in vacuo. The pH of the reaction mixture was made basic by the addition of solid potassium carbonate. The aqueous layer was extracted with dichloromethane (5×50 mL) and the combined organic layers were concentrated in vacuo. To the crude product was added ethyl ether. The solid filtered off to afford the desired product (0.30 g, 27%) which was used without further purification. $^1$H NMR (400 MHz, CDCl$_3$) δ 3.05-2.96 (m, 3H), 2.76 (s, 2H), 2.72-2.66 (m, 2H), 2.09-2.01 (m, 1H), 1.78-1.71 (m, 1H) ppm.

The 1-azabicyclo[2.2.1]heptan-3-one (0.30 g, 2.7 mmol) in ethanol (2-3 mL) was reduced over PtO$_2$ (50 wt %) under a H$_2$ atmosphere. After stirring 4 hours, the catalyst was filtered off and the filtercake washed with ethanol. The ethanol was removed in vacuo to afford the desired product (0.29 g, 95%). $^1$H NMR (400 MHz, CDCl$_3$) δ 4.36-4.35 (m, 1H), 3.10-3.05 (m, 1H), 2.95-2.88 (m, 1H), 2.72-2.66 (m, 1H), 2.63-2.57 (m, 2H), 2.48-2.44 (dd, J=10.0, 3.2 Hz, 1H), 2.11-2.05 (m, 2H), 1.51-1.44 (m, 1H) ppm.

Preparation G

Intermediate 10

(R)-3-methylquinuclidin-3-amine and (S)-3-methylquinuclidin-3-amine

To a well-stirred solution of MeLi [3.0M/diethyl ether] (67.0 mL, 201 mmol) in anhydrous diethyl ether (150 mL) at −78° C. was added, dropwise, a solution of quinuclidin-3-one (12.5 g, 100 mmol) in diethyl ether (100 mL). The resulting solution was maintained at −78° C. for 1 hour, then at room temperature for 18 hours. Water (60 mL) was added dropwise at 0° C. and the mixture was concentrated in vacuo to give a residue, which was purified by neutral aluminum oxide column chromatography (0-20% MeOH in CHCl$_3$) to give 3-methylquinuclidin-3-ol (10.0 g, 71%) as a light yellow solid. To stirred acetonitrile (250 mL) at 0° C. was slowly added concentrated sulfuric acid (100 mL). The resulting solution was added dropwise to a mixture of 3-methylquinuclidin-3-ol (9.10 g, 64.5 mmol) in acetonitrile (250 mL) at 0° C. The reaction mixture was stirred at room temperature for 60 hours, then cooled with an ice bath and basified with aqueous sodium hydroxide solution to pH 10. The mixture was extracted with 5:1 (v/v) CHC$_3$/i-PrOH. The organic layer was concentrated to afford a residue which was diluted with 2N aq. HCl and washed with 5:1 (v/v) CHC$_3$/i-PrOH. The remaining aqueous layer was then basified with 2N NaOH and extracted with 5:1 (v/v) CHCl$_3$/i-PrOH. The combined organic layers were washed with water, dried (Na$_2$SO$_4$) and concentrated to give 9.5 g (82%) of the desired compound as a light yellow oil. The 2 enantiomers of the above intermediate are separated from each other by using chiral column on supercritical fluid chromatography (SFC) system.

A solution of the above chiral acetamide intermediate (9.50 g, 52.0 mmol) in conc. HCl (100 mL) was refluxed for 3 days, cooled with an ice bath and neutralised with aqueous sodium hydroxide solution to pH 1. The mixture was washed with 5:1 (v/v) CHCl$_3$/i-PrOH. The aqueous layer was then basified with 2N NaOH and extracted with 5:1 (v/v) CHCl$_3$/i-PrOH). The combined extracts were washed with water, dried (Na$_2$SO$_4$) and concentrated to give 5.00 g (69%) of the desired chiral compound as a light yellow semi-solid. $^1$H NMR (500 MHz, DMSO-d$_6$) δ 2.72-2.39 (m, 6H), 2.01-1.96 (m, 1H), 1.67-1.61 (m, 1H), 1.43-1.36 (m, 2H), 1.23-1.17 (m, 1H), 1.09 (s, 3H) ppm. $^{13}$C NMR (125 MHz, DMSO-d$_6$) δ65.3, 48.3, 46.6, 46.4, 34.2, 30.0, 24.8, 22.8 ppm. Purity: >99% (GC-MS); retention time 6.63 min; (M) 140.1.

Preparation H

Intermediate 11

2-(3-(4-fluorophenyl)isothiazol-5-yl)propan-2-amine

To a stirred suspension of 4-fluorobenzamide (70.00 g, 503.1 mmol) in toluene (900 mL) was added chlorocarbonyl sulfenyl chloride (83.0 mL, 1.00 mol). The mixture was heated overnight at 60° C. and concentrated. The resulting tan solid was triturated with methylene chloride (200 mL), collected by suction filtration and rinsed with additional methylene chloride (4×70 mL). The crude product was impregnated onto silica (100 g) and chromatographed in a large filter funnel dry loaded with silica using a hexane/ethyl acetate gradient. The product 5-(4-fluorophenyl)-1,3,4-oxathiazol-2-one was afforded as an off-white solid (55.98 g, 56%).

To a stirred solution of 5-(4-fluorophenyl)-1,3,4-oxathiazol-2-one (42.80 g, 217.1 mmol) in o-dichlorobenzene (600 mL) was added ethyl propiolate (66.0 mL, 651 mmol). The mixture was heated overnight at 135° C. and concentrated. The residual oil was purified by flash chromatography using a hexane/ethyl acetate gradient to afford ethyl 3-(4-fluorophenyl)isothiazole-5-carboxylate as a pale golden solid (17.35 g, 32%). The more polar, ethyl 3-(4-fluorophenyl)isothiazole-4-carboxylate isomer (generated in ~57/43 ratio versus the desired product) was discarded.

To a stirred and cooled (0° C.) solution of ethyl 3-(4-fluorophenyl)isothiazole-5-carboxylate (38.50 g, 153.2 mmol) in THF (400 mL) was added a solution of methylmagnesium bromide in diethyl ether (3.0 M, 128 mL, 384 mmol), dropwise over 20 minutes. After another 1.5 hours at 0° C. the reaction was quenched by the slow addition of ethyl acetate (20 mL) and concentrated. The residue was taken up in aqueous NH$_4$Cl (400 mL) and extracted with ethyl acetate (2×150 mL). The combined extracts were dried (Na$_2$SO$_4$) and concentrated. The resulting amber syrup was purified by flash chromatography using a hexane/ethyl acetate gradient to afford 2-(3-(4-fluorophenyl)isothiazol-5-yl)propan-2-ol as soft, golden solid (29.02 g, 80%).

2-(3-(4-Fluorophenyl)isothiazol-5-yl)propan-2-ol (29.00 g, 122.2 mmol) was taken up in thionyl chloride (75 mL). The mixture was cooled (ice bath) briefly and stirred. After 4 hours the reaction was concentrated and the residue was partitioned between ethyl acetate (200 mL) and aqueous NaHCO$_3$ (300 mL). The organic layer was combined with a backextract of the aqueous layer (ethyl acetate, 1×100 mL), dried (Na$_2$SO$_4$) and concentrated to afford a mixture of 5-(2-chloropropan-2-yl)-3-(4-fluorophenyl)isothiazole product and 3-(4-fluorophenyl)-5-(prop-1-en-2-yl)isothiazole elimination byproduct (~63/39 ratio) as a dark amber oil (29.37 g). This material was used without purification in the next reaction.

To a stirred solution of the product of the previous step in DMSO (80 mL) was added sodium azide (14.89 g, 229.0 mmol). The mixture was heated at 50° C. overnight, diluted with ethyl acetate (250 mL) and washed with water (6×400 mL). The organic layer was dried (Na$_2$SO$_4$) and concentrated to afford a mixture of 5-(2-azidopropan-2-yl)-3-(4-fluorophenyl)isothiazole and 3-(4-fluorophenyl)-5-(prop-1-en-2-yl)isothiazole (~56/44 ratio) as a dark amber oil (29.10 g). This material was used without purification in the next reaction.

The product of the previous step was combined with 10% palladium on carbon (50% water; 7.50 g) and taken up in methanol (350 mL). The stirred suspension was cycled between vacuum and a nitrogen purge three times. After an additional evacuation, the reaction was backfilled with hydrogen gas (balloon reservoir) and stirred overnight. The reaction was filtered through Celite. The filtrate was combined with methanol rinsings of the Celite and concentrated. The resulting dark amber oil purified by flash chromatography using a methylene chloride/methanol gradient to afford 2-(3-(4-fluorophenyl)isothiazol-5-yl)propan-2-amine as viscous, amber oil (14.23 g, 49% over 3 steps).

Several approaches are being used or pursued for the treatment of LSDs, most of which focus on enzyme replacement therapy for use alone in disease management. Numerous approved enzyme replacement therapies are commercially available for treating LSDs (e.g., Myozyme® for Pompe disease, Aldurazyme® for Mucopolysaccharidosis I, Cerezyme® for Gaucher disease and Fabrazyme® for Fabry disease). Additionally, the inventors have identified a number of small molecules for use alone in the management of LSDs. The therapeutic methods of the invention described herein provide treatment options for the practitioner faced with management of various lysosomal storage diseases, as described in detail below.

In certain aspects of the invention, the compounds of the present invention may be used to treat a metabolic disease, such as a lysosomal storage disease (LSD), either alone or as a combination therapy with an enzyme replacement therapy. In other aspects of the invention, the compounds of the present invention may be used to inhibit or reduce GCS activity in a subject diagnosed with a metabolic disease, such as an LSD, either alone or as a combination therapy with an enzyme replacement therapy. In other aspects of the invention, the compounds of the present invention may be used to reduce and/or inhibit the accumulation of a stored material (e.g., lysosomal substrate) in a subject diagnosed with a metabolic disease, such as an LSD. In certain embodiments of the foregoing aspects, the LSD is Gaucher (type 1, type 2 or type 3), Fabry, $G_{M1}$-gangliosidosis or $G_{M2}$-gangliosidoses (e.g., GM2 Activator Deficiency, Tay-Sachs and Sandhoff). Table 1 lists numerous LSDs and identifies the corresponding deficient enzyme that may be used as an ERT in the foregoing aspects of the invention.

In other scenarios it may be necessary to provide SMT to a patient whose condition requires the reduction of substrates in the brain and thus is not treatable by systemic administration of ERT. While direct intracerebroventricular or intrathecal administration can reduce substrate levels in the brain, systemic administration of ERT is not amenable for LSD's with Central Nervous System (CNS) involvement due to its incapacity to cross the Blood Brain Barrier (BBB) and SMT may prove beneficial in patients having residual enzymatic activities in the CNS.

In accordance with the present invention, SMT is provided to a patient to treat a cancer and/or metabolic disease, such as, a lysosomal storage disease. The SMT may include one or more small molecules. The SMT includes administering to the patient compounds of the present invention. In particular embodiments, the compound is (S)-Quinuclidin-3-yl (2-(2-(4-fluorophenyl)thiazol-4-yl)propan-2-yl)carbamate or Quinuclidin-3-yl (2-(4'-fluoro-[1,1'-biphenyl]-3-yl)propan-2-yl) carbamate, or combinations thereof.

In certain embodiments, compounds of the invention, such as, for example, (S)-Quinuclidin-3-yl (2-(2-(4-fluorophenyl) thiazol-4-yl)propan-2-yl)carbamate and Quinuclidin-3-yl (2-(4'-fluoro-[1,1'-biphenyl]-3-yl)propan-2-yl)carbamate may be used for treatment of virtually any storage disease resulting from a defect in the glycosphingolipid pathway (e.g. Gaucher (i.e., type 1, type 2 type 3), Fabry, $G_{M1}$-gangliosidosis, $G_{M2}$-gangliosidoses (e.g., GM2 Activator Deficiency. Tay-Sachs and Sandhoff)). In a particularly preferred embodiment, (S)-Quinuclidin-3-yl (2-(2-(4-fluorophenyl)thiazol-4-yl)propan-2-yl)carbamate or a pharmaceutically acceptable salt or prodrug thereof is used to inhibit and/or reduce the accumulation of Gb3 and/or lyso-Gb3 in a patient with Fabry disease, either alone or as a combination therapy with enzyme replacement therapy (see Examples). In a preferred embodiment, the enzyme replacement therapy includes administering alpha-galactosidase A to the Fabry patient. Indeed, the Examples below demonstrate that a GCS inhibitor of the invention effectively reduces Gb3 and lyso-Gb3 storage in a mouse model of Fabry disease, thus supporting its use as a viable approach for the treatment of Fabry disease. Furthermore, in vivo combination therapy data provided in the Examples strongly suggest that a combined therapeutic approach could be both additive and complementary.

In certain embodiments, compounds of the invention, such as, for example, (S)-Quinuclidin-3-yl (2-(2-(4-fluorophenyl) thiazol-4-yl)propan-2-yl)carbamate and Quinuclidin-3-yl (2-(4'-fluoro-[1,1'-biphenyl]-3-yl)propan-2-yl)carbamate may be used for reducing the level of GluCer and GluSph in the brain of a subject diagnosed with neuropathic Gaucher disease, either alone or in combination with ERT (e.g., glucocerebrosidase administration).

Dosage regimens for a small molecule therapy component of a combination therapy of the invention are generally determined by the skilled clinician and are expected to vary significantly depending on the particular storage disease being treated and the clinical status of the particular affected individual. The general principles for determining a dosage regimen for a given SMT of the invention for the treatment of any storage disease are well known to the skilled artisan. Guidance for dosage regimens can be obtained from any of the many well known references in the art on this topic. Further guidance is available, inter alia, from a review of the specific references cited herein. In certain embodiments, such dosages may range from about 0.5 mg/kg to about 300 mg/kg, preferably from about 5 mg/kg to about 60 mg/kg (e.g., 5 mg/kg, 10 mg/kg, 15, mg/kg, 20 mg/kg, 25 mg/kg, 30 mg/kg, 35 mg/kg, 40 mg/kg, 45 mg/kg, 50 mg/kg, 55 mg/kg and 60 mg/kg) by intraperitoneal, oral or equivalent administration from one to five times daily. Such dosages may range from about 5 mg/kg to about 5 g/kg, preferably from about 10 mg/kg to about 1 g/kg by oral, intraperitoneal or equivalent administration from one to five times daily. In one embodiment, doses range from about 10 mg/day to about 500 mg/day (e.g., 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 220 mg/day, 230 mg/day, 240 mg/day, 250 mg/day, 260 mg/day, 270 mg/day, 280 mg/day, 290 mg/day, 300 mg/day). A particularly preferred oral dose range is from about 50 mg to about 100 mg, wherein the dose is administered twice daily. A particular oral dose range for a compound of the present invention is from about 5 mg/kg/day to about 600 mg/kg/day. In a particular oral dose range for a compound of the present invention is from about 1 mg/kg/day to about 120 mg/kg/day, e.g., 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day, 50 mg/kg/day, 55 mg/kg/day or 60 mg/kg/day, 65 mg/kg/day, 70 mg/kg/day, 75 mg/kg/day, 80 mg/kg/day, 85 mg/kg/day, 90 mg/kg/day, 95 mg/kg/day, 100 mg/kg/day, 105 mg/kg/day, 110 mg/kg/day, 115 mg/kg/day or 120 mg/kg/day.

In certain embodiments, the invention relates to combination therapies of SMT using compounds of the invention and ERT therapy for the treatment of lysosomal storage diseases. A partial list of known lysosomal storage diseases that can be treated in accordance with the invention is set forth in Table 1, including common disease name, material stored, and corresponding enzyme deficiency (adapted from Table 38-4 of Kolodny et al., 1998, Id.).

TABLE 1

| \multicolumn{3}{c}{Lysosomal Storage Diseases} | | |
|---|---|---|
| Disease | Material Stored | Enzyme Deficiency |
| \multicolumn{3}{c}{Sphingolipidoses} | | |
| Gaucher | Glucocerebroside, glucosylsphingosine | Glucocerebrosidase |
| Niemann-Pick | Sphingomyelin | Sphingomyelinase |
| Niemann-Pick B | Sphingomyelin | Sphingomyelinase |
| Farber | Ceramide | Ceramidase |
| $G_{M1}$-gangliosidosis | $G_{M1}$-ganglioside, glycoprotein | $G_{M1}$-ganglioside-β-galactosidase |
| $G_{M2}$-gangliosidosis (Sandhoff) | $G_{M2}$-ganglioside, globoside | Hexosaminidase A and B |
| Tay-Sachs | $G_{M2}$-ganglioside | Hexosaminidase A |
| Krabbe | Galactosylceramide | β-Galactocerebrosidase |
| \multicolumn{3}{c}{Mucopolysaccharidoses} | | |
| Hurler-Scheie (MPS I) | Dermatan sulfate, heparin Sulfate | α-L-iduronidase |
| Hunter (MPS II) | Dermatan sulfate, heparin sulfate | Iduronate sulfatase |
| \multicolumn{3}{c}{Sanfilippo (MPS III)} | | |
| Type A | Heparan sulfate | Heparan-N-sulfatase |
| Type B | Heparan sulfate | N-acetyl-α-glucosaminidase |
| Type C | Heparan sulfate | Acetyl CoA:α-glucosaminide acetyl-transferase |
| Type D | Heparan sulfate | N-acetyl-α-glucosamine-6-sulfatase |
| \multicolumn{3}{c}{Marquio (MPS IV)} | | |
| Type A | Keratan sulfate | Galactosamine-6-sulfatase |
| Type B | Keratan sulfate | β-galactosidase |
| Maroteaux-Lamy (MPS VI) | Dermatan sulfate | Galactosamine-4-sulfatase (arylsulfatase B) |
| Sly (MPS VII) | Dermatan sulfate, heparan Sulfate | β-glucuronidase |
| Mucosulfatidosis | Sulfatides, mucopolysaccharides | Arylsulfatase A, B and C, other sulfatases |
| \multicolumn{3}{c}{Mucolipidoses} | | |
| Sialidoses | Sialyloligosaccharides, glycoproteins | α-neuraminidase |
| Mucolipidosis II | Sialyloligosaccharides, glycoproteins, glycolipids | High serum, low fibroblast enzymes; N-acetyl-glucosamine-1-phosphate transferase |
| Mucolipidosis III | Glycoproteins, glycolipids | Same as above |
| Mucolipidosis IV | Glycolipids, glycoproteins | Mcoln1 transm protein |

TABLE 1-continued

Lysosomal Storage Diseases

| Disease | Material Stored | Enzyme Deficiency |
| --- | --- | --- |
| Other Diseases of Complex Carbohydrate Metabolism | | |
| Fabry | Globotriaosylceramide(Gb3), lyso-Gb3 | α-galactosidase A |
| Schindler | O-linked glycopeptides | α-N-acetylgalactosaminidase |
| Pompe | Glycogen | α-glucosidase |
| Sialic acid storage disease | Free sialic acid | Unknown |
| Fucosidosis | Fucoglycolipids, fucosyloligosaccharides | α-fucosidase |
| Mannosidosis | Mannosyloligosaccharides | α-mannosidase |
| Aspartylglucosaminuria | Aspartylglucosamine | Aspartylglucosamine amidase |
| Wolman | Cholesteryl esters, Triglycerides | Acid lipase |
| Neuronal Ceroid Lipofuscinoses (NCLs)* | | |
| Infintile NCL | Granular osmophilic deposits, Saposins A and D | Palmitoyl-protein thioesterase (PPT1) |
| Late Infantile | Curvilinear profiles, ATP synthase subunit c | Tripeptidyl protease 1 (TPP1) |
| Finnish variant | Fingerprint/Rectilinear profiles, ATP synthase subunit c | CLN5 |
| Variant | Fingerprint/Rectilinear profiles, ATP synthase subunit c | CLN6 |
| Juvenile | Fingerprint profile, ATP synthase subunit c | CLN3 |
| Adult | Variable | Unknown |
| Northern Epilepsy | Rectilinear profile, ATP synthase subunit c | CLN8 |
| Turkish variant | Fingerprint/Rectilinear profiles - constituents unknown | Unknown |
| Lysosomal diseases of cholesterol transport and metabolism | | |
| Niemann-Pick type C | Unesterified cholesterol | NPC1 or NPC2 |

*Davidson et al., The Neuronal Ceroid Lipofuscinosis, Clinical Features and Molecular Basis of Disease. In Barranger JA and Cabrera-Salazar MA (Eds) Lysosomal Storage Disorders, 2007. pp. 371-388. Springer, New York, U.S.A.

Any method known to the skilled artisan may be used to monitor disease status and the effectiveness of a combination therapy of the invention. Clinical monitors of disease status may include but are not limited to organ volume (e.g. liver, spleen), hemoglobin, erythrocyte count, hematocrit, thrombocytopenia, cachexia (wasting), and plasma chitinase levels (e.g. chitotriosidase). Chitotriosidase, an enzyme of the chitinase family, is known to be produced by macrophages in high levels in subjects with lysosomal storage diseases (see Guo et al., 1995, J. Inherit. Metab. Dis. 18, 717-722; den Tandt et al., 1996, J. Inherit. Metab. Dis. 19, 344-350; Dodelson de Kremer et al., 1997, Medicina (Buenos Aires) 57, 677-684; Czartoryska et al., 2000, Clin. Biochem. 33, 147-149; Czartoryska et al., 1998, Clin. Biochem. 31, 417-420; Mistry et al., 1997, Baillieres Clin. Haematol. 10, 817-838; Young et al., 1997, J. Inherit. Metab. Dis. 20, 595-602; Hollak et al., 1994, J. Clin. Invest. 93, 1288-1292). Chitotriosidase is preferably measured in conjunction with angiotensin converting enzyme and non tartrate resistant acid phosphatase to monitor response to treatment of Gaucher patients.

Methods and formulations for administering the combination therapies of the invention include all methods and formulations well known in the art (see, e.g., Remington's Pharmaceutical Sciences, 1980 and subsequent years, 16th ed. and subsequent editions, A. Oslo editor, Easton Pa.; Controlled Drug Delivery, 1987, 2nd rev., Joseph R. Robinson & Vincent H. L. Lee, eds., Marcel Dekker, ISBN: 0824775880; Encyclopedia of Controlled Drug Delivery, 1999, Edith Mathiowitz, John Wiley & Sons, ISBN: 0471148288; U.S. Pat. No. 6,066,626 and references cited therein; see also, references cited in sections below).

According to the invention, the following general approaches are provided for combination therapy in the treatment of lysosomal storage diseases. Each general approach involves combining enzyme replacement therapy with small molecule therapy in a manner consistent with optimizing clinical benefit while minimizing disadvantages associated with using each therapy alone.

In one embodiment of the invention, enzyme replacement therapy (alone or in combination with small molecule therapy) is administered to initiate treatment (i.e., to debulk the subject), and small molecule therapy is administered after the de-bulking phase to achieve and maintain a stable, long-term therapeutic effect without the need for frequent intravenous ERT injections. For example, enzyme replacement therapy may be administered intravenously (e.g. over a one to two hour period) once, on a weekly basis, once every two weeks, or once every two months, for several weeks or months, or longer (e.g., until an involved indicator organ such as spleen or liver shows a decrease in size). Moreover, the ERT phase of initial de-bulking treatment can be performed alone or in combination with a small molecule therapy. A small molecule therapeutic component is particularly preferred where the small molecule is compatible with oral administration, thus providing further relief from frequent intravenous intervention.

Alternating among ERT and SMT, or supplementing SMT with ERT as needed, provides a strategy for simultaneously taking advantage of the strengths and addressing the weaknesses associated with each therapy when used alone. An advantage of ERT, whether used for de-bulking and/or for more long-term care, is the much broader clinical experience available to inform the practitioner's decisions. Moreover, a subject can be effectively titrated with ERT during the debulking phase by, for example, monitoring biochemical metabolites in urine or other body samples, or by measuring affected organ volume. A disadvantage of ERT, however, is the frequency of the administration required, typically involving intravenous injection on a weekly or bi-weekly basis due to the constant re-accumulation of the substrate. The use of small molecule therapy to reduce the amount of or inhibit substrate accumulation in a patient can in turn reduce the administration frequency of ERT. For example, a bi-weekly enzyme replacement therapy dosing regimen can be offered an "ERT holiday" (e.g., using a SMT) so that frequent enzyme injections are not required therapy. Furthermore, treating a lysosomal storage disease with combination therapy can provide complementary therapeutic approaches. Indeed, as demonstrated in the Examples below, a combination therapy of SMT and ERT can provide significant improvements over either therapeutic platform alone. These data suggest that combination therapy using SMT and ERT can be both additive and complementary. In one embodiment, ERT may be used as a de-bulking strategy (i.e., to initiate treatment), followed by or simultaneously supplemented with SMT using a compound of the present invention. In another embodiment, a patient is first treated with SMT using a compound of the present invention, followed by or simultaneously supplemented with ERT. In other embodiments, a SMT is used to inhibit or reduce further accumulation of substrate (or re-accumulation of substrate if used after debulking with ERT) in a patient with a lysosomal storage disease, and optionally provided ERT as needed to reduce any further substrate accumulation. In one embodiment, this invention provides a method of combination therapy for treatment of a subject diagnosed as having a lysosomal storage disease comprising alternating between administration of an enzyme replacement therapy and a small molecule therapy. In another embodiment, this invention provides a method of combination therapy for treatment of a subject diagnosed as having a lysosomal storage disease comprising simultaneously administering an enzyme replacement therapy and a small molecule therapy. In the various combination therapies of the invention, it will be understood that administering small molecule therapy may occur prior to, concurrently with, or after, administration of enzyme replacement therapy. Similarly, administering enzyme replacement therapy may occur prior to, concurrently with, or after, administration of small molecule therapy.

In any of the embodiments of the invention, the lysosomal storage disease is selected from the group consisting of Gaucher (types 1, 2 and 3), Niemann-Pick, Farber, $G_{M1}$-gangliosidosis, $G_{M2}$-gangliosidoses (e.g., GM2 Activator Deficiency, Tay-Sachs and Sandhoff), Krabbe, Hurler-Scheie (MPS I), Hunter (MPS II), Sanfilippo (MPS III) Type A, Sanfilippo (MPS III) Type B, Sanfilippo (MPS III) Type C, Sanfilippo (MPS III) Type D, Marquio (MPS IV) Type A, Marquio (MPS IV) Type B, Maroteaux-Lamy (MPS VI), Sly (MPS VII), mucosulfatidosis, sialidoses, mucolipidosis II, mucolipidosis III, mucolipidosis IV, Fabry, Schindler, Pompe, sialic acid storage disease, fucosidosis, mannosidosis, aspartylglucosaminuria, Wolman, and neuronal ceroid lipofucsinoses.

Further, the ERT provides an effective amount of at least one of the following enzymes; glucocerebrosidase, sphingomyelinase, ceramidase, $G_{M1}$-ganglioside-beta-galactosidase, hexosaminidase A, hexosaminidase B, beta-galactocerebrosidase, alpha-L-iduronidase, iduronate sulfatase, heparan-N-sulfatase, N-acetyl-alpha-glucosaminidase, acetyl CoA:alpha-glucosaminide acetyl-transferase, N-acetyl-alpha-glucosamine-6-sulfatase, galactosamine-6-sulfatase, beta-galactosidase, galactosamine-4-sulfatase (arylsulfatase B), beta-glucuronidase, arylsulfatase A, arylsulfatase C, alpha-neuraminidase, N-acetyl-glucosamine-1-phosphate transferase, alpha-galactosidase A, alpha-N-acetylgalactosaminidase, alpha-glucosidase, alpha-fucosidase, alpha-mannosidase, aspartylglucosamine amidase, acid lipase, palmitoyl-protein thioesterase (CLN-1), PPT1, TPP1, CLN3, CLN5, CLN6, CLN8, NPC1 or NPC2.

In accordance with the invention, the SMT and/or ERT produce a diminution in at least one of the following stored materials; glucocerebroside, sphingomyelin, ceramide, $G_{M1}$-ganglioside, $G_{M2}$-ganglioside, globoside, galactosylceramide, dermatan sulfate, heparan sulfate, keratan sulfate, sulfatides, mucopolysaccharides, sialyloligosaccharides, glycoproteins, sialyloligosaccharides, glycolipids, globotriaosylceramide, O-linked glycopeptides, glycogen, free sialic acid, fucoglycolipids, fucosyloligosaccharides, mannosyloligosaccharides, aspartylglucosamine, cholesteryl esters, triglycerides, granular osmophilic deposits—Saposins A and D, ATP synthase subunit c, NPC1 or NPC2.

Figure 2A:
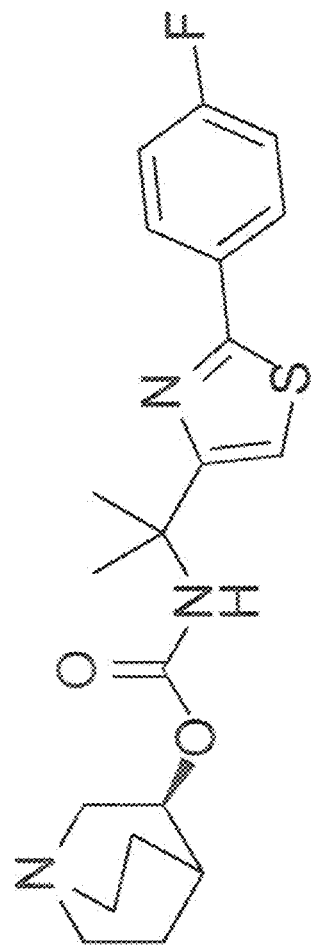
FIG. 2A Chemical structure of (S)-Quinuclidin-3-yl (2-(2-(4-fluorophenyl)thiazol-4-yl)propan-2-yl)carbamate FIG. 2B Chemical structure of Quinuclidin-3-yl (2-(4'-fluoro-[1,1'-biphenyl]-3-yl)propan-2-yl)carbamate FIG. 3
Gb3 concentration in kidney (A) and heart (B) from 12 month old Fabry mice treated with 300 mg/kg/day (1R,2R)-Octanoic acid[2-(2',3'-dihydro-benzo[1,4]dioxin-6'-yl)-2-hydroxy-1-pyrrolidin-1-ylmethyl-ethyl]-amide-L-tartaric acid salt ("GZ 638") or 60 mg/kg/day (S)-Quinuclidin-3-yl (2-(2-(4-fluorophenyl)thiazol-4-yl)propan-2-yl)carbamate (S)-2-hydroxysuccinate salt ("GZ 452").
Figure 2B:
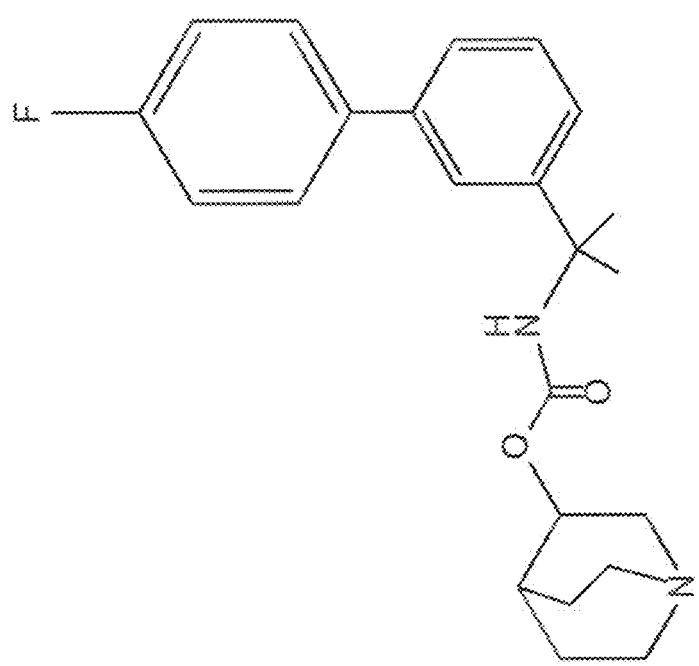

In certain embodiments of the invention, the small molecule therapy comprises administering to the subject an effective amount of (S)-Quinuclidin-3-yl (2-(2-(4-fluorophenyl)thiazol-4-yl)propan-2-yl)carbamate (see FIG. 2A). In other embodiments, the small molecule therapy comprises administering to the subject an effective amount of Quinuclidin-3-yl (2-(4'-fluoro-[1,1'-biphenyl]-3-yl)propan-2-yl)carbamate (see FIG. 2B). The small molecule therapy may include administering to a subject one or more compounds. In certain embodiments, at least one of the compounds is a compound of the present invention, such as those shown in FIGS. 2A and/or 2B.

Enzyme replacement therapy can provoke unwanted immune responses. Accordingly, immunosuppressant agents may be used together with an enzyme replacement therapy component of a combination therapy of the invention. Such agents may also be used with a small molecule therapy component, but the need for intervention here is generally less likely. Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000. Scand. J. Immunol. 51, 224-230; Ideguchi et al., 2000, Neuroscience 95, 217-226; Potter et. al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352: Ito et al., 2000, J. Immunol. 164, 1230-1235).

Any combination of immunosuppressant agents known to the skilled artisan can be used together with a combination therapy of the invention. One immunosuppressant agent combination of particular utility is tacrolimus (FK506) plus sirolimus (rapamycin) plus daclizumab (anti-IL2 receptor .alpha.-subunit antibody). This combination is proven effective as an alternative to steroids and cyclosporine, and when specifically targeting the liver. Moreover, this combination has recently been shown to permit successful pancreatic islet cell transplants. See Denise Grady, The New York Times, Saturday, May 27, 2000, pages A1 and A11. See also A. M. Shapiro et al., Jul. 27, 2000, "Islet Transplantation In Seven Patients With Type 1 Diabetes Mellitus Using A Glucocorticoid-Free Immunosuppressive Regimen", N. Engl. J. Med. 343, 230-238; Ryan et al., 2001, Diabetes 50, 710-719. Plasmaphoresis by any method known in the art may also be used to remove or deplete antibodies that may develop against various components of a combination therapy.

Immune status indicators of use with the invention include but are not limited to antibodies and any of the cytokines known to the skilled artisan, e.g., the interleukins, CSFs and interferons (see generally, Leonard et al., 2000, J. Allergy Clin. Immunol. 105, 877-888, Oberholzer et al., 2000, Crit. Care Med. 28 (4 Suppl.), N3-N12; Rubinstein et al., 1998, Cytokine Growth Factor Rev. 9, 175-181). For example, antibodies specifically immunoreactive with the replacement enzyme can be monitored to determine immune status of the subject. Among the two dozen or so interleukins known, particularly preferred immune status indicators are IL-1.alpha., IL-2, IL-4, IL-8 and IL-10. Among the colony stimulating factors (CSFs), particularly preferred immune status indicators are G-CSF, GM-CSF and M-CSF. Among the interferons, one or more alpha, beta or gamma interferons are preferred as immune status indicators.

In the sections which follow, various components that may be used for eight specific lysosomal storage diseases are provided (i.e., Gaucher (including types 1, 2 and 3), Fabry, Niemann-Pick B, Hunter, Morquio, Maroteaux-Lamy, Pompe, and Hurler-Scheie). In subsequent sections, further enabling disclosure for enzyme replacement therapy and small molecule therapy components of a combination therapy of the invention are provided.

Gaucher

As noted above, Gaucher's disease is caused by the deficiency of the enzyme glucocerebrosidase (beta-D-glucosyl-N-acylsphingosine glucohydrolase, EC 3.2.1.45) and accumulation of glucocerebroside (glucosylceramide). For an enzyme replacement therapy component of a combination therapy of the invention for the treatment of Gaucher's disease, a number of references are available which set forth satisfactory dosage regimens and other useful information relating to treatment (see Morales, 1996, Gaucher's Disease: A Review, The Annals of Pharmacotherapy 30, 381-388; Rosenthal et al., 1995, Enzyme Replacement Therapy for Gaucher Disease: Skeletal Responses to Macrophage-targeted Glucocerebrosidase, Pediatrics 96, 629-637; Barton et al., 1991, Replacement Therapy for Inherited Enzyme Deficiency-Macrophage-targeted Glucocerebrosidase for Gaucher's Disease, New England Journal of Medicine 324, 1464-1470; Grabowski et al., 1995, Enzyme Therapy in Type 1 Gaucher Disease: Comparative Efficacy of Mannose-terminated Glucocerebrosidase from Natural and Recombinant Sources, Annals of Internal Medicine 122, 33-39; Pastores et al., 1993, Enzyme Therapy in Gaucher Disease Type 1: Dosage Efficacy and Adverse Effects in 33 Patients treated for 6 to 24 Months, Blood 82, 408-416); and Weinreb et al., Am. J. Med.; 113(2):112-9 (2002).

In one embodiment, an ERT dosage regimen of from 2.5 units per kilogram (U/kg) three times a week to 60 U/kg once every two weeks is provided, where the enzyme is administered by intravenous infusion over 1-2 hours. A unit of glucocerebrosidase is defined as the amount of enzyme that catalyzes the hydrolysis of one micromole of the synthetic substrate para-nitrophenyl-p-D-glucopyranoside per minute at 37° C. In another embodiment, a dosage regimen of from 1 U/kg three times a week to 120 U/kg once every two weeks is provided. In yet another embodiment, a dosage regimen of from 0.25 U/kg daily or three times a week to 600 U/kg once every two to six weeks is provided.

Since 1991, alglucerase (Ceredase®) has been available from Genzyme Corporation. Alglucerase is a placentally-derived modified form of glucocerebrosidase. In 1994, imiglucerase (Cerezyme®) also became available from Genzyme Corporation. Imiglucerase is a modified form of glucocerebrosidase derived from expression of recombinant DNA in a mammalian cell culture system (Chinese hamster ovary cells). Imiglucerase is a monomeric glycoprotein of 497 amino acids containing four N-linked glycosylation sites. Imiglucerase has the advantages of a theoretically unlimited supply and a reduced chance of biological contaminants relative to placentally-derived aglucerase. These enzymes are modified at their glycosylation sites to expose mannose residues, a maneuver which improves lysosomal targeting via the mannose-6-phosphate receptor. Imiglucerase differs from placental glucocerebrosidase by one amino acid at position 495 where histidine is substituted for arginine. Several dosage regimens of these products are known to be effective (see Morales, 1996, Id.; Rosenthal et al., 1995, Id.; Barton et al., 1991, Id.; Grabowski et al., 1995, Id.; Pastores et al., 1993, Id.). For example, a dosage regimen of 60 U/kg once every two weeks is of clinical benefit in subjects with moderate to severe disease. The references cited above and the package inserts for these products should be consulted by the skilled practitioner for additional dosage regimen and administration information. See also U.S. Pat. Nos. 5,236,838 and 5,549,892 assigned to Genzyme Corporation.

As noted above, Gaucher Disease results from a deficiency of the lysosomal enzyme glucocerebrosidase (GC). In the most common phenotype of Gaucher disease (type 1), pathology is limited to the reticuloendothelial and skeletal systems and there are no neuropathic symptoms. See Barranger, Glucosylceramide lipidosis: Gaucher disease. In: Scriver C R B A, Sly W S, Valle D, editor. The Metabolic Basis of Inherited Disease. New York: McGraw-Hill. pp. 3635-3668 (2001). In neuropathic Gaucher disease (nGD), subdivided into type 2 and type 3 Gaucher disease, the deficiency of glucocerebrosidase (GC) causes glucosylceramide (GluCer; GL-1) and glucosylsphingosine (GluSph) to accumulate in the brain, leading to neurologic impairment. Type 2 Gaucher disease is characterized by early onset, rapid progression, extensive pathology in the viscera and central nervous system, and death usually by 2 years of age. Type 3 Gaucher disease, also known as subacute nGD, is an intermediate phenotype with varying age of onset and different degrees of severity and rates of progression. Goker-Alpan et al., The Journal of Pediatrics 143: 273-276 (2003). A recent development has produced the K14 lnl/lnl mouse model of type 2 Gaucher disease (hereinafter, the "K14 mouse"); this mouse model closely recapitulates the human disease showing ataxia, seizures, spasticity and a reduced median lifespan of only 14 days. Enquist et al., PNAS 104: 17483-17488 (2007).

As in patients with nGD, several mouse models of the disease have increased levels of GluCer and GluSph in the brain due to the deficiency in GC activity. Liu et al., PNAS 95: 2503-2508 (1998) and Nilsson, J. Neurochem 39: 709-718 (1982). The "K14" mice display a neuropathic phenotype that shares many pathologic features with type 2 Gaucher disease, such as neurodegeneration, astrogliosis, microglial proliferation, and increased levels of GluCer and GluSph in specific brain regions. Enquist et al. (2007).

Clinical management of patients affected by nGD poses a challenge for treating physicians both because of the severity of type 2 disease and the inability of the current therapies to cross the blood brain barrier (BBB). Current treatment of non-nGD relies on the intravenous delivery of recombinant human glucocerebrosidase (Imiglucerase, Cerezyme™) to replace the missing enzyme or the administration of glucosylceramide synthase inhibitors to attenuate substrate (GL-1) production. However, these drugs do not cross the blood brain barrier, and thus are not expected to provide therapeutic benefit for nGD patients. Current small molecule glucosylceramide synthase inhibitors in the clinic are not likely to address the neuropathic phenotypes of nGD. An evaluation of a compound of the present invention, Quinuclidin-3-yl (2-(4'-fluoro-[1,1'-biphenyl]-3-yl)propan-2-yl)carbamate (hereinafter, "Gz161"), in the K14 mouse model of type 2 Gaucher disease demonstrated that it could indeed reduce brain GluCer and GluSph (see Examples 122-125). It also reduced brain neuropathology and extended the lifespan of this model. Moreover, a combined approach using both enzyme replacement and small molecule substrate reduction may represent a superior therapy for type 2 Gaucher disease.

Fabry

As noted previously, Fabry's disease is caused by the deficiency of the lysosomal enzyme alpha-galactosidase A. The enzymatic defect leads to systemic deposition of glycosphingolipids having terminal alpha-galactosyl moieties, predominantly globotriaosylceramide (GL3 or Gb3) and, to a lesser extent, galabiosylceramide and blood group B glycosphingolipids.

Several assays are available to monitor disease progression and to determine when to switch from one treatment modality to another. In one embodiment, an assay to determine the specific activity of alpha-galactosidase A in a tissue sample may be used. In another embodiment, an assay to determine the accumulation of Gb3 may be used. In another embodiment, the practitioner may assay for deposition of glycosphingolipid substrates in body fluids and in lysosomes of vascular endothelial, perithelial and smooth muscle cells of blood vessels. Other clinical manifestations which may be useful indicators of disease management include proteinuria, or other signs of renal impairment such as red cells or lipid globules in the urine, and elevated erythrocyte sedimentation rate. One can also monitor anemia, decreased serum iron concentration, high concentration of beta-thromboglobulin, and elevated reticulocyte counts or platelet aggregation. Indeed, any approach for monitoring disease progression which is known to the skilled artisan may be used (See generally Desnick R J et al., 1995, .alpha.-Galactosidase A Deficiency: Fabry Disease, In: The Metabolic and Molecular Bases of Inherited Disease, Scriver et al., eds., McGraw-Hill, N.Y., 7.sup.th ed., pages 2741-2784). A preferred surrogate marker is pain for monitoring Fabry disease management. Other preferred methods include the measurement of total clearance of the enzyme and/or substrate from a bodily fluid or biopsy specimen. A preferred dosage regimen for enzyme replacement therapy in Fabry disease is 1-10 mg/kg i.v. every other day. A dosage regimen from 0.1 to 100 mg/kg i.v. at a frequency of from every other day to once weekly or every two weeks can be used.

Niemann-Pick B

As previously noted, Niemann-Pick B disease is caused by reduced activity of the lysosomal enzyme acid sphingomyelinase and accumulation of membrane lipid, primarily sphingomyelin. An effective dosage of replacement acid sphingomyelinase to be delivered may range from about 0.01 mg/kg to about 10 mg/kg body weight at a frequency of from every other day to weekly, once every two weeks, or once every two months. In other embodiments an effective dosage may range from about 0.03 mg/kg to about 1 mg/kg; from about 0.03 mg/kg to about 0.1 mg/kg; and/or from about 0.3 mg/kg to about 0.6 mg/kg. In a particular embodiment, a patient is administering acid sphingomyelinase in an escalating dose regimen at the following sequential doses: 0.1 mg/kg; 0.3 mg/kg; 0.6 mg/kg; and 1.0 mg/kg, wherein each dose of acid sphingomyelinase is administered at least twice, and each dose is administered at two week intervals, and wherein the patient is monitored for toxic side effects before elevating the dose to the next level (See U.S. Patent Application Publication No. 2011/0052559.

Hurler-Scheie (MPS I)

Hurler, Scheie, and Hurler-Scheie disease, also known as MPS I, are caused by inactivation of alpha-iduronidase and accumulation of dermatan sulfate and heparan sulfate. Several assays are available to monitor MPS I disease progression. For example, alpha-iduronidase enzyme activity can be monitored in tissue biopsy specimens or cultured cells obtained from peripheral blood. In addition, a convenient measure of disease progression in MPS I and other mucopolysaccharidoses is the urinary excretion of the glycosaminoglycans dermatan sulfate and heparan sulfate (see Neufeld et al., 1995, Id.). In a particular embodiment, alpha-iduronidase enzyme is administered once weekly as an intravenous infusion at a dosage of 0.58 mg/kg of body weight.

Hunter (MPS II)

Hunter's disease (a.k.a. MPS II) is caused by inactivation of iduronate sulfatase and accumulation of dermatan sulfate and heparan sulfate. Hunter's disease presents clinically in severe and mild forms. A dosage regimen of therapeutic enzyme from 1.5 mg/kg every two weeks to 50 mg/kg every week is preferred.

Morquio (MPS IV)

Morquio's syndrome (a.k.a. MPS IV) results from accumulation of keratan sulfate due to inactivation of either of two enzymes. In MPS IVA the inactivated enzyme is galactosamine-6-sulfatase and in MPS IVB the inactivated enzyme is beta-galactosidase. A dosage regimen of therapeutic enzyme from 1.5 mg/kg every two weeks to 50 mg/kg every week is preferred.

Maroteaux-Lamy (MPS VI)

Maroteaux-Lamy syndrome (a.k.a. MPS VI) is caused by inactivation of alactosamine-4-sulfatase (arylsulfatase B) and accumulation of dermatan sulfate. A dosage regimen of from 1.5 mg/kg every two weeks to 50 mg/kg every week is a preferred range of effective therapeutic enzyme provided by ERT. Optimally, the dosage employed is less than or equal to 10 mg/kg per week. A preferred surrogate marker for MPS VI disease progression is roteoglycan levels.

Pompe

Pompe's disease is caused by inactivation of the acid alpha-glucosidase enzyme and accumulation of glycogen. The acid alpha-glucosidase gene resides on human chromosome 17 and is designated GAA. H. G. Hers first proposed the concept of inborn lysosomal disease based on his studies of this disease, which he referred to as type II glycogen storage disease (GSD II) and which is now also termed acid maltase deficiency (AMD) (see Hers, 1965, Gastroenterology 48, 625). In a particular embodiment, GAA is administered every 2 weeks as an intravenous infusion at a dosage of 20 mg/kg body weight.

Several assays are available to monitor Pompe disease progression. Any assay known to the skilled artisan may be used. For example, one can assay for intra-lysosomal accumulation of glycogen granules, particularly in myocardium, liver and skeletal muscle fibers obtained from biopsy. Alpha-glucosidase enzyme activity can also be monitored in biopsy specimens or cultured cells obtained from peripheral blood. Serum elevation of creatine kinase (CK) can be monitored as an indication of disease progression. Serum CK can be elevated up to ten-fold in infantile-onset patients and is usually elevated to a lesser degree in adult-onset patients. See Hirschhorn R, 1995, Glycogen Storage Disease Type II: Acid alpha-Glucosidase (Acid Maltase) Deficiency, In: The Metabolic and Molecular Bases of Inherited Disease, Scriver et al., eds., McGraw-Hill, N.Y., 7.sup.th ed., pages 2443-2464.

Enzyme Replacement Therapy

The following sections set forth specific disclosure and alternative embodiments available for the enzyme replacement therapy component of a combination therapy of the invention. Generally, dosage regimens for an enzyme replacement therapy component of a combination therapy of the invention are generally determined by the skilled clinician. Several examples of dosage regimens for the treatment of Gaucher's disease with glucocerebrosidase are provided above. The general principles for determining a dosage regimen for any given ERT component of a combination therapy of the invention for the treatment of any LSD will be apparent to the skilled artisan from publically available information, such as, for example, a review of the specific references cited in the sections for each specific LSD. An ERT may be administered to a patient by intravenous infusion. Intracerebroventricular and/or intrathecal infusion may be used (e.g., in addition to intravenous infusion) to administer ERT to a patient diagnosed with a lysosomal storage disease having CNS manifestations.

Any method known in the art may be used for the manufacture of the enzymes to be used in an enzyme replacement therapy component of a combination therapy of the invention. Many such methods are known and include but are not limited to the Gene Activation technology developed by Shire plc (see U.S. Pat. Nos. 5,968,502 and 5,272,071).

Small Molecule Therapy

The following section also sets forth specific disclosures and alternative embodiments available for the small molecule therapy component of a combination therapy of the invention. Dosage regimens for a small molecule therapy component of a combination therapy of the invention are generally determined by the skilled clinician and are expected to vary significantly depending on the particular storage disease being treated and the clinical status of the particular affected individual. The general principles for determining a dosage regimen for a given SMT component of any combination therapy of the invention for the treatment of any storage disease are well known to the skilled artisan. Guidance for dosage regimens can be obtained from any of the many well known references in the art on this topic. Further guidance is available, inter alia, from a review of the specific references cited herein.

Generally, compounds of the present invention, such as, for example, (S)-Quinuclidin-3-yl (2-(2-(4-fluorophenyl)thiazol-4-yl)propan-2-yl)carbamate and Quinuclidin-3-yl (2-(4'-fluoro-[1,1'-biphenyl]-3-yl)propan-2-yl)carbamate may be used in the combination therapies of the invention for treatment of virtually any storage disease resulting from a lesion in the glycosphingolipid pathway (e.g. Gaucher, Fabry. $G_{M1}$-gangliosidosis and $G_{M2}$-gangliosidoses (e.g., GM2 Activator Deficiency, Tay-Sachs and Sandhoff)). Likewise, aminoglycosides (e.g. gentamicin, G418) may be used in the combination therapies of the invention for any storage disease individual having a premature stop-codon mutation (i.e., nonsense mutation). Such mutations are particularly prevalent in Hurler syndrome. A small molecule therapy component of a combination therapy of the invention is particularly preferred where there is a central nervous system manifestation to the storage disease being treated (e.g., Sandhoff. Tay-Sachs, Niemann-Pick Type A, and Gaucher types 2 and 3), since small molecules can generally cross the blood-brain barrier with ease when compared to other therapies.

Preferred dosages of substrate inhibitors used in a combination therapy of the invention are easily determined by the skilled artisan. In certain embodiments, such dosages may range from about 0.5 mg/kg to about 300 mg/kg, preferably from about 5 mg/kg to about 60 mg/kg (e.g., 5 mg/kg, 10 mg/kg, 15, mg/kg, 20 mg/kg, 25 mg/kg, 30 mg/kg, 35 mg/kg, 40 mg/kg, 45 mg/kg, 50 mg/kg, 55 mg/kg and 60 mg/kg) by intraperitoneal, oral or equivalent administration from one to five times daily. Such dosages may range from about 5 mg/kg to about 5 g/kg, preferably from about 10 mg/kg to about 1 g/kg by oral, intraperitoneal or equivalent administration from one to five times daily. In one embodiment, doses range from about 10 mg/day to about 500 mg/day (e.g., 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 220 mg/day, 230 mg/day, 240 mg/day, 250 mg/day, 260 mg/day, 270 mg/day, 280 mg/day, 290 mg/day, 300 mg/day). A particularly preferred oral dose range is from about 50 mg to about 100 mg, wherein the dose is administered twice daily. A particular oral dose range for a compound of the present invention is from about 5 mg/kg/day to about 600 mg/kg/day. In a particular oral dose range for a compound of the present invention is from about 1 mg/kg/day to about 100 mg/kg/day, e.g., 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day, 50 mg/kg/day, 55 mg/kg/day or 60 mg/kg/day, 65 mg/kg/day, 70 mg/kg/day, 75 mg/kg/day, 80 mg/kg/day, 85 mg/kg/day, 90 mg/kg/day, 95 mg/kg/day or 100 mg/kg/day.

A rotating combination of therapeutic platforms (i.e., enzyme replacement and small molecule therapy) is preferred. However, subjects may also be treated by overlapping both approaches as needed, as determined by the skilled clinician. Examples of treatment schedules may include but are not limited to: (1) SMT followed by ERT; (2) ERT followed by SMT; and (3) ERT and SMT provided at about the same time. As noted previously, temporal overlap of therapeutic platforms may also be performed, as needed, depending on the clinical course of a given storage disease in a given subject.

Treatment intervals for various combination therapies can vary widely and may generally be different among different storage diseases and different individuals depending on how aggressively storage products are accumulated. For example, Fabry storage product accumulation may be slow compared to rapid storage product accumulation in Pompe. Titration of a particular storage disease in a particular individual is carried out by the skilled artisan by monitoring the clinical signs of disease progression and treatment success.

The various macromolecules that accumulate in lysosomal storage diseases are not uniformly distributed, but instead are deposited in certain preferred anatomic sites for each disease. However, an exogenously supplied enzyme is generally taken up by cells of the reticuloendothelial system and sorted to the lysosomal compartment where it acts to hydrolyze the accumulated substrate. Moreover, cellular uptake of therapeutic enzyme can be augmented by certain maneuvers to increase lysosomal targeting (see e.g. U.S. Pat. No. 5,549,892 by Friedman et al., assigned to Genzyme Corporation, which describes recombinant glucocerebrosidase having improved pharmacokinetics by virtue of remodeled oligosaccharide side chains recognized by cell surface mannose receptors which are endocytosed and transported to lysosomes).

Figure 6B:
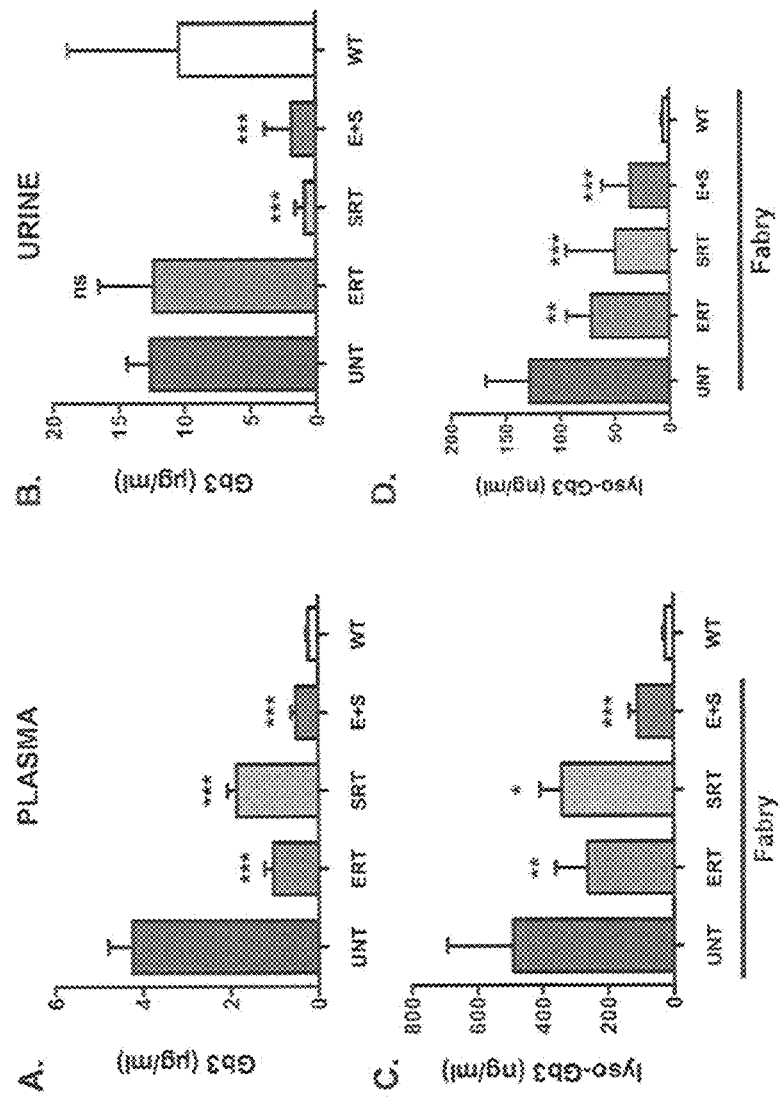
FIG. 6B
Plasma (A&C) and urine (B&D) Gb3 (A&C) and lyso-Gb3 (C&D) concentrations from 5 month old Fabry mice treated with alpha-galactosidase A alone (ERT), GZ 452 alone (SRT) or a combination of the two (E+S) for 2 months.

Some treatment modalities target some affected organs better than others. In Fabry, for example, if ERT does not reach the kidney well enough for a satisfactory clinical outcome, SMT can be used to reduce the substrate levels in the kidney. As demonstrated in Example 112 and FIG. 6B, SMT effectively reduced Gb3 levels (i.e., the substrate accumulated in Fabry patients) in the urine of a Fabry mouse model to a greater extent than ERT. The kidneys are believed to be the major source of urine Gb3. In contrast, FIG. 6B shows ERT effectively reduced the Gb3 levels in the plasma to a greater extent than SMT. These results demonstrate that a combination therapy of ERT and SMT provides a complementary therapeutic strategy that takes advantage of the strengths and addresses the weaknesses associated with each therapy employed alone. SMT is able to cross the BBB, providing a powerful approach, when combined with ERT, for treating LSDs having CNS manifestations, such as Niemann Pick Type A and Neuropathic Gaucher disease (nGD). Moreover, substrate reduction by SMT combined with enzyme replacement address the storage problem at separate and distinct intervention points which may enhance clinical outcome.

It will be understood that reference to simultaneous or concurrent administration of two or more therapies does not require that they be administered at the same time, just that they be acting in the subject at the same time.

Example 1 quinuclidin-3-yl 1-phenylcyclobutylcarbamate

Using general procedure A, 1-phenylcyclobutanamine hydrochloride (100 mg, 0.540 mmol) and quinuclidin-3-ol (103 mg, 0.810 mmol) gave quinuclidin-3-yl 1-phenylcyclobutylcarbamate (76 mg, 47%) as a white solid. $^1$H NMR (400 MHz, CDCl$_3$) δ 7.43 (d, J=7.9 Hz, 2H), 7.34 (t, J=7.7 Hz, 2H), 7.23 (t, J=7.3 Hz, 1H), 5.75-5.25 (m, 1H), 4.60 (br s, 1H), 3.25-2.22 (m, 9H), 2.16-2.03 (m, 1H), 2.02-0.94 (m, 6H), 0.88 (t, J=6.8 Hz, 1H) ppm. $^{13}$C NMR (100 MHz, CDCl$_3$) δ 158.1, 128.5, 126.9, 125.6, 71.4, 59.4, 55.7, 47.5, 46.6, 34.0, 31.8, 29.9, 25.5, 24.7, 22.9, 19.7, 15.3, 14.4 ppm. Purity: >99.9% UPLCMS (210 nm); retention time 0.62 min; (M+1) 331.

Example 2 quinuclidin-3-yl 2-(benzo[d][1,3]dioxol-5-yl)propan-2-ylcarbamate

Using general procedure B, benzo[d][1,3]dioxole-5-carbonitrile (1.00 g, 6.81 mmol) was converted to 2-(benzo[d][1,3]dioxol-5-yl)propan-2-amine hydrochloride (692 mg, 47%).

Using general procedure A, the above ammonium chloride intermediate (150 mg, 0.695 mmol) and quinuclidin-3-ol gave quinuclidin-3-yl 2-(benzo[d][1,3]dioxol-5-yl)propan-2-ylcarbamate (125 mg, 54%) as a white solid. $^1$H NMR (400 MHz, CDCl$_3$) δ 6.91 (dd, J=1.9 Hz, 1H), 6.87 (dd, J=1.9, 8.2 Hz, 1H), 6.75 (d, J=8.2 Hz, 1H), 5.93 (s, 2H), 5.12 (s, 1H), 4.69-4.66 (m, 1H), 3.26-2.11 (m, 7H), 2.03-1.07 (m, 4H), 1.63 (s, 6H) ppm. $^{13}$C NMR (100 MHz, CDCl$_3$) δ 156.7, 147.9, 118.0, 108.1, 106.1, 101.2, 71.2, 55.9, 55.3, 47.6, 46.7, 29.9, 29.7, 25.6, 24.8, 19.8 ppm. Purity: 97.5% UPLCMS (210 nm); retention time 0.65 min; (M+1) 333.

Example 3 quinuclidin-3-yl 2-(naphthalen-1-yl)propan-2-ylcarbamate

Using general procedure A, 2-(naphthalen-1-yl)propan-2-amine hydrochloride (100 mg, 0.450 mmol) and quinuclidin-3-ol gave quinuclidin-3-yl 2-(naphthalen-1-yl)propan-2-ylcarbamate (115 mg, 59%) as a white solid. $^1$H NMR (400 MHz, CDCl$_3$) δ 8.79-8.46 (m, 1H), 7.99-7.72 (m, 2H), 7.69-7.36 (m, 4H), 5.86-5.37 (m, 1H), 4.72-4.34 (m, 1H), 3.25-2.20 (m, 6H), 2.16-0.41 (m, 5H), 1.93 (s, 6H) ppm. $^{13}$C NMR (100 MHz, CDCl$_3$) δ 154.6, 135.2, 130.7, 129.7, 128.8, 125.9, 125.3, 123.9, 72.2, 71.1, 56.5, 55.7, 47.6, 46.6, 31.8, 31.2, 25.5, 24.8, 22.9, 19.7, 14.4 ppm. Purity: 100% UPLCMS (210 nm); retention time 0.80 min: (M+1) 339.

Preparation I

Example 4

(R)-quinuclidin-3-yl 2-(3-(prop-1-en-2-yl)phenyl) propan-2-ylcarbamate

To a solution of (R)-quinuclidin-3-ol (194 mg, 1.52 mmol) in THF (5 mL) at room temperature was added NaH [60%, oil] (64 mg, 1.6 mmol). The reaction mixture was stirred for 15 min and 1-(2-isocyanatopropan-2-yl)-3-(prop-1-en-2-yl) benzene (302 uL, 1.53 mmol) was added dropwise. The reaction was stirred for a period of 30 min and quenched with brine. The solution was extracted with EtOAc and the organic layer was dried over Na$_2$SO$_4$ and concentrated. The crude material was purified on a combiflash (SiO$_2$ cartridge, CHCl$_3$ and 2N NH$_3$ in MeOH) to afford the corresponding carbamate (475 mg, 95%) as a clear oil. $^1$H NMR (400 MHz, CDCl$_3$) δ 7.49 (s, 1H), 7.31 (br s, 3H), 5.33 (s, 1H), 5.17 (s, 1H), 5.08 (s, 1H), 4.77-4.61 (m, 1H), 3.33-2.27 (m, 5H), 2.14 (s, 3H), 2.25-0.75 (m, 6H), 1.68 (br s, 6H) ppm. $^{13}$C NMR (100 MHz, CDCl$_3$) δ 154.7, 147.2, 143.7, 141.6, 128.5, 124.2, 122.1, 112.8, 70.9, 55.7, 55.5, 47.5, 46.6, 32.2, 31.5, 29.9, 29.6, 25.5, 24.6, 22.9, 22.2, 19.6 ppm. Purity: 100% UPLCMS (210 nm); retention time 0.84 min; (M+1) 329.2. Anal. Calcd. for C$_{20}$H$_{28}$N$_2$O$_2$.0.06 (CHCl$_3$): C, 71.59; H, 8.40; N, 8.58. Found: C, 71.51; H, 9.05; N, 8.60.

Preparation J

Example 5 quinuclidin-3-yl 2-(3-isopropoxyphenyl)propan-2-ylcarbamate

A solution of 3-cyanophenol (1.00 g, 8.39 mmol), 2-iodopropane (839 uL, 8.39 mmol) and cesium carbonate (2.73 g, 8.39 mmol) in 1:1 CH$_2$Cl$_2$/CH$_3$CN (16 mL) was stirred at reflux for 18 h. The reaction mixture was cooled to room temperature and filtered through Celite. The filtrate was concentrated and the crude material purified on a combiflash (SiO$_2$ cartridge, CH$_2$Cl$_2$) to afford the corresponding ether (763 mg, 57%) as a white solid.

Using general procedure B, 3-isopropoxybenzonitrile (763 mg, 4.24 mmol) was converted to the corresponding 2-(3-isopropoxyphenyl)propan-2-amine (362 mg, 45%) as a clear oil.

Using general procedure A, the above amine (100 mg, 0.520 mmol) and quinuclidin-3-ol gave quinuclidin-3-yl 2-(3-isopropoxyphenyl)propan-2-ylcarbamate (110 mg, 61%) as a white solid. $^1$H NMR (400 MHz, CDCl$_3$) δ 7.17 (t, J=7.9 Hz, 1H), 6.92 (d, J=7.8 Hz, 1H), 6.89 (t, J=2.1 Hz, 1H), 6.70 (d, J=8.1 Hz, 1H), 5.38-5.13 (m, 1H), 4.58 (br s, 1H), 4.49 (hept, J=6.1 Hz, 1H), 3.31-2.04 (m, 6H), 2.00-0.79 (m, 5H) 1.60 (br s, 6H), 1.28 (d, J=6.1 Hz, 6H) ppm. $^{13}$C NMR (100 MHz, CDCl$_3$) δ 158.1, 129.5, 117.2, 113.6, 71.1, 69.9, 55.8, 55.4, 47.6, 46.6, 29.4, 25.6, 24.8, 22.3, 19.7 ppm. Purity: >99.9% UPLCMS (210 nm); retention time 0.83 min; (M+1) 347.

Example 6 quinuclidin-3-yl 2-(3-bromo-2-fluorophenyl)propan-2-ylcarbamate

Using general procedure A, 2-(3-bromo-2-fluorophenyl)propan-2-amine (1.0 g, 4.3 mmol) and quinuclidin-3-ol gave quinuclidin-3-yl 2-(3-bromo-2-fluorophenyl)propan-2-ylcarbamate (957 mg, 58%) as a white solid. $^1$H NMR (400 MHz, CDCl$_3$) δ 7.45 (ddd, J=1.6, 6.3, 7.9 Hz, 1H), 7.31 (td, J=1.6, 7.7 Hz, 1H), 6.99 (td, J=1.0, 8.0 Hz, 1H), 5.31-5.15 (br s, 1H), 4.59 (br s, 1H), 3.25-2.19 (m, 6H), 2.06-0.81 (m, 5H), 1.73 (s, 3H), 1.71 (s, 3H) ppm. $^{13}$C NMR (100 MHz, CDCl$_3$) δ 158.1, 155.6, 132.5, 127.1, 127.0, 124.8, 124.8, 110.6, 110.4, 71.5, 55.7, 54.2, 47.5, 46.7, 29.9, 28.4, 25.5, 24.8, 19.7 ppm. Purity: >99.9% UPLCMS (210 nm); retention time 0.79 min; (M+1) 385.

Example 7

(+/−) quinuclidin-3-yl (1R,2S)-2-phenylcyclopropylcarbamate

Using general procedure A, (+/−) ((1S,2R)-2-isocyanato-cyclopropyl)benzene (117 uL, 0.780 mmol) and quinuclidin-3-ol gave (+/−) quinuclidin-3-yl (1R,2S)-2-phenylcyclopropylcarbamate (63 mg, 28%) as a white solid. $^1$H NMR (400 MHz, CDCl$_3$) δ 7.30-7.05 (m, 5H), 5.43 (br s, 1H), 4.77 (br s, 1H), 3.23 (dd, J=9.0, 14.0 Hz, 1H), 2.97-2.65 (m, 6H), 2.15-1.12 (m, 8H) ppm. $^{13}$C NMR (100 MHz, CDCl$_3$) δ 157.1, 140.7, 140.2, 128.5, 126.8, 126.3, 71.5, 55.7, 47.5, 46.6, 32.7, 25.6, 25.2, 24.5, 19.5, 16.2 ppm. Purity: >99.9% UPLCMS (210 nm); retention time 0.67 min; (M+1) 287.

Example 8 quinuclidin-3-yl 1-phenylcyclohexylcarbamate

Using general procedure A, 1-phenylcyclohexanamine (36 mg, 0.21 mmol) and quinuclidin-3-ol gave quinuclidin-3-yl 1-phenylcyclohexylcarbamate (40 mg, 58%) as a white solid. $^1$H NMR (400 MHz, CDCl$_3$) δ 7.41 (d, J=7.4 Hz, 2H), 7.32 (t, J=7.7 Hz, 2H), 7.21 (t, J=7.3 Hz, 1H), 5.19-4.98 (br s, 1H), 4.70-4.56 (s, 1H), 3.34-0.83 (m, 21H) ppm. $^{13}$C NMR (100 MHz, CDCl$_3$) δ 158.4, 128.3, 126.5, 124.9, 57.2, 46.3, 36.1, 25.4, 24.2, 22.0, 19.2, 15.2 ppm. Purity: >99.9% UPLCMS (210 nm); retention time 0.84 min; (M+1) 329.

Preparation K

Example 9

(R)-1-(2-(3-(prop-1-en-2-yl)phenyl)propan-2-yl)-3-(quinuclidin-3-yl)urea

To a solution of (R)-quinuclidin-3-amine dihydrochloride (120 mg, 0.603 mmol) and 1-(2-isocyanatopropan-2-yl)-3-(prop-1-en-2-yl)benzene (119 mg, 0.597 mmol) in THF (3 mL) was added triethylamine (168 uL, 1.21 mmol). The reaction mixture was stirred at room temperature for 18 h and then quenched with brine. The mixture was extracted with CHCl$_3$ and the organic layer was dried (Na$_2$SO$_4$) and concentrated. The crude material was purified on a combiflash (SiO$_2$ cartridge, CHCl$_3$ and 2N NH$_3$ in MeOH) to afford the corresponding urea (163 mg, 50%) as a white solid. $^1$H NMR (400 MHz, CDCl$_3$) δ 7.62 (t, J=1.6 Hz, 1H), 7.44 (dt, J=1.9, 7.0 Hz, 1H), 7.41-7.33 (m, 2H), 5.35 (br s, 1H), 5.11 (p, J=1.4 Hz, 1H), 4.84 (s, 1H), 4.21 (d, J=7.5 Hz, 1H), 3.70-3.61 (m, 1H), 3.13 (ddd, J=2.3, 9.3, 14.2 Hz, 1H), 2.71-2.54 (m, 3H), 2.30-2.22 (m, 1H), 2.15 (dd, J=0.8, 1.4, 3H), 2.05-1.96 (m, 1H), 1.65 (s, 3H), 1.64 (s, 3H), 1.65-1.60 (m, 1H) 1.54-1.45 (m, 2H), 1.22-1.12 (m, 1H), 0.95-0.80 (m, 1H) ppm. $^{13}$C NMR (400 MHz, CDCl$_3$) δ 157.4, 148.5, 143.8, 141.3, 128.4, 124.4, 123.8, 122.2, 112.6, 55.2, 53.4, 46.2, 46.1, 44.5, 30.5, 30.4, 25.0, 22.2, 17.7, 8.9 ppm. Purity: 97.5% UPLCMS (210 nm); retention time 0.83 min; (M+1) 328.

Example 10

1-(2-(naphthalen-2-yl)propan-2-yl)-3-(quinuclidin-3-yl)urea

Using general procedure B, naphthalene-2-carbonitrile (1.00 g, 6.53 mmol) was converted to the corresponding 2-(naphthalen-2-yl)propan-2-amine (294 mg, 25%) as a clear oil.

Using general procedure C, quinuclidin-3-amine (102 mg, 0.808 mmol), CDI (131 mg, 0.808 mmol) and 2-(naphthalen-2-yl)propan-2-amine (150 mg, 0.819 mmol) gave 1-(2-(naphthalen-2-yl)propan-2-yl)-3-(quinuclidin-3-yl)urea (132 mg, 49%) as a white solid. $^1$H NMR (400 MHz, CDCl$_3$) δ 7.94-7.78 (m, 4H), 7.69 (dd, J=2.0, 8.7 Hz, 1H), 7.53-7.46 (m, 2H), 4.84 (s, 1H), 4.23 (d, J=8.0 Hz, 1H), 3.68-3.54 (m, 1H), 3.07 (ddd, J=2.3, 9.3, 14.1 Hz, 1H), 2.61-2.51 (m, 2H), 2.42-2.32 (m, 1H), 1.95-1.83 (m, 2H), 1.75 (s, 3H), 1.74 (s, 3H), 1.58-1.54 (m, 1H), 1.46-1.40 (m, 2H), 1.03-0.91 (m, 1H), 0.72-0.60 (m, 1H) ppm. $^{13}$C NMR (100 MHz, CDCl$_3$) δ 157.5, 143.7, 133.4, 132.8, 129.3, 128.1, 127.8, 126.9, 126.7, 124.4, 124.0, 57.0, 55.0, 47.1, 47.1, 46.6, 30.5, 30.3, 26.0, 25.9, 20.0 ppm. Purity: >99.9% UPLCMS (210 nm); retention time 0.71 min; (M+1) 338.

Example 11

1-(2-methyl-2-(m-tolyl)propyl)-3-(3-methylquinuclidin-3-yl)urea

Using general procedure D, 2-methyl-2-(m-tolyl)propan-1-amine hydrochloride (100 mg, 0.501 mmol), triethylamine (279 uL, 2.00 mmol), triphosgene (47 mg, 0.18 mmol) and 3-methylquinuclidin-3-amine 2,2,2-trifluoroacetate (140 mg, 0.550 mmol) gave 1-(2-methyl-2-(m-tolyl)propyl)-3-(3-methylquinuclidin-3-yl)urea (41 mg, 25%) as a white solid. $^1$H NMR (400 MHz, CDCl$_3$) δ 7.23 (t, J=7.7 Hz, 1H), 7.18-7.12 (m, 2H), 7.04 (d, J=7.5 Hz, 1H), 4.12 (s, 1H), 4.08 (t, J=6.0 Hz, 1H), 3.39-3.22 (m, 2H), 2.81-2.62 (m, 6H), 2.34 (s, 3H), 1.98-1.89 (m, 1H), 1.80-1.63 (m, 2H), 1.51-1.23 (m, J=26.9 Hz, 2H), 1.37 (s, 3H), 1.30 (s, 6H) ppm. $^{13}$C NMR (100 MHz, CDCl$_3$) δ 157.9, 147.1, 138.2, 128.6, 127.1, 127.1, 123.3, 64.0, 52.2, 52.1, 46.9, 46.7, 39.2, 31.2, 27.1, 26.8, 25.4, 23.5, 22.7, 21.9. Purity: >99.9% UPLCMS (210 nm); retention time 0.79 min; (M+1) 330.

Example 12

1-(2-(3-methoxyphenyl)propan-2-yl)-3-(quinuclidin-3-yl)urea

Using general procedure C, quinuclidin-3-amine (380 mg, 3.01 mmol), CDI (489 mg, 3.01 mmol) and 2-(3-methoxyphenyl)propan-2-amine (506 mg, 3.07 mmol) gave 1-(2-(3-methoxyphenyl)propan-2-yl)-3-(quinuclidin-3-yl)urea (560 mg, 59%) as a white solid. $^1$H NMR (400 MHz, CDCl$_3$) δ 7.35-7.29 (m, 1H), 7.14-7.07 (m, 2H), 6.87-6.81 (ddd, 1H), 4.76 (s, 1H), 4.19 (d, 1H), 3.81 (s, 3H), 3.70-3.62 (m, 1H), 3.19-3.10 (m, 1H), 2.74-2.59 (m, 3H), 2.37-2.26 (m, 1H), 2.07-1.98 (dd, 1H), 1.80 (br s, 1H), 1.69-1.63 (m, 1H), 1.63 (s, 3H), 1.62 (s, 3H), 1.58-1.44 (m, 2H), 1.28-1.14 (m, 1H), 1.02-0.90 (m, 1H) ppm. $^{13}$C NMR (100 MHz, CDCl$_3$) δ 160.0, 157.5, 148.4, 129.9, 117.7, 112.0, 111.9, 56.7, 55.3, 54.6, 47.2, 46.8, 46.4, 30.1, 25.8, 20.0 ppm. Purity: >99.4% UPLCMS (210 nm); retention time 1.73 min; (M+1) 318.

Example 13 quinuclidin-3-yl 2-(3-methoxyphenyl)propan-2-ylcarbamate

Using general procedure A, 1-(3-methoxyphenyl)propan-2-amine (327 mg, 1.98 mmol) and quinuclidin-3-ol gave quinuclidin-3-yl 2-(3-methoxyphenyl)propan-2-ylcarbamate (370 mg, 59%) as a white solid. $^1$H NMR (400 MHz, CDCl$_3$) δ 7.30-7.20 (m, 1H), 7.03-6.97 (m, 1H), 6.97-6.93 (m, 1H), 6.80-6.74 (dd, 1H), 5.18-5.00 (br s, 1H), 4.67-4.57 (m, 1H), 3.80 (s, 3H), 3.30-2.12 (br m, 7H), 2.02-1.00 (m, 10H) ppm. $^{13}$C NMR (100 MHz, CDCl$_3$) δ 159.7, 154.5, 149.0, 129.3, 117.2, 111.4, 111.0, 70.9, 55.7, 55.1, 47.4, 46.5, 29.4, 25.4, 24.6, 19.6 ppm. Purity: >99.9% UPLCMS (210 nm); retention time 1.85 min; (M+1) 319.

Example 14 quinuclidin-3-yl 2-(3-methoxyphenyl)propan-2-ylcarbamate

Using general procedure A, 1-(4-methoxyphenyl)propan-2-amine hydrochloride (316 mg, 1.57 mmol) and quinuclidin-3-ol gave quinuclidin-3-yl 2-(3-methoxyphenyl)propan-2-ylcarbamate (370 mg, 59%) as a white solid. $^1$H NMR (400 MHz, CDCl$_3$) δ 7.33 (d, 2H), 6.86 (d, 2H), 5.15-5.01 (br s, 1H), 4.66-4.57 (m, 1H), 3.79 (s, 3H), 3.33-2.12 (m, 7H), 2.10-0.96 (m, 10H) ppm. $^{13}$C NMR (100 MHz, CDCl$_3$) δ 158.1, 154.5, 139.2, 125.8, 113.5, 70.7, 55.7, 55.2, 54.6, 47.2, 46.3, 31.2, 29.4, 25.3, 24.5, 19.4 ppm. Purity: >94.1% UPLCMS (210 nm); retention time 1.81 min; (M+1) 319.

Example 15 quinuclidin-3-yl 2-(4-tert-butylphenyl)propan-2-ylcarbamate

Using general procedure A, 1-(4-tert-butylphenyl)propan-2-amine (348 mg, 1.82 mmol) and quinuclidin-3-ol gave quinuclidin-3-yl 2-(4-tert-butylphenyl)propan-2-ylcarbamate (427 mg, 68%) as a white solid. $^1$H NMR (400 MHz, CDCl$_3$) δ 7.34 (s, 4H), 5.09 (br s, 1H), 4.69-4.52 (m, 1H), 3.47-2.05 (m, 7H), 3.33-2.12 (m, 7H), 2.00-0.80 (m, 20H) ppm. $^{13}$C NMR (100 MHz, CDCl$_3$) δ 156.2, 149.4, 144.5, 125.3, 124.5, 70.9, 55.8, 55.1, 47.5, 46.6, 34.4, 31.4, 29.8, 29.3, 25.5, 24.6, 19.6 ppm. Purity: >98.2% UPLCMS (210 nm); retention time 2.29 min; (M+1) 345.

Example 16 quinuclidin-3-yl 2-(4-isopropylphenyl)propan-2-ylcarbamate

Using general procedure A, 1-(4-isopropylphenyl)propan-2-amine (158 mg, 0.891 mmol) and quinuclidin-3-ol gave quinuclidin-3-yl 2-(4-isopropylphenyl)propan-2-ylcarbamate (205 mg, 70%) as a white solid. $^1$H NMR (400 MHz, CDCl$_3$) δ 7.33 (d, J=7.3 Hz, 2H), 7.19 (s, 1H), 7.17 (s, 1H), 5.09 (s, 1H) 4.69-4.51 (br s, 1H) 3.30-1.30 (m, 17H), 1.24 (s, 3H), 1.22 (s, 3H), 1.06-0.77 (m, 1H) ppm. $^{13}$C NMR (100 MHz, CDCl$_3$) δ 156.2, 147.1, 144.4, 126.4, 124.7, 70.9, 55.7, 55.0, 47.4, 46.5, 33.6, 29.8, 29.4, 25.4, 24.6, 24.0, 19.5 ppm. Purity: >98.3% UPLCMS (210 nm); retention time 2.19 min; (M+1) 331.

Example 17 quinuclidin-3-yl 2-(4-ethylphenyl)propan-2-ylcarbamate

Using general procedure A, 1-(4-ethylphenyl)propan-2-amine (230 mg, 1.41 mmol) and quinuclidin-3-ol gave quinuclidin-3-yl 2-(4-ethylphenyl)propan-2-ylcarbamate (248 mg, 56%) as a white solid. $^1$H NMR (400 MHz, CDCl$_3$) δ 7.33 (d, J=7.3 Hz, 2H), 7.19 (s, 1H), 7.17 (s, 1H), 5.09 (s, 1H) 4.69-4.51 (br s, 1H) 3.34-0.73 (m, 22H) ppm. $^{13}$C NMR (100 MHz, CDCl$_3$) δ 154.5, 144.3, 142.4, 127.8, 124.7, 71.0, 55.6, 55.1, 47.4, 46.5, 29.6, 28.3, 25.4, 24.6, 19.5, 15.8, 15.4 ppm. Purity: >99.5% UPLCMS (210 nm); retention time 2.07 min; (M+1) 317.

Example 18 quinuclidin-3-yl 2-o-tolylpropan-2-ylcarbamate

Using general procedure A, 2-o-tolylpropan-2-amine (230 mg, 1.52 mmol) and quinuclidin-3-ol gave quinuclidin-3-yl 2-o-tolylpropan-2-ylcarbamate (200 mg, 44%) as a white solid. $^1$H NMR (400 MHz, CDCl$_3$) (rotamers) δ 7.33 (s, br, 1H), 7.15-7.10 (m, 3H), 5.35-5.20 (m, 1H), 4.60 (br s, 1H), 3.20-2.60 (m, 5H), 2.5 (s, 3H), 2.15 (br s, 1H), 1.80-1.30 (m, 10H). $^{13}$C NMR (100 MHz, CDCl$_3$) (rotamers) δ 154.2, 144.5, 140.2, 133.0, 127.1, 126.2, 126.1, 72.2, 71, 56.0, 46.6, 46.7, 31.0, 29.0, 26.0, 24.7, 22.3, 19.7. Purity: >95% UPLCMS (210 nm); (M+1) 303.

Example 19 quinuclidin-3-yl 2-(2-methoxyphenyl)propan-2-ylcarbamate

Using general procedure A, 2-(2-methoxyphenyl)propan-2-amine (150 mg, 0.908 mmol) and quinuclidin-3-ol gave quinuclidin-3-yl 2-(2-methoxyphenyl)propan-2-ylcarbamate (60 mg, 21%) as a white solid. $^1$H NMR (400 MHz, CDCl$_3$) (rotamers) δ 7.3 (m, 1H), 7.2 (m, 1H), 6.9 (m, 2H), 5.4 (s, br, 1H), 4.6 (m, 1H), 3.8 (s, 1H), 3.1 (m, 1H), 2.4-2.8 (m, 5H), 1.9 (s, 1H), 1.3-1.7 (m, 10H). $^{13}$C NMR (100 MHz, CDCl$_3$) (rotamers) δ 157, 155, 140, 134, 129, 127, 121, 111, 70, 56, 55, 48, 47, 29, 26, 25, 20. Purity: >99% UPLCMS (210 nm); (M+1) 319.

Preparation L

Example 20

1-(3-cyanoquinuclidin-3-yl)-3-(2-(3-(prop-1-en-2-yl)phenyl)propan-2-yl)urea

3-Amino-3-cyanoquinuclidine was prepared as described in the literature (Fernandez, M. A.; Gonzalez, G.; Martinez, M.; Galvez, E. *Anales de la Real Academia de Farmacia* 1988, 54, 502).

To a solution of 3-amino-3-cyanoquinuclidine (100 mg, 0.661 mmol) in CH$_2$Cl$_2$ (5 mL) was added, dropwise, 3-isoprenyl-☐,☐-dimethylbenzyl isocyanate (0.13 mL, 0.66 mmol). The reaction mixture was stirred at room temperature for 18 hours, concentrated and subjected to flash chromatography over silica gel (19:1 CH$_2$Cl$_2$/7M NH$_3$(CH$_3$OH)). The title product was obtained as a white solid (155 mg, 67%). $^1$H NMR (400 MHz, CD$_3$OD) δ 7.52 (s, 1H), 7.35-7.25 (m, 3H), 5.34 (s, 1H), 5.05 (s, 1H), 2.60-3.41 (m, 6H), 2.25-2.32 (m, 1H), 2.13 (s, 3H), 1.42-2.10 (m, 4H), 1.64 (s, 6H) ppm. $^{13}$C NMR (100 MHz, CD$_3$OD) δ 157.0, 147.9, 144.0, 141.4, 128.1, 124.0, 123.4, 121.9, 121.7, 111.5, 61.0, 55.1, 50.4, 30.9, 23.3, 22.5, 21.0 19.0 ppm. Purity: >99.9% UPLCMS (210 nm); retention time 0.82 min; (M+1) 353.

Preparation M

Example 21

1-[(3S)-1-azabicyclo[2.2.2]oct-3-yl]-3-{2-[3-(prop-1-en-2-yl)phenyl]propan-2-yl}urea To a suspension of (S)-(−)-3-aminoquinculidine dihydrochloride (120 mg, 0.603 mmol) and triethylamine (168 uL, 1.21 mmol) in THF (2 mL) at room temperature was added 3-isopropenyl-☐,☐-dimethylbenzyl-isocyanate (121 mg, 0.601 mmol). The reaction mixture was stirred for 18 hr and then washed with saturated aqueous NaHCO$_3$. The organic phase was dried over Na$_2$SO$_4$ and concentrated. The crude material was purified on a combiflash (SiO$_2$ cartridge, CHCl$_3$ and 2N NH$_3$ in MeOH) to afford the title compound (29 mg, 47%) as an off-white solid. $^1$H NMR (400 MHz, CD$_3$OD) δ 7.51 (dt, J=2.5, 1.2 Hz, 1H), 7.41-7.14 (m, 3H), 5.32 (dd, J=1.6, 0.8 Hz, 1H), 5.06 (s, 1H), 3.74-3.60 (m, 1H), 3.31-3.29 (m, 2H), 3.19 (ddd, J=13.7, 9.5, 1.6 Hz, 1H), 2.88-2.50 (m, 4H), 2.37 (ddd, J=14.0, 4.9, 2.2 Hz, 1H), 2.14 (ddd, J=2.3, 1.8, 1.0 Hz, 3H), 1.81-1.63 (m, 4H), 1.62 (d, J=6.2 Hz, 6H), 1.55-1.38 (m, 1H) ppm. $^{13}$C NMR (100 MHz, CD$_3$OD) δ 158.4, 148.4, 144.0, 141.3, 128.0, 124.1, 123.3, 121.9, 111.4, 55.7, 54.7, 46.7, 46.4, 46.0, 29.6, 29.4, 28.4, 26.1, 25.1, 21.0, 19.4 ppm. Purity: >96% UPLCMS (210 nm); retention time 0.81 min; (M+1) 329.5.

Preparation N

Example 22

1-(1-azabicyclo[2.2.2]oct-3-yl)-3-{2-[3-(propan-2-yl)phenyl]propan-2-yl}urea

To a solution of 3-aminoquinuclidine (150 mg, 1.19 mmol) in THF (5 mL) was added 3-isopropenyl-☐, ☐-dimethylbenzylisocyanate. The solution was stirred at room temperature for 30 min, then concentrated onto silica gel and purified on a combiflash (SiO$_2$ cartridge, CHCl$_3$ and 2N NH$_3$ in MeOH) to afford an off-white solid (299 mg, 77%).

Using general procedure F, the above isoprenyl urea (150 mg, 1.19 mmol) and palladium hydroxide (30 mg, 20 wt. % on carbon) gave 1-(1-azabicyclo[2.2.2]oct-3-yl)-3-{2-[3-(propan-2-yl)phenyl]propan-2-yl}urea (116 mg, 77%) as an off-white solid. $^1$H NMR (400 MHz, CDCl$_3$) δ 7.38-7.28 (m, 3H), 7.16 (dt, J=6.9, 1.6 Hz, 1H), 4.93 (s, 1H), 4.26 (d, J=7.5 Hz, 1H), 3.70-3.58 (m, 1H), 3.11 (ddd, J=14.1, 9.4, 2.3 Hz, 1H), 2.90 (hept, J=6.9 Hz, 1H), 2.71-2.52 (m, 4H), 2.31-2.19 (m, 1H), 1.98 (dd, J=14.2, 2.9 Hz, 1H), 1.61 (d, J=2.0 Hz, 6H), 1.52-1.43 (m, 2H), 1.23 (d, J=6.9 Hz, 6H), 1.19-1.09 (m, 1H), 0.92-0.79 (m, 1H) ppm. $^{13}$C NMR (100 MHz, CDCl$_3$) δ 157.6, 150.1, 146.1, 129.2, 125.8, 124.1, 123.3, 57.1, 54.9, 47.4, 47.0, 46.6, 34.5, 30.7, 30.5, 26.1, 26.0, 24.3, 24.2, 20.3 ppm. Purity: 94% UPLCMS (210 nm); retention time 0.87 min; (M+1) 329.3.

Example 23

1-(1-azabicyclo[2.2.2]oct-3-yl)-3-[1-(naphthalen-1-yl)ethyl]urea

3-Aminoquinculidene dihydrochloride (150 mg, 0.753 mmol) was mixed with THF (3 mL) and triethylamine (152 mg, 1.50 mmol) before adding 1-(1-naphthyl)ethylisocyanate (149 mg, 0.752 mmol). The mixture was stirred 48 h at room temperature. The reaction solution was concentrated and purified on a combiflash (SiO$_2$ cartridge, CHCl$_3$ and 2N NH$_3$ in MeOH) to afford the title compound as an off-white solid (46 mg, 19%). $^1$H NMR (400 MHz, CDCl$_3$) δ 8.20-8.05 (m, 1H), 7.85 (dd. J=7.9, 1.5 Hz, 1H), 7.75 (d, J=8.1 Hz, 1H), 7.59-7.34 (m, 4H), 5.55 (hept, 1H), 5.35-5.19 (m, 1H), 4.84 (dd, 1H), 3.70-3.53 (m, 1H), 3.09 (ddd, 1H), 2.74-2.28 (m, 4H), 2.17 (ddd, J=1.8, 4.5, 14.1 Hz, 1H), 1.75-1.62 (m, 1H), 1.55 (dd, J=1.8, 6.8 Hz, 3H), 1.52-1.06 (m, 4H) ppm. $^{13}$C NMR (100 MHz, CDCl$_3$) δ 157.7, 140.0, 134.1, 130.9, 129.2, 128.3, 126.8, 126.7, 126.7, 126.0, 125.6, 123.2, 123.1, 122.8, 122.7, 56.9, 56.7, 47.4, 47.3, 46.7, 46.4, 26.1, 25.9, 22.7, 22.6, 20.1, 20.0 ppm. Purity: 97% UPLCMS (210 nm); retention time 0.68 min; (M+1) 324.2

Example 24

1-(1-azabicyclo[2.2.2]oct-3-yl)-3-[2-(3-bromophenyl)propan-2-yl]urea

Using general procedure C, quinuclidin-3-amine (100 mg, 0.792 mmol), CDI (128 mg, 0.789 mmol) and 2-(3-bromophenyl)propan-2-amine (170 mg, 0.791 mmol) gave the title compound as a white solid (166 mg, 75%). $^1$H NMR (400 MHz, CDCl$_3$) δ 7.50 (s, 1H), 7.30 (t, J=7.2 Hz, 2H), 7.15 (t, J=7.9 Hz, 1H), 5.54 (d, J=22.7 Hz, 1H), 5.16 (d, J=29.7 Hz, 1H), 3.60 (s, 1H), 3.14 (ddd, J=13.3, 9.4, 1.6 Hz, 1H), 2.61 (d, J=52.6 Hz, 4H), 2.18 (dd, J=14.1, 2.8 Hz, 1H), 1.66 (d, J=3.0 Hz, 2H), 1.51 (d, J=7.6 Hz, 6H), 1.28 (s, 3H) ppm. $^{13}$C NMR (100 MHz, CDCl$_3$) δ 157.1, 150.4, 130.3, 130.0, 128.6, 124.0, 123.0, 57.0, 54.6, 47.6, 47.2, 46.8, 30.5, 30.3, 26.3, 26.2, 20.2 ppm. Purity: 100% UPLCMS (210 nm); retention time 0.66 min; (M+1) 367.8.

Example 25

1-(1-azabicyclo[2.2.2]oct-3-yl)-3-[2-(biphenyl-3-yl) propan-2-yl]urea

Using general procedure E, 1-(1-azabicyclo[2.2.2]oct-3-yl)-3-[2-(3-bromophenyl)propan-2-yl]urea (111 mg, 0.301 mmol), phenylboronic acid (78.8 mg, 0.606 mmol) and tetrakis(triphenylphosphine)palladium(0) gave the title compound as an off-white solid (21 mg, 11%). $^1$H NMR (400 MHz, CDCl$_3$) δ 7.74 (s, 1H), 7.52-7.40 (m, 8H), 4.89 (s, 1H), 4.28 (d, J=7.3 Hz, 1H), 3.75-3.59 (m, 1H), 3.15 (ddd, J=1.9, 9.3, 13.9 Hz, 1H), 2.46 (m, 4H), 2.05 (dd, J=3.5, 14.0 Hz, 1H), 1.68 (d, J=4.7 Hz, 6H), 1.66-0.76 (m, 5H) ppm. $^{13}$C NMR (100 MHz, CDCl$_3$) δ 157.4, 146.9, 142.5, 141.1, 129.7, 129.1, 127.8, 127.4, 126.7, 124.8, 124.7, 57.1, 55.1, 30.7, 30.1, 26.1, 26.0, 20.2 ppm. Purity: 100% UPLCMS (210 nm); retention time 0.78 min; (M+1) 364.0.

Example 26

1-azabicyclo[2.2.2]oct-3-yl {2-[3-(propan-2-yl)phenyl]propan-2-yl}carbamate

Using general procedure F, 1-azabicyclo[2.2.2]oct-3-yl {2-[3-(prop-1-en-2-yl)phenyl]propan-2-yl}carbamate (48.8 mg, 0.146 mmol) and palladium hydroxide (30 mg, 20 wt. % on carbon) gave the title compound as an off-white solid (16 mg, 33%). $^1$H NMR (400 MHz, CDCl$_3$) δ 7.24 (d, J=5.1 Hz, 3H), 7.10 (d, 1H), 5.12 (s, 1H), 4.63 (s, 1H), 3.54-2.96 (m, 1H), 2.89 (s, 1H), 2.68 (s, 5H), 2.17-1.75 (m, 2H), 1.67 (s, 6H), 1.62-1.30 (m, 2H), 1.24 (d, J=6.9 Hz, 6H), 1.15-0.85 (m, 1H) ppm. $^{13}$C NMR (100 MHz, CDCl$_3$) δ 149.1, 128.5, 124.9, 123.1, 122.5, 55.8, 55.6, 46.6, 34.5, 25.6, 24.6, 24.3, 19.7 ppm. Purity: 94% UPLCMS (210 nm); retention time 0.89 min; (M+1) 331.1.

Example 27

1-azabicyclo[2.2.2]oct-3-yl[2-(3-bromophenyl)propan-2-yl]carbamate

Using general procedure A, 2-(3-bromophenyl)propan-2-amine hydrochloride (2.00 g, 7.89 mmol) and quinuclidin-3-ol gave the title compound as a white solid (2.23 g, 76%). $^1$H NMR (400 MHz, CDCl$_3$) δ 7.54 (s, 1H), 7.41-7.30 (m, 2H), 7.19 (t, J=7.9 Hz, 1H), 5.11 (s, 1H), 4.68-4.54 (m, 1H), 3.51-2.11 (m, 6H), 2.04-1.68 (m, 2H), 1.63 (d, J=10.2 Hz, 6H), 1.51-0.67 (m, 3H) ppm. $^{13}$C NMR (100 MHz, CDCl$_3$) δ 156.0, 154.7, 150.6, 149.7, 130.2, 130.0, 128.4, 123.7, 72.5, 71.6, 71.5, 55.8, 55.1, 47.6, 46.7, 31.2, 29.9, 29.8, 29.5, 25.6, 24.8, 19.7 ppm. Purity: 100% UPLCMS (210 nm); retention time 0.69 min; (M+1) 368.8.

Example 28

1-azabicyclo[2.2.2]oct-3-yl 12-(3-cyclopropylphenyl)propan-2-ylcarbamate

Using general procedure E, 11-azabicyclo[2.2.2]oct-3-yl [2-(3-bromophenyl)propan-2-yl]carbamate (44.3 mg, 0.121 mmol), cyclopropyl boronic acid (14 mg, 0.16 mmol) and palladium (II) acetate gave the title compound as an off-white solid (21 mg, 11%). $^1$H NMR (400 MHz, CDCl$_3$) δ 7.54 (s, 1H), 7.41-7.30 (m, 2H), 7.19 (t, J=7.9 Hz, 1H), 5.11 (s, 1H), 4.68-4.54 (m, 1H), 3.51-2.11 (m, 6H), 2.04-1.68 (m, 2H), 1.63 (d, J=10.2 Hz, 6H), 1.36 (d, J=9.5 Hz, 3H) ppm. $^{13}$C NMR (100 MHz, CDCl$_3$) δ 147.2, 144.2, 128.6, 128.4, 125.0, 123.7, 122.8, 122.1, 10.0, 72.2, 71.4, 55.9, 55.4, 47.7, 47.3, 46.7, 33.1, 31.6, 30.0, 29.6, 25.6, 24.8, 19.8, 19.3, 15.8, 9.5 ppm. Purity: 91% UPLCMS (210 nm); retention time 0.75 min; (M+1) 329.0.

Example 29

1-azabicyclo[2.2.2]oct-3-yl[2-(biphenyl-3-yl)propan-2-yl]carbamate

Using general procedure E, 1-azabicyclo[2.2.2]oct-3-yl[2-(3-bromophenyl)propan-2-yl]carbamate (600 mg, 1.63 mmol), phenylboronic acid (398 mg, 3.27 mmol) and palladium (II) acetate gave the title compound as a white solid (379 mg, 64%). $^1$H NMR (400 MHz, CDCl$_3$) δ 7.61 (s, 1H), 7.56 (d, J=7.4 Hz, 2H), 7.50-7.38 (m, 4H), 7.34 (m, 2H), 5.16 (s, 1H), 4.63 (s, 1H), 3.39-2.09 (m, 6H), 1.72 (s, 6H), 2.02-0.73 (m, 5H) ppm. $^{13}$C NMR (100 MHz, CDCl$_3$) δ 154.8, 147.8, 141.6, 129.0, 129.0, 128.6, 127.5, 125.8, 125.0, 124.0, 71.6, 71.3, 55.9, 55.5, 47.6, 46.8, 31.5, 30.2, 30.0, 29.5, 25.6, 24.8, 19.8 ppm. Purity: 99% UPLCMS (210 nm); retention time 0.84 min; (M+1) 365.0. Anal. Calcd. for C$_{23}$H$_{28}$N$_2$O$_2$.0.29 (CHC$_3$): C, 70.02; H, 7.14; N, 7.01. Found: C, 70.02; H, 7.37; N, 6.84.

Example 30

1-azabicyclo[2.2.2]oct-3-yl {2-[3-(2-methylpropyl)phenyl]propan-2-yl}carbamate

Using general procedure E, 1-azabicyclo[2.2.2]oct-3-yl[2-(3-bromophenyl)propan-2-yl]carbamate (75 mg, 0.20 mmol), 2-methylpropyl boronic acid (28.1 mg, 0.276 mmol) and palladium (II) acetate gave the title compound as a white solid (50 mg, 71%). $^1$H NMR (400 MHz, CDCl$_3$) 7.21 (d, J=4.9 Hz, 2H), 7.16 (s, 1H), 7.00 (s, 1H), 5.17 (s, 1H), 4.60 (s, 1H), 3.35-2.10 (m, 6H), 2.45 (d, J=7.1 Hz, 2H), 1.82 (dt, J=6.8, 13.5 Hz, 1H), 2.03-0.94 (m, 5H), 1.65 (s, 6H), 0.89 (d, J=6.6 Hz, 6H) ppm. $^{13}$C NMR (100 MHz, CDCl$_3$) δ 172.6, 172.1, 170.8, 170.2, 160.1, 160.0, 157.8, 157.7, 140.4, 139.8, 130.5, 130.4, 130.0, 129.8, 129.5, 129.3, 127.9, 127.7, 120.8, 120.7, 120.3, 113.9, 113.6, 113.2, 113.0, 110.5, 110.4, 66.6, 66.5, 56.8, 56.3, 55.4, 55.4, 54.0, 53.7, 51.1, 46.6, 43.8, 43.7, 42.0, 38.4, 37.8, 37.7, 33.8, 33.2, 27.4, 27.0, 25.7, 25.5, 20.9, 20.9 ppm. Purity: 90% UPLCMS (210 nm): retention time 0.89 min: (M+1) 345.

Example 31

1-azabicyclo[2.2.2]oct-3-yl[2-(5-bromo-2-fluorophenyl)propan-2-yl]carbamate

Using general procedure A, 2-(5-bromo-2-fluorophenyl)propan-2-amine hydrochloride (100 mg, 0.372 mmol) and quinuclidin-3-ol gave the title compound as a white solid (90.3 mg, 98%). $^1$H NMR (400 MHz, CDCl$_3$) δ 7.45 (dd, J=2.3, 7.3 Hz, 1H), 7.31 (ddd, J=2.5, 4.2, 8.6 Hz, 1H), 6.88 (dd, J=8.6, 11.9 Hz, 1H), 5.38 (s, 1H), 4.82-4.33 (m, 1H), 3.28-2.28 (m, 6H), 1.68 (d, J=9.0 Hz, 6H), 1.98-1.27 (m, 5H) ppm. $^{13}$C NMR (100 MHz, CDCl$_3$) δ 161.1, 158.6, 131.7, 131.6, 131.0, 131.0, 118.6, 118.3, 116.8, 55.8, 54.0, 47.6, 46.7, 28.5, 25.6, 24.8, 19.7 ppm. Purity: 100% UPLCMS (210 nm); retention time 0.81 min; (M+1) 386.7. Anal. Calcd. for $C_{17}H_{22}BrFN_2O_2.0.37$ (CHCl$_3$): C, 52.20; H, 5.66; N, 7.14. Found: C, 52.21; H, 5.57; N, 7.13.

Example 32

1-azabicyclo[2.2.21 oct-3-yl 12-(4'-fluorobiphenyl-3-yl)propan-2-yl]carbamate Using general procedure E, 1-azabicyclo[2.2.2]oct-3-yl[2-(3-bromophenyl)propan-2-yl]carbamate (600 mg, 1.63 mmol), 4-fluorophenyl boronic acid (457 mg, 3.27 mmol) and palladium (II) acetate gave the title compound as a white solid (373 mg, 60%). $^1$H NMR (400 MHz, CDCl$_3$) δ 7.56 (s, 1H), 7.52 (dd, J=5.4, 8.4 Hz, 2H), 7.42-7.38 (m, 3H), 7.12 (m, 2H), 5.18 (s, 1H), 4.62 (s, 1H), 2.66 (m, 6H), 1.72 (s, 6H), 2.01-0.83 (m, 5H) ppm. $^{13}$C NMR (100 MHz, CDCl$_3$) δ 125.0, 124.0, 123.8, 116.0, 116.0, 71.3, 55.9, 55.5, 47.6, 46.7, 29.6, 25.6, 24.8, 19.8 ppm. Purity: 98.0% UPLCMS (210 nm); retention time 0.95 min; (M+1) 382.9. Anal. Calcd. for $C_{23}H_{27}FN_2O_2.0.37$ (CHCl$_3$): C, 65.86; H, 6.47; N, 6.57. Found: C, 65.85; H, 6.69; N, 6.49.

Example 33

1-azabicyclo[2.2.2]oct-3-yl[2-(4-fluorobiphenyl-3-yl)propan-2-yl]carbamate

Using general procedure E, 1-azabicyclo[2.2.2]oct-3-yl[2-(5-bromo-2-fluorophenyl)propan-2-yl]carbamate (990 mg, 2.57 mmol), phenylboronic acid (209 mg, 1.71 mmol) and palladium (II) acetate gave the title compound as a white solid (257 mg, 26%). $^1$H NMR (400 MHz, CDCl$_3$) δ 7.58-7.49 (m, 3H), 7.44-7.38 (m, 3H), 7.35-7.29 (m, 1H), 7.08 (dd, J=8.4, 12.1 Hz, 1H), 5.30 (s, 1H), 4.75-4.42 (m, 1H), 2.89 (d, J=10.2 Hz, 6H), 1.81-1.66 (m, 6H), 2.04-1.18 (m, 5H) ppm. $^{13}$C NMR (100 MHz, CDCl$_3$) δ 161.7, 159.3, 140.7, 137.3, 137.3, 131.7, 131.7, 131.0, 129.0, 127.5, 127.3, 126.7, 117.1, 116.9, 71.4, 55.8, 54.3, 47.6, 46.7, 28.6, 25.6, 24.8, 19.8 ppm. Purity: 92.0% UPLCMS (210 nm); retention time 0.95 min: (M+1) 382.9. Anal. Calcd. for $C_{23}H_{27}FN_2O_2.0.4$ (CHCl$_3$): C, 65.39; H, 6.43; N, 6.52. Found: C, 65.39; H, 6.51; N, 6.42.

Example 34

1-azabicyclo[2.2.2]oct-3-yl{2-[2-fluoro-5-(2-methylpropyl)phenyl]propan-2-yl}carbamate Using general procedure E, 1-azabicyclo[2.2.2]oct-3-yl[2-(5-bromo-2-fluorophenyl)propan-2-yl]carbamate (120 mg, 0.312 mmol), 2-methylpropylboronic acid (79.4 mg, 0.779 mmol) and palladium (II) acetate gave the title as a white solid compound (37 mg, 33%). $^1$H NMR (400 MHz, CDCl$_3$) 7.08 (dd, J=2.0, 8.2 Hz, 1H), 6.95 (d, J=4.9 Hz, 1H), 6.93-6.85 (m, 1H), 5.23 (s, 1H), 4.72-4.52 (m, 1H), 3.20-2.47 (m, 6H), 2.41 (d, J=7.1 Hz, 2H), 1.89-1.76 (m, 1H), 2.02-1.26 (m, 5H), 1.70 (d, J=7.6 Hz, 6H), 0.88 (d, J=6.6 Hz, 6H) ppm. $^{13}$C NMR (100 MHz, CDCl$_3$) δ 160.4, 158.0, 137.1, 137.1, 129.2, 129.1, 128.1, 116.2, 116.0, 71.2, 55.8, 54.2, 47.6, 46.7, 45.1, 30.5, 29.9, 28.6, 27.0, 25.6, 24.8, 22.5, 19.8, 19.5 ppm. Purity: 95.0% UPLCMS (210 nm); retention time 1.02 min; (M+1) 363.

Example 35

1-azabicyclo[2.2.2]oct-3-yl[2-(5-cyclopropyl-2-fluorophenyl)propan-2-yl]carbamate Using general procedure E, 1-azabicyclo[2.2.2]oct-3-yl[2-(5-bromo-2-fluorophenyl)propan-2-yl]carbamate (750 mg, 0.649 mmol), cyclopropylboronic acid (139 mg, 1.62 mmol) and palladium (II) acetate gave the title compound as a white solid (727 mg, 86%). $^1$H NMR (400 MHz, CDCl$_3$) δ 7.08 (d, J=6.4 Hz, 1H), 6.97-6.78 (m, 2H), 5.19 (s, 1H), 4.65-4.57 (m, 1H), 2.66 (s, 6H), 1.85 (tt, J=5.1, 8.4 Hz, 1H), 2.00-1.17 (m, 5H), 1.71 (d, J=8.7 Hz, 6H), 0.92 (ddd, J=4.6, 6.3, 8.4 Hz, 2H), 0.62 (dt, J=4.7, 6.4 Hz, 2H) ppm. $^{13}$C NMR (100 MHz, CDCl$_3$) δ 160.2, 157.8, 139.2, 139.2, 125.6, 125.5, 125.4, 116.5, 116.3, 71.3, 55.8, 54.2, 47.6, 46.7, 29.9, 29.6, 28.6, 25.6, 24.8, 19.6, 15.2, 9.1 ppm. Purity: 100% UPLCMS (210 nm); retention time 0.87 min; (M+1) 347.2. Anal. Calcd. for $C_{20}H_{27}FN_2O_2.0.07$ (CHCl$_3$): C, 68.00; H, 7.70; N, 7.90. Found: C, 67.99; H, 7.86; N, 7.81.

Example 36

1-azabicyclo[2.2.2]oct-3-yl[2-(3-bromo-4-fluorophenyl)propan-2-yl]carbamate

Using general procedure A, 2-(3-bromo-4-fluorophenyl)propan-2-amine hydrochloride (1.00 g, 3.72 mmol) and quinuclidin-3-ol gave the title compound as a white solid (434 mg, 30%). $^1$H NMR (400 MHz, CDCl$_3$) δ 7.57 (s, 1H), 7.38-7.25 (m, 1H), 7.06 (t, J=8.5 Hz, 1H), 5.62 (s, 1H), 4.86-4.32 (m, 1H), 3.33-2.12 (m, 6H), 1.73 (t, J=7.2 Hz, 5H), 1.61 (d, J=9.6 Hz, 6H) ppm. $^{13}$C NMR (100 MHz, CDCl$_3$) δ 159.1, 156.7, 154.6, 130.4, 125.8, 125.7, 116.4, 116.2, 109.1, 108.9, 71.3, 55.7, 54.7, 47.4, 46.5, 29.9, 29.6, 25.5, 24.6, 22.9, 19.6 ppm. Purity: 100% UPLCMS (210 nm); retention time 0.79 min; (M+1) 387.8. Anal. Calcd. for $C_{17}H_{22}BrFN_2O_2.0.27$ (CHCl$_3$): C, 49.68; H, 5.38; N, 6.71. Found: C, 49.67; H, 5.39; N, 6.74.

Example 37

1-azabicyclo[2.2.2]oct-3-yl[2-(6-fluorobiphenyl-3-yl)propan-2-yl]carbamate

Using general procedure E, 1-azabicyclo[2.2.2]oct-3-yl[2-(3-bromo-4-fluorophenyl)propan-2-yl]carbamate (750 mg, 1.95 mmol), phenyl boronic acid (418 mg, 4.87 mmol) and palladium (II) acetate gave the title compound as a white solid (195 mg, 29%). $^1$H NMR (400 MHz, CDCl$_3$) δ 7.49 (s, 2H), 7.46-7.38 (m, 3H), 7.35 (dd, J=4.3, 11.7 Hz, 2H), 7.08 (dd, J=8.6, 10.1 Hz, 1H), 5.10 (s, 1H), 4.60 (s, 1H), 3.33-2.10 (m, 6H), 1.67 (d, J=7.9 Hz, 6H), 1.67 (m, 5H) ppm. $^{13}$C NMR (100 MHz, CDCl$_3$) δ 159.9, 157.4, 136.2, 129.3, 129.0, 128.7, 127.9, 127.6, 125.7, 125.6, 71.0, 66.1, 55.7, 55.1, 47.5, 46.6, 29.9, 29.6, 25.5, 24.5, 19.5, 15.5 ppm. Purity: 98% UPLCMS (210 nm); retention time 0.95 min; (M+1) 382.9. Anal. Calcd. for $C_{23}H_{27}FN_2O_2.0.29$ (CHCl$_3$): C, 67.08; H, 6.60; N, 6.72. Found: C, 67.09; H, 6.95; N, 6.37.

Example 38

1-azabicyclo[2.2.2]oct-3-yl{2-[4-fluoro-3-(2-methylpropyl)phenyl]propan-2-yl}carbamate Using general procedure E, 1-azabicyclo[2.2.2]oct-3-yl[2-(3-bromo-4-fluorophenyl)propan-2-yl]carbamate (125 mg, 0.324 mmol), 2-methylpropylboronic acid (66 mg, 0.65 mmol) and palladium (II) acetate gave the title compound as a white solid (27 mg, 23%). $^1$H NMR (400 MHz, CDCl$_3$) δ 7.23-7.11 (m, 2H), 7.04-6.82 (m, 1H), 5.11 (s, 1H), 4.59 (s, 1H), 3.32-2.12 (m, 6H), 2.48 (d, J=7.2 Hz, 2H), 1.86 (d, J=6.7, Hz, 1H), 2.05-0.96 (m, 5H), 1.62 (d, J=5.8 Hz, 6H), 0.90 (d, J=6.6 Hz, 6H) ppm. $^{13}$C NMR (100 MHz, CDCl$_3$) 161.4, 159.0, 154.7, 142.5, 128.3, 124.0, 115.1, 114.9, 71.2, 66.1, 55.8, 55.0, 47.6, 46.7, 38.7, 29.9, 29.6, 25.6, 24.8, 22.6, 19.7, ppm. Purity: 85% UPLCMS (210 nm); retention time 1.0 min; (M+1) 362.9.

Example 39

1-azabicyclo[2.2.2]oct-3-yl[2-(4',6-difluorobiphenyl-3-yl)propan-2-yl]carbamate

Using general procedure E, 1-azabicyclo[2.2.2]oct-3-yl[2-(3-bromo-4-fluorophenyl)propan-2-yl]carbamate (125 mg, 0.324 mmol), 4-fluoroboronic acid (64 mg, 0.46 mmol) and palladium (II) acetate gave the title compound as a white solid (76 mg, 56%). $^1$H NMR (400 MHz, CDCl$_3$) δ 7.48 (t, 2H), 7.44-7.29 (m, 2H), 7.21-7.00 (m, 3H), 5.27 (s, 1H), 4.68-4.55 (m, 1H), 3.29-2.10 (m, 6H), 1.67 (d, J=9.4 Hz, 6H), 2.01-0.69 (m, 5H) ppm. $^{13}$C NMR (100 MHz, CDCl$_3$) δ 163.9, 161.4, 159.8, 157.3, 154.8, 143.5, 132.2, 130.9, 127.9, 127.8, 127.4, 125.9, 125.8, 116.2, 116.0, 115.7, 115.5, 71.4, 66.1, 55.9, 47.6, 46.7, 30.0, 39.7, 25.6, 24.8, 19.8 ppm. Purity: 98% UPLCMS (210 nm): retention time 0.96 min; (M+1) 400.9.

Example 40

1-azabicyclo[2.2.2]oct-3-yl{2-[4-fluoro-3-(pyrimidin-5-yl)phenyl]propan-2-yl}carbamate Using general procedure E, 1-azabicyclo[2.2.2]oct-3-yl[2-(3-bromo-4-fluorophenyl)propan-2-yl]carbamate (150 mg, 0.389 mmol), pyrimidine-5-boronic acid (75.9 mg, 0.613 mmol) and tris(dibenzylideneacetone)dipalladium(0) gave the title compound as a white solid (49 mg, 31%). $^1$H NMR (400 MHz, CDCl$_3$) δ 9.22 (s, 1H), 8.92 (s, 2H), 7.55-7.41 (m, 2H), 7.19 (dd, J=8.7, 9.9 Hz, 1H), 5.37 (s, 1H), 4.72-4.49 (m, 1H), 3.34-2.04 (m, 6H), 2.04-0.98 (m, 5H), 1.66 (t, J=10.9 Hz, 6H) ppm. $^{13}$C NMR (100 MHz, CDCl$_3$) δ 159.9, 157.9, 157.4, 156.6, 154.7, 130.2, 127.85, 127.77, 126.9, 122.0, 121.8, 116.7, 116.5, 116.2, 71.6, 55.9, 54.9, 47.6, 46.7, 30.3, 29.6, 25.6, 24.8, 19.8 ppm. Purity: 93% UPLCMS (210 nm); retention time 0.63 min; (M+1) 384.9

Example 41

1-azabicyclo[2.2.2]oct-3-yl {2-[4-fluoro-3-(pyridin-3-yl)phenyl]propan-2-yl}carbamate Using general procedure E, 1-azabicyclo[2.2.2]oct-3-yl[2-(3-bromo-4-fluorophenyl)propan-2-yl]carbamate (110 mg, 0.286 mmol), pyridine-3-boronic acid (53 mg, 0.43 mmol) and tris(dibenzylideneacetone)dipalladium(0) gave the title compound as a white solid (42 mg, 39%). $^1$H NMR (400 MHz, CDCl$_3$) δ 8.78 (s, 1H), 8.62 (d, J=3.5 Hz, 1H), 7.86 (s, 1H), 7.46 (d, J=7.2 Hz, 2H), 7.38 (dd, J=4.9, 7.9 Hz, 1H), 7.15 (dd, J=8.7, 9.9 Hz, 1H), 5.32 (s, 1H), 4.69-4.57 (m, 1H), 2.68 (s, 6H), 1.70 (d, J=11.3 Hz, 6H), 2.08-0.94 (m, 5H) ppm. $^{13}$C NMR (100 MHz, CDCl$_3$) δ 160.0, 157.5, 149.9, 149.0, 136.6, 132.1, 127.3, 126.8, 126.7, 125.5, 125.3, 123.5, 116.4, 116.2, 71.5, 55.9, 55.0, 47.6, 46.7, 30.1, 29.66, 25.6, 24.8, 19.7 ppm. Purity: 100% UPLCMS (210 nm); retention time 0.54 min; (M+1) 367.8.

Example 42

1-azabicyclo[2.2.2]oct-3-yl {2-[4-fluoro-3-(furan-3-yl)phenyl]propan-2-yl}carbamate Using general procedure E, 1-azabicyclo[2.2.2]oct-3-yl[2-(3-bromo-4-fluorophenyl)propan-2-yl]carbamate (110 mg, 0.296 mmol), furan-3-boronic acid (47.9 mg, 0.428 mmol) and tris(dibenzylideneacetone)dipalladium(0) gave the title compound as a white solid (47 mg, 44%). $^1$H NMR (400 MHz, CDCl$_3$) δ 7.88 (ddd, J=0.9, 1.5, 2.5 Hz, 1H), 7.53 (dd, J=2.5, 7.1 Hz, 1H), 7.50 (t, J=1.7 Hz, 1H), 7.31-7.23 (m, 1H), 7.08 (dd, J=8.6, 10.6 Hz, 1H), 6.76 (dt, J=0.8, 1.7 Hz, 1H), 5.22 (s, 1H), 4.62 (s, 1H), 3.40-2.11 (m, 6H), 2.02-0.87 (m, 5H), 1.59 (dd, J=11.6, 70.3 Hz, 6H) ppm. $^{13}$C NMR (100 MHz, CDCl$_3$) δ 160.0, 157.5, 150.2, 143.9, 127.44, 127.36, 127.0, 126.1, 123.8, 116.6, 116.4, 71.5, 55.9, 55.0, 47.6, 46.7, 30.1, 29.9, 25.6, 24.8, 19.8 ppm. Purity: 96% UPLCMS (210 nm); retention time 0.85 min; (M+1) 372.9.

Example 43

1-azabicyclo[2.2.2]oct-3-yl {2-[4-fluoro-3-(pyridin-4-yl)phenyl]propan-2-yl}carbamate Using general procedure E, 1-azabicyclo[2.2.2]oct-3-yl[2-(3-bromo-4-fluorophenyl)propan-2-yl]carbamate (130 mg, 0.291 mmol), pyridine-4-boronic acid (54 mg, 0.43 mmol) and tris(dibenzylideneacetone)dipalladium(0) gave the title compound as a white solid (46 mg, 41%). $^1$H NMR (400 MHz, CDCl$_3$) δ 8.68 (dd, J=1.6, 4.5 Hz, 2H), 7.61-7.39 (m, 4H), 7.15 (dd, J=8.6, 10.2 Hz, 1H), 5.31 (s, 1H), 4.69-4.57 (m, 1H), 3.40-2.07 (m, 6H), 1.69 (d, J=10.8 Hz, 6H), 2.06-0.74 (m, 5H) ppm. $^{13}$C NMR (100 MHz, CDCl$_3$) δ 160.0, 157.6, 143.3, 141.6, 141.5, 126.7, 126.6, 124.9, 124.8, 120.1, 119.9, 116.1, 115.9, 115.4, 115.1, 109.2, 71.4, 55.9, 55.0, 47.6, 46.7, 29.9, 25.6, 24.8, 19.8 ppm. Purity: 97% UPLCMS (210 nm); retention time 0.82 min; (M+1) 384.6.

Example 44

1-(1-azabicyclo[2.2.2.2]oct-3-yl)-3-(2-phenylpropan-2-yl)urea

Using general procedure C, quinuclidin-3-amine (102 mg, 0.6 mmol), CDI (131 mg, 0.789 mmol) and cumylamine (95 mg, 0.70 mmol) gave the title compound as a white solid (21 mg, 10%). $^1$H NMR (400 MHz, CDCl$_3$) δ 7.61-7.47 (m, 2H), 7.44-7.37 (m, 2H), 7.34-7.28 (m, 1H), 4.86 (s, 1H), 4.20 (d. J=7.3 Hz, 1H), 3.71-3.60 (m, 1H), 3.14 (ddd, J=2.3, 9.4, 14.2 Hz, 1H), 2.79-1.89 (m, 6H), 1.64 (d, J=3.3 Hz, 6H), 1.58-1.10 (m, 5H) ppm. $^{13}$C NMR (100 MHz, CDCl$_3$) δ 157.4, 146.2, 129.3, 127.8, 125.8, 57.1, 54.9, 47.7, 47.1, 46.7, 30.6, 30.5, 26.0, 20.3 ppm. Purity: 79% UPLCMS (210 nm); retention time 0.61 min; (M+1) 288.2.

Preparation O

Example 45

3-cyano-1-azabicyclo[2.2.2]oct-3-yl {2-[3-(prop-1-en-2-yl)phenyl]propan-2-yl}carbamate To a solution of 3-hydroxyquinuclidine-3-carbonitrile (38 mg, 0.25 mmol) in acetonitrile/dioxane (3 mL) at room temperature was added triethylamine (7.0 uL, 0.05 mmol). The reaction mixture was stirred for 15 min and 1-(2-isocyanatopropan-2-yl)-3-(prop-1-en-2-yl)benzene (49.0 uL, 0.248 mmol) was added dropwise. The reaction was stirred for a period of 18 h at 65° C. and concentrated. The crude material was purified on a combiflash (SiO$_2$ cartridge, CHCl$_3$ and 2N NH$_3$ in MeOH) to afford the corresponding carbamate as a clear oil (57 mg, 65%). $^1$H NMR (400 MHz, CDCl$_3$) δ 7.42-7.20 (s, 5H), 6.61 (s, 1H), 5.11 (s, 1H), 3.29 (d, J=12.0 Hz, 1H), 3.09 (d, J=12.0 Hz, 1H), 2.93 (d, J=4.0 Hz, 2H), 2.79-2.68 (m, 2H), 2.13 (s, 6H) 2.05-2.00 (m, 2H), 1.91 (s, 3H), 1.87 (s, 2H), 1.50-1.37 (m, 2H) ppm. $^{13}$C NMR (100 MHz, CDCl$_3$) δ 135.4, 128.7, 125.2, 124.5, 124.0, 122.0, 112.9, 61.2, 47.0, 46.2, 32.4, 31.8, 29.9, 29.4, 29.2, 26.6, 25.7, 23.7, 22.8, 22.2, 19.2 ppm. Purity: >99% UPLCMS (210 nm); retention time 0.81 min; (M+1) 354.

Preparation P

Example 46

N-(2-(3-(prop-1-en-2-yl)phenyl)propan-2-yl)-1,4-diazabicyclo[3.2.2]nonane-4-carboxamide To a solution of 1,4-diazabicyclo[3.2.2]nonane (350 mg, 2.77 mmol) and 1-(2-isocyanatopropan-2-yl)-3-(prop-1-en-2-yl)benzene (1.09 mL, 5.55 mmol) in chloroform (2 mL) was added 3-4 pieces of molecular sieves. The reaction mixture was stirred at room temperature for 18 h and then concentrated. The crude material was purified on a combiflash (SiO$_2$ cartridge, CHCl$_3$ and 2N NH$_3$ in MeOH) to afford the corresponding urea as an off-white solid (650 mg, 36%). $^1$H NMR (400 MHz, CDCl$_3$) δ 7.48 (s, 1H), 7.31-7.26 (m, 3H), 5.34 (s, 1H), 5.07 (s, 1H), 4.73 (br s, 1H), 4.03 (BR s, 1H), 3.64 (m, 2H), 3.14-3.03 (m, 6H), 2.15 (s, 3H) 2.06 (m, 2H), 1.72 (m, 8H) ppm. $^{13}$C NMR (100 MHz, CDCl$_3$) δ 155.7, 148.3, 143.8, 141.3, 128.5, 124.1, 123.9, 122.0, 112.5, 57.8, 55.8, 48.1, 46.4 (2×), 41.2, 30.2 (2×), 27.3 (2×), 22.1 ppm. Purity: >98% UPLCMS (210 nm); retention time 0.71 min; (M+1) 328

Example 47 biphenyl-2-yl 1,4-diazabicyclo[3.2.2]nonane-4-carboxylate

Biphenyl-2-yl carbonochloridate (83.0 mg, 0.358 mmol) was treated with 1,4-diazabicyclo[3.2.2]nonane (113 mg, 0.896 mmol) using the same procedure reported in example 46 to afford the title compound as an off-white solid (17 mg, 15%). Purity: >99% UPLCMS (210 nm); retention time 0.75 min; (M+1) 323.

Example 48

N-{2-[3-(propan-2-yl)phenyl]propan-2-yl}-1,4-diazabicyclo[3.2.2]nonane-4-carboxamide Using general procedure F, N-(2-(3-(prop-1-en-2-yl)phenyl)propan-2-yl)-1,4-diazabicyclo[3.2.2]nonane-4-carboxamide (100 mg, 0.305 mmol) and palladium, (20 mg, 20 wt. % on carbon) gave the title compound as an off-white solid (60 mg, 57%). $^1$H NMR (400 MHz, CDCl$_3$) δ 7.28-7.21 (m, 3H), 7.11 (d, J=8.0 Hz, 1H), 4.71 (s, 1H), 4.02 (s, 1H), 3.66 (t, J=8.0 Hz, 2H) 3.15 (m, 7H), 2.06 (br s, 2H), 1.77 (s, 7H) 1.26 (d, J=4.0 Hz, 6H) ppm. $^{13}$C NMR (100 MHz, CDCl$_3$) δ 155.8, 148.9, 148.5, 128.5.1, 124.7, 123.1, 122.4, 57.8, 56.0, 48.1, 46.4, 41.2, 34.5, 32.2, 30.4, 30.0, 29.9, 27.3, 24.3, 22.9 ppm. Purity: >91% UPLCMS (210 nm); retention time 0.74 min; (M+1) 330.

Preparation Q

Example 49

(+/−)-(3S,4S)-1-azabicyclo[2.2.1]heptan-3-yl-2-(3-(prop-1-en-2-yl)phenyl)propan-2-ylcarbamate To a solution of (+/−)-(3S,4S)-1-azabicyclo[2.2.1]heptan-3-ol (294 mg, 2.6 mmol) in THF (5 mL) at room temperature was added NaH [60%, oil](107 mg, 2.67 mmol). The reaction mixture was stirred for 15 min and 1-(2-isocyanatopropan-2-yl)-3-(prop-1-en-2-yl)benzene (344 uL, 1.73 mmol) was added dropwise. The reaction was stirred for a period of 30 min and quenched with brine. The solution was extracted with EtOAc and the organic layer was dried over Na$_2$SO$_4$ and concentrated. The crude material was purified on a combiflash (SiO$_2$ cartridge, CHCl$_3$ and 2N NH$_3$ in MeOH) to afford the corresponding carbamate as a clear oil (140 mg, 26%). $^1$H NMR (400 MHz, CDCl$_3$) δ 7.26-7.20 (m, 3H), 7.11 (m, 1H), 5.18 (s, 1H), 5.19 (br s, 1H), 5.01 (s, 1H), 4.81 (br s, 1H), 2.99 (br s, 1H), 2.82 (br s, 1H), 2.70 (br s, 1H), 2.53 (br s, 2H), 2.33 (br s, 1H), 2.02 (s, 3H), 1.76 (br s, 1H) 1.61 (br s, 6H), 1.52 (br s, 1H), 1.37 (br s, 1H) ppm. $^{13}$C NMR (100 MHz, CDCl$_3$) δ 147.1, 143.7, 141.5, 128.5, 124.1, 122.1, 112.7, 75.6, 60.6, 59.4, 55.4, 54.3, 53.9, 41.5, 29.9, 29.8, 29.4, 22.2, 21.6 ppm. Purity: >98% UPLCMS (210 nm); retention time 0.83 min; (M+1) 315

Example 50

(+/−)-(3S,4S)-1-azabicyclo[2.2.11 hept-3-yl{2-3-(propan-2-yl)phenyl]propan-2-yl}carbamate Using general procedure F, (+/−)-(3S,4S)-1-azabicyclo [2.2.1]heptan-3-yl 2-(3-(prop-1-en-2-yl)phenyl)propan-2-ylcarbamate (110 mg, 0.350 mmol) and palladium (20 mg, 20 wt. % on carbon) gave the title compound as an off-white solid (36 mg, 46%). $^1$H NMR (400 MHz, CDCl$_3$) δ 7.25-7.19 (m, 3H), 7.11 (d, J=8.0 Hz, 1H), 5.19 (s, 1H), 4.91 (s, 1H), 3.44 (t, J=4.0 Hz, 2H) 3.19 (br s, 1H), 3.02 (br s, 1H), 2.89 (m, 2H), 2.69 (br s, 1H), 2.39 (br s, 1H), 1.91 (br s, 1H), 1.66 (br s, 7H) 1.26 (d, J=4.0 Hz, 6H) ppm. $^{13}$C NMR (100 MHz, CDCl$_3$) δ 128.5 (2×), 124.8, 123.1 (2×), 122.4 (2×), 77.4, 60.6, 59.4, 55.5, 41.5, 34.5, 29.9, 29.9, 29.5, 24.3 (2×), 21.6 ppm. Purity: >95% UPLCMS (210 nm); retention time 0.88 min; (M+1) 317.

Example 51

N-[2-(3-bromo-4-fluorophenyl)propan-2-yl]-1,4-diazabicyclo[3.2.2]nonane-4-carboxamide Using general procedure A, 2-(3-bromo-4-fluorophenyl) propan-2-amine hydrochloride (1.00 g, 3.72 mmol) and 1,4-diazabicyclo[3.2.2]nonane gave the title compound as a white solid (265 mg, 18%). $^1$H NMR (400 MHz, CDCl$_3$) δ 7.54-7.52 (m, 1H), 7.31-7.25 (m, 1H), 7.04 (t, J=8.0 Hz, 1H), 4.71 (s, 1H), 3.99 (br s, 1H), 3.59 (t, J=8.0 Hz, 2H), 3.13-2.95 (m, 6H), 2.04-1.97 (m, 2H) 1.77-1.67 (m, 2H), 1.65 (s, 6H) ppm. $^{13}$C NMR (100 MHz, CDCl$_3$) δ 158.9, 156.4, 155.4, 145.9, 130.2, 125.6, 116.2, 57.8, 54.9, 48.3, 46.6, 46.6, 41.6, 30.5, 30.5, 27.6, 27.6 ppm. Purity: >99% UPLCMS (210 nm); retention time 0.73 min: (M+1) 384.

Example 52

N-[2-(6-fluorobiphenyl-3-yl)propan-2-yl]-1,4-diazabicyclo[3.2.2]nonane-4-carboxamide Using general procedure E, N-[2-(3-bromo-4-fluorophenyl)propan-2-yl]-1,4-diazabicyclo[3.2.2]nonane-4-carboxamide (100 mg, 0.261 mmol), phenylboronic acid (79 mg, 0.65 mmol) and palladium (II) acetate gave the title compound as an off-white solid (66 mg, 66%). $^1$H NMR (400 MHz, CDCl$_3$) δ 7.54 (m, 2H), 7.44-7.40 (m, 5H), 7.08 (m, 1H), 4.78 (br s, 1H), 4.00 (br s, 1H), 3.60 (m, 2H), 3.11-2.92 (m, 6H), 2.00 (m, 2H) 1.67 (m, 7H), 1.26 (s, 1H) ppm. $^{13}$C NMR (100 MHz, CDCl$_3$) δ 159.6, 155.6, 144.6, 136.5, 129.3, 128.6, 128.5, 127.8, 127.5, 125.7, 125.6, 116.1, 115.9, 57.9, 55.3, 48.2, 46.4, 46.4, 41.6, 30.6, 30.5, 29.9, 27.6 ppm. Purity: >99% UPLCMS (210 nm); retention time 0.88 min; (M+1) 382.

Example 53

N-[2-(4',6-difluorobiphenyl-3-yl)propan-2-yl]-1,4-diazabicyclo[3.2.2]nonane-4-carboxamide Using general procedure E, N-[2-(3-bromo-4-fluorophenyl)propan-2-yl]-1,4-diazabicyclo[3.2.2]nonane-4-carboxamide (100 mg, 0.261 mmol), 4-fluorophenyl boronic acid (91 mg, 0.65 mmol) and palladium (II) acetate gave the title compound as an off-white solid (64 mg, 62%). $^1$H NMR (400 MHz, CDCl$_3$) δ 7.48 (m, 2H), 7.37-7.30 (m, 2H), 7.10-7.03 (m, 3H), 4.77 (s, 1H), 3.99 (br s, 1H), 3.58 (m, 2H), 3.10-2.90 (m, 6H), 1.98 (m, 2H) 1.71 (m, 8H) ppm. $^{13}$C NMR (100 MHz, CDCl$_3$) δ 163.7, 161.3, 159.5, 157.1, 155.6, 144.6, 131.0, 130.9, 127.4, 127.2, 125.7, 116.1, 115.6, 57.9, 55.2, 48.2, 46.4, 46.4, 41.5, 30.6, 30.6, 27.6, 27.6 ppm. Purity: >99% UPLCMS (210 nm); retention time 0.90 min; (M+1) 400.

Example 54

N-[2-(naphthalen-1-yl)propan-2-yl]-1,4-diazabicyclo[3.2.2]nonane-4-carboxamide

Using general procedure A, 2-(naphthalen-1-yl)propan-2-amine hydrochloride (227 mg, 1.23 mmol) and 1,4-diazabicyclo[3.2.2]nonane gave the title compound as a white solid (206 mg, 50%). $^1$H NMR (400 MHz, CDCl$_3$) δ 8.63-8.60 (m, 1H), 7.90-7.87 (m, 1H), 7.78 (d, J=8.0 Hz, 1H), 7.63 (d, J=8.0 Hz, 1H), 7.47-7.42 (m, 3H), 4.86 (s, 1H), 3.94 (br s, 1H), 3.61 (m, 2H), 3.11-2.88 (m, 7H), 2.01-1.91 (m, 7H), 1.68-1.62 (m, 2H) ppm. $^{13}$C NMR (100 MHz, CDCl$_3$) δ 176.2, 155.5, 142.6, 135.3, 130.6, 129.9, 128.8, 126.3, 125.4, 125.2, 123.9, 57.3, 57.1, 47.7, 45.8, 45.8, 40.7, 29.4, 29.4, 26.9, 26.9 ppm. Purity: >99% UPLCMS (210 nm); retention time 0.72 min; (M+1) 338.

Example 55

N-(2-(5-bromo-2-fluorophenyl)propan-2-yl)-1,4-diazabicyclo[3.2.2]nonane-4-carboxamide Using general procedure A, 2-(5-bromo-2-fluorophenyl)propan-2-amine hydrochloride (100 mg, 0.372 mmol) and 1,4-diazabicyclo[3.2.2]nonane gave the title compound as a white solid (70 mg, 49%). $^1$H NMR (400 MHz, CDCl$_3$) δ 7.48 (m, 1H), 7.28 (m, 1H), 6.86 (m, 1H), 4.85 (s, 1H), 3.98 (br s, 1H), 3.56 (m, 2H), 3.14-2.91 (m, 7H), 1.99 (m, 2H) 1.71 (m, 7H) ppm. $^{13}$C NMR (100 MHz, CDCl$_3$) δ 161.1, 158.6, 155.7, 131.3, 113.1, 118.3, 118.0 57.8, 54.0, 48.1, 46.4, 46.4, 41.5, 29.1, 29.1, 27.5, 27.5 ppm. Purity: >99% UPLCMS (210 nm); retention time 0.73 min; (M+1) 384.

Example 56

N-[2-(4-fluorobiphenyl-3-yl)propan-2-yl]-1,4-diazabicyclo[3.2.2]nonane-4-carboxamide Using general procedure E, N-(2-(5-bromo-2-fluorophenyl)propan-2-yl)-1,4-diazabicyclo[3.2.2]nonane-4-carboxamide (100 mg, 0.261 mmol), phenyl boronic acid (30 mg, 0.25 mmol) and palladium (II) acetate gave the title compound as an off-white solid (27 mg, 39%). $^1$H NMR (400 MHz, CDCl$_3$) δ 7.56-7.51 (m, 3H), 7.41-7.37 (m, 3H), 7.32-7.30 (m, 1H), 7.03 (m, 1H), 4.90 (s, 1H), 4.00 (br s, 1H), 3.59 (m, 2H), 3.11-2.92 (m, 6H), 2.04-1.98 (m, 2H) 1.78 (s, 6H), 1.73-1.67 (m, 2H) ppm. $^{13}$C NMR (100 MHz, CDCl$_3$) δ 161.8, 159.4, 155.9, 140.9, 137.2, 134.6, 128.9, 127.4, 127.3, 127.2, 127.1, 127.0, 116.9, 57.9, 54.4, 48.1, 46.5, 46.5, 41.4, 29.9, 29.3, 27.5, 27.5 ppm. Purity: >99% UPLCMS (210 nm); retention time 0.90 min; (M+1) 400.

Example 57

N-(2-(3-isopropoxyphenyl)propan-2-yl)-1,4-diazabicyclo[3.2.2]nonane-4-carboxamide Using general procedure A, 2-(3-isopropoxyphenyl)propan-2-amine hydrochloride (60 mg, 0.31 mmol) and 1,4-diazabicyclo[3.2.2]nonane gave the title compound as a white solid (70 mg, 57%). $^1$H NMR (400 MHz, CDCl$_3$) 7.17 (t, J=8.0 Hz, 1H), 6.92-6.87 (m, 2H), 6.69 (d, J=8.0 Hz, 1H) 4.66 (br s, 1H), 4.48 (m, 1H), 3.94 (br s, 1H) 3.56 (m, 2H), 3.08-2.90 (m, 5H), 1.96 (m, 2H) 1.69-1.60 (m, 7H), 1.27 (d, J=8.0 Hz, 6H), 1.17 (br s, 2H) ppm. $^{13}$C NMR (100 MHz, CDCl$_3$) δ 158.0, 155.7, 150.3, 129.4, 117.1, 113.4, 113.1, 77.5, 69.8, 55.7, 48.2, 46.4, 46.4, 46.3, 41.5, 30.3, 30.0, 29.9, 27.6, 22.3 ppm. Purity: >99% UPLCMS (210 nm); retention time 0.75 min; (M+1) 346.

Example 58

N-(biphenyl-3-yl)-1,4-diazabicyclo[3.2.2]nonane-4-carboxamide

Using general procedure A, biphenyl-3-amine (100 mg, 0.592 mmol) and 1,4-diazabicyclo[3.2.2]nonane gave the title compound as an off white solid (93 mg, 49%). $^1$H NMR (400 MHz, CDCl$_3$) δ 7.60 (m, 1H), 7.56-53 (m, 2H), 7.39-7.21 (m, 6H), 6.67 (br s, 1H), 4.85 (s, 1H), 4.16 (br s, 1H), 3.66-3.61 (m, 2H), 3.07-2.86 (m, 6H), 1.97 (m, 2H) 1.68 (m, 2H) ppm. $^{13}$C NMR (100 MHz, CDCl$_3$) δ 154.7, 142.0, 141.1, 139.9, 129.3, 128.8, 128.8, 127.5, 127.3, 127.3, 122.0, 119.4, 119.2, 57.5, 48.4, 46.3, 46.3, 42.1, 27.5, 27.5 ppm. Purity: >96% UPLCMS (210 nm): retention time 0.75 min: (M+1) 333.

Example 59

N-{2-[2-fluoro-5-(2-methylpropyl)phenyl]propan-2-yl}-1,4-diazabicyclo[3.2.2]nonane-4-carboxamide Using general procedure E, N-(2-(5-bromo-2-fluorophenyl)propan-2-yl)-1,4-diazabicyclo[3.2.2]nonane-4-carboxamide (100 mg, 0.261 mmol), with isopropyl boronic acid (66 mg, 0.65 mmol) and palladium (II)

acetate gave the title compound as an off-white solid (27 mg, 39%). $^1$H NMR (400 MHz, CDCl$_3$) δ 7.08 (d, J=8.0 Hz, 1H), 6.93-6.81 (m, 2H), 4.85 (s, 1H), 3.96 (br s, 1H), 3.65 (q, J=8.0 Hz, 1H), 3.55 (t, J=8.0 Hz, 2H), 3.09-2.90 (m, 5H), 2.40 (d, J=4.0 Hz, 1H), 2.01-1.92 (m, 2H) 1.81-1.61 (m, 8H), 1.22-1.17 (m, 2H), 0.87 (d, J=8.0 Hz, 6H) ppm. $^{13}$C NMR (100 MHz, CDCl$_3$) δ 160.5, 158.0, 155.9, 137.0, 133.6, 128.8, 116.0, 57.9, 54.3, 48.1, 46.4 (2×), 45.2, 41.4, 30.5, 29.9, 29.2, 29.2, 27.5, 22.6, 22.6 ppm. Purity: >99% UPLCMS (210 nm); retention time 0.94 min; (M+1) 362.

Example 60

N-(biphenyl-2-yl)-1,4-diazabicyclo[3.2.2]nonane-4-carboxamide

Using general procedure A, 1-isocyanatobiphenyl (50 mg, 0.26 mmol) and 1,4-diazabicyclo[3.2.2]nonane gave the title compound as a white solid (55 mg, 65%). $^1$H NMR (400 MHz, CDCl$_3$) δ 8.15 (d, J=8.0 Hz, 1H), 7.45-7.31 (m, 6H), 7.16 (d, J=8.0 Hz, 1H), 7.04 (t, J=8.0 Hz, 1H), 6.47 (br s, 1H), 3.63 (br s, 1H), 3.57 (t, J=8.0 Hz, 2H), 3.00-2.80 (m, 6H), 1.68 (m, 2H) 1.43 (m, 2H) ppm. $^{13}$C NMR (100 MHz, CDCl$_3$) δ 154.2, 138.9, 136.6, 131.7, 129.7, 129.5, 129.5, 129.3, 129.3, 128.7, 128.1, 122.6, 120.5, 57.6, 48.5, 46.2, 46.2, 41.6, 29.9, 27.3 ppm. Purity: >99% UPLCMS (210 nm); retention time 0.64 min; (M+1) 322.

Example 61

N-(naphthalen-1-yl)-1,4-diazabicyclo[3.2.2]nonane-4-carboxamide

Using general procedure A, 1-isocyanatonaphthalene (208 mg, 1.23 mmol) and 1,4-diazabicyclo[3.2.2]nonane gave the title compound as a white solid (150 mg, 48%). $^1$H NMR (400 MHz, CDCl$_3$) δ 7.80-7.72 (m, 2H), 7.64 (d, J=8.0 Hz, 1H), 7.56 (d, J=8.0 Hz, 1H), 7.44-7.35 (m, 3H), 6.65 (br s, 1H), 4.18 (br s, 1H), 3.64 (t, J=8.0 Hz, 2H), 3.09-2.91 (m, 6H), 2.08-1.93 (m, 2H) 1.74-1.66 (m, 2H) ppm. $^{13}$C NMR (100 MHz, CDCl$_3$) δ 155.3, 134.4, 134.3, 128.9, 128.2, 126.2, 126.1, 126.0, 125.1, 121.2, 121.0, 57.6, 48.7, 46.4, 46.4, 42.2, 27.6, 27.6 ppm. Purity: >99% UPLCMS (210 nm); retention time 0.53 min; (M+1) 296.

Example 62

(S)-quinuclidin-3-yl 2-(biphenyl-4-yl)propan-2-ylcarbamate

Using general procedure B, bromobenzonitrile (2.00 g, 11.0 mmol) was converted to the corresponding 2-(4-bromophenyl)propan-2-amine (1.20 g, 51%) as a brown oil.

Using general procedure A, 2-(4-bromophenyl)propan-2-amine (1.0 g, 4.7 mmol) and (S)-quinuclidin-3-ol gave (S)-quinuclidin-3-yl 2-(4-bromophenyl)propan-2-ylcarbamate (1.0 g, 58%) as a brown oil.

Using general procedure E, the above bromide (200 mg, 0.540 mmol), phenylboronic acid (133 mg, 1.10 mmol) and [PdCl$_2$(pddf)]CH$_2$Cl$_2$ gave the title compound as a white solid (70 mg, 35%). $^1$H NMR (500 MHz, CDCl$_3$) δ 7.60-7.53 (m, 4H), 7.47 (d, J=8.5 Hz, 2H), 7.42 (t. J=7.5 Hz, 2H), 7.33 (t, J=7.5 Hz, 1H), 5.26 (br s, 1H), 4.64 (m, 1H), 3.33-3.15 (m, 1H), 3.10-2.45 (m, 5H), 2.40-1.80 (m, 2H), 1.78-1.58 (m, 7H), 1.55-1.33 (m, 2H) ppm. $^{13}$C NMR (125 MHz, CDCl$_3$) δ 154.5, 146.1, 140.8, 139.5, 128.7, 127.2, 127.1, 127.1, 125.2, 70.9, 55.5, 55.1, 47.4, 46.4, 31.1, 29.5, 25.3, 24.5, 19.5 ppm. Purity: 100% LCMS (214 nm & 254 nm); retention time 1.56 min; (M+1) 365.

Example 63 quinuclidin-3-yl 2-(4-(pyrimidin-5-yl)phenyl)propan-2-ylcarbamate

Using general procedure E, quinuclidin-3-yl 2-(4-bromophenyl)propan-2-ylcarbamate (200 mg, 0.540 mmol), pyrimidin-5-ylboronic acid (136 mg, 1.12 mmol) and [PdCl$_2$(pddf)]CH$_2$Cl$_2$ gave the title compound as a white solid (80 mg, 40%). $^1$H NMR (500 MHz, CDCl$_3$) δ 9.17 (s, 1H), 8.92 (s, 2H), 7.58-7.51 (m, 4H), 5.34 (s, 1H), 4.61 (m, 1H), 3.20-3.10 (m, 1H), 2.92-2.41 (m, 5H), 2.00-1.76 (m, 2H), 1.72-1.53 (m, 7H), 1.52-1.32 (m, 2H) ppm. $^{13}$C NMR (125 MHz, CDCl$_3$) δ 157.4, 154.8, 154.5, 148.2, 134.0, 132.5, 127.0, 126.0, 71.2, 55.6, 55.0, 47.4, 46.3, 29.7, 29.4, 25.4, 24.5, 19.5 ppm. Purity: >96% LCMS (214 nm & 254 nm); retention time 1.34 min; (M+1) 366.

Example 64 quinuclidin-3-yl 1-(biphenyl-4-yl)cyclopropylcarbamate

Using general procedure G, bromobenzonitrile (3.00 g, 16.5 mmol) was converted to the corresponding 1-(4-bromophenyl)cyclopropanamine (1.80 g, 51%) as a yellow solid.

Using general procedure A, 1-(4-bromophenyl)cyclopropanamine (1.0 g, 4.7 mmol) and quinuclidin-3-ol gave quinuclidin-3-yl 1-(4-bromophenyl)cyclopropylcarbamate (1.3 g, 75%) as a white semi-solid.

Using general procedure E, the above carbamate (400 mg, 1.12 mmol), phenylboronic acid (267 mg, 2.22 mmol) and [PdCl$_2$(pddf)]CH$_2$Cl$_2$ the title compound as a viscous oil (100 mg, 25%). $^1$H NMR (500 MHz, CDCl$_3$) δ 7.47 (d, J=7.5 Hz, 2H), 7.43 (d, J=8.0 Hz, 2H), 7.33 (t, J=7.5 Hz, 2H), 7.26-7.15 (m, 3H), 5.93 (br s, 0.6H), 5.89 (br s, 0.4H), 4.67 (m, 1H), 3.20-3.06 (m, 1H), 2.88-2.42 (m, 5H), 1.98-1.08 (m, 9H) ppm. $^{13}$C NMR (125 MHz, CDCl$_3$) δ 155.0, 141.0, 139.7, 138.2, 127.7, 126.1, 126.0, 124.8, 124.1, 70.0, 54.5, 46.3, 45.4, 34.1, 24.3, 23.2, 18.3, 17.0 ppm. Purity: 100% LCMC (214 nm & 254 nm); retention time 1.52 min; (M+1) 363.

Preparation R

Example 65 quinuclidin-3-yl 1-(4-(pyridin-2-yl)phenyl)cyclopropylcarbamate

To a solution of quinuclidin-3-yl 1-(4-bromophenyl)cyclopropylcarbamate (870 mg, 2.43 mmol) in 30 mL 1,4-dioxane, was added bis(pinacolato)diboron (1.81 g, 7.22 mmol), CH$_3$COOK (2.10 g, 21.4 mmol), and [PdCl$_2$(pddf)]CH$_2$Cl$_2$ (97 mg, 0.12 mmol). The mixture was stirred at 80° C. for 18 h. The solvent was evaporated and the residue was extracted with EtOAc. The extracts were concentrated and purified by silica gel column chromatography (eluting with EtOAc/methanol from 20/1 to 10/1, containing 1% of TEA) to give quinuclidin-3-yl 1-(4-(4,4,5,5-tetramethyl-1,3,2-dioxaborolan-2-yl)phenyl)cyclopropylcarbamate (260 mg, 33%) as a brown semi-solid.

Using general procedure E, the above boronate (260 mg, 0.632 mmol), 2-bromopyridine (149 mg, 0.941 mmol) and Pd$_2$(dba)$_3$ (32.0 mg, 0.036 mmol) gave the title as a white semi-solid compound (70 mg, 31%). $^1$H NMR (500 MHz, CDCl$_3$) δ 8.58 (d, J=4.5 Hz, 1H), 7.82 (d, J=7.0 Hz, 2H), 7.66-7.57 (m, 2H), 7.23-7.15 (m, 2H), 7.11 (t, J=5.0 Hz, 1H), 6.16 (br s, 0.6H), 5.97 (br s, 0.4H), 4.63 (m, 1H), 3.17-3.02 (m, 1H), 2.90-2.38 (m, 5H), 1.90-1.10 (m, 9H) ppm. $^{13}$C NMR (125 MHz, CDCl$_3$) δ 156.1, 155.2, 148.6, 143.0, 136.3, 135.7, 125.9, 124.5, 120.9, 119.4, 70.3, 54.6, 46.3, 45.4, 34.1, 24.4, 23.5, 18.5, 17.3 ppm. Purity: 100% LCMS (214 nm & 254 nm); retention time 1.18 (M+H) 364.

Example 66 quinuclidin-3-yl 1-(4-(pyrimidin-5-yl)phenyl)cyclopropylcarbamate

Using general procedure E, the above quinuclidin-3-yl 1-(4-bromophenyl)cyclopropyl-carbamate (400 mg, 1.10 mmol), pyrimidin-5-ylboronic acid (204 mg, 1.64 mmol) and [PdCl$_2$(pddf)]CH$_2$Cl$_2$ gave the title compound as a viscous oil (110 mg, 28%). $^1$H NMR (500 MHz, CDCl$_3$) δ(s, 1H), □□ (s, 2H), 7.44 (d. J=8.5 Hz, 2H), 7.33-7.25 (m, 2H), 6.02 (br s, 0.7H), 6.02 (br s, 0.3H), 4.65 (m, 1H), 3.20-3.05 (m, 1H), 2.86-2.40 (m, 5H), 1.98-1.12 (m, 9H) ppm. $^{13}$C NMR (125 MHz, CDCl$_3$) δ 156.3, 155.1, 153.7, 143.3, 132.9, 131.1, 126.0, 125.3, 70.5, 54.7, 46.4, 45.4, 34.1, 24.4, 23.5, 18.5, 17.5 ppm. Purity: 100% LCMS (214 nm & 254 nm); retention time 1.29 min; (M+1) 365.

Example 67

(S)-quinuclidin-3-yl 1-(4'-fluorobiphenyl-4-yl)cyclopropylcarbamate

Using general procedure E, (S)-quinuclidin-3-yl 1-(4-bromophenyl)cyclopropyl carbamate, 4-F-phenylboronic acid and [PdCl$_2$(pddf)]CH$_2$Cl$_2$ gave the title compound as a white solid (45%). $^1$H NMR (500 MHz, DMSO-d$_6$) δ 8.06-7.83 (d, 1H), 7.69-7.66 (m, 2H), 7.59-7.55 (m, 2H), 7.29-7.22 (m, 4H), 4.56-4.54 (m, 1H), 3.13-2.32 (m, 6H), 1.91-1.19 (m, 9H) ppm. $^{13}$C NMR (125 MHz, DMSO-d$_6$) δ 163.2, 161.2, 156.4, 143.7, 136.9, 128.9, 128.8, 126.8, 125.6, 116.2, 116.0, 70.7, 55.8, 47.4, 46.4, 34.8, 25.7, 24.6, 19.6, 18.7, 18.6 ppm. Purity: >97% LCMS (214 nm & 254 nm); retention time 1.96 min; (M+1) 381.2.

Example 68

1-azabicyclo[3.2.2]nonan-4-yl 1-(4'-fluorobiphenyl-4-yl)cyclopropylcarbamate

Using general procedure E, 1-azabicyclo[3.2.2]nonan-4-yl 1-(4-bromophenyl)-cyclopropyl carbamate, 4-F-phenylboronic acid and [PdCl$_2$(pddf)]CH$_2$Cl$_2$ gave the title compound as a white solid (27%). $^1$H NMR (500 MHz, CDCl$_3$) δ 7.52-7.48 (m, 4H), 7.33-7.28 (m, 2H), 7.14-7.11 (t, J=8.5 Hz, 2H), 5.47-5.33 (d, 1H), 4.93-4.89 (m, 1H), 3.15-2.75 (m, 6H), 2.10-0.88 (m, 11H) ppm. $^{13}$C NMR (125 MHz, CDCl$_3$) δ 163.4, 161.4, 155.7, 142.1, 138.3, 136.9, 128.5, 128.5, 127.0, 125.9, 125.4, 115.7, 115.5, 78.8, 51.7, 48.3, 44.9, 35.2, 33.7, 30.6, 29.7, 24.8, 22.2, 18.1 ppm. Purity: >99% LCMS (214 nm & 254 nm): retention time 1.56 min: (M+1) 395.2.

Example 69

(S)-quinuclidin-3-yl 1-(4-(5-fluoropyridin-2-yl)phenyl)cyclopropylcarbamate

Using general procedure E, (S)-quinuclidin-3-yl (1-(4-(4,4,5,5-tetramethyl-1,3,2-dioxa-borolan-2-yl)phenyl)cyclopropyl)carbamate, 2-bromo-5-fluoropyridine and [PdCl$_2$(pddf)]CH$_2$Cl$_2$ gave the title compound as a white solid (34%). $^1$H NMR (500 MHz, CDCl$_3$) δ 8.51-8.52 (d, J=3.5 Hz, 1H), 7.87-7.85 (d, J=10.5 Hz, 2H), 7.69-7.67 (m, 1H), 7.47-7.42 (m, 1H), 7.32-7.27 (m, 2H), 5.79-5.66 (d, 1H), 4.73-4.71 (t, J=5.0 Hz, 1H), 3.22-3.19 (m, 1H), 2.87-2.61 (m, 5H), 2.01-1.22 (m, 9H) ppm. $^{13}$C NMR (125 MHz, CDCl$_3$) δ 160.8, 157.4, 156.1, 153.5, 144.4, 137.8, 136.3, 126.7, 125.7, 124.9, 123.6, 121.1, 71.6, 55.7, 47.4, 46.5, 35.3, 29.7, 25.4, 24.8, 19.4, 18.2 ppm. Purity: >99% LCMS (214 nm & 254 nm); retention time 1.41 min; (M+1) 382.2.

Preparation S

Example 70

(S)-1-(1-(4'-fluorobiphenyl-4-yl)cyclopropyl)-3-(3-methylquinuclidin-3-yl)urea

In a three-necked round-bottomed flask fitted with two pressure-equalizing addition funnels and a rubber tube connected with a gas flowmeter, a suspension of 1-(4'-fluoro-[1,1'-biphenyl]-4-yl)cyclopropanamine (1.50 g, 7.07 mmol) in a mixture of 20 mL of water and 1 mL of conc. HCl was stirred for 10 min. Toluene (10 mL) was added and the solution was maintained under vigorous stirring and cooled down to 0° C. A solution of triphosgene (3.10 g, 10.6 mmol) in 20 mL of toluene and 40 mL of saturated aqueous NaHCO$_3$ was added dropwise over 1 h period. The reactionnal mixture was stirred for an additional 30 min. The stirring was stopped and the upper toluene layer was then separated out, dried (Na$_2$SO$_4$) and concentrated to afford the corresponding isocyanate which is used in the next step without further purification.

To a solution of the above isocyanate (134 mg, 0.571 mmol) in 15 mL of toluene was added (S)-3-methylquinuclidin-3-amine (80 mg, 0.57 mmol). The resulting mixture was heated at reflux overnight, cooled to ambient temperature and concentrated in vacuo to give a residue, which was purified by reverse phase chromatography on a combiflash (0-20% MeCN in water) to afford the title compound as a white solid (73 mg, 33%). $^1$H NMR (500 MHz CDCl$_3$) δ 7.52-7.48 (m, 4H), 7.27-7.25 (d, J=10.0 Hz, 2H), 7.13-7.09 (m, 2H), 5.39 (s, 1H), 4.78 (s, 1H), 2.95-2.71 (m, 5H), 2.65-2.64 (m, 1H), 1.94-1.93 (m, 1H), 1.69-1.68 (m, 1H), 1.46-1.38 (m, 5H), 1.36-1.33 (m, 4H), 1.26-1.23 (m, 1H) ppm. $^{13}$C NMR (125 MHz CDCl$_3$) δ 163.5, 161.5, 157.5, 141.5, 138.5, 136.6, 136.6, 128.5, 128.4, 127.2, 124.7, 115.8, 115.6, 63.8, 52.3, 46.6, 46.3, 34.9, 31.0, 25.0, 23.2, 22.5, 20.2, 20.0 ppm. Purity: >99% LCMS (214 nm & 254 nm); retention time 1.51 min; (M+H$^+$) 394.2.

Example 71

(S)-1-azabicyclo[2.2.2]oct-3-yl[1-(2',4'-difluorobiphenyl-4-yl)cyclopropyl]carbamate Using general procedure E, (S)-quinuclidin-3-yl 1-(4-bromophenyl)cyclopropylcarbamate (0.446 g, 1.22 mmol), 2,4-difluorophenyl boronic acid (0.386 g, 2.44 mmol) and Pd(OAc)$_2$ (0.015 g, 0.067 mmol) gave the title compound as a tan solid (0.111 g, 23%). $^1$H NMR (CDCl$_3$) δ 7.43 (dd, J=8.4, 1.6 Hz, 2H), 7.40-7.33 (m, 1H), 7.31 (d, J=7.7 Hz, 2H), 6.99-6.81 (m, 2H), 5.54 (d, J=48.0 Hz, 1H), 4.82-4.65 (m, 1H), 3.30-3.07 (m, 1H), 2.98-2.44 (m, 5H), 1.97 (d, J=32.7 Hz, 1H), 1.83 (d, J=10.3 Hz, 1H), 1.64 (s, 1H), 1.52 (s, 1H), 1.39 (s, 1H), 1.31 (d, J=6.8 Hz, 4H) ppm. $^{13}$C NMR major rotomer (CDCl$_3$) δ 162.2 (dd, J=12.8, 249.1 Hz), 159.8 (dd, J=11.8, 251.0 Hz), 156.9, 156.0, 142.6, 133.1, 131.3 (m), 128.9, 125.6, 124.9, 111.5 (dd, J=3.9, 21.2 Hz) 104.4 (dd, J=25.2, 29.4 Hz), 72.1, 71.6, 55.7, 47.4, 46.5, 35.7, 35.3, 25.5, 24.6, 24.4, 19.5, 18.1 ppm. Purity: LCMS >99.3% (214 nm & 254 nm): retention time 0.90 min: (M+1) 399.0

Example 72

1-azabicyclo[2.2.2]oct-3-yl[1-(4'-methoxybiphenyl-4-yl)cyclopropyl]carbamate

Using general procedure E, quinuclidin-3-yl 1-(4-bromophenyl)cyclopropylcarbamate (0.485 g, 1.33 mmol), 4-methoxyphenyl boronic acid (0.404 g, 2.66 mmol) and Pd(OAc)$_2$ (0.016 g, 0.071 mmol) gave the title compound as a grey solid (0.337 mg, 65%). $^1$H NMR (CDCl$_3$) δ 7.48 (dd, J=8.6, 5.5 Hz, 4H), 7.29 (d, J=7.6 Hz, 2H), 6.96 (d, J=8.8 Hz, 2H), 5.58 (d, J=48.7 Hz, 1H), 4.83-4.63 (m, 1H), 3.84 (s, 3H), 3.20 (dd, J=24.0, 15.5 Hz, 1H), 2.97-2.42 (m, 5H), 1.97 (d, J=30.9 Hz, 1H), 1.81 (s, 1H), 1.75-1.33 (m, 3H), 1.28 (d, J=6.8 Hz, 4H) ppm. $^{13}$C NMR major rotomer (CDCl$_3$) δ 159.1, 156.0, 141.4, 139.0, 133.4, 128.0, 126.7, 125.9, 114.2, 71.5, 55.7, 55.3, 47.4, 46.5, 35.3, 25.5, 24.6, 19.6, 17.8 ppm. Purity: LCMS >97.1% (214 nm & 254 nm): retention time 0.88 min: (M+1) 393.4.

Preparation T

Example 73 quinuclidin-3-yl 2-(5-(4-fluorophenyl)thiophen-3-yl)propan-2-ylcarbamate

To a stirred and cooled (0° C.) solution of ethyl 5-bromothiophene-3-carboxylate (13.30 g, 56.57 mmol) in THF (100 mL) was added a solution of methylmagnesium bromide in diethyl ether [3.0 M] (55.0 mL, 165 mmol), dropwise over 20 minutes. After 2 hours, the reaction solution was concentrated. The residue was taken up in aqueous NH$_4$Cl (200 mL) and extracted with ethyl acetate (2×100 mL). The combined extracts were dried (Na$_2$SO$_4$) and concentrated. The resulting amber oil was purified by flash chromatography using a hexane/ethyl acetate gradient to afford 2-(5-bromothiophen-3-yl)propan-2-ol as a pale amber oil (8.05 g, 64%).

To a stirred solution of 2-(5-bromothiophen-3-yl)propan-2-ol (8.03 g, 36.3 mmol) in methylene chloride (80 mL) was added sodium azide (7.08 g, 109 mmol) followed by trifluoroacetic acid (8.0 mL: dropwise over 5-6 minutes). The thickening suspension was stirred for 1.5 hour before diluting with water (350 mL) and extracting with ethyl acetate (1×200 mL). The organic layer was washed with aqueous NaHCO$_3$ (1×250 mL), dried (Na$_2$SO$_4$) and concentrated to afford the crude azide product. To a stirred solution of this material in THF (160 mL) was added water (11 mL) followed by triphenylphosphine (23.8 g, 90.7 mmol). The reaction was stirred for 2 days before concentrating. The resulting residue was dissolved in ethyl acetate (250 mL) and extracted with 1 N aqueous HCl (4×75 mL). The combined extracts were basified with concentrated NH$_4$OH and extracted with ethyl acetate (2×100 mL). These extracts were, in turn, dried (Na$_2$SO$_4$) and concentrated. The resulting amber oil was purified by flash chromatography using a methylene chloride/methanol/ammonia gradient to afford a mixture of 2-(5-bromothiophen-3-yl)propan-2-amine and triphenylphosphine oxide (~70/30 ratio) as a viscous amber oil (1.32 g, 17%).

To a stirred solution of 3-quinuclidinol (3.00 g, 23.6 mmol) in THF (100 mL) was added 4-nitrophenyl chloroformate (5.94 g, 29.5). After stirring for 4 hours, the precipitate was filtered off, rinsed with THF and air dried on the frit under house vacuum. The filtercake was dissolved in ethyl acetate (150 mL) and washed with aqueous NaHCO$_3$ (1×150 mL) and water (2×150 mL). The organic layer was dried (Na$_2$SO$_4$) and concentrated to afford crude 4-nitrophenyl quinuclidin-3-yl carbonate product, which was used in the next step without purification.

To a stirred solution of 2-(5-bromothiophen-3-yl)propan-2-amine (0.366 g, 1.66 mmol) in THF (10 mL) was added 4-nitrophenyl quinuclidin-3-yl carbonate (0.571 g, 1.95 mmol) and a few granules of 4-(dimethylamino)pyridine. The mixture was refluxed overnight, concentrated and partitioned between ethyl acetate (50 mL) and aqueous NaHCO$_3$ (50 mL). The organic layer was washed again with aqueous NaHCO$_3$ (1×50 mL), dried (Na$_2$SO$_4$) and concentrated. The resulting dirty yellow gum was purified by flash chromatography using a chloroform/methanol/ammonia gradient to afford quinuclidin-3-yl (1-(5-bromothiophen-3-yl)cyclopropyl)carbamate as an off-white solid (0.305 g, 49%).

Using general procedure E, quinuclidin-3-yl (1-(5-bromothiophen-3-yl)cyclopropyl)carbamate (0.227 g, 0.742 mmol), 4-fluorophenyl boronic acid (0.208 g, 1.49 mmol), tricyclohexylphosphine (0.021 g, 0.075 mmol), potassium phosphate (0.866, 4.08 mmol) and palladium acetate (8.0 mg, 36 □mol) gave the title compound as a gray solid (0.142 g, 49%). $^1$H NMR (400 MHz, CDCl$_3$) δ 7.60-7.45 (m, 2H), 7.24-7.19 (m, 1H), 7.10-6.97 (m, 3H), 5.23 (br s, 1H), 4.72-4.61 (m, 1H), 3.30-3.04 (m, 1H), 3.03-2.25 (m, 5H), 2.09-1.02 (m, 11H) ppm. $^{13}$C NMR (400 MHz, CDCl$_3$) δ 162.3 (d, J=247.1 Hz), 154.5, 149.8, 143.6, 130.7, 127.4 (d, J=8.1 Hz), 121.8, 118.9, 115.8 (d, J=21.6 Hz), 70.8, 55.5, 53.4, 47.3, 46.4, 29.0, 25.4, 24.4, 19.4 ppm. Purity: 95.8% UPLCMS (210 nm & 254 nm); retention time 0.90 min; (M+1) 389.

Preparation U

Example 74

(S)-quinuclidin-3-yl 2-(3-(4-fluorophenyl)isothiazol-5-yl)propan-2-ylcarbamate

To stirred solution of 2-(3-(4-fluorophenyl)isothiazol-5-yl)propan-2-amine (1.21 g, 5.12 mmol) in toluene was added a solution of phosgene in toluene[~1.9 M] (10.8 mL, 20.5 mmol). The reaction was heated at reflux for two hours and then concentrated. The residue was coevaporated with toluene (2×15 mL) to afford the crude isocyanate intermediate as golden oil. This material was taken up in toluene (10 mL) and treated with (S)-3-quinuclidinol (0.749 g, 5.89 mmol). The reaction was heated at reflux overnight and concentrated. The residue was purified by flash chromatography using a chloroform/methanol/ammonia gradient to afford the title compound as a white solid (0.971 g, 49%). $^1$H NMR (400 MHz, DMSO-d$_6$) δ 8.09-8.00 (m, 2H), 7.87 (br s, 1H), 7.75 (s, 1H), 7.35-7.25 (m, 2H), 4.54-4.45 (m, 1H), 3.14-2.92 (m, 1H), 2.87-2.17 (m, 5H), 1.98-0.98 (m, 11H) ppm. $^{13}$C NMR (400 MHz, DMSO-d$_6$) δ 180.1, 165.6, 162.6 (d, J=246.4 Hz), 154.7, 131.2 (d, J=3.0 Hz), 128.7 (d, J=8.4 Hz), 118.2, 115.7 (d, J=21.8 Hz), 70.6, 55.3, 52.8, 46.9, 45.9, 29.9, 25.2, 24.2, 19.2 ppm. Purity: 100% UPLCMS (210 nm & 254 nm); retention time 0.82 min; (M+1) 390.

Preparation V

Example 75

(S)-quinuclidin-3-yl 2-(2-(4-fluorophenyl)thiazol-4-yl)propan-2-ylcarbamate

To a stirred solution of 4-fluorothiobenzamide (8.94 g, 57.6 mmol) in ethanol (70 mL) was added ethyl 4-chloroacetoacetate (7.8 mL, 58 mmol). The reaction was heated at reflux for 4 hours, treated with an addition aliquot of ethyl 4-chloroacetoacetate (1.0 mL, 7.4 mmol) and refluxed for an additional 3.5 hours. The reaction was then concentrated and the residue was partitioned between ethyl acetate (200 mL) and aqueous NaHCO$_3$ (200 mL). The organic layer was combined with a backextract of the aqueous layer (ethyl acetate, 1×75 mL), dried (Na$_2$SO$_4$) and concentrated. The resulting amber oil was purified by flash chromatography using a hexane/ethyl acetate gradient to afford ethyl 2-(2-(4-fluorophenyl)thiazol-4-yl)acetate as a low melting, nearly colorless solid (13.58 g, 89%).

To a stirred solution of ethyl 2-(2-(4-fluorophenyl)thiazol-4-yl)acetate (6.28 g, 23.7 mmol) in DMF (50 mL) was added sodium hydride [60% dispersion in mineral oil] (2.84 g, 71.0 mmol). The frothy mixture was stirred for 15 minutes before cooling in an ice bath and adding iodomethane (4.4 mL, 71 mmol). The reaction was stirred overnight, allowing the cooling bath to slowly warm to room temperature. The mixture was then concentrated and the residue partitioned between ethyl acetate (80 mL) and water (200 mL). The organic layer was washed with a second portion of water (1×200 mL), dried (Na$_2$SO$_4$) and concentrated. The resulting amber oil was purified by flash chromatography using a hexane/ethyl acetate gradient to afford ethyl 2-(2-(4-fluorophenyl)thiazol-4-yl)-2-methylpropanoate as a colorless oil (4.57 g, 66%).

To a stirred solution of ethyl 2-(2-(4-fluorophenyl)thiazol-4-yl)-2-methylpropanoate (4.56 g, 15.5 mmol) in 1:1:1 THF/ethanol/water (45 mL) was added lithium hydroxide monohydrate (2.93 g, 69.8 mmol). The reaction was stirred overnight, concentrated and redissolved in water (175 mL). The solution was washed with ether (1×100 mL), acidified by the addition of 1.0 N HCl (80 mL) and extracted with ethyl acetate (2×70 mL). The combined extracts were dried (Na$_2$SO$_4$) and concentrated to afford 2-(2-(4-fluorophenyl)thiazol-4-yl)-2-methylpropanoic acid as a white solid (4.04 g, 98%). This material was used in the next step without purification.

To a stirred and cooled (0° C.) solution of 2-(2-(4-fluorophenyl)thiazol-4-yl)-2-methylpropanoic acid (4.02 g, 15.2 mmol) in THF (100 mL) was added triethylamine (4.2 mL, 30 mmol) followed by isobutyl chloroformate (3.0 mL, 23 mmol). The reaction was stirred cold for another 1 hour before adding a solution of sodium azide (1.98 g, 30.5 mmol) in water (20 mL). The reaction was stirred overnight, allowing the cooling bath to slowly warm to room temperature. The mixture was then diluted with water (100 mL) and extracted with ethyl acetate (2×60 mL). The combined extracts were washed with aqueous NaHCO$_3$ (1×150 mL) and brine (1×100 mL), dried (Na$_2$SO$_4$) and concentrated. After coevaporating with toluene (2×50 mL), the resulting white solid was taken up in toluene (100 mL) and refluxed for 4 hours. (S)-3-quinuclidinol (3.87 g, 30.4 mmol) was then added and reflux was continued overnight. The reaction was concentrated and the residue partitioned between ethyl acetate (100 mL) and aqueous NaHCO$_3$ (150 mL). The organic layer was washed with water (1×150 mL), dried (Na$_2$SO$_4$) and concentrated. The resulting off-white solid was purified by flash chromatography using a chloroform/methanol/ammonia gradient to afford the title compound as a white solid (4.34 g, 73%). $^1$H NMR (400 MHz, CDCl$_3$) δ 7.96-7.88 (m, 2H), 7.16-7.04 (m, 3H), 5.55 (br s, 1H), 4.69-4.62 (m, 1H), 3.24-3.11 (m, 1H), 3.00-2.50 (m, 5H), 2.01-1.26 (m, 11H) ppm. $^{13}$C NMR (400 MHz, CDCl$_3$) δ 166.4, 165.1, 163.8 (d, J=250.3 Hz), 162.9, 155.0, 130.1 (d, J=3.3 Hz), 128.4 (d, J=8.5 Hz), 115.9 (d, J=22.3 Hz), 112.5, 71.2, 55.7, 54.2, 47.5, 46.5, 28.0, 25.5, 24.7, 19.6 ppm. Purity: 100% UPLCMS (210 nm & 254 nm): retention time 0.83 min: (M+1) 390.

Preparation W

Example 76

(S)-quinuclidin-3-yl 2-(4-(4-fluorophenyl)thiazol-2-yl)propan-2-ylcarbamate

To a stirred solution of ethyl 3-amino-3-thioxopropanoate (20.00 g, 135.9 mmol) in ethanol (120 mL) was added 2-bromo-4'-fluoroacetophenone (29.49 g, 135.9 mmol). The mixture was refluxed for 1 hour, concentrated and partitioned between ethyl acetate (300 mL) and aqueous NaHCO$_3$ (400 mL). The organic layer was combined with a backextract of the aqueous layer (ethyl acetate, 1×100 mL), dried (Na$_2$SO$_4$) and concentrated. The resulting light brown solid was purified by flash chromatography using a hexane/ethyl acetate gradient to afford ethyl 2-(4-(4-fluorophenyl)thiazol-2-yl)acetate as an off-white solid (29.92 g, 83%).

To a stirred and cooled (−78° C.) solution of ethyl 2-(4-(4-fluorophenyl)thiazol-2-yl)acetate (10.00 g, 37.69 mmol) in THF (250 mL) was added a solution of potassium t-butoxide in THF [1.0 M] (136 mL, 136 mmol), dropwise over 15 minutes, followed by 18-crown-6 (1.6 mL, 7.5 mmol). After an additional 30 minutes at −78° C., iodomethane (8.5 mL) was added, dropwise over 5 minutes. The reaction was stirred cold for another 2 hours before pouring into water (450 mL) and extracting with ethyl acetate (2×150 mL). The combined extracts were washed with brine (1×200 mL), dried (Na$_2$SO$_4$) and concentrated. The resulting brown oil was purified by flash chromatography using a hexane/ethyl acetate gradient to afford ethyl 2-(4-(4-fluorophenyl)thiazol-2-yl)-2-methylpropanoate as a pale amber oil (8.64 g, 78%).

To a stirred solution of ethyl 2-(4-(4-fluorophenyl)thiazol-2-yl)-2-methylpropanoate (0.900 g, 3.07 mmol) in 1:1:1 THF/ethanol/water (15 mL) was added lithium hydroxide monohydrate (0.451 g, 10.7 mmol). After overnight stirring, the reaction was concentrated and redissolved in water (80 mL). The solution was washed with ether (1×50 mL), acidified with the addition of 1 N HCl (15 mL) and extracted with ethyl acetate (2×50 mL). The combined extracts were dried (Na$_2$SO$_4$) and concentrated to afford 2-(4-(4-fluorophenyl)thiazol-2-yl)-2-methylpropanoic acid as a pale golden solid (0.808 g, 99%).

To stirred and cooled (0° C.) solution of 2-(4-(4-fluorophenyl)thiazol-2-yl)-2-methylpropanoic acid (0.784 g, 2.96 mmol) in THF (25 mL) was added triethylamine (0.82 mL, 5.9 mmol) followed by isobutyl chloroformate (0.58 mL, 4.4 mmol). The reaction was stirred cold for another 1 hour before adding a solution of sodium azide (0.385 g, 5.92 mmol) in water (7 mL). The reaction was stirred overnight, allowing the cooling bath to slowly warm to room temperature. The mixture was then diluted with water (100 mL) and extracted with ethyl acetate (2×60 mL). The combined extracts were washed with aqueous NaHCO$_3$ (1×150 mL) and brine (1×100 mL), dried (Na$_2$SO$_4$) and concentrated. After coevaporating with toluene (2×30 mL), the resulting off-white solid was taken up in toluene (25 mL) and refluxed for 4 hours. (S)-3-quinuclidinol (0.753 g, 5.92 mmol) was then added and reflux was continued for 3 hours. The reaction was concentrated and the residue was purified by flash chromatography using a chloroform/methanol/ammonia gradient to afford the title compound as a white solid (0.793 g, 69%). $^1$H NMR (400 MHz, CDCl$_3$) δ 7.90-7.81 (m, 2H), 7.32 (s, 1H), 7.14-7.05 (m, 2H), 5.76 (br s, 1H), 4.72-4.65 (m, 1H), 3.26-3.10 (m, 1H), 3.03-2.37 (m, 5H), 2.05-1.23 (m, 1H) ppm. $^{13}$C NMR (400 MHz, CDCl$_3$) δ 177.6, 162.6 (d, J=248.4 Hz), 154.8, 153.6, 130.8 (d, J=3.2 Hz), 128.1 (d, J=8.1 Hz), 115.9 (d, J=21.7 Hz), 112.2, 71.6, 55.7, 47.4, 46.5, 29.1, 25.4, 24.7, 19.6 ppm. Purity: 100% UPLCMS (210 nm & 254 nm): retention time 0.82 min: (M+1) 390.

Example 77 quinuclidin-3-yl 1-(4-(benzyloxy)phenyl)cyclopropylcarbamate

A mixture of 4-cyanophenol (5.0 g, 42 mmol), benzylbromide (8.6 g, 50 mmol), potassium carbonate (11.6 g, 84.0 mmol) in DMF (40 mL) was stirred at 100° C. for 3 h. The precipitate was filtered off and the filtrate was diluted with EtOAc and washed with water. The organic layer was dried (Na$_2$SO$_4$) and concentrated. The resulting crude product was purified by silica gel column chromatography (eluting with petroleum ether/EtOAc from 20/1 to 5/1) to give 4-(benzyloxy)benzonitrile as a white solid (8.1 g, 92%).

Using general procedure G, 4-(benzyloxy)benzonitrile (6.00 g, 28.7 mmol) was converted to the corresponding 1-(4-(benzyloxy)phenyl)cyclopropanamine as a yellow solid (1.8 g, 26%).

Using general procedure A, 1-(4-(benzyloxy)phenyl)cyclopropanamine (600 mg, 2.51 mmol) and quinuclidin-3-ol gave the title compound as a viscous oil (170 mg, 17%). $^1$H NMR (500 MHz, CDCl$_3$) δ 7.34 (d, J=7.0 Hz, 2H), 7.30 (t, J=7.0 Hz, 2H), 7.25 (t, J=7.0 Hz, 1H), 7.16 (d, J=8.5 Hz, 1H), 7.07 (d, J=7.0 Hz, 1H), 6.83 (d, J=8.0 Hz, 2H), 5.50 (br s, 0.6H), 5.40 (br s, 0.4H), 4.96 (s, 2H), 4.64 (m, 1H), 3.20-3.15 (m, 1H), 2.88-2.50 (m, 5H), 1.95-1.05 (m, 9H) ppm. $^{13}$C NMR (125 MHz, CDCl$_3$) δ 156.6, 154.8, 136.0, 134.2, 127.6, 126.9, 126.4, 125.4, 113.7, 70.0, 69.0, 54.5, 46.3, 45.4, 34.2, 24.3, 23.3, 18.3, 15.8 ppm. Purity: >90% LCMS (214 nm & 254 nm); retention time 1.57 min; (M+1) 393.

Example 78 quinuclidin-3-yl biphenyl-3-ylmethylcarbamate

To a stirred and cooled (0° C.) solution of triphosgene (0.80 g, 2.7 mmol) in THF (20 mL) was added, dropwise, a mixture of (3-bromophenyl)methanamine (1.0 g, 5.4 mmol) and triethylamine (1.08 g, 10.7 mmol) in THF (30 mL) over 2 h. After the addition was complete, the mixture was refluxed for 1 h and then cooled to room temperature. Quinuclidin-3-ol (1.40 g, 10.7 mmol) was added, and the mixture was refluxed for 18 h. The solvent was removed in vacuo, and the residue was dissolved in EtOAc, washed with water, dried over Na$_2$SO$_4$, and concentrated. The crude residue was purified by silica gel column chromatography (eluting with EtOAc/methanol=10/1) to give quinuclidin-3-yl 3-bromobenzylcarbamate as a colourless liquid (0.68 g, 37%).

Using general procedure E, quinuclidin-3-yl 3-bromobenzylcarbamate (237 mg, 0.700 mmol), phenylboronic acid (171 mg, 1.4 mmol) and [PdCl$_2$(pddf)]CH$_2$Cl$_2$ gave the title compound as a viscous semi-solid (110 mg, 47%). $^1$H NMR (500 MHz, CDCl$_3$) δ 7.57 (d, J=7.5 Hz, 2H), 7.50 (m, 2H), 7.62-7.38 (m, 3H), 7.35 (t, J=7.5 Hz, 1H), 7.28 (d, J=8.0 Hz, 1H), 5.32-5.17 (m, 1H), 7.78 (m, 1H), 4.42 (d, J=6.0 Hz, 2H), 3.26 (m, 1H), 2.95-2.65 (m, 5H), 2.05 (m, 1H), 1.84 (m, 1H), 1.70 (m, 1H), 1.58 (m, 1H), 1.42 (m, 1H) ppm. $^{13}$C NMR (125 MHz, CDCl$_3$) δ 155.2, 140.7, 139.8, 138.0, 128.1, 127.8, 126.4, 126.1, 125.5, 125.4, 125.3, 70.1, 54.4, 46.2, 45.3, 44.1, 24.3, 23.1, 18.2 ppm. Purity: >98% LCMS (214 nm & 254 nm); retention time 1.44 min; (M+1) 337.

Example 79 quinuclidin-3-yl 3-(pyrimidin-5-yl)benzylcarbamate

Using general procedure E, quinuclidin-3-yl 3-bromobenzylcarbamate (203 mg, 0.600 mmol), pyrimidin-5-ylboronic acid (149 mg, 1.2 mmol) and [PdCl$_2$(pddf)]CH$_2$Cl$_2$ gave the title compound as a viscous semi-solid (110 mg, 54%). $^1$H NMR (500 MHz, CDCl$_3$) δ 9.20 (s, 1H), 8.94 (s, 2H), 7.51 (m, 3H), 7.40 (m, 1H), 5.62 (m, 1H), 4.81 (m, 1H), 4.50-4.40 (m, 2H), 3.30 (m, 1H), 2.97-2.65 (m, 5H), 2.12 (m, 1H), 1.92-1.82 (m, 1H), 1.79-1.69 (m, 1H), 1.65-1.56 (m, 1H), 1.50-1.42 (m, 1H) ppm. $^{13}$C NMR (125 MHz, CDCl$_3$) δ 157.6, 156.2, 154.9, 140.1, 134.7, 134.1, 129.8, 128.2, 126.2, 70.9, 55.2, 47.2, 46.2, 44.8, 25.2, 23.8, 19.0 ppm. Purity: >95% LCMS (214 nm & 254 nm); retention time 1.22 min; (M+1) 339.

Example 80 quinuclidin-3-yl 3-(benzyloxy)benzylcarbamate

A mixture of 2-(3-hydroxyphenyl)acetic acid (0.6 g, 3.95 mmol), benzyl bromide (0.710 g, 4.14 mmol), potassium hydroxide (0.550 g, 9.87 mmol), KI (13 mg, 0.079 mmol) in THF (20 mL) was refluxed for 18 h. The solvent was removed and the residue was dissolved in 50 mL of water and extracted with ether. The aqueous layer was acidified with aqueous 1N HCl and the white precipitate that formed was filtered off to afford 2-(3-(benzyloxy)phenyl)acetic acid as a gray solid (0.87 g, 91%).

Using general procedure H, 2-(3-(benzyloxy)phenyl)acetic acid (242 mg, 1.00 mmol) and quinuclidin-3-ol gave the title compound as a viscous semi-solid (200 mg, 55%). $^1$H NMR (500 MHz, CDCl$_3$) δ 7.42 (d, J=7.5 Hz, 2H), 7.38 (t, J=7.5 Hz, 2H), 7.32 (t, J=7.0 Hz, 1H), 7.24 (d, J=7.5 Hz, 1H), 6.92 (s, 1H), 6.88 (d, J=7.0 Hz, 2H), 5.30 (m, 1H), 5.05 (s, 2H), 4.75 (m, 1H), 4.32 (d, J=6.0 Hz, 2H), 3.23 (m, 1H), 2.93-2.60 (m, 5H), 2.08-1.96 (m, 1H), 1.88-1.75 (m, 1H), 1.72-1.62 (m, 1H), 1.60-1.50 (m, 1H), 1.42-1.34 (m, 1H) ppm. $^{13}$C NMR (125 MHz, CDCl$_3$) δ 159.1, 156.3, 140.2, 136.8, 129.7, 128.6, 128.0, 127.5, 120.0, 114.1, 113.6, 71.3, 70.0, 55.5, 47.3, 46.4, 45.0, 25.4, 24.3, 19.3 ppm. Purity: >95% LCMS (214 nm & 254 nm); retention time 1.51 min; (M+1) 367

Example 81 quinuclidin-3-yl 4-phenoxybenzylcarbamate

Using general procedure H, 2-(3-phenoxyphenyl)acetic acid (228 mg, 1.00 mmol), and quinuclidin-3-ol gave the title compound as a viscous semi-solid (70 mg, 20%). $^1$H NMR (500 MHz, CDCl$_3$) δ 7.29-7.18 (m, 3H), 7.03 (t, J=7.5 Hz, 1H), 6.96-6.90 (m, 3H), 6.86 (s, 1H), 6.82 (d, J=8.5 Hz, 1H), 5.40-5.15 (m, 1H), 4.70 (m, 1H), 4.25 (d, J=6.0 Hz, 2H), 3.18 (m, 1H), 2.90-2.60 (m, 5H), 2.03-1.92 (m, 1H), 1.82-1.74 (m, 1H), 1.68-1.60 (m, 1H), 1.57-1.45 (m, 1H), 1.40-1.32 (m, 1H)

ppm. $^{13}$C NMR (125 MHz, CDCl$_3$) δ 156.6, 155.9, 155.1, 139.6, 129.0, 128.8, 122.4, 121.1, 118.0, 116.7, 69.7, 54.1, 46.1, 45.2, 43.7, 24.2, 22.7, 18.0 ppm. Purity: 100% LCMS (214 nm & 254 nm); retention time 1.50 min; (M+1) 353.

Example 82 quinuclidin-3-yl 3-isopropoxybenzylcarbamate

A mixture containing 2-(3-hydroxyphenyl)acetic acid (0.800 g, 5.26 mmol), 2-bromopropane (0.971 g, 7.89 mmol), potassium hydroxide (0.740 g, 13.2 mmol), KI (18 mg, 0.11 mmol) in 20 mL EtOH was refluxed for 18 h. The solvent was removed and the residue was dissolved in 50 mL of water and extracted with ether. The aqueous layer was acidified with aqueous 1N HCl and extracted with EtOAc. The organic layers were dried (Na$_2$SO$_4$) and concentrated to afford a residue which was purified by silica gel chromatography (petroleum ether/EtOAc 4:1) to get 2-(3-(benzyloxy)phenyl) acetic acid as a white solid (0.45 g, 44%).

Using general procedure H, 2-(3-isopropoxyphenyl)acetic acid (291 mg, 1.50 mmol), and quinuclidin-3-ol gave the title compound as a viscous semi-solid (120 mg, 25%). $^1$H-NMR (500 MHz, CDCl$_3$) δ 7.23 (t, J=7.5 Hz, 1H), 6.86-6.77 (m, 3H), 5.16-5.00 (m, 1H), 4.78 (m, 1H), 4.55 (m, 1H), 4.32 (d, J=5.0 Hz, 2H), 3.26 (m, 1H), 2.95-2.70 (m, 5H), 2.10-2.05 (m, 1H), 1.90-1.80 (m, 1H), 1.75-1.65 (m, 1H), 1.63-1.53 (m, 1H), 1.47-1.37 (m, 1H), 1.33 (d, J=5.5 Hz, 6H) ppm. $^{13}$C NMR (125 MHz, CDCl$_3$) δ 158.1, 156.2, 140.1, 129.7, 119.6, 115.2, 114.6, 71.0, 69.8, 55.3, 47.2, 46.3, 45.0, 25.3, 24.1, 22.0, 19.2 ppm. Purity: >90% LCMS (214 nm & 254 nm); retention time 1.42 min; (M+1) 319.

Example 83 quinuclidin-3-yl 3-isobutoxybenzylcarbamate

A mixture containing 2-(3-hydroxyphenyl)acetic acid (1.0 g, 6.6 mmol), 1-bromo-2-methylpropane (1.08 g, 7.91 mmol), potassium hydroxide (0.920 g, 16.4 mmol), KI (22 mg, 0.13 mmol) in EtOH (20 mL) was refluxed for 18 h. The solvent was removed and the residue was dissolved in 50 mL of water and extracted with ether. The aqueous layer was acidified with aqueous 1N HCl and extracted with EtOAc. The organic layers were dried (Na$_2$SO$_4$) and concentrated to afford a residue which was purified by silica gel chromatography (petroleum ether/EtOAc 4:1) to get 2-(3-(benzyloxy) phenyl)acetic acid as a white solid (0.42 g, 31%).

Using general procedure H, 2-(3-isobutoxyphenyl)acetic acid (208 mg, 1.00 mmol) and quinuclidin-3-ol gave the title compound as a viscous semi-solid (130 mg, 39%). $^1$H NMR (500 MHz, CDCl$_3$) δ 7.23 (t, J=7.5 Hz, 1H), 6.86-6.76 (m, 3H), 5.35-5.10 (m, 1H), 4.77 (m, 1H), 4.31 (d, J=5.5 Hz, 2H), 3.69 (d, J=6.5 Hz, 2H), 3.26 (m, 1H), 2.95-2.70 (m, 5H), 2.10-2.00 (m, 2H), 1.88-1.80 (m, 1H), 1.75-1.63 (m, 1H), 1.62-1.52 (m, 1H), 1.45-1.36 (m, 1H), 1.01 (d, J=6.5 Hz, 6H) ppm. $^{13}$C NMR (125 MHz, CDCl$_3$) δ 159.6, 156.1, 139.9, 129.7, 119.6, 113.9, 113.4, 74.4, 70.9, 55.3, 47.2, 46.3, 45.1, 28.3, 25.3, 23.9, 19.3, 19.1 ppm. Purity: >95% LCMS (214 nm & 254 nm); retention time 1.50 min; (M+1) 333.

Example 84 quinuclidin-3-yl 3-(cyclopropylmethoxy)benzylcarbamate

A mixture containing 2-(3-hydroxyphenyl)acetic acid (1.0 g, 6.6 mmol), (bromomethyl)cyclopropane (0.97 g, 7.2 mmol), potassium hydroxide (0.920 g, 16.4 mmol), KI (22 mg, 0.13 mmol) in EtOH (20 mL) was refluxed for 18 h. The solvent was removed in vacuo, and the residue was dissolved in 50 mL of water and extracted with ether. The aqueous layer was acidified with aqueous 1N HCl and extracted with EtOAc. The organic layers were dried (Na$_2$SO$_4$) and concentrated to afford a residue which was purified by silica gel chromatography (petroleum ether/EtOAc 4:1) to get 2-(3-(cyclopropylmethoxy)phenyl)acetic acid as a white solid (0.80 g, 59%).

Using general procedure H, 2-(3-(cyclopropylmethoxy) phenyl)acetic acid (300 mg, 1.50 mmol) and quinuclidin-3-ol gave the title compound as a viscous oil (90 mg, 19%). $^1$H NMR (500 MHz, CDCl$_3$) δ 7.24 (t, J=7.5 Hz, 1H), 6.88-6.78 (m, 3H), 5.13-4.95 (m, 1H), 4.74 (m, 1H), 4.33 (d, J=6.0 Hz, 2H), 3.79 (d, J=7.0 Hz, 2H), 3.23 (m, 1H), 2.93-2.63 (m, 5H), 2.04-1.98 (m, 1H), 1.85-1.76 (m, 1H), 1.72-1.60 (m, 1H), 1.58-1.50 (m, 1H), 1.41-1.22 (m, 2H), 0.68-0.62 (m, 2H), 0.37-0.32 (m, 2H) ppm. $^{13}$C NMR (125 MHz, CDCl$_3$) δ 158.2, 155.5, 139.3, 128.6, 118.6, 112.8, 112.3, 71.7, 70.4, 54.5, 46.2, 45.3, 43.9, 24.4, 23.5, 18.5, 9.3, 2.2 ppm. Purity: >95% LCMS (214 nm & 254 nm); retention time 1.44 min; (M+1) 331.

Preparation X

Example 85

N-(2-(biphenyl-4-yl)propan-2-yl)-2-(quinuclidin-3-yl)acetamide

To a solution of 2-(quinuclidin-3-yl)acetic acid hydrochloride (0.97 g, 4.7 mmol) in DMF (30 mL) was added HATU (1.79 g, 4.72 mmol), 2-(4-bromophenyl)propan-2-amine (1.0 g, 4.7 mmol), and triethylamine (3.9 mL, 28 mmol). The resulting mixture was stirred at 60° C. for 16 h. The mixture was concentrated in vacuo, diluted with EtOAc and washed with brine. The organic layer was dried over Na$_2$SO$_4$ and evaporated to afford crude product, which was purified by silica gel column chromatography (EtOAc/methanol 50/1 to 3/1) to obtain N-(2-(4-bromophenyl)propan-2-yl)-2-(quinuclidin-3-yl)acetamide as a yellow solid (1.3 g, 76%).

Using general procedure E, N-(2-(4-bromophenyl)propan-2-yl)-2-(quinuclidin-3-yl)acetamide (200 mg, 0.550 mmol), phenylboronic acid (134 mg, 1.00 mmol) and [PdCl$_2$(pddf)] CH$_2$Cl$_2$ gave the title compound as a viscous brown oil (58 mg, 32%). $^1$H NMR (500 MHz, CDCl$_3$) δ 7.58-7.50 (m, 4H), 7.44-7.37 (m, 4H), 7.31 (t, J=7.0 Hz, 1H), 6.50 (s, 1H), 3.16 (m, 1H), 3.02 (m, 1H), 2.92-2.78 (m, 3H), 2.60 (m, 1H), 2.40-2.20 (m, 3H), 1.47-1.90 (m, 11H) ppm. $^{13}$C NMR (125 MHz, CDCl$_3$) δ 170.5, 146.1, 140.7, 139.2, 128.8, 127.2, 127.0 125.2, 55.6, 53.1, 46.8, 46.2, 40.3, 31.7, 29.3, 29.2, 26.0, 24.4, 19.7 ppm. Purity: 100% LCMS (214 nm & 254 nm); retention time 1.55 min; (M+1) 363.

Example 86 quinuclidin-3-yl biphenyl-3-ylcarbamate

To a solution of quinuclidin-3-ol (635 mg, 5.00 mmol) in THF (15 mL) was added NaH [60% dispersion in mineral oil](260 mg, 6.50 mmol) at room temperature. The mixture was stirred for 15 min and 3-bromophenyl isocyanate (990 mg, 5.00 mmol) was added under stirring. The resulting mixture was stirred at room temperature for 18 h, quenched with brine and extracted with EtOAc. The organic layers were combined, dried over Na$_2$SO$_4$ and concentrated. The crude product was purified by silica gel column chromatography (eluting with EtOAc/methanol 3:1) to give quinuclidin-3-yl 3-bromophenylcarbamate as a white solid (0.70 g, 43%).

Using general procedure E, above carbamate intermediate (130 mg, 0.402 mmol), phenylboronic acid (72 mg, 0.6 mmol) and [PdCl$_2$(pddf)]CH$_2$Cl$_2$ gave the title compound as a white solid (75 mg, 58%). $^1$H NMR (500 MHz, CDCl$_3$) δ 7.67 (br s, 1H), 7.59 (d, J=7.5 Hz, 2H), 7.43 (t, J=7.5 Hz, 2H), 7.41-7.28 (m, 4H), 6.77 (br s, 1H), 4.85 (m, 1H), 3.30 (m, 1H), 2.98-2.75 (m, 5H), 2.12 (m, 1H), 1.93-1.68 (m, 2H), 1.64-1.55 (m, 1H), 1.47-1.40 (m, 1H) ppm. $^{13}$C NMR (125 MHz, CDCl$_3$) δ 153.3, 142.3, 140.7, 138.3, 129.5, 128.8, 127.5, 127.2, 122.3, 117.4, 72.1, 55.4, 47.4, 46.5, 30.9, 25.4, 24.5, 19.5 ppm. Purity: 100% LCMS (214 nm & 254 nm); retention time 1.53 min; (M+1) 323.

Example 87 quinuclidin-3-yl 2'-methoxybiphenyl-3-ylcarbamate

Using general procedure E, quinuclidin-3-yl 3-bromophenylcarbamate, 2-methoxy-phenylboronic acid and [PdCl$_2$(pddf)]CH$_2$Cl$_2$ gave the title compound as a white solid (75 mg, 58%). $^1$H NMR (500 MHz, CDCl$_3$) δ 7.49 (br s, 1H), 7.41 (br s, 1H), 7.37-7.28 (m, 3H), 7.23 (d, J=7.5 Hz, 1H), 7.04-6.94 (m, 3H), 4.83 (m, 1H), 3.80 (s, 3H), 3.29 (m, 1H), 2.97-2.70 (m, 5H), 2.10 (m, 1H), 1.91-1.82 (m, 1H), 1.74-1.65 (m, 1H), 1.62-1.53 (m, 1H), 1.46-1.37 (m, 1H) ppm. $^{13}$C NMR (125 MHz, CDCl$_3$) δ 156.4, 153.4, 139.4, 137.6, 130.9, 130.2, 128.8, 128.6, 124.8, 120.8, 119.9, 117.3, 111.2, 72.0, 55.6, 55.4, 47.4, 46.5, 25.4, 24.5, 19.5 ppm. Purity: >95% LCMS (214 nm & 254 nm); retention time 1.52 min; (M+1) 353.

Example 88 quinuclidin-3-yl 2'-ethylbiphenyl-3-ylcarbamate

Using general procedure E, quinuclidin-3-yl 3-bromophenylcarbamate, 2-ethylphenylboronic acid and [PdCl$_2$(pddf)]CH$_2$Cl$_2$ gave the title v compound as a white solid (110 mg, 78%). $^1$H NMR (400 MHz, CDCl$_3$) δ 7.42-7.28 (m, 5H), 7.25-7.16 (m, 2H), 7.03-7.00 (m, 1H), 6.88 (br s, 1H), 4.83 (m, 1H), 3.27 (m, 1H), 2.98-2.70 (m, 5H), 2.61 (q, J=7.6 Hz, 2H), 2.08 (m, 1H), 1.92-1.80 (m, 1H), 1.75-1.65 (m, 1H), 1.63-1.55 (m, 1H), 1.46-1.37 (m, 1H), 1.10 (t, J=7.6 Hz, 3H) ppm. $^{13}$C NMR (100 MHz, CDCl$_3$) δ 152.1, 141.7, 140.4, 139.9, 136.4, 128.6, 127.5, 127.4, 126.4, 124.3, 123.2, 118.4, 115.9, 71.0, 54.3, 46.2, 45.3, 25.0, 24.2, 23.4, 18.3, 14.5 ppm. Purity: 100% LCMS (214 nm & 254 nm); retention time 1.61 min; (M+1) 351.

Example 89 quinuclidin-3-yl 3'-methoxybiphenyl-3-ylcarbamate

Using general procedure E, quinuclidin-3-yl 3-bromophenylcarbamate, 3-methoxyphenylboronic acid and [PdCl$_2$(pddf)]CH$_2$Cl$_2$ gave the title compound as a white solid (100 mg, 71%). $^1$H NMR (500 MHz, CDCl$_3$) δ 7.63 (br s, 1H), 7.40-7.27 (m, 4H), 7.17 (d, J=8.0 Hz, 1H), 7.11 (m, 1H), 7.07 (br s, 1H), 6.89 (dd, J=8.0, 2.0 Hz, 1H), 4.85 (m, 1H), 3.85 (s, 3H), 3.30 (m, 1H), 2.99-2.70 (m, 5H), 2.12 (m, 1H), 1.92-1.84 (m, 1H), 1.75-1.68 (m, 1H), 1.62-1.55 (m, 1H), 1.48-1.40 (m, 1H) ppm. $^{13}$C NMR (125 MHz, CDCl$_3$) δ 159.9, 153.4, 142.3, 142.1, 138.4, 129.8, 129.4, 122.3, 119.7, 117.7, 112.9, 112.8, 72.0, 55.4, 55.3, 47.4, 46.5, 25.4, 24.5, 19.5 ppm. Purity: >97% LCMS (214 nm & 254 nm); retention time 1.52 min; (M+1) 353

Example 90 quinuclidin-3-yl 3'-ethylbiphenyl-3-ylcarbamate

To a solution of 1-bromo-3-ethylbenzene (370 mg, 2.00 mmol) in 5 mL 1,4-dioxane, was added bis(pinacolato)diboron (609 mg, 2.40 mmol), CH$_3$COOK (589 mg, 6.02 mmol), and [PdCl$_2$(pddf)]CH$_2$Cl$_2$ (75 mg, 0.09 mmol). The mixture was stirred at 80° C. for 5 h. The mixture was cooled, diluted with water, and extracted with EtOAc. The combined extracts were dried (Na$_2$SO$_4$) and concentrated to afford the crude boronate (410 mg, >100%), which was used without purification in the next step.

Using general procedure E, quinuclidin-3-yl 3-bromophenylcarbamate, 3-ethylphenylboronic acid and [PdCl$_2$(pddf)]CH$_2$Cl$_2$ gave the title compound as a white solid (78 mg, 56%). $^1$H NMR (500 MHz, CDCl$_3$) δ 7.64 (br s, 1H), 7.43-7.27 (m, 6H), 7.24 (br s, 1H), 7.18 (d, J=8.0 Hz, 1H), 4.85 (m, 1H), 3.30 (m, 1H), 2.99-2.73 (m, 5H), 2.70 (q, J=7.5 Hz, 2H), 2.12 (m, 1H), 1.92-1.84 (m, 1H), 1.75-1.67 (m, 1H), 1.62-1.55 (m, 1H), 1.48-1.38 (m, 1H), 1.27 (t, J=7.5 Hz, 3H) ppm. $^{13}$C NMR (125 MHz, CDCl$_3$) δ 153.5, 144.8, 142.4, 140.8, 138.4, 129.4, 128.8, 127.1, 126.8, 124.6, 122.3, 117.4, 72.1, 55.4, 47.4, 46.5, 29.0, 25.4, 24.5, 19.5, 15.7 ppm. Purity: >98% LCMS (214 nm & 254 nm); retention time 1.66 min: (M+1) 351.

Example 91 quinuclidin-3-yl biphenyl-2-ylcarbamate

To a solution of quinuclidin-3-ol (382 mg, 3.00 mmol) in THF (15 mL) was added NaH [60% dispersion in mineral oil](156 mg, 3.90 mmol) at room temperature. The mixture was stirred for 15 min and 2-bromophenyl isocyanate (594 mg, 3.00 mmol) was added under stirring. The resulting mixture was stirred at room temperature for 18 h, quenched with brine and extracted with EtOAc. The organic layers were combined, dried over Na$_2$SO$_4$ and concentrated. The resulting crude product was purified by silica gel column chromatography (EtOAc/methanol 3:1) to give the product quinuclidin-3-yl 2-bromophenylcarbamate as viscous oil (0.80 g, 82%).

Using general procedure E, quinuclidin-3-yl 2-bromophenylcarbamate (130 mg, 0.400 mmol), phenylboronic acid (96 mg, 0.8 mmol) and [PdCl$_2$(pddf)]CH$_2$Cl$_2$ gave the title compound as a white solid (112 mg, 87%). $^1$H NMR (400 MHz, CDCl$_3$) δ 8.07 (br s, 1H), 7.55-7.33 (m, 6H), 7.25-7.21 (dd, J=7.6 & 1.6 Hz, 1H), 7.43 (td, J=8.0, 1.2 Hz, 1H), 6.65 (br s, 1H), 4.78 (m, 1H), 3.24 (m, 1H), 2.90-2.68 (m, 5H), 2.04 (m, 1H), 1.80-1.62 (m, 2H), 1.61-1.50 (m, 1H), 1.41-1.30 (m, 1H) ppm. $^{13}$C NMR (100 MHz, CDCl$_3$) δ 151.2, 135.9, 132.5, 129.5, 128.0, 127.0, 126.9, 126.2, 125.7, 121.4, 117.9, 69.9, 53.1, 45.1, 44.3, 23.1, 22.3, 17.2 ppm. Purity: 100% LCMS (214 nm & 254 nm); retention time 1.47 min: (M+1) 323.

Example 92 quinuclidin-3-yl 2'-methoxybiphenyl-2-ylcarbamate

Using general procedure E, quinuclidin-3-yl 2-bromophenylcarbamate, 2-methoxyphenylboronic acid and [PdCl$_2$(pddf)]CH$_2$Cl$_2$ gave the title compound as a white solid (102 mg, 72%). ¹H NMR (500 MHz, CDCl₃) δ 7.95 (br s, 1H), 7.42 (t, J=7.5 Hz, 1H), 7.37 (t, J=7.5 Hz, 1H), 7.25 (d, J=7.5 Hz, 1H), 7.15 (t, J=7.5 Hz, 1H), 7.09 (t, J=7.5 Hz, 1H), 7.04 (d, J=8.5 Hz, 1H), 6.72 (br s, 1H), 4.76 (m, 1H), 3.82 (s, 3H), 3.23 (m, 1H), 2.90-2.64 (m, 5H), 1.98-2.08 (m, 1H), 1.81-1.63 (m, 2H), 1.60-1.50 (m, 1H), 1.42-1.30 (m, 1H) ppm. ¹³C NMR (125 MHz, CDCl₃) δ 156.2, 153.8, 135.6, 132.1, 130.9, 129.7, 128.3, 127.1, 123.8, 121.5, 111.3, 71.8, 55.7, 55.5, 47.3, 46.5, 25.3, 24.5, 19.4 ppm. Purity: 100% LCMS (214 nm & 254 nm); retention time 1.48 min; (M+1) 353.

Example 93 quinuclidin-3-yl 2'-ethylbiphenyl-2-ylcarbamate

Using general procedure E, quinuclidin-3-yl 2-bromophenylcarbamate, 2-ethylphenylboronic and [PdCl₂(pddf)]CH₂Cl₂ gave the title compound as a white solid (71 mg, 51%). ¹H NMR (500 MHz, CDCl₃) δ 8.11 (br s, 1H), 7.43-7.34 (m, 3H), 7.33-7.28 (m, 1H), 7.18-7.08 (m, 3H), 6.24 (br s, 1H), 4.75 (m, 1H), 3.23 (m, 1H), 2.85-2.65 (m, 5H), 2.40 (m, 2H), 2.02 (m, 1H), 1.73-1.62 (m, 2H), 1.61-1.50 (m, 1H), 1.40-1.30 (m, 1H), 1.05 (m, 3H) ppm. ¹³C NMR (125 MHz, CDCl₃) δ 153.3, 142.9, 136.4, 135.3, 130.6, 130.3, 130.1, 129.0, 128.7, 128.4, 126.4, 123.0, 119.1, 72.1, 55.2, 47.3, 46.4, 26.0, 25.3, 24.5, 19.3, 15.2 ppm. Purity: >98% LCMS (214 nm & 254 nm); retention time 1.55 min; (M+1) 351.

Example 94 quinuclidin-3-yl 3'-methoxybiphenyl-2-ylcarbamate

Using general procedure E, quinuclidin-3-yl 2-bromophenylcarbamate, 3-methoxyphenylboronic acid and [PdCl₂(pddf)]CH₂Cl₂ gave the title compound as a white solid (120 mg, 85%). ¹H NMR (500 MHz, CDCl₃) δ 8.08 (br s, 1H), 7.40 (t, J=7.5 Hz, 1H), 7.36 (t, J=7.5 Hz, 1H), 7.23 (dd, J=7.5, 1.5 Hz, 1H), 7.13 (td, J=7.5, 1.5 Hz, 1H), 6.96 (dd, J=8.0, 2.0 Hz, 2H), 6.91 (t, J=1.5 Hz, 1H), 6.73 (br s, 1H), 4.79 (m, 1H), 3.84 (s, 3H), 3.24 (m, 1H), 2.90-2.70 (m, 5H), 2.05 (m, 1H), 1.80-1.70 (m, 2H), 1.62-1.52 (m, 1H), 1.41-1.32 (m, 1H) ppm. ¹³C NMR (125 MHz, CDCl₃) δ 160.1, 153.4, 139.5, 134.7, 131.5, 130.1, 130.1, 128.5, 123.5, 121.4, 119.9, 114.7, 113.6, 72.1, 55.3, 55.3, 47.3, 46.5, 25.3, 24.5, 19.4 ppm. Purity: >98% LCMS (214 nm & 254 nm); retention time 1.48 min; (M+1) 353

Example 95 quinuclidin-3-yl 3'-ethylbiphenyl-2-ylcarbamate

Using general procedure E, quinuclidin-3-yl 2-bromophenylcarbamate, 3-ethylphenylboronic acid and [PdCl₂(pddf)]CH₂Cl₂ gave the title compound as a white solid (120 mg, 86%). ¹H NMR (500 MHz, CDCl₃) δ 8.09 (br s, 1H), 7.41 (t, J=7.5 Hz, 1H), 7.36 (t, J=7.5 Hz, 1H), 7.26-7.18 (m, 4H), 7.14 (t, J=7.5 Hz, 1H), 6.71 (br s, 1H), 4.79 (m, 1H), 3.25 (m, 1H), 2.90-2.65 (m, 7H), 2.05 (m, 1H), 1.80-1.64 (m, 2H), 1.62-1.52 (m, 1H), 1.40-1.32 (m, 1H), 1.28 (t, J=7.5 Hz, 3H) ppm. ¹³C NMR (125 MHz, CDCl₃) 153.4, 145.2, 138.1, 134.7, 131.8, 130.2, 129.1, 128.8, 128.4, 127.5, 126.6, 123.5, 120.1, 72.0, 55.3, 47.3, 46.4, 28.9, 25.3, 24.5, 19.4, 15.7 ppm. Purity: >95% LCMS (214 nm & 254 nm): retention time 1.55 min: (M+1) 351.

Preparation Y

Example 96 quinuclidin-3-yl 2-isopropoxyphenylcarbamate

To a mixture of 3-aminophenol (1.50 g, 13.8 mmol), isopropanol (3.3 g, 55 mmol), and triphenylphosphine (14.4 g, 54.9 mmol) in THF (15 mL), was added dropwise diethylazodicarboxylate (9.60 g, 55.0 mmol) over a 30 min period. The mixture was stirred at room temperature for 3 h and concentrated. The residue was diluted with water, acidified with aqueous 2N HCl and extracted with ether. The aqueous phase was basified with aqueous 2N NaOH and extracted with EtOAc. The combined organic layers were dried (Na₂SO4) and concentrated. The resulting crude product was purified by silica gel column chromatograph (petroleum ether/EtOAc 10:1 to 5:1) to afford 3-isopropoxybenzenamine as yellow oil (1.3 g, 64%).

Using general procedure A, 3-isopropoxybenzenamine (300 mg, 2.00 mmol) and quinuclidin-3-ol gave the title compound as a viscous oil (130 mg, 22%). ¹H NMR (500 MHz, CDCl₃) δ 7.20 (br s, 1H), 7.09 (t, J=8.5 Hz, 1H), 7.05 (br s, 1H), 6.77 (d, J=8.0 Hz, 1H), 6.51 (d, J=8.5 Hz, 1H), 4.75 (m, 1H), 4.46 (m, 1H), 3.26-3.18 (m, 1H), 2.92-2.65 (m, 5H), 2.04 (m, 1H), 1.80 (m, 1H), 1.63 (m, 1H), 1.52 (m, 1H), 1.35 (m, 1H), 1.28 (d, J=5.5 Hz, 6H) ppm. ¹³C NMR (125 MHz, CDCl₃) δ 157.5, 152.2, 138.2, 128.7, 110.1, 109.6, 105.1, 70.7, 68.9, 54.3, 46.3, 45.4, 28.7, 24.3, 23.3, 21.0, 18.3 ppm. Purity: >90% LCMS (214 nm & 254 nm); retention time 1.43 min; (M+1) 305.

Example 97 quinuclidin-3-yl 2-isobutoxyphenylcarbamate

To a mixture of 3-aminophenol (500 mg, 4.60 mmol), 2-methylpropan-1-ol (1.40 g, 18.9 mmol) and triphenylphosphine (4.80 g, 16.2 mmol) in THF (10 mL) was added dropwise diethylazodicarboxylate (3.20 g, 18.3 mmol) over a 30 min period. The mixture was stirred at room temperature for 3 h. The solvent was evaporated and the residue was diluted with water, acidified with aqueous 2N HCl and extracted with ether. The aqueous phase was basified with aqueous 2N NaOH and extracted with EtOAc. The combined organic layers were dried (Na₂SO₄) and concentrated. The resulting crude product was purified by silica gel column chromatograph (petroleum ether/EtOAc 15:1) to afford 3-isobutoxybenzenamine as yellow oil (330 mg, 45%).

Using general procedure A, 3-isobutoxybenzenamine (330 mg, 2.00 mmol) and quinuclidin-3-ol gave the title compound as a viscous oil (140 mg, 22%). ¹H NMR (500 MHz, CDCl₃) δ 7.17 (t, J=8.0 Hz, 1H), 7.15 (br s, 1H), 6.81 (d, J=8.5 Hz, 1H), 6.80 (br s, 1H), 6.61 (d, J=8.5 Hz, 1H), 4.83 (m, 1H), 3.71 (d, J=6.5 Hz, 2H), 3.34-3.21 (m, 1H), 2.97-2.72 (m, 5H), 2.12-2.04 (m, 2H), 1.90-1.84 (m, 1H), 1.75-1.67 (m, 1H), 1.55-1.63 (m, 1H), 1.46-1.38 (m, 1H), 1.01 (d, J=6.5 Hz, 6H) ppm. ¹³C NMR (100 MHz, CDCl₃) δ 159.9, 153.4, 139.3, 129.6, 110.6, 109.7, 105.0, 74.4, 72.0, 55.4, 47.3, 46.5, 28.3, 25.4, 24.5, 19.5, 19.3 ppm. Purity: 100% LCMS (214 nm & 254 nm); retention time 1.56 min; (M+1) 319.

Example 98 quinuclidin-3-yl 2-(cyclopropylmethoxy)phenylcarbamate

To a mixture of 3-aminophenol (300 mg, 2.70 mmol), cyclopropylmethanol (793 mg, 11.0 mmol) and triphenylphosphine (2.90 g, 11.0 mmol) in THF (6 mL) was added dropwise diethylazodicarboxylate (1.90 g, 11.0 mmol) over a 30 min period. The mixture was stirred at room temperature for 3 h. The solvent was evaporated and the residue was diluted with water, acidified with aqueous 2N HCl and extracted with ether. The aqueous phase was basified with aqueous 2N NaOH and extracted with EtOAc. The combined organic layers were dried ($Na_2SO_4$) and concentrated. The resulting crude product was purified by silica gel column chromatograph (petroleum ether/EtOAc 15:1) to afford 3-(cyclopropylmethoxy)benzenamine as a brown oil (260 mg, 58%).

Using general procedure A, 3-(cyclopropylmethoxy)benzenamine (260 mg, 1.60 mmol) and quinuclidin-3-ol gave the title compound as a viscous oil (80 mg, 16%). $^1$H NMR (400 MHz, $CDCl_3$) δ 7.72 (br s, 1H), 7.14 (br s, 1H), 7.13 (t, J=8.0 Hz, 1H), 6.85 (d, J=8.0 Hz, 1H), 6.57 (dd, J=8.0, 2.0 Hz, 1H), 4.85 (m, 1H), 3.75 (d, J=6.8 Hz, 2H), 3.35-3.26 (m, 1H), 3.05-2.78 (m, 5H), 2.18-2.12 (m, 1H), 1.97-1.86 (m, 1H), 1.80-1.67 (m, 1H), 1.66-1.55 (m, 1H), 1.52-1.42 (m, 1H), 1.26-1.15 (m, 1H), 0.61-0.55 (m, 2H), 0.31-0.26 (m, 2H) ppm. $^{13}$C NMR (100 MHz, $CDCl_3$) δ 158.6, 152.1, 138.3, 128.6, 109.9, 108.9, 104.0, 71.7, 69.7, 53.8, 46.0, 45.2, 28.7, 24.1, 22.4, 17.8, 9.2, 2.2 ppm. Purity: 100% LCMS (214 nm & 254 nm); retention time 1.46 min; (M+1) 317.

Example 99

1-benzyl-3-(quinuclidin-3-yl)imidazolidin-2-one

To a stirred solution of quinuclidin-3-amine hydrochloride (324 mg, 0.199 mmol) in DMF (30 ml) was added triethylamine (3 drops) followed by (isocyanatomethyl)benzene (275 mg, 2.10 mmol) carefully. The resultant mixture was stirred at 25° C. for 18 h. After HPLC separation, 1-benzyl-3-(quinuclidin-3-yl)urea (283 mg, 55%) was obtained.

To a solution of 1-benzyl-3-(quinuclidin-3-yl)urea (260 mg, 1.00 mmol) in DMF (30 ml) was added NaH [60% dispersion in mineral oil](96 mg, 2.4 mmol) with ice bath cooling. The resultant mixture was stirred for 2 h before $BrCH_2CH_2Br$ (0.75 g, 4.0 mmol) was added carefully. The reaction was stirred for an additional 18 h at about 25° C. After HPLC separation, the aqueous layer was lyophilized and purified by prep-TLC ($CHCl_3$ to 5% MeOH in $CHCl_3$ to 5% 2N $NH_3$(MeOH) in $CHCl_3$) to give the title compound (81 mg, 28%). $^1$H NMR (400 MHz, $CDCl_3$) δ 7.19-7.22 (m, 4H), 7.11-7.14 (m, 1H), 6.09 (dd, J=15.2, 8.4 Hz, 1H), 5.45 (dd, J=15.6, 4.0 Hz, 1H), 5.30 (dd, J=8.0, 3.6 Hz, 1H), 4.17-4.29 (m, 4H), 3.66-3.75 (m, 2H), 3.47 (d, J=12.4 Hz, 1H), 3.19-3.27 (m, 3H), 2.34 (br s, 1H), 2.22 (d, J=2.4 Hz, 1H), 1.92 (br s, 2H), 1.75 (br s, 1H) ppm. $^{13}$C NMR (400 MHz, $CDCl_3$) δ 158.9, 141.1, 140.4, 128.7, 127.4, 127.3, 113.6, 63.6, 57.1, 56.0, 45.6, 43.9, 25.2, 23.0, 18.8 ppm. Purity: 93.8% HPLCMS (210 nm); retention time 1.84 min; (M+1) 286.

Example 100

N-(1 aza-bicyclo[2.2.2]oct-3-yl)-4-p-tolyl-butyramide

Using general procedure I, 1-aza-bicyclo[2.2.2]oct-3-ylamine (200 mg, 1.00 mmol) and -p-tolyl-butyric acid (220 mg, 1.2 mmol) gave N-(1-aza-bicyclo[2.2.2]oct-3-yl)-4-p-tolyl-butyramide (114 mg, 40%) as a white solid. $^1$H NMR (400 MHz, $CDCl_3$) δ 7.06 (s, 4H), 4.19 (m, 1H), 3.66-3.73 (t, J=8.4 Hz, 1H), 3.29-3.33 (m, 4H), 2.91 (dd, J=8.0, J=3.6 Hz, 1H), 2.59 (t, J=7.6 Hz, 2H), 2.28 (s, 3H), 2.24 (t, J=7.6 Hz, 2H), 2.15-2.16 (m, 1H), 2.02-2.14 (m, 1H), 1.92-2.01 (m, 2H), 1.81-1.91 (m, 3H) ppm. $^{13}$C NMR (400 MHz, $CDCl_3$) δ 175.1, 138.6, 135.1, 128.8, 128.2, 52.7, 47.4, 47.3, 44.5, 34.8, 27.3, 24.3, 21.6, 19.8, 17.1 ppm. Purity: 99.7% HPLCMS (210 nm); retention time 1.76 min; (M+1) 287.

Example 101

N-(1-aza-bicyclo[2.2.2]oct-3-yl)-4-(4-methoxy-phenyl)-butyramide

Using general procedure I, 1-aza-bicyclo[2.2.2]oct-3-ylamine (200 mg, 1.00 mmol) and 4-(4-methoxy-phenyl)-butyric acid gave the title compound as a white solid (85 mg, 28%). $^1$H NMR (400 MHz, $CD_3OD$) δ 7.08 (d, J=8.4 Hz, 2H), 6.81 (d, J=8.4 Hz, 2H), 4.18 (br s, 1H), 3.74 (s, 3H), 3.68 (d, J=11.6 Hz, 1H), 3.24-3.33 (m, 4H), 2.98-3.03 (m, 1H), 2.57 (t, J=7.6 Hz, 2H), 2.24 (t, J=7.6 Hz, 2H), 2.03-2.16 (m, 2H), 2.02 (br s, 2H), 1.85-1.91 (m, 3H) ppm. $^{13}$C NMR (400 MHz, $CD_3OD$) δ 175.2, 158.3, 133.6, 129.2, 113.6, 54.5, 52.6, 47.2, 46.4, 44.5, 34.9, 34.2, 27.5, 24.4, 21.5, 17.1 ppm. Purity: 96.4% HPLCMS (210 nm); retention time 1.76 min; (M+1) 303.

Example 102

Biphenyl-3-carboxylic acid (1-aza-bicyclo[2.2.2]oct-3-yl)-amide

Using general procedure I, 1-aza-bicyclo[2.2.2]oct-3-ylamine (200 mg, 1.00 mmol) and biphenyl-3-carboxylic acid gave the title compound as a white solid (211 mg, 68%). $^1$H NMR (400 MHz, $CD_3OD$) δ 7.86 (s, 1H), 7.59 (d, J=7.6 Hz, 1H), 7.53 (d, J=8.0 Hz, 1H), 7.40 (d, J=7.6 Hz, 2H), 7.28 (t, J=7.6 Hz, 1H), 7.19 (t, J=7.6 Hz, 2H), 7.11 (t, J=7.6 Hz, 1H), 4.21 (br s, 1H), 3.56 (t. J=11.6 Hz, 1H), 3.11-3.22 (m, 1H), 3.05-3.10 (m, 4H), 2.10 (q, J=3.2 Hz, 1H), 1.95 (br s, 1H), 1.79-1.83 (m, 2H), 1.59-1.20 (m, 1H) ppm. $^{13}$C NMR (400 MHz, $CD_3OD$) δ 169.6, 141.6, 140.2, 134.5, 130.3, 129.0, 127.7, 126.9, 126.3, 125.9, 51.9, 46.4, 46.0, 45.6, 24.6, 21.6, 17.3 ppm. Purity: 99.8% HPLCMS (210 nm); retention time 1.60 min; (M+1) 307.

Example 103

N-(1-aza-bicyclo[2.2.2]oct-3-yl)-2-biphenyl-4-yl-acetamide

Using general procedure I, 1-aza-bicyclo[2.2.2]oct-3-ylamine (200 mg, 1.00 mmol) and biphenyl-4-yl-acetic acid gave the title compound as a white solid (140 mg, 44%). $^1$H NMR (400 MHz, $CD_3OD$) δ 7.56 (t, J=8.0 Hz, 4H), 7.29-7.41 (m, 5H), 4.19 (br s, 1H), 3.70 (t, J=7.2 Hz, 1H), 3.58 (s, 2H), 3.24-3.31 (m, 5H), 3.12-3.19 (m, 1H), 2.16-2.17 (m, 2H), 1.95-1.98 (m, 2H), 1.82 (br s, 1H) ppm. $^{13}$C NMR (400 MHz, $CD_3OD$) δ 173.1, 140.8, 140.0, 134.7, 129.4, 128.7, 126.9, 52.3, 46.4, 45.9, 44.3, 41.9, 24.4, 21.5, 17.1 ppm. Purity: 93.9% HPLCMS (210 nm); retention time 2.87 min; (M+1) 321.

Preparation Z

Example 104

2-(quinuclidin-3-yl)-N-(1-p-tolylcyclopropyl)acetamide

To a solution of methyl 2-(dimethoxyphosphoryl)acetate (2.70 g, 14.8 mmol) in THF (200 ml) at 0° C. was added NaH

[60% dispersion in mineral oil] (600 mg, 15.0 mmol). After 1 h of stirring, quinuclidin-3-one (2.00 g, 12.4 mmol) was added and the resultant mixture was stirred at room temperature for 18 h. The reaction was quenched with 50 ml water at 0° C. and the mixture was extracted with EtOAc. The organic layers were combined and concentrated under reduced pressure to afford crude methyl 2-(quinuclidin-3-ylidene)acetate, which was used in next step without purification (1.2 g, 70%).

A mixture of methyl 2-(quinuclidin-3-ylidene)acetate (70 mg, 0.38 mmol) and Pd/C (100 mg, 20% w/w) in EtOH (10 mL) was stirred under $H_2$ (20 psi) at room temperature for 18 h. The reaction solution was filtered through Celite and the filtrate was concentrated under reduced pressure to afford crude methyl 2-(quinuclidin-3-yl)acetate (60 mg, 85%), which was used with purification in the next step.

A mixture of methyl 2-(quinuclidin-3-yl)acetate (1.1 g, 6.0 mmol) and 50 mL of conc. HCl [12M] was stirred at 70° C. for 18 h. The reaction mixture was concentrated under reduced pressure to afford crude 2-(quinuclidin-3-yl)acetic acid, which was used without purification in the next step (900 mg, 86%).

Using general procedure I, 2-(quinuclidin-3-yl)acetic acid (169 mg, 1.00 mmol) and 1-p-tolylcyclopropanamine (149 mg, 1.10 mmol) gave the title compound as a white solid (60 mg, 18%). $^1$H NMR (400 MHz, CDCl$_3$) δ 7.86 (s, 1H), 6.96-7.07 (m, 4H), 3.22-3.37 (m, 2H), 2.85-3.05 (m, 4H), 2.39-2.45 (m, 2H), 2.21 (s, 3H), 1.45-1.92 (m, 5H), 1.07-1.23 (m, 5H) ppm. $^{13}$C NMR (400 MHz, CDCl$_3$) δ 171.6, 139.8, 136.1, 129.2, 125.6, 52.1, 50.9, 46.5, 46.0, 39.2, 34.9, 30.8, 24.5, 21.1, 18.7, 17.6 ppm. Purity: 96.2% HPLCMS (210 nm); retention time 1.21 min; (M+1) 299.

Example 105

N-(2-(3-methoxyphenyl)propan-2-yl)-2-(quinuclidin-3-yl)acetamide

Using general procedure I, 2-(quinuclidin-3-yl)acetic acid (169 mg, 1.00 mmol) and 2-(3-methoxyphenyl)propan-2-amine (182 mg, 1.10 mmol) gave the title compound as a white solid (126 mg, 40%). $^1$H NMR (400 MHz, CDCl$_3$) δ 7.39 (s, 1H), 7.20 (t, J=8.0 Hz, 1H), 6.92 (d, J=8.0 Hz, 1H), 6.87 (d, J=2.0 Hz, 1H), 6.71 (dd, J=8.0, 2.0 Hz, 1H), 3.75 (s, 3H), 3.31-3.42 (m, 2H), 3.00-3.19 (m, 4H), 2.47-2.60 (m, 2H), 2.27 (dd, J=14.0, 6.0 Hz, 1H), 1.83-2.06 (m, 4H), 1.64-1.74 (m, 1H), 1.61 (d, J=12.4 Hz, 6H) ppm. $^{13}$C NMR (400 MHz, CDCl$_3$) δ 170.0, 159.7, 149.3, 129.5, 117.5, 111.8, 111.0, 55.9, 55.4, 52.0, 50.6, 46.6, 46.0, 39.7, 30.9, 29.7, 29.1, 24.3, 18.8 ppm. Purity: 93.7% HPLCMS (210 nm); retention time 0.76 min; (M+1) 317.

Example 106

2-(1-aza-bicyclo[2.2.2]oct-3-yl)-N-[1-(3-isopropyl-phenyl)-1-methyl-ethyl]-acetamide To a solution of 1-(1-isocyanato-1-methyl-ethyl)-3-isopropenyl-benzene (10 g, 50 mmol) in t-BuOH (1000 mL) was added KOH (40.0 g, 71.6 mmol). The mixture was stirred at reflux for 3 h. The resultant mixture was cooled down to room temperature, concentrated and dissolved in CH$_2$Cl$_2$. Solid residue was filtered off and the organic layer was adjusted to pH<7 using conc. HCl. The ammonium salt was extracted with water. The aqueous layer was made basic using an aqueous NaOH solution [5% w/w, 200 ml] and free based amine was then extracted with CH$_2$Cl$_2$. The organic layers were combined, dried over Na$_2$SO$_4$, filtered and concentrated under reduced pressure to give 1-(3-isopropenyl-phenyl)-1-methyl-ethylamine (3.3 g, 63%).

A solution of the above compound (8.5 g, 48 mmol) and PtO$_2$ (1.8 g, 8.0 mmol) in EtOH (600 mL) was stirred at room temperature under 1 atm of H$_2$ for 18 h. The reaction was filtered through Celite and concentrated under reduced pressure to give 1-(3-isopropyl-phenyl)-1-methyl-ethylamine (5.0 g, 58%).

Using general procedure I, (1-aza-bicyclo[2.2.2]oct-3-yl)-acetic acid (200 mg, 1.20 mmol) and 1-(3-isopropyl-phenyl)-1-methyl-ethylamine gave the title compound as a white solid (42 mg, 10%). $^1$H NMR (400 MHz, DMSO-d) δ 7.15-1.20 (m, 3H), 7.05 (d, J=8.4 Hz, 1H), 3.41-3.45 (m, 1H), 3.26 (s, 2H), 3.15-3.22 (m, 2H), 2.71-2.82 (m, 2H), 2.41-2.47 (m, 3H), 2.05-2.12 (m, 1H), 1.79-1.90 (m, 4H), 1.61 (d, J=8.0 Hz, 6H), 1.21 (d, J=6.4 Hz, 6H) ppm. $^{13}$C NMR (400 MHz, DMSO-d) δ 171.1, 148.7, 147.3, 128.1, 123.9, 122.8, 122.2, 55.6, 52.1, 46.5, 45.9, 38.8, 34.5, 30.7, 28.9, 28.5, 23.8, 23.4, 18.0 ppm. Purity: 96.8% HPLCMS (210 nm); retention time 1.93 min; (M+1) 329.

Example 107

2-(1-aza-bicyclo[2.2.2]oct-3-yl)-N-[2-(2-methoxy-phenyl)-ethyl]-acetamide

Using general procedure I, (1-aza-bicyclo[2.2.2]oct-3-yl)-acetic acid (200 mg, 1.20 mmol) and 2-(2-methoxy-phenyl)-ethylamine gave the title compound as a white solid (60 mg, 15%). $^1$H NMR (400 MHz, CD$_3$OD) δ 7.17 (t, J=7.2 Hz, 1H), 7.08 (d, J=7.2 Hz, 1H), 6.89 (d, J=8.4 Hz, 1H), 6.84 (t, J=7.6 Hz, 1H), 3.89 (s, 3H), 3.35-3.45 (m, 3H), 3.21-3.31 (m, 3H), 2.76-2.83 (m, 3H), 2.29-2.45 (m, 3H), 1.82-2.01 (m, 3H), 1.72-1.81 (m, 2H) ppm. $^{13}$C NMR (400 MHz, CD$_3$OD) δ 172.0, 158.0, 130.4, 127.8, 127.2, 120.2, 110.4, 54.6, 52.0, 46.4, 45.9, 39.1, 38.3, 30.7, 30.2, 23.8, 17.9 ppm. Purity: 92.4% HPLCMS (210 nm); retention time 1.59 min; (M+1) 303.

Example 108

1-(1-aza-bicyclo[2.2.2]oct-3-yl)-3-[1-(3-isopropyl-phenyl)-cyclopropyl]-urea

A mixture of 3-isopropyl-benzoic acid (5.00 g, 30.4 mmol) in SOCl$_2$ (50 ml) was stirred at 100° C. for 2 h. The reaction mixture was concentrated to give 3-isopropyl-benzoyl chloride (5.00 g, 91%).

Into a solution of the above acid chloride (5.00 g, 27.0 mmol) in CH$_2$Cl$_2$ (20 ml) at −70° C. was added, dropwise, a solution of NH$_3$/CH$_2$Cl$_2$ (200 mL). The mixture was stirred at room temperature for 18 h and then concentrated to give 3-isopropyl-benzamide (4.2 g, 93%).

A solution of the above amide (4.20 g, 25.7 mmol) in POCl$_3$ (36.0 g, 236 mmol) was stirred at 80° C. for 18 h. The solution was concentrated and the residue was poured into water (100 mL). The mixture was exacted with EtOAc. The organic layers were combined, washed by brine, dried over Na$_2$SO$_4$ and concentrated to give 3-isopropyl-benzonitrile (3.00 g, 80%).

Using general procedure G, 3-isopropyl-benzonitrile (3.00 g, 20.6 mmol) was converted to the corresponding 1-(3-isopropyl-phenyl)-cyclopropylamine (0.80 g, 22%).

Using general procedure C, the above amine (300 mg, 1.71 mmol), quinuclidin-3-amine (215 mg, 1.71 mmol) and CDI (290 mg, 2.05 mmol) gave the title compound as a white solid (88 mg, 46%). $^1$H NMR (400 MHz, CD$_3$OD) δ 7.18 (t, J=8.0

Hz, 1H), 7.12 (s, 1H), 7.01 (dd, J=19.2, 7.6 Hz, 2H), 3.74-3.77 (m, 1H), 3.18-3.24 (m, 1H), 2.71-2.87 (m, 5H), 2.42-2.47 (m, 1H), 1.63-1.82 (m, 4H), 1.45 (br s, 1H), 1.21-1.26 (m, 10H) ppm. $^{13}$C NMR (400 MHz, CD$_3$OD) δ 193.0, 168.7, 160.1, 128.2, 122.7, 121.9, 55.3, 46.8, 46.1, 34.1, 25.9, 25.0, 23.5, 19.6, 18.2 ppm. Purity: 92.4% HPLCMS (210 nm); retention time 2.53 min; (M+1) 328.

Example 109

2-(1-aza-bicyclo[2.2.2]oct-3-yl)-N-[1-(3-isopropyl-phenyl)-cyclopropyl]-acetamide Using general procedure I, 1-(3-isopropyl-phenyl)-cyclopropylamine (278 mg, 1.58 mmol) and (1-aza-bicyclo[2.2.2]oct-3-yl)-acetic acid (267 mg, 1.58 mmol) gave the title compound as a white solid (70 mg, 14%). $^1$H NMR (400 MHz, CD$_3$OD) δ 7.16 (t, J=8.0 Hz, 1H), 7.07 (s, 1H), 6.97 (dd, J=19.2, 7.6 Hz, 2H), 3.16-3.23 (m, 1H), 2.79-2.97 (m, 5H), 2.51-2.58 (m, 1H), 2.23-2.41 (m, 3H), 1.83-1.92 (m, 1H), 1.68-1.81 (m, 3H), 1.54-1.62 (m, 1H), 1.15-1.25 (m, 10H) ppm. $^{13}$C NMR (400 MHz, CD$_3$OD) δ 173.6, 148.5, 142.4, 127.8, 123.6, 123.1, 122.0, 73.0, 53.1, 46.6, 45.9, 39.3, 34.1, 32.3, 28.1, 26.4, 24.4, 19.7, 16.8 ppm. Purity: 96.9% HPLCMS (210 nm); retention time 2.55 min; (M+1) 327.

Example 110

[1-(3-isopropyl-phenyl)-cyclopropyl]-carbamic acid 1-aza-bicyclo[2.2.2]oct-3-yl ester Using general procedure A, 1-(3-isopropyl-phenyl)-cyclopropylamine (278 mg, 1.58 mmol) and quinuclidin-3-ol gave the title compound as a white solid (75 mg, 22%). $^1$H NMR (400 MHz, CD$_3$OD) δ 7.17 (m, 1H), 7.09 (s, 1H), 6.97-7.08 (m, 2H), 4.72-4.79 (m, 1H), 3.36-3.42 (m, 1H), 2.79-3.08 (m, 5H), 1.93-2.17 (m, 2H), 1.81-1.90 (m, 1H), 1.67-1.78 (m, 2H), 1.31-1.54 (m, 1H), 1.13-1.28 (m, 10H) ppm. $^{13}$C NMR (400 MHz, CD$_3$OD) δ 157.1, 148.4, 143.1, 128.1, 123.9, 123.0, 122.4, 69.2, 54.4, 46.7, 45.7, 34.7, 34.3, 24.9, 23.3, 22.0, 18.0, 17.3 ppm. Purity: 99.2% HPLCMS (210 nm); retention time 1.83 min; (M+1) 329.

Example 111

In Vivo Efficacy Studies of Small Molecule Therapy Using (S)-Quinuclidin-3-yl(2-(2-(4-fluorophenyl)thiazol-4-yl)propan-2-yl)carbamate (S)-2-hydroxysuccinate salt on Fabry Mouse Model Here, in vivo experiments are described using a GCS inhibitor in a Fabry mouse model and demonstrate that substrate reduction therapy (SRT) is equally effective at reducing the levels of both Gb3 and lyso-Gb3 in the plasma, kidney and urine of Fabry mice. The study was designed to evaluate whether substrate inhibition (i.e. "substrate reduction therapy") using a compounds of the invention types could reduce the accumulation of the storage material globotriaosylceramide (Gb3) and lysoglobotriaosylceramide (lyso-Gb3). Recently it has been proposed that urinary lyso-Gb3 may represent a reliable biomarker of clinical relevance for Fabry disease (Aerts et al., PNAS USA 105:2812-2817 (2008); and Auray-Blais et al., Clin Chim Acta 411:1906-1914 (2010)). The metabolic origin of the lyso-Gb3 is not known and can conceivably be derived through either deacylation of Gb3 or through anabolic synthesis from glucosyl-sphingosine.

In FIG. 2, black arrows indicate demonstrated pathways, gray arrows are undocumented pathways. ERT using α-Galactosidase A is known to degrade both Gb3 and lyso-Gb3. Accordingly, SRT using a GCS inhibitor would be most effective at limiting lyso-Gb3 accumulation if the lyso-Gb3 is generated primarily through deacylation of Gb3, a GCS dependent pathway. These experiments demonstrate that SRT using GCS inhibitors in a mouse model of Fabry disease reduced both Gb3 and lyso-Gb3, thus supporting the use of compounds of the invention as viable therapeutic options for Fabry patients.

In the following experiments, mice dosed with GCS inhibitors at either ~60 mg/kg/day of (S)-Quinuclidin-3-yl (2-(2-(4-fluorophenyl)thiazol-4-yl)propan-2-yl)carbamate (S)-2-hydroxysuccinate salt (hereinafter "GZ 452") or ~300 mg/kg/day of (1R,2R)-Octanoic acid[2-(2',3'-dihydro-benzo[1,4]dioxin-6'-yl)-2-hydroxy-1-pyrrolidin-1-ylmethyl-ethyl]-amide-L-tartaric acid salt (hereinafter "GZ 638") as a component of the pelleted food diet provided ad libitum. Lipid analysis was by ESLMS as described in Marshall et al., PLoS ONE 5:e15033 (2010). As discussed in further detail below, treatment started when the mice were 3, 8 or 12 months of age to test the efficacy at different disease severities. Blood and urine was collected monthly and periodic tissue harvests provided materials to evaluate efficacy of the therapy (Gb3 and lyso-Gb3 levels). Previous studies demonstrated that earlier generation glucosylceramide synthase inhibitors (of the P4-like class) could delay the rate of Gb3 accumulation, however, as discussed below, treatment with Genz-452 could not only prevent or delay further accumulation but effected reductions of the absolute levels of both Gb3 and lyso-Gb3 in the tissues tested (liver, heart, urine, plasma). As further discussed below, the efficacy of SMT was affected by the age of the mice at the start of treatment. Generally, the older the mouse, the higher the levels of Gb3 stored and thus a longer period of treatment was required in order to affect similar therapeutic benefit (see FIG. 4). The experiments and results are described further below.

GCS Inhibitor Reduces Gb3 Levels in Fabry Mouse Visceral Tissue

Figure 3:
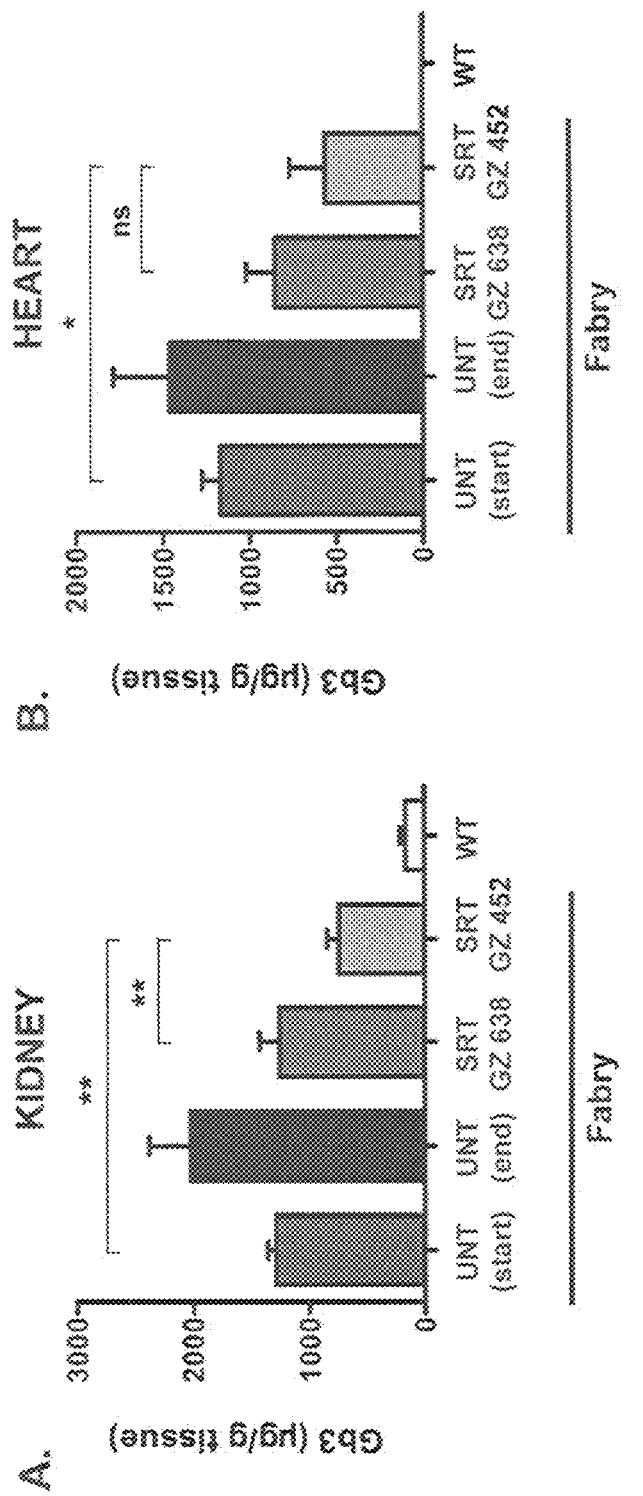

In this experiment, Fabry mice were treated with GCS inhibitors in their diet for 4 months starting at 8 months old. We have previously reported that eliglustat tartrate (GZ 638) at 300 mg/kg/day (SRT GZ 638) is effective at inhibiting further accumulation of tissue Gb3 (as shown here by the non-significant changes in Gb3 relative to the starting levels UNT (start)). As shown in FIG. 3, a more potent GCS inhibitor, GZ 452, was also evaluated (at 60 mg/kg/day) (SRT-Gz452) and found not only to prevent further accumulation but also to significantly reduce stored Gb3 relative to the starting levels (UNT (start)). Age-matched wild-type levels (WT) are also shown. These results demonstrate that GZ 638 is a potent GCS inhibitor and effectively reduces Gb3 levels in visceral tissues of the Fabry mouse.

SRT Reduces Urine and Plasma Gb3 in Both Younger and Older Fabry Mice

Figure 4B:
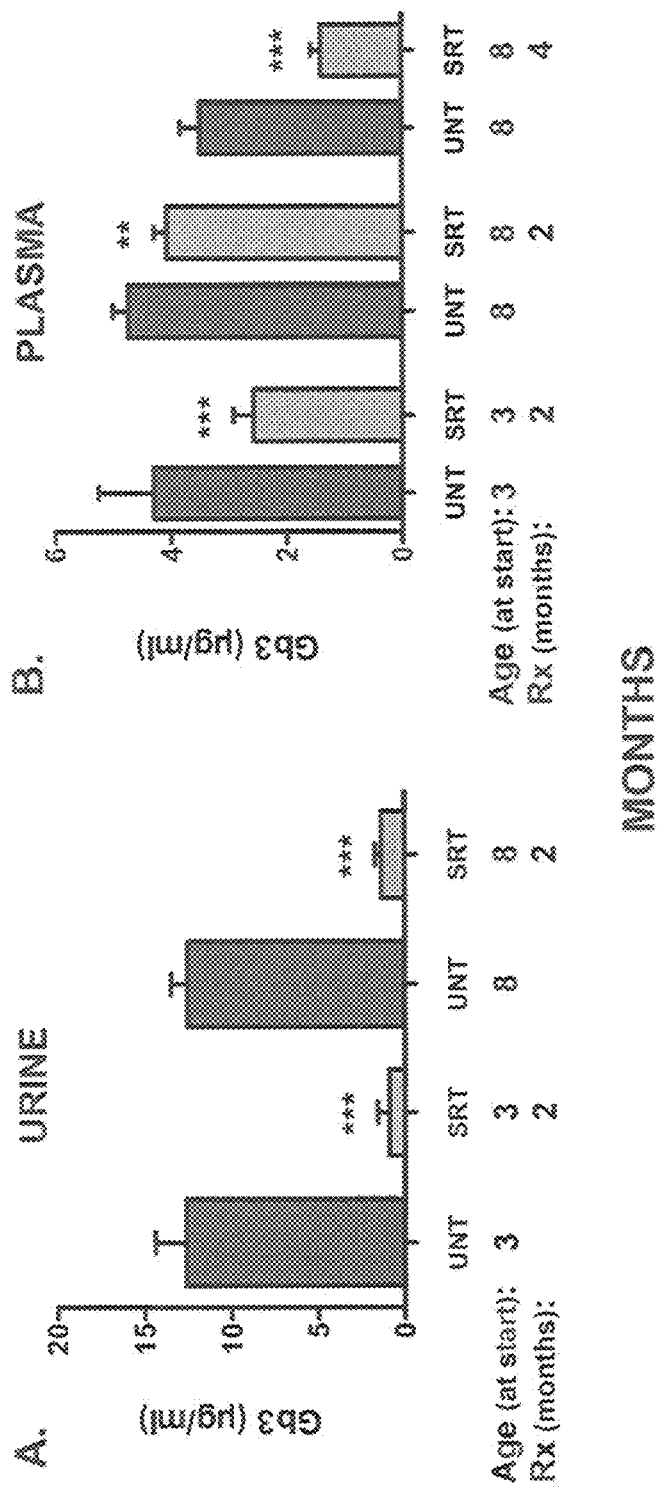
FIG. 4B
Gb3 concentration in urine (A) and plasma (B) from Fabry mice starting treatment with 60 mg/kg/day GZ 452 at either 3 or 8 months of age. Drug treatment (Rx) was for either 2 or 4 months.

In this experiment, Fabry mice were treated with GZ 452 in their diet (Rx:) for 2 or 4 months starting at either 3 or 8 months of age (Age:) as indicated in FIGS. 4A and 4B. The urine Gb3 levels of younger and older mice were equally responsive to SRT treatment, achieving ~90% reduction with 2 months of treatment. Plasma levels of Gb3 were slower to respond to treatment, with older mice requiring twice the treatment time of younger mice (4 vs. 2 months) to achieve ~50% reduction. These results demonstrate that GZ 638 effectively reduces Gb3 levels in urine and plasma in younger and older Fabry mice.

SRT Reduces Both Gb3 and Lyso-Gb3 in Fabry Mouse Kidney

Figure 5:
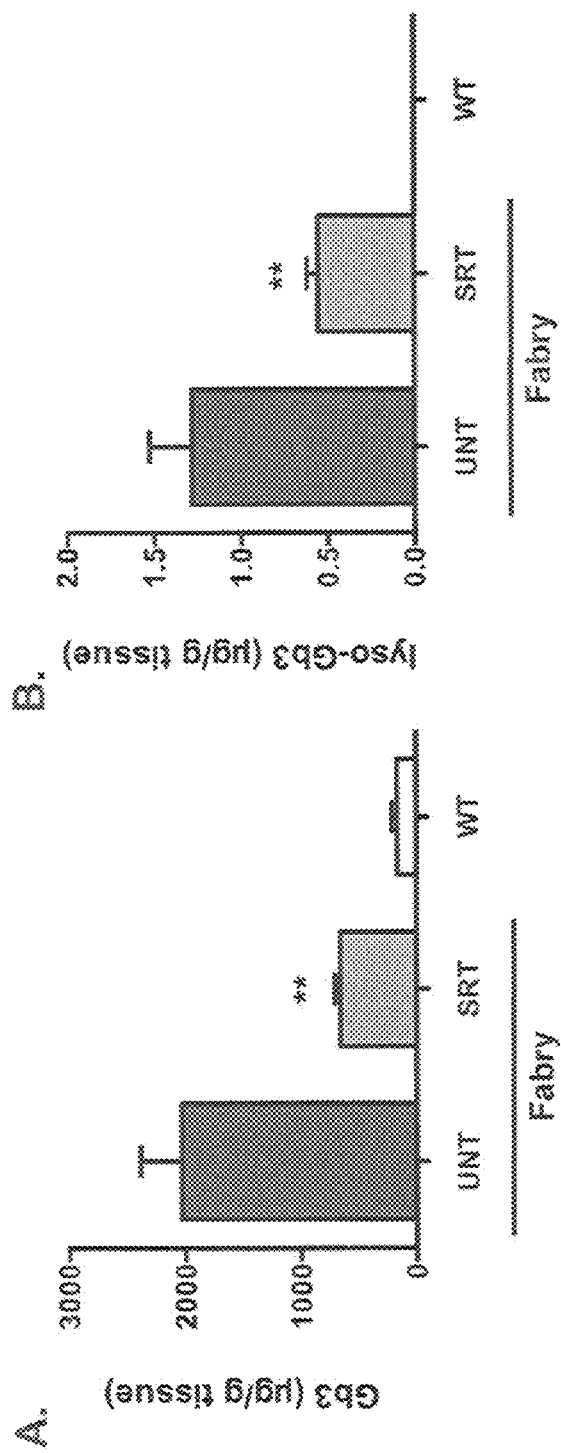
FIG. 5
Gb3 (A) and lyso-Gb3 (B) concentration in kidney tissue from 12 month old Fabry mice that were either untreated (UNT) or treated with 60 mg/kg/day GZ 452 for 4 months (SRT).

In this experiment, Fabry mice were treated with Genz-452 in their diet for 4 months starting at 8 months of age. As shown in FIG. 5, kidney tissue was analyzed for (A) Gb3 and (B) lyso-Gb3 from age-matched untreated Fabry mice (UNT), GZ 452-treated Fabry mice (SRT) and wild-type control mice (WT). SRT resulted in similar significant relative reductions in levels (60-70%) for both Gb3 and lyso-Gb3. These results demonstrate that GZ 638 effectively reduces both Gb3 and Lyso-Gb3 levels in kidney tissues of Fabry mice.

Example 112

In Vivo Efficacy Studies of Combination Therapy on Fabry Mouse Model Using GZ 452 and Alpha-Galactosidase A Fabry mice were used to test the in vivo efficacy of combining enzyme replacement therapy with small molecule therapy in a concurrent treatment format. The study was designed to evaluate whether substrate inhibition (i.e. "substrate reduction therapy") using the GZ 452 compound could reduce re-accumulation of the storage material Gb3 and lyso-Gb3. The study protocol called for three distinct treatment groups of 3 month old male Fabry mice (FIG. 6A). The first group received intravenous injections of alpha-galactosidase A enzyme (ERT) at 1 mg/kg to reduce Gb3 levels and was repeated every 2 months. The second group received the same enzyme injections as group 1, but also were dosed with GZ 452 at ~60 mg/kg/day as a component of the pelleted diet. The third group received only the daily dosing of GZ 452 in their diet. A fourth group received no treatment to serve as vehicle controls and a fifth group of wild-type animals provided 'normal' Gb3 and lyso-Gb3 values. Monthly urine and blood collections and three monthly tissue harvests provide materials to evaluate relative efficacy of the therapies (FIG. 6A).

After 2 months (mice were 5 months old), plasma (FIG. 6B, panels A and C) and urine (FIG. 6B, panels B & D) were analyzed for Gb3 (FIG. 6B, panels A and B) and lyso-Gb3 (FIG. 6B, panels C and D). In plasma, ERT and SRT reduced both Gb3 (panel A) and lyso-Gb3 (panel C) levels, and combining ERT and SRT resulted in significant improvements over either therapeutic alone. Urine Gb3 levels were unaffected by ERT, but significantly reduced by SRT (panel B). Urine lyso-Gb3 was similarly reduced by all treatments (panel D), suggesting that urine Gb3 and lyso-Gb3 may originate from distinct sources. The results from these studies show that the SMT was effective at reducing Gb3 in the kidney and urine. ERT was more effective than SMT at reducing Gb3 in the plasma, however the most effective therapy was derived from combining the two therapies. SMT therapy alone or in combination with ERT was also capable of affecting (reducing accumulation) of lyso-Gb3.

Example 113

Gb3 Acyl Chain Isoform Profile

Figure 7:
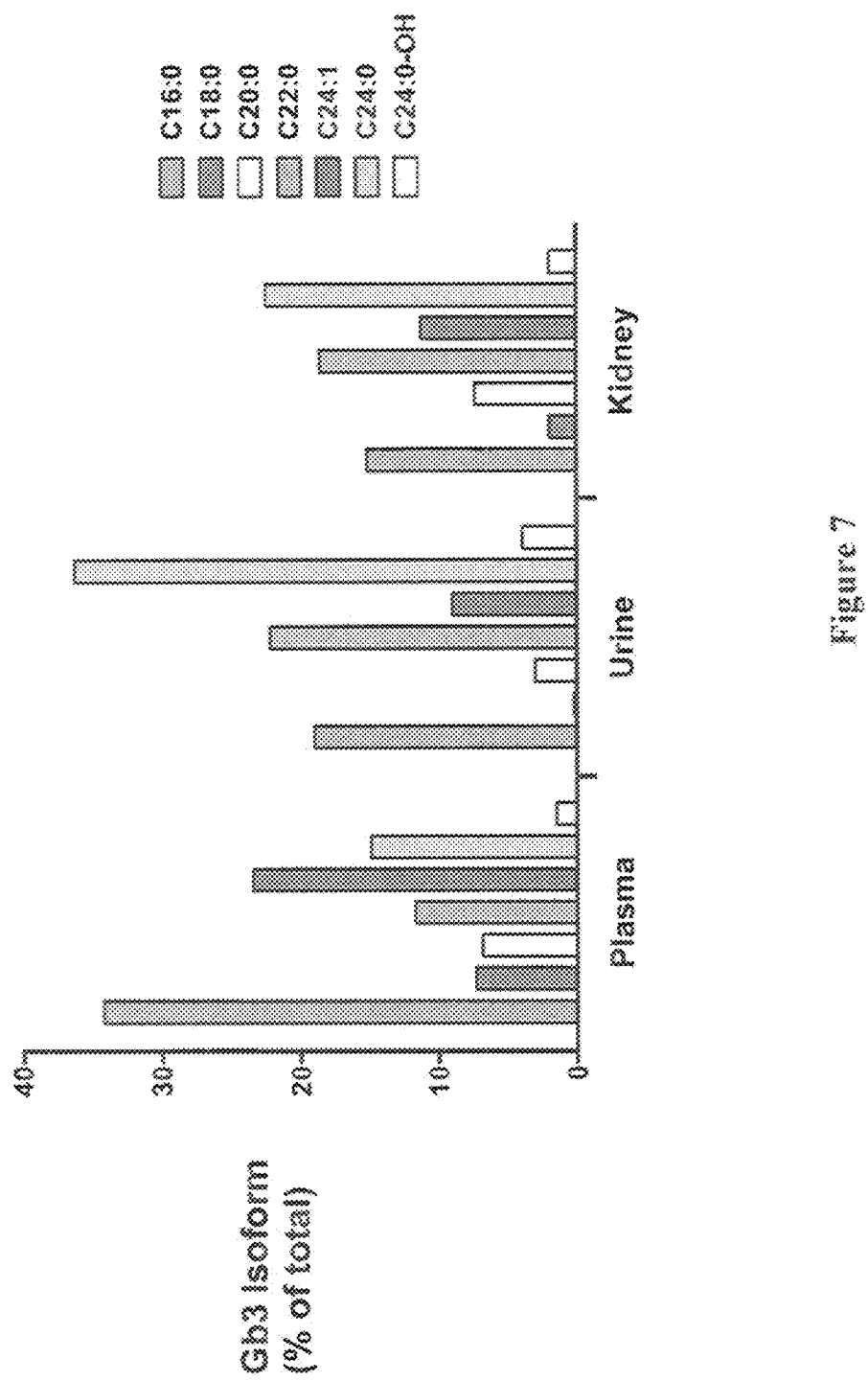
FIG. 7
N-linked acyl chain isoform analysis of Gb3 isolated from Fabry mouse plasma, urine and kidney.

The relative abundance of the different carbon chain length amido-linked acyl groups was determined for Gb3 from plasma, urine and kidney of Fabry mice. As shown in FIG. 7, major plasma isoforms were C16:0 and C24:1. Urine and kidney isoform profiles were nearly identical, with C24:0 and C22:0 being the predominant chain lengths. These data are consistent with urine Gb3 coming predominantly from the kidney—probably through epidermal exosomal shedding. Correlating these results with those in FIG. 6, in which ERT reduced plasma and urine lyso-Gb3 but not urine Gb3, suggests that the lyso-Gb3 in urine is derived from plasma filtrate. This differentiation of source for urine Gb3 and lyso-Gb3, if also true for patients, may explain why lyso-Gb3 is thought to be a more accurate predictor of disease severity and treatment efficacy than urine Gb3.

Example 114

SRT but not ERT Significantly Delays Loss of Thermal Nociceptive Response

Figure 8:
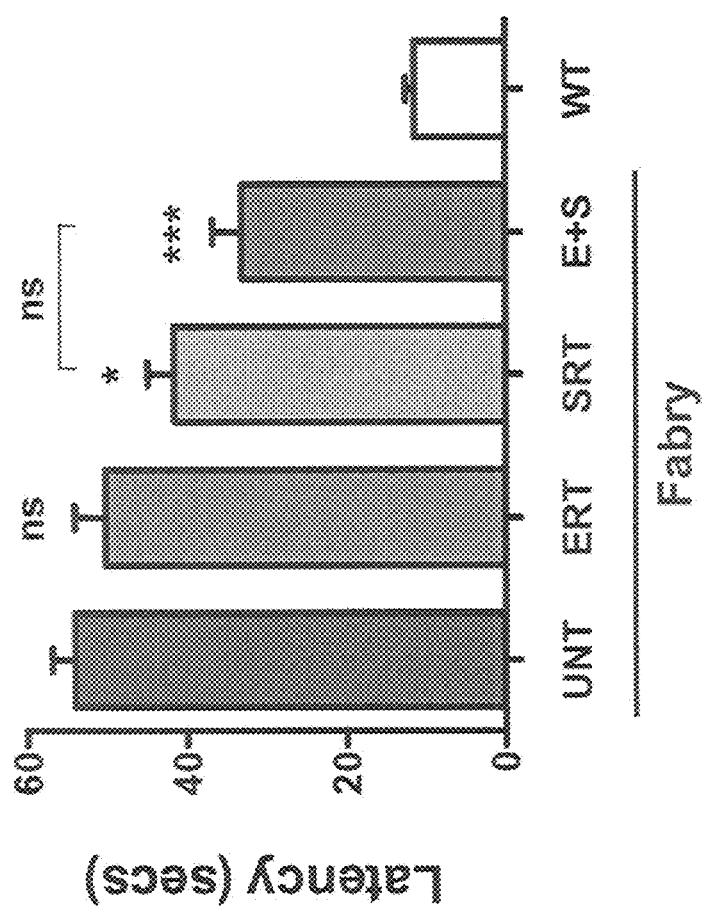
FIG. 8
Latency (time to respond) to a heat stimulus (55° C. hot-plate) of 10 month old Fabry mice following 7 months treatment with alpha-galactosidase A (ERT), GZ 452 (SRT) or a combination of the two (E+S) relative to untreated mice (UNT) and wild-type mice (WT).

Three month old Fabry mice were treated with GZ 452 in their diet (SRT), αgal once every 2 months (ERT), or a combination of the 2 treatments (E+S), as described above. After 6 months of combination therapy, the thermal nociceptive response time (latency) was evaluated by placing the mice on a 55° C. hotplate and recording the time to respond (i.e., a distinctive hind-paw flick). As shown in FIG. 8, after 7 months of treatment (10 month old mice) the ERT-only treated group was not significantly different to the untreated group (UNT). The SRT and combination treated groups had significantly shorter response times to the heat stimulus. These results demonstrate that SRT (but not ERT) delayed the loss of a thermal nociceptive response, a surrogate for the peripheral neuropathy often seen in Fabry patients.

Example 115 nGD Mouse Model for In Vivo Studies of SMT Using Gz161

K14 lnl/lnl (abbreviated as K14) mice were obtained from Lund University (Enquist et al. (2007)) and bred under a protocol approved by the Institutional Animal Care and Use Committee. Pups obtained from heterozygote matings were tail clipped and genotyped within one day of birth (by P1). The DNA was extracted using a lysis buffer of 5 mM EDTA, 0.2% SDS, 200 mM NaCl, 100 mM Tris pH 8.0 supplemented with 0.25 mg/ml Proteinase K (Invitrogen, Carlsbad, Calif.), precipitated with 100% isopropanol and redissolved in 1×Tris EDTA buffer. The DNA was then used for polymerase chain reaction (PCR) to determine the presence of the GC gene under the K14 keratin promoter (CRE) (Enquist et al. (2007)). To determine the Neomycin resistance site disruption of the murine glucocerebrosidase gene (NEO) we used a three primer approach: GC WT Fwd 5'-TGTTCCCCAACACAAT-GCTCTTT-3'; Rev 5'-TCTGTGACTCTGATGCCAC-CTTG-3' and Neo Rev 5'-AAGACAGAATAAAACG-CACGG GTG-3' as previously described in Cabrera-Salazar et al., Experimental Neurology 225: 436-444 (2010).

Newborn mice received daily 5 mg/kg intraperitoneal injections of Quinuclidin-3-yl (2-(4'-fluoro-[1,1'-biphenyl]-3-yl)propan-2-yl)carbamate (hereinafter "GZ 161") in a volume of 10 µl/gram of body weight starting at postnatal day 4. K14 mice and wild type littermates were humanely sacrificed at postnatal day 10 (pre-symptomatic) and at day 14 (humane endpoint) to evaluate glycosphingolipid (GSL) levels. Mice received a 150 mg/kg dose of pentobarbital (Euthasol, Virbac Inc, Forth Worth, Tex.) and were transcardially perfused with cold 0.9% NaCl solution. Brains were dissected and divided; one hemisphere was used for GSL analysis and the other was fixed in 4% paraformaldehyde for 96 hours and processed for histology.

To determine if further benefits could be achieved by prenatal exposure to GZ 161, a subset of pregnant K14 females received GZ 161 in food using a formulation calculated to provide 20 mg/kg/day during the final 5-7 days of gestation. Females receiving GZ 161 were switched to standard diet after delivery and the pups received daily IP injections of GZ 161 at a dose of 5 mg/kg (10 μl per gram of body weight) starting at P1. A set of WT pups born to females receiving the drug or standard formula was sacrificed immediately after birth to determine whether in utero exposure to GZ 161 could reduce brain GSL levels.

Example 116

Glycosphingolipid Quantitation

Quantitative sphingolipid analysis was performed by liquid chromatography and tandem mass spectrometry (LC/MS/MS) as previously described in Merrill et al., Methods 36: 207-224 (2005). Briefly, 101 of brain tissue homogenate (tissue weight/water:100 mg/ml) was extracted with 1.00 ml of an organic solvent mixture (97% acetonitrile, 2% methanol, and 1% acetic acid, v/v) and vortexed vigorously for 10 min. Extracted sphingolipids (GluCer and GluSph) were directly separated by hydrophilic liquid chromatography (Atlantis HILIC column, Waters Corp.) and analyzed by triple quadrupole tandem mass spectrometry (API 4000, Applied Biosystems/MDS SCIEX) and compared with sphingolipid standards (Matreya, LLC; Pleasant Gap, Pa.)

Example 117

Reformulation of Recombinant Human Glucocerebrosidase

Recombinant human glucocerebrosidase (rhGC) was reformulated as previously described in Cabrera-Salazar et al. (2010). Briefly, rhGC was bound using a cation-exchange (CM Sepharose) and human serum albumin (HSA) was added to the eluate as a stabilizer. The formulation for ICV administration was 2 mg/ml rhGC in a 10 mM sodium phosphate buffer at pH 7.2 containing 135 mM sodium chloride, 5 mg/ml HSA and 0.01% polysorbate 80.

Example 118

Intracerebroventricular Injections

An animal model of neuropathic Gaucher disease (nGD) identified as K14 were cryoanesthesized and received 2 μl bilateral intracerebroventricular (ICV) injections of either rhGC at 2 mg/ml or vehicle as previously described. (Cabrera-Salazar et al. (2010)) The injected pups were monitored for recovery and returned to the mother following the procedure.

Example 119

Histopathology

After genotype confirmation, animals were humanely sacrificed at 10 days of age, At this age K14 mice are asymptomatic. Mice received an intraperitoneal injection of 150 mg/kg sodium pentobarbital ((Euthasol, Virbac Inc, Forth Worth, Tex.) and were perfused by an intracardial infusion of chilled 0.9% sodium chloride. Brains were removed and post fixed in 4% paraformaldehyde for 72 hours. Tissue was transferred to PBS and paraffin embedded. Sagital sections 5 μm thick were cut and stained as described below. Gliosis and the presence of cells of the macrophage lineage were evaluated by means of glial fibrillary acidic protein staining and expression of CD68 and F4/80 pan-macrophage markers using the Leica Bond Max Immunostainer system (Leica Microsystems, Wetzlar, Germany).

GFAP staining: Paraffin sections were placed on mounting slides and processed using the Bond Polymer Refine IHC system (Leica Microsystems, Wetlzar, Germany) blocked for 10 minutes in serum-free protein block (Dako systems, Glostrup, Denmark), incubated for 30 minutes in a 1:1500 dilution of primary anti-GFAP antibody in Dako antibody diluent (Dako, Glostrup, Denmark), and stained using the Bond Polymer Refine detection kit (Leica Microsystems, Wetzlar, Germany).

F4/80 staining: Paraffin sections were placed on mounting slides and processed using the Bond Polymer Refine IHC system (Leica Microsystems, Wetlzar, Germany), incubated for 30 minutes in a 1:2500 dilution of rat anti-mouse F4/80 antibody (eBioscience, San Diego, Calif.) or Rat IgG2a (eBioscience, San Diego, Calif.) as an isotype control. Slides were then incubated with a 1:250 dilution of rabbit anti-rat secondary antibody (Vector laboratories, Burlingame, Calif.) and stained using the Bond Polymer Refine detection kit (Leica Microsystems, Wetzlar, Germany).

CD68 staining: Paraffin sections were placed on mounting slides and processed using the Bond Polymer Refine IHC system (Leica Microsystems, Wetlzar, Germany), incubated for 30 minutes in a 1:2500 dilution of rat anti-mouse CD68 clone FA-11 antibody (AbD Serotec, Oxford, UK) or Rat IgG2a isotype control (AbD Serotec, Oxford, UK). Slides were then incubated with a 1:250 dilution of rabbit anti-rat secondary antibody (Vector laboratories, Burlingame, Calif.) and stained using the Bond Polymer Refine detection kit (Leica Microsystems, Wetzlar, Germany).

For each staining technique exposure-matched digital images were obtained from similar brain regions of each experimental group using the Aperio ScanScope XT system (Aperio Technologies, Vista, Calif.). Stained slides were digitalized in high resolution and six areas of interest were highlighted in each slide and analyzed independently by histomorphometry. Positively stained area and nuclei were determined and quantitative data were analyzed by a one-way analysis of variance followed by Tukey's multiple comparison test using the Graph Pad Prism V 4.0 (GraphPad Software, San Diego, Calif.). Differences between group means with $p<0.05$ were considered significant.

Example 119

Survival

K14 mice received daily intraperitoneal injections of GZ 161 at a dose of 5 mg/kg of body weight as described above. A separate cohort of animals also received ICV injections of GC at postnatal days 1, 2 and 3 followed by daily IP injections of GZ 161. Animals that reached weaning age received GZ 161 in a special chow designed to provide a dose of 60 mg/kg/day. All animals were monitored daily for the development of neurological complications. Mice were sacrificed when they reached a humane endpoint (inability to right within 10 seconds after being placed in lateral recumbence) by an injection of 150 mg/kg sodium pentobarbital (Euthasol, Virbac Inc, Forth Worth, Tex.). This time point was recorded as end of life and analyzed using Kaplan-Meier plots.

Example 120

Statistical Analysis

Values shown correspond to means and error bars represent standard error of the mean. Comparisons between groups were analyzed by a one-way analysis of variance followed by Tukey's multiple comparison test. Comparison of substrate reduction in utero was analyzed by the unpaired t test with Welch's correction. Kaplan-Meier survival curves were analyzed using the log-rank test equivalent to the Mantel-Haenszel test. All statistical analyses were performed using GraphPad Prism v4.0 (GraphPad Software, San Diego, Calif.). Differences between group means with $p<0.05$ were considered significant.

Example 121

Substrate Accumulation in K14 Mouse Brain

Figure 9:
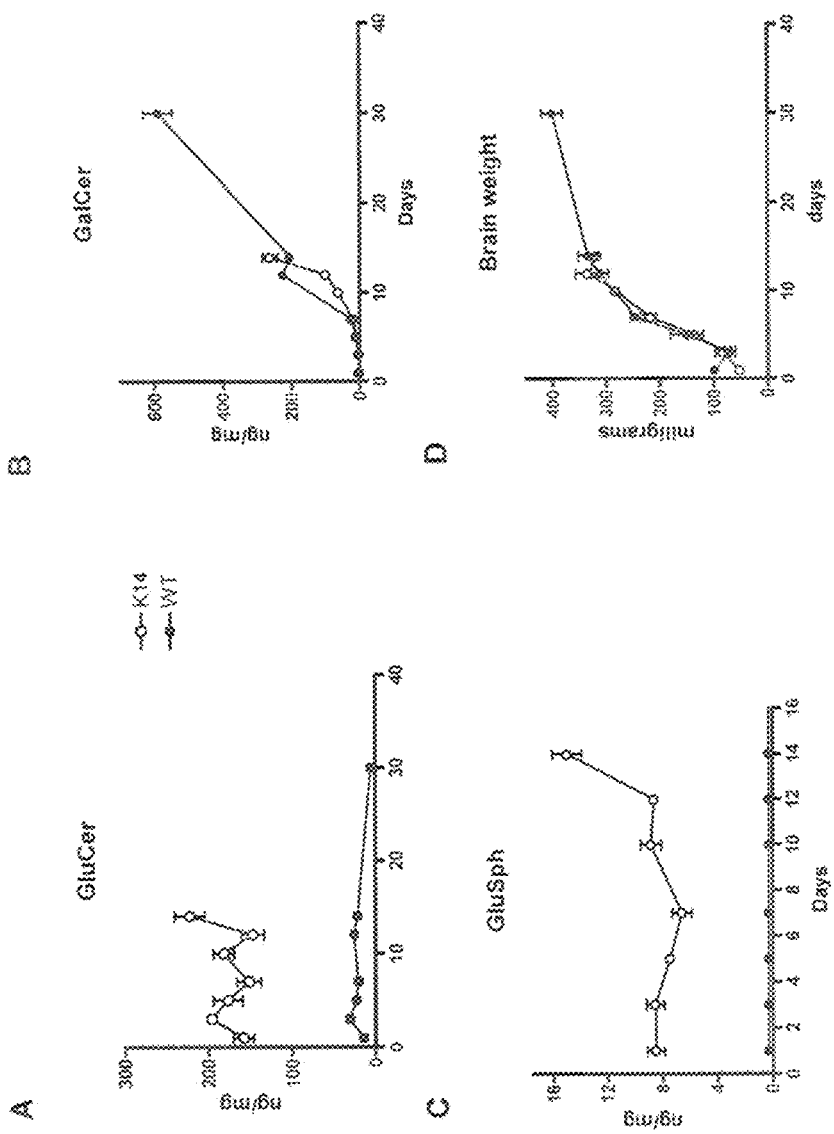
FIG. 9 Glucosyl ceramide (GluCer) and Glucosyl sphingosine (GluSph) are significantly elevated in the brains of neonatal K14 mice. Mass spectrometry analysis of glucosyl- and galactosylceramides shows that (A) GluCer was elevated 10-fold in K14 mice (an animal model of Neonatal Gaucher disease, also known as Gaucher disease Type 2) compared to WT mice through the first 2 weeks of life, (B) GalCer levels were similar over time for both K14 and WT mice, (C) GluSph levels were ≥10-fold higher in K14 mice than age-matched WT mice over the first 2 weeks of life; GluSph levels in WT animals were below the level of detection (<0.3 ng/mg). (D) There were no significant differences in brain weights between K14 and WT mice over the first 2 weeks of life. Data points represent mean values and error bars SEM for N=4.

Before evaluating drug effects on brain lipids, we compared the time dependent changes in GluCer, GalCer and GluSph levels in the K14 mouse brain to those of a wild type (WT) mouse control. FIG. 9, panels A and B show that in WT mouse brain, the predominant GL-1 isomer in the first few days of life was GluCer; by postnatal day 14 (P14) the predominant isomer was GalCer. These results are consistent with those of a study in rat brain, which found that GluCer is synthesized at a higher rate during the first week of life and is followed by an increased synthesis of GalCer starting at P8 (Brenkert et al., Brain Research 36: 183-193 (1972)). FIG. 9, panel A also shows that in K14 mice GluCer was elevated 10-fold relative to WT mice and that this increase was sustained through the first 2 weeks of life until the mice died around P14.

In agreement with previous mouse models of neuropathic Gaucher disease (Liu et al., PNAS 95: 2503-2508 (1998)), FIG. 9, panel C shows that at birth the lysoglycosphingolipid GluSph was elevated >20-fold in the brains of the K14 mouse model relative to WT mice. This increase was sustained through the first 2 weeks of life and was even higher in animals sacrificed at end stage (FIG. 9, panel C). In WT littermates of the K14 mice, GluSph levels were below the threshold of detection (0.3 ng/mg of tissue). FIG. 9, panel D shows that these elevated glycosphingolipids and lysoglycosphingolipids in the K14 mouse did not appear to have an impact on brain weight (relative to that of WT mice). Given the known toxicity of GluSph, therapeutic strategies geared towards reducing the accumulation of these substrates in the K14 mouse brain might be expected to have an impact on the pathologic features of the disease and the lifespan of the animals.

Example 122

Figure 10:
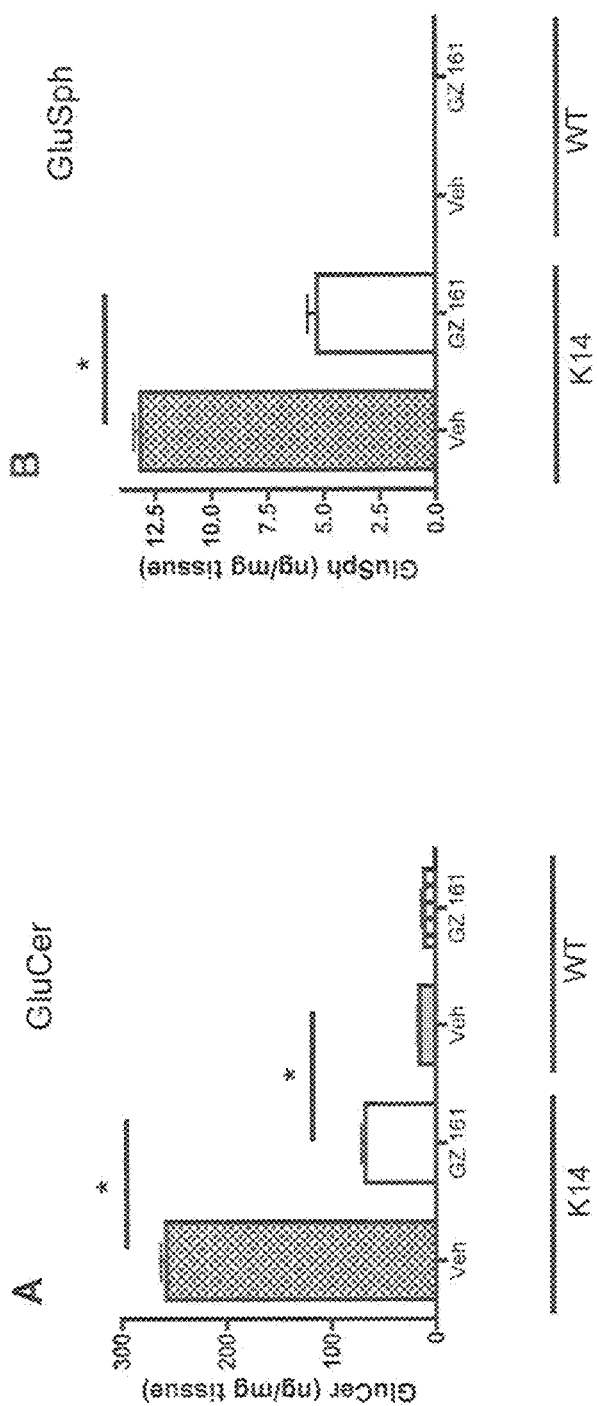
FIG. 10 Systemic administration of Quinuclidin-3-yl (2-(4'-fluoro-[1,1'-biphenyl]-3-yl)propan-2-yl)carbamate ("GZ 161") reduces GluCer and GluSph levels in the K14 mouse brain. K14 and WT mice were treated daily (IP) beginning at P4 with vehicle or 5 mg/kg GZ 161, and brains analyzed for GluCer and GluSph at P10. GZ 161-treated animals were asymptomatic at this time. Treatment with GZ 161 reduced K14 (A) GluCer levels by ~70% and (B) GluSph levels by ~60%. Post-treatment levels of both glycosphingolipids remained significantly elevated compared to their WT litter-mates and genotypes were confirmed by post-mortem DNA analysis. *$p<0.05$. N=4/group.

Intraperitoneal Administration of GZ 161 Reduces GluCer and GluSph Levels in the Brains of K14 Mice FIG. 10 shows that compared to vehicle-treated K14 mice at the humane endpoint (14-15 days of age), daily intraperitoneal (IP) administration of GZ 161 reduced brain levels of both GluCer and GluSph by >60%. K14 mice treated with GZ 161 were asymptomatic at this time point. Even though GZ 161 administration significantly reduced the levels of these glycosphingolipids, FIG. 10 shows that they nonetheless remained elevated several-fold over those of age-matched wild-type mice; GluSph was not detected in samples analyzed from WT or heterozygote littermates. The reduction of brain glycosphingolipids as a consequence of systemic drug administration strongly suggests that GZ 161 is both capable of crossing the blood brain barrier and inhibiting its target enzyme, GCS.

Example 123

Figure 11:
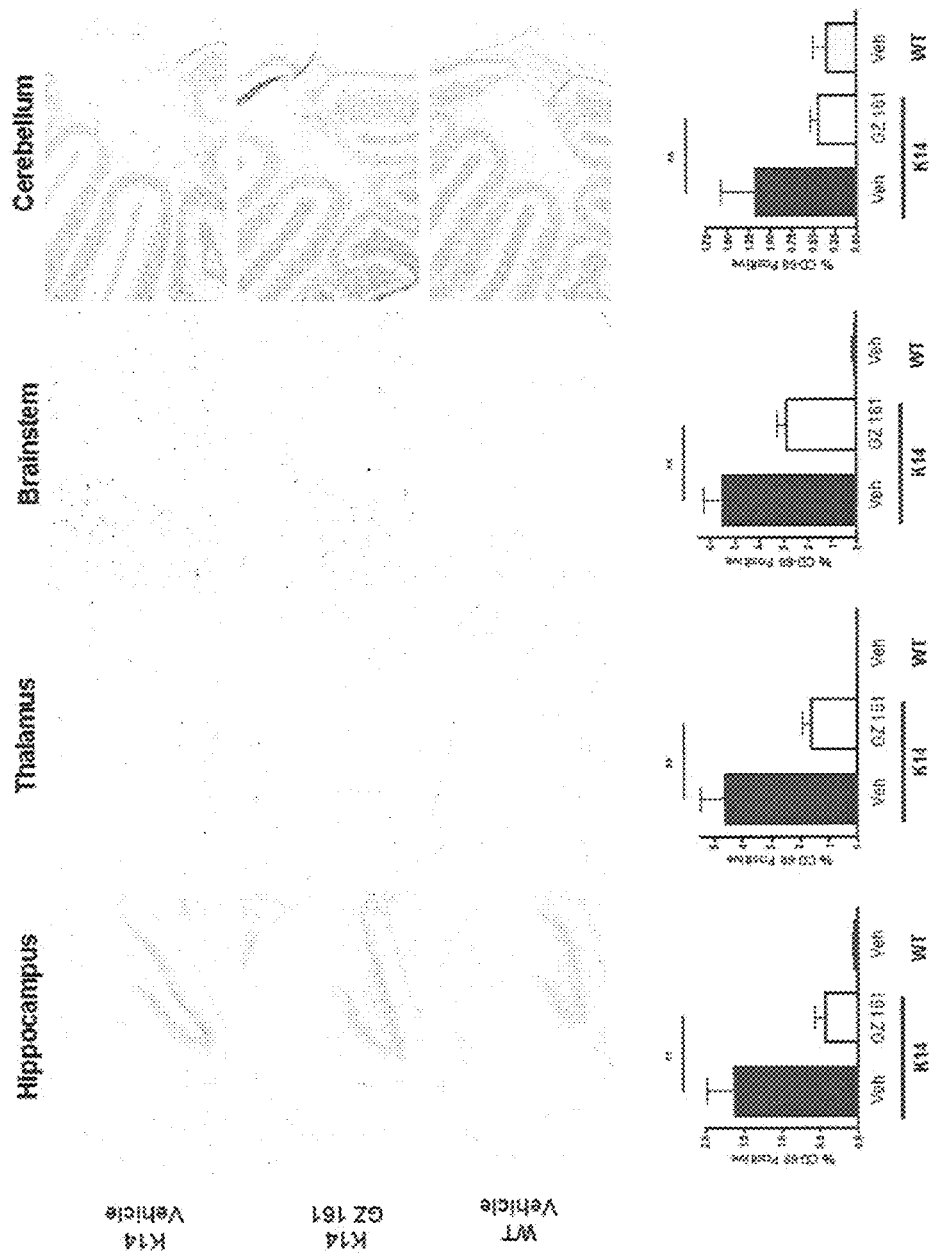
Figure 12:
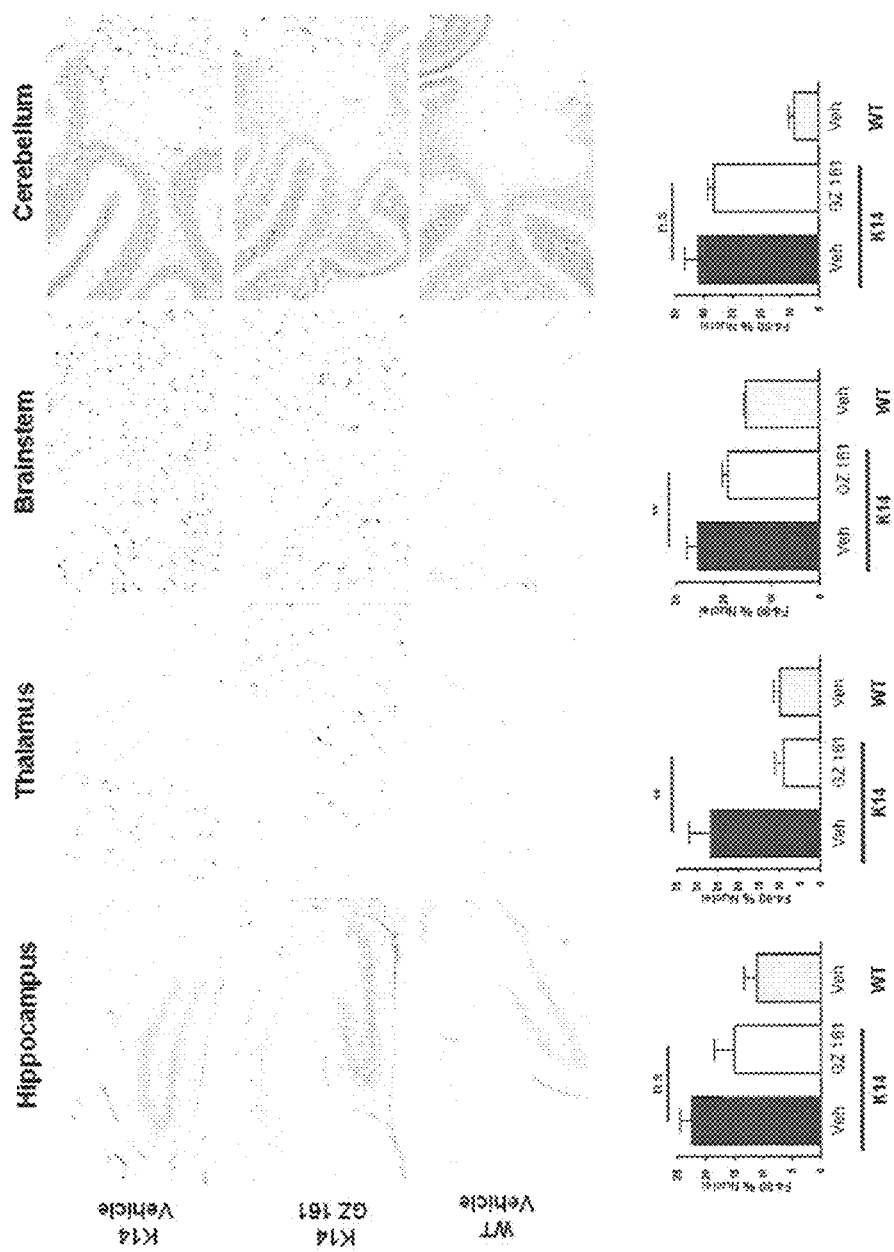

Intraperitoneal Administration of Gz 161 Reduces Microglial/Macrophage Staining Throughout the Brain of K14 Mice Cells of the myeloid lineage can be detected in the murine brain using antibodies to antigens such as F4/80 and CD68. F4/80 is a transmembrane glycoprotein found on ramified (quiescent) microglia and macrophages, while CD68 is a lysosomal protein expressed at relatively high levels in macrophages and activated (reactive) microglia, and at lower levels in ramified microglia. Increased F4/80 and CD68 staining in the brain may occur through recruitment of monocytes or microglial proliferation, and is a normal response to injury and inflammation. FIG. 11 shows qualitatively and quantitatively that compared to wild type mice at 10 days of age (P10), the K14 mouse brain has increased numbers of CD68+ cells in multiple locations (hippocampus, thalamus, brainstem, cerebellum). The greatest concentration of CD68+ cells was seen in the thalamus and brainstem, two sites that also show pathology in type 2 Gaucher patients. (Conradi et al., Acta Neuropathologica 65: 99-109 (1984); Conradi et al., Acta Neuropathologica 82: 152-157 (1991); and Wong et al., Molecular Genetics and Metabolism 82: 192-207 (2004)). FIG. 11 also shows that systemic administration of GZ 161 reduces the numbers of CD68+ cells in all of these locations; treatment also reduced CD68+ cells in the olfactory bulb and frontal cortex (data not shown). Consistent with the CD68 histopathology, FIG. 12 shows increased F4/80 staining relative to WT animals in vehicle treated K14 mice at P10. Daily IP injections of GZ 161 reduced the numbers of F4/80+ cells in the thalamus and brainstem, but had marginal effects in other brain regions. Taken together with the CD68 data, these results suggest that systemic treatment of the K14 mouse with GZ 161 results in decreased numbers of macrophages/microglia in multiple brain regions.

Example 124

Figure 13:
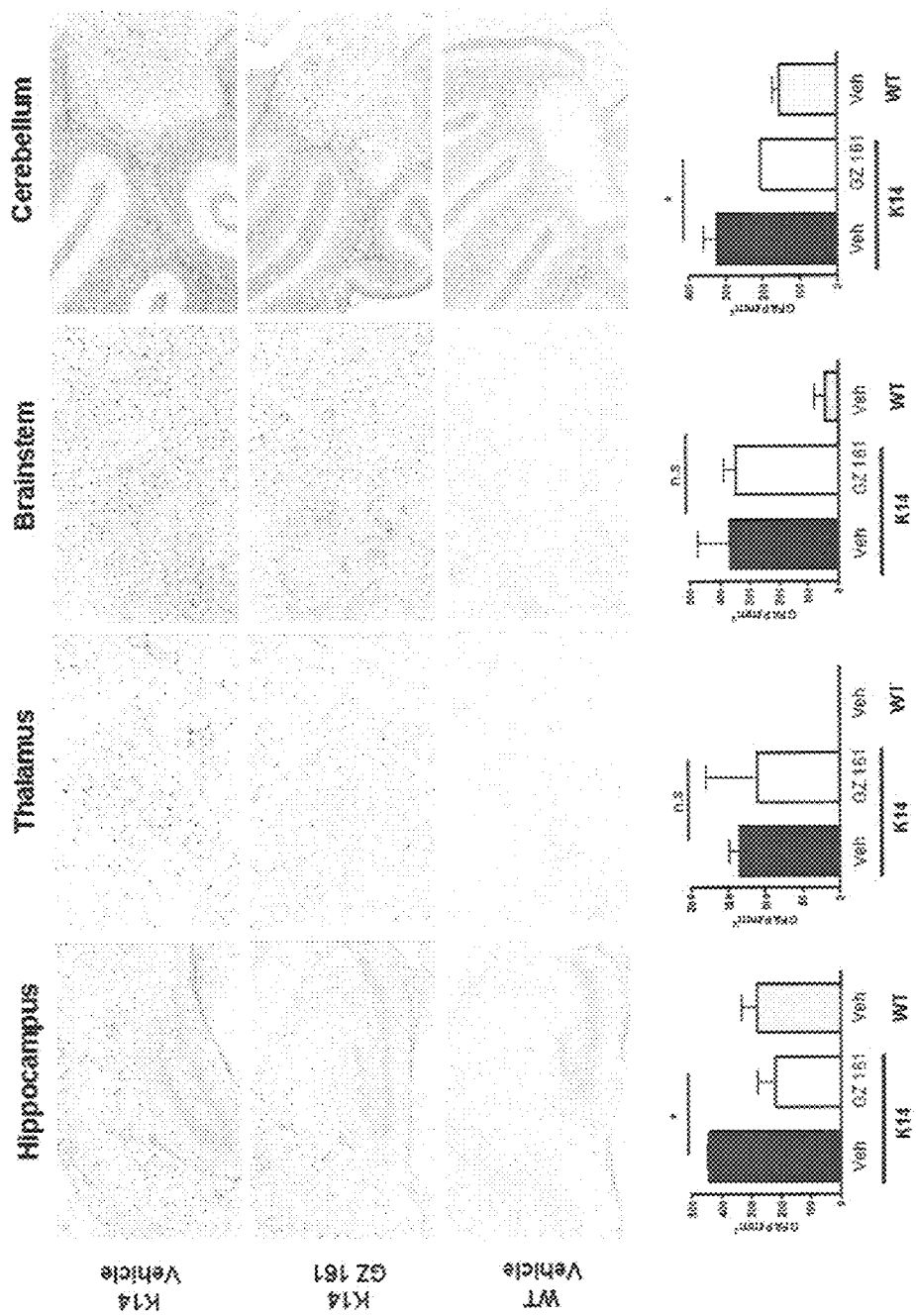

Intraperitoneal Administration of GZ 161 Reduces Gliosis in Several Brain Regions of K14 Mice Astrocytes can undergo hypertrophy or proliferate in response to inflammation and neuronal damage or death, a process known as astrogliosis. Glial fibrillary acidic protein (GFAP) is an intermediate filament protein that is heavily expressed in activated (reactive) astrocytes, and can therefore be used to monitor astrogliosis. FIG. 13 shows that at P10 GFAP staining was increased compared to WT levels in several brain regions (hippocampus, thalamus, brainstem, cerebellum) of the K14 mouse, indicating the presence of reactive astrocytes. FIG. 13 also shows that systemic treatment of K14 mice with GZ 161 led to decreased GFAP staining in the hippocampus and cerebellum at P10: staining was also decreased in the olfactory bulb and frontal cortex (data not shown). Thus, these GFAP results are consistent with the above macrophage/microglial data demonstrating that the K14 mouse likely has an ongoing inflammatory process that can be attenuated to some degree by systemic administration of GZ 161.

Example 125

Intraperitoneal Administration of GZ 161 Increases Survival of K14 Mice

Figure 14:
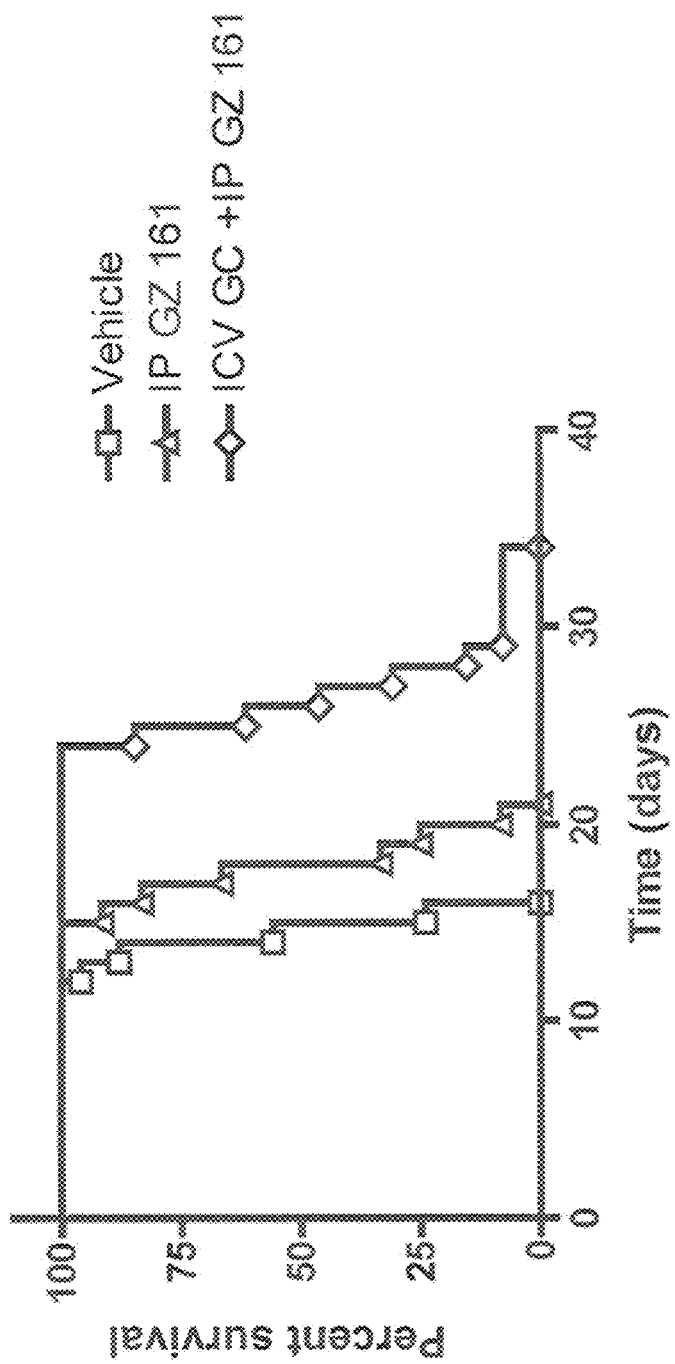
FIG. 14 Systemic administration of GZ 161 increases the median lifespan of K14 mice. K14 mice were injected (IP) daily beginning at P4 with vehicle or GZ 161 or given a combined treatment of three intracerebroventricular (ICV) injections of rhGC at P1, 2, 3 together with daily (IP) injections of GZ 161 beginning at P4. Vehicle treated mice had a 15 day median lifespan (N=25); GZ 161 treated mice had an 18 day median lifespan (N=12; $p<0.0001$ compared to vehicle-treated); mice coadministered GZ 161 and rhGC had a 26 day median lifespan (N=13)

Given the positive effects of GZ 161 treatment on brain glycosphingolipids and histopathology, we asked whether these effects translated into increased survival of the K14 mouse. FIG. 14 demonstrates that vehicle treated K14 mice have a median lifespan of 15 days, consistent with our previous findings in this mouse model (Cabrera-Salazar et al. (2010)). Systemic (IP) treatment of K14 mice with GZ 161 resulted in an extension in median lifespan to 18 days ($p<0.0001$), consistent with a benefit of the molecular and cellular effects of the drug in the brain shown above.

In previous experiments, it was shown in the K14 mouse that neonatal (P1-P3) intracerebroventricular injections of GC could extend median survival even further, viz., to 23 days (Cabrera-Salazar et al. (2010)). Because GC and GZ 161 both have the potential to decrease levels of the same glycosphingolipid, namely GluCer (GC by degrading GluCer; GZ 161 by inhibiting its synthesis) we also asked whether the combination of Gz161 and intracerebroventricular (ICV) administration of GC would provide survival benefit superior to that resulting from either individual agent. FIG. 14 demonstrates that the combination of ICV GC (at P1,2,3) and daily IP Gz161 led to a median survival of 26 days, significantly greater than GZ 161 alone or ICV GC ($p=0.0007$). Thus, systemic administration of GZ 161 appears to be additive to ICV GC, and provides additional survival benefit.

Example 126

Prenatal Administration of GZ 161 Fails to Increase Survival of K14 Mice

Figure 15:
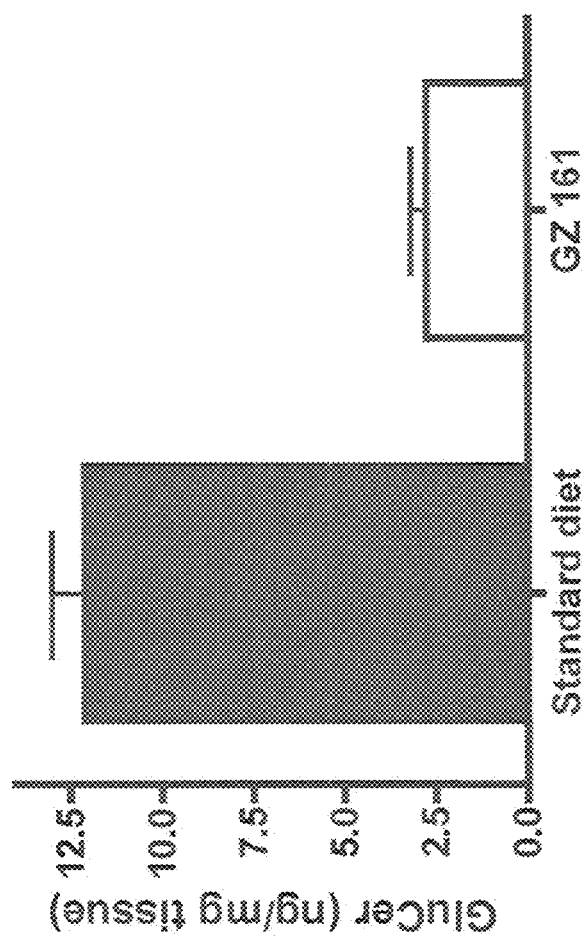
FIG. 15 GZ 161 appears to cross the blood/placental barrier. Systemic administration (20 mg/kg/day in food) of GZ 161 to pregnant WT mice reduces the GluCer load in whole brain homogenates of mice at birth (P0). N=7; $p<0.0001$)
Figure 16:
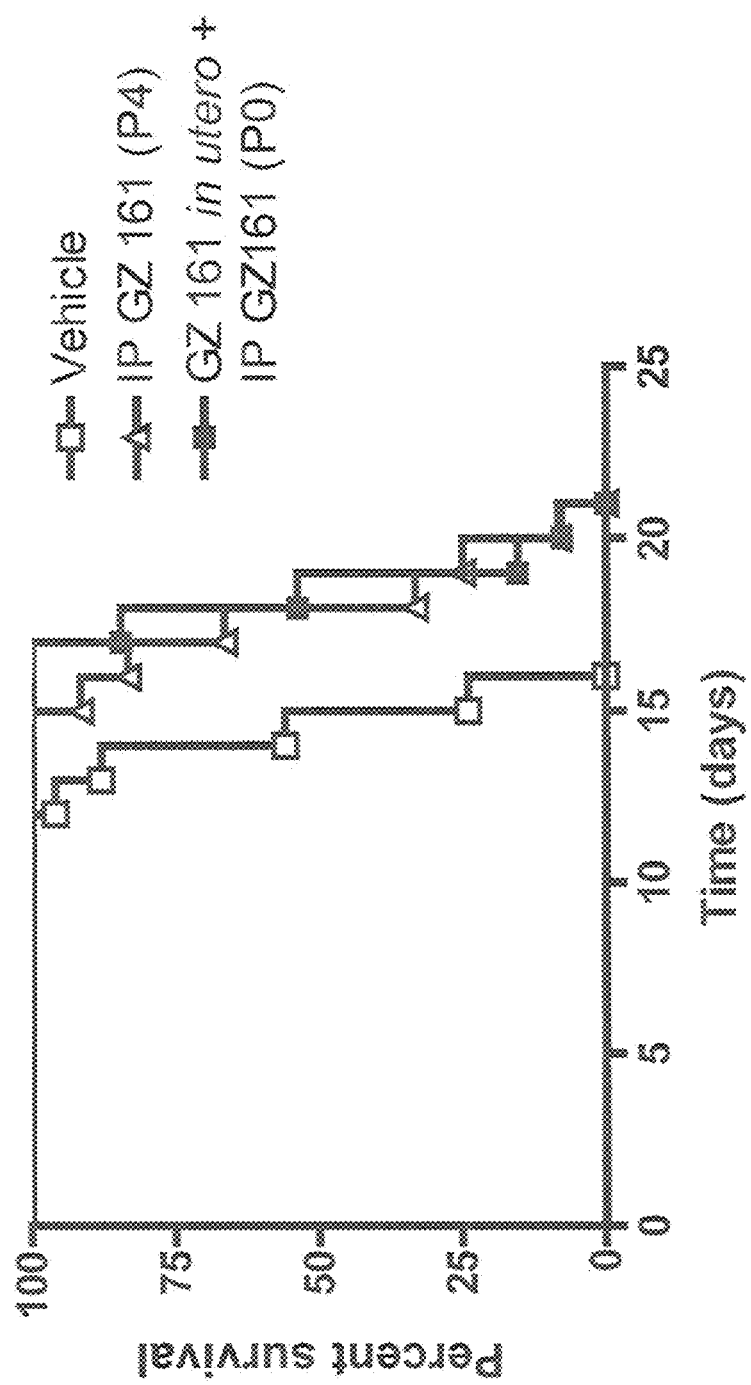
FIG. 16 Treating K14 mice with GZ 161 in utero has a minimal effect on survival. K14 mice treated daily (IP) beginning at P4 with vehicle had a median lifespan of 14 days (N=13). Systemic administration (20 mg/kg/day in food) of GZ 161 to pregnant K14 mice and then daily systemic (IP) administration of GZ 161 (5 mg/kg) to the pups beginning at P0 extended lifespan to 19 days (N=13), a result similar to treating pups daily systemically (IP) with GZ 161 at 5 mg/kg beginning at P4 (N=12).

Because the GluSph levels in the K14 mouse brain were found to be elevated at least 10-fold over normal at P1, and it has been documented that GluSph is elevated in the brains of mice and humans affected by nGD even prenatally (Orvisky et al., Pediatric Research 48: 233-237 (2000)), it was investigated whether a survival advantage could be gained by treating K14 mice with GZ 161 in utero. FIG. 15 shows that treating WT mouse dams with GZ 161 led to an ~5-fold decrease in GluCer levels in the newborn mouse brain (P0), suggesting that GZ 161 could cross the blood/placental barrier. However, giving K14 dams GZ 161 and then treating the resulting pups IP with GZ 161 failed to extend survival beyond that of mice given systemic GZ 161 postnatally alone (18 days) (FIGS. 14 and 16). These data are thus consistent with the results described in FIG. 14, and imply that although GZ 161 can effect reductions in glycosphingolipids and neuropathology, the current treatment regime is insufficient to rescue the CNS. These results are consistent with our previous results in this model using intracerebroventricular injections of recombinant human glucocerebrosidase (Cabrera-Salazar et al. (2010)), and together suggest that more robust and continuous depletion of glycosphingolipids such as GluCer will be necessary to improve survival further.

These data show both qualitatively and quantitatively that systemic (IP) administration of GZ 161 to neonatal K14 mice significantly reduces substrate load, ameliorates the pathological features of the disease and increases median lifespan. When combined with ICV-delivered rhGC, systemic administration of GZ 161 resulted in additive increases in lifespan, implying that such a combination might be more efficacious than either monotherapy alone in nGD patients. Given the implications of these studies that GZ 161 can apparently cross the BBB and inhibit its target enzyme, glucosylceramide synthase, it is reasonable to assume that this molecule could also be used to treat other LSDs resulting from a buildup of substrates downstream from GluCer.

It is important to note that in the current studies, GZ 161 was administered to K14 mice in a time frame in which GluCer and GluSph were being produced in the developing mouse brain at relatively high levels compared to WT mice (FIG. 9); Brenkert et al., 1972). Daily IP treatment with GZ 161 successfully reduced, but did not normalize GluCer and GluSph levels in the K14 brain (FIG. 10). There are several lines of evidence suggesting that GluSph and other lysosphingolipids such as galactosyl sphingosine may contribute to CNS pathology by initiating the production of inflammatory mediators Girl et al., Journal of lipid research 47: 1478-1492 (2006) and Gräler et al., Molecular and Cell Biology of Lipids 1582: 168-174 (2002). The ability of GZ 161 to decrease GluSph levels and concurrently result in decreased macrophage/microglial and astrocyte staining (FIGS. 11-13) is consistent with this hypothesis. Because GluSph also has known neurotoxic properties (Schueler et al., Neurobiology of Disease 14: 595-601 (2003); Orvisky et al., Molecular Genetics and Metabolism 76: 262-270 (2002); Sun et al., Hum Mol Genet. 19: 1088-1097 (2010); and Pelled et al., Journal of Inherited Metabolic Disease 23: 175-184 (2000)), the inability of GZ 161 treatment to normalize GluSph levels is consistent with GluSph as a potential contributor to the early death seen in this model.

Taken together, the preclinical results in the K14 mouse model shown here suggest that administration of GZ 161 may mitigate disease progression and neurologic symptoms in type 2 and type 3 Gaucher disease patients. However, it is difficult to predict the potential benefits of such a therapeutic approach in symptomatic type 2 patients since it is known that their brains contain very high levels of GluSph that date back to prenatal life. Goker-Alpan et al., The Journal of Pediatrics 143: 273-276 (2003). Type 3 Gaucher disease may be more amenable to treatment since the brain levels of GluSph are lower (Nilsson, J Neurochem 39: 709-718 (1982), the progression of the disease is slower despite being part of a phenotypic continuum (Goker-Alpan et al. (2003)), and in some cases the patients can be identified by mutational analysis before the onset of the neuropathic phenotype (Ida et al., Human Genetics 105: 120-126 (1999)). Based on the current results, it would appear that an early, aggressive approach will be needed to treat these patients. Small molecule inhibitors of glucosylceramide synthase may represent one arm of a comprehensive approach.

Example 127

SMT of Male and Female Fabry Mice Treated with GZ 452, GZ 161 and GZ 638

Figure 17:
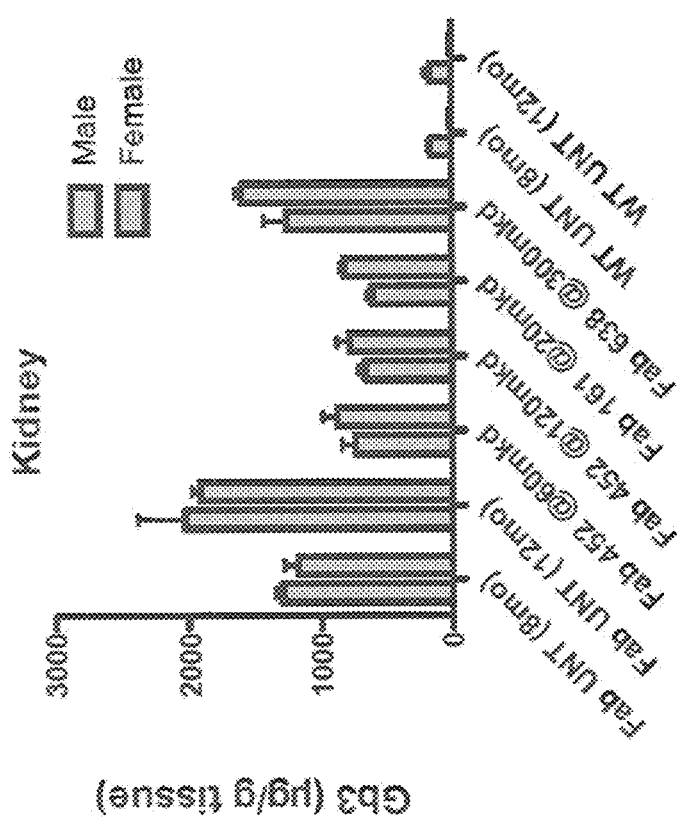
FIG. 17 Gb3 levels in kidney tissue from 12 month old male and female Fabry mice treated with GZ 452, GZ 161 and GZ 638. Mice began treatment at ~8 months old and were treated for 4 months with: 60 mg/kg/day GZ 452, 120 mg/kg/day GZ 452, 20 mg/kg/day GZ 161, 300 mg/kg/day GZ 638, plus WT and UNT controls.

Fabry mice began treatment at ~8 months old and were treated for 4 months with: 60 mg/kg/day GZ 452 (Fab 452@60 mkd), 120 mg/kg/day GZ 452 (Fab 452@120 mkd), 20 mg/kg/day GZ 161 (Fab 161@20 mkd), 300 mg/kg/day GZ 638 (Fab 638@300 mkd). Kidney tissue from 12 month old male and female Fabry mice were tested for Gb3 levels. As shown in FIG. 17, GZ 161 and GZ 452 significantly reduced the amount of Gb3 present in kidney tissue relative to untreated controls (Fab UNT 12 mo).

The invention claimed is:
1. A compound represented by the following structural formula,

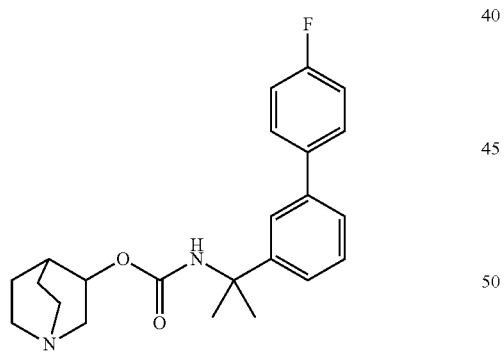

or a pharmaceutically acceptable salt thereof.

* * * * *